US012297243B2

(12) United States Patent
Emtage et al.

(10) Patent No.: US 12,297,243 B2
(45) Date of Patent: May 13, 2025

(54) METHODS AND COMPOSITIONS FOR REDUCING THE IMMUNOGENICITY OF CHIMERIC NOTCH RECEPTORS

(71) Applicant: Cell Design Labs, Inc., Emeryville, CA (US)

(72) Inventors: Peter Emtage, Lafayette, CA (US); Amy E. Gilbert, San Francisco, CA (US); Anselm Levskaya, Oakland, CA (US); Spencer Scott, San Francisco, CA (US); Vladimir Anatolievich Slepushkin, Vallejo, CA (US)

(73) Assignee: Cell Design Labs, Inc., Emeryville, CA (US)

( * ) Notice: Subject to any disclaimer, the term of this patent is extended or adjusted under 35 U.S.C. 154(b) by 0 days.

(21) Appl. No.: 17/716,630

(22) Filed: Apr. 8, 2022

(65) Prior Publication Data

US 2022/0372090 A1 Nov. 24, 2022

Related U.S. Application Data

(62) Division of application No. 16/010,805, filed on Jun. 18, 2018, now Pat. No. 11,325,957.

(60) Provisional application No. 62/603,993, filed on Jun. 19, 2017, provisional application No. 62/556,765, filed on Sep. 11, 2017.

(51) Int. Cl.

| | |
|---|---|
| ***C07K 14/47*** | (2006.01) |
| ***A61K 48/00*** | (2006.01) |
| ***C07K 14/705*** | (2006.01) |
| ***C07K 14/71*** | (2006.01) |
| ***C07K 16/18*** | (2006.01) |
| ***C07K 16/28*** | (2006.01) |
| ***C07K 19/00*** | (2006.01) |
| ***C12N 5/0786*** | (2010.01) |
| ***C12N 5/10*** | (2006.01) |
| ***C12N 15/63*** | (2006.01) |
| ***C12N 15/85*** | (2006.01) |
| *A61K 39/00* | (2006.01) |
| *A61P 35/04* | (2006.01) |
| *C07K 16/46* | (2006.01) |

(52) U.S. Cl.

CPC .......... *C07K 14/4702* (2013.01); *A61K 48/00* (2013.01); *C07K 14/4705* (2013.01); *C07K 14/705* (2013.01); *C07K 14/70517* (2013.01); *C07K 14/71* (2013.01); *C07K 16/28* (2013.01); *C07K 16/2803* (2013.01); *C07K 19/00* (2013.01); *C12N 5/0645* (2013.01); *C12N 5/10* (2013.01); *C12N 15/63* (2013.01); *C12N 15/85* (2013.01); *A61K 2039/5156* (2013.01); *A61P 35/04* (2018.01); *C07K 16/462* (2013.01); *C07K 2317/569* (2013.01); *C07K 2317/622* (2013.01); *C07K 2317/626* (2013.01); *C07K 2317/70* (2013.01); *C07K 2319/00* (2013.01); *C07K 2319/02* (2013.01); *C07K 2319/03* (2013.01); *C07K 2319/09* (2013.01); *C07K 2319/33* (2013.01); *C07K 2319/41* (2013.01); *C07K 2319/50* (2013.01); *C07K 2319/70* (2013.01); *C07K 2319/71* (2013.01); *C07K 2319/80* (2013.01); *C07K 2319/95* (2013.01); *C12N 2740/16043* (2013.01); *C12N 2830/15* (2013.01); *C12N 2830/85* (2013.01)

(58) Field of Classification Search

CPC .......... A61K 2039/505; A61K 39/3955; A61K 48/00; A61K 2039/5156; A61K 38/177; C07K 16/28; C07K 16/2803; C07K 16/2851; C07K 16/2896; C07K 16/30; C07K 16/2866; C07K 16/2863; C07K 19/00; C07K 2319/00; C07K 2319/02; C07K 2319/03; C07K 2319/09; C07K 2319/33; C07K 2319/50; C07K 2319/71; C07K 2319/70; C07K 2319/80; C07K 2319/91; C07K 14/705

See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 5,225,539 | A | 7/1993 | Winter |
| 5,476,786 | A | 12/1995 | Huston et al. |
| 7,612,181 | B2 | 11/2009 | Wu et al. |
| 8,258,268 | B2 | 9/2012 | Wu et al. |
| 8,586,714 | B2 | 11/2013 | Ghayur et al. |
| 8,716,450 | B2 | 5/2014 | Ghayur et al. |

(Continued)

FOREIGN PATENT DOCUMENTS

| | | | |
|---|---|---|---|
| CN | 101883786 | A | 11/2010 |
| EP | 0404097 | B1 | 9/1996 |

(Continued)

OTHER PUBLICATIONS

Borggrefe et al. The Notch signaling pathway: Transcriptional regulation at Notch target genes. Cell Mol Life Sci 66: 1631-1646, 2009.*

(Continued)

*Primary Examiner* — Bridget E Bunner

(74) *Attorney, Agent, or Firm* — Barnes & Thornburg LLP

(57) ABSTRACT

The present invention relates to methods and compositions for reducing the immunogenicity of chimeric Notch receptors, and specifically to transcription factors useful for controlling gene expression delivered to tissues by such chimeric Notch receptors.

9 Claims, 7 Drawing Sheets

Specification includes a Sequence Listing.

(56) References Cited

U.S. PATENT DOCUMENTS

| | | | |
|---|---|---|---|
| 8,722,855 B2 | 5/2014 | Ghayur et al. | |
| 8,735,546 B2 | 5/2014 | Ghayur et al. | |
| 8,822,645 B2 | 9/2014 | Ghayur et al. | |
| 9,670,281 B2 | 6/2017 | Lim et al. | |
| 9,834,608 B2 | 12/2017 | Lim et al. | |
| 2003/0109678 A1 | 6/2003 | Cortese et al. | |
| 2016/0264665 A1 | 9/2016 | Lim et al. | |
| 2018/0362603 A1 | 12/2018 | Gilbert et al. | |
| 2019/0202918 A1* | 7/2019 | Lim | C07K 16/2803 |

FOREIGN PATENT DOCUMENTS

| | | | |
|---|---|---|---|
| WO | 1986001533 A1 | 3/1986 | |
| WO | 1993011161 A1 | 6/1993 | |
| WO | 2009025867 A2 | 2/2009 | |
| WO | 2014127261 A1 | 8/2014 | |
| WO | 2016138034 A1 | 9/2016 | |
| WO | 2017123559 A2 | 7/2017 | |
| WO | 2019164979 A1 | 8/2019 | |
| WO | WO-2018039247 A1 * | 3/2023 | |

OTHER PUBLICATIONS

Groot et al. Regulated Proteolysis of Notch2 and Notch3 Receptors by Adam10 and Presenilins. Mol Cell Biol 34(15): 2822-2832, 2014.*

Habets et al. Human Notch2 Is Resistant to Ligand-independent Activation by Metalloprotease Adam17. J Biol Chem 290(23): 14705-14716, 2005.*

Lobry et al. Notch signaling: switching an oncogene to a tumor suppressor. Blood 123(16): 2451-2459, 2014.*

Sadelain Michel. "Chimeric antigen receptors: driving immunology towards synthetic biology." Current opinion in Immunology 41 (2016): 68-76.

Barrett et al., "Chimeric antigen receptor therapy for cancer," Ann. Rev. Med. 65:333-347, Jan. 2014.

Beatty et al., "Chimeric Antigen Receptor-Modified T Cells for the Treatment of Solid Tumors: Defining the Challenges and Next Steps," Pharmacology & Therapeutics, vol. 166, (2015), pp. 30-39.

Bird et al., "Single-chain antigen-binding proteins," Science 242:423-426, Oct. 1988.

Bork, "Go Hunting in Sequence Databases but watch out for Traps," Tig, vol. 12, No. 10, (1996), pp. 425-427.

Bork, "Powers and Pitfalls in Sequence Analysis: The 70% Hurdle," Genome Res., vol. 10, (2000), pp. 398-400.

Brenner, "Errors in Genome Annotation," Tig, vol. 15, No. 4, (1999), pp. 132-133.

Cartellieri et al., "Chimeric antigen receptor-engineered T cells for immunotherapy of cancer," J Biomed. Biotechnol. vol. 2010, Article ID 956304, May 2010.

Cheadle et al., "Cart cells: driving the road from the labratory to the clinic," Immunol. Rev.257(1):91-106, Jan. 2014.

Chen et al., "Fusion protein linkers: property, design and functionality," Adv. Drug Deliv. Rev.65:1357-1369, Oct. 2013.

Doerks, "Protein Annotation: Detective Work for Function Prediction," Tig, vol. 14, No. 6, (1998), pp. 248-250.

Fedorov et al., "PD-1- and CTLA-4-based inhibitory chimeric antigen receptors (iCARs) divert off-target immunotherapy responses," Sci. Transl. Med. 5(215):215ral72, Dec. 2013.

Frain, "The liver-specific transcription factor LF-B1 contains a highly diverged homeobox DNA binding domain," Cell 59:145-157, Oct. 1990.

Furukawa et al., "Crx, a novel otx-like homeobox gene, shows photoreceptor-specific expression and regulates photoreceptor differentiation," Cell 91(4):531-541, Nov. 1997.

Galfre and Milstein, "Preparation of Monoclonal Antibodies: Strategies and Procedures," Methods Enzymol. 73 (B):3-46, 1981.

Glienke et al., "Advantages and applications of CAR-expressing natural killer cells," Front. Pharmacol. 6:21, Feb. 2015.

Gordon et al. The molecular logic of Notch signaling—a structural and biochemical perspective. J Cell Sci 121:3109-3119, 2008.

Graham et al., "Characteristics of a human cell line transformed by DNA from human adenovirus type 5," J Gen. Virol. 36:59-74, Jul. 1977.

Holliger et al., "Diabodies: small bivalent and bispecific antibody fragments," Proc. Natl. Acad. Sci. U.S.A. 90:6444-6448, Jul. 1993.

Holt et al., "Domain antibodies: proteins for therapy," Trends Biotechnol. 21:484-490, Nov. 2003.

Hong et al., "TAZ, a transcriptional modulator of mesenchymal stem cell differentiation," Science 309 (5737):1074-1078, Aug. 2005.

Hrecka et al., "Vpx relieves the inhibition of HIV-1 infection of macrophages mediated by the SAMHDI protein," Nature 474(7353):658-661, Jun. 2011.

International Preliminary Report on Patentability, issued in PCT/US2019/0018813, dated Aug. 27, 2020.

International Search Report, issued in PCT/US2019/018813, dated Jun. 11, 2019.

Jacobson et al., "Structure of Pit-1 POU domain bound to DNA as a dimer: unexpected arrangement and flexibility," Genes Develop. 11(2):198-212, Jan. 1997.

Kakarla and Gottschalk, "Cart cells for solid tumors: armed and ready to go?" Cancer J 20(2):151-155, Mar.-Apr. 2014.

Kipniss et al., "Engineering Cell Sensing and Responses using a GPCR-Coupled CRISPR-Cas System," Nature Communications, vol. 8, No. 1, (2017), pp. 1-10.

Klebanoff et al., "Customizing Functionality and Payload Delivery for Receptor-Engineered T Cells," Cell 167 (2):304-306, Oct. 2016.

Klein et al., "Design and characterization of structured protein linkers with differing flexibilities," Protein Eng Design Select. 27(10): 325-330, Oct. 2014.

Kojika et al., "Notch Receptors and Hematopoiesis," Experimental Hematology, vol. 29, (2001), pp. 1041-1052.

Lian et al., "The role of YAP transcription coactivator in regulating stem cell self-renewal and differentiation," Genes Develop. 24(11):1106-1118, Jun. 2010.

Liu et al., "Comparative Analysis of Notch1 and Notch2 Binding Sites in the Genome of BxPC3 Pancreatic Cancer Cells," Journal of Cancer, vol. 8, (2017), pp. 65-73.

Long et al., "Harnessing the antitumor potential of macrophages for cancer immunotherapy ,"Oncoimmunology 2: e26860, Dec. 2013.

Mizutani et al. Conservation of the biochemical mechanisms of signal transduction among mammalian Notch family members. Proc Natl Acad Sci USA 98(16): 9026-9031, 2001.

Morsut et al., "Engineering Customized Cell Sensing and Response Behaviors Using Synthetic Notch Receptors," Cell 164(4):780-791, Feb. 2016.

Moyes et al., "Genetically Engineered Macrophages: A Potential Platform for Cancer Immunotherapy," Human Gene Therapy 28(2):200-215, Feb. 2017.

Najafabadi et al., "C2H2 zinc finger proteins greatly expand the human regulatory lexicon," Nature Biotechnol. 33 (5):555-562, May 2015.

Ngo et al., "Computational Copmlexity, Protein Structure Prediction, and the Levinthal Paradox," The Protein Folding Problems and Tertiary Structure Prediction, (1994), pp. 492-495.

Omori et al., "CREB-H: a novel mammalian transcription factor belonging to the CREB/ATF family and functioning via the box-B element with a liver-specific expression," Nucleic Acids Res., 29(10):2154-2162, May 2001.

Pancewicz and Nicot, "Current views on the role of Notch signaling and the pathogenesis of human leukemia," BMC Cancer 11(1):502, Dec. 2011.

PCT International Search Report and Written Opinion in International Appln. No. PCT/US2018/038218, dated Sep. 14, 2018, 16 pages.

Pegram et al., "CD28z CARs and Armored CARs," CancerJ 20(2):127-133, Mar. 2014.

Pluckthun, "Antibodies from *Escherichia coli*," Pharmacol. Monoclonal Antibodies 113:269-315, 1994.

Priyanka et al., "Linkers in the structural biology of protein-protein interactions," Protein Sci. 22(2):153-167, Feb. 2013.

(56) References Cited

OTHER PUBLICATIONS

Riddell et al., "Adoptive Therapy with Chimeric Antigen Receptor Modified T Cells of Defined Subset Composition," Cancer J 20(2):141-144, Mar. 2014.
Roybal et al., "Precision Tumor Recognition by T Cells With Combinatorial Antigen-Sensing Circuits," Cell 164 (4):770-779, Feb. 2016.
Roybal et al., "Engineering T Cells with Customized Therapeutic Response Programs Using Synthetic Notch Receptors," Cell, vol. 167, No. 2, (2016), pp. 419-432.e1-e6.
Sadelain et al., "The basic principles of chimeric antigen receptor (CAR) design," Cancer Discov. 3(4):388-398, Apr. 2013.
Skolnick et al., "From Genes to Protein Structure and Function: Novel Applications of Computational Approaches in the Genomic Era," Trends in Biotech, vol. 18, No. 1, (2000), pp. 34-39.
Smith et al., The Challenges of Genome Sequence Annotation or "The Devil is in the Details," Nature Biotech, vol. 15, (1997), pp. 1222-1223.
Thiel et al., "Regulation of life and death by the zinc finger transcription factor Egr-1," J Cell. Physiol. 193(3):287-282, Dec. 2002.
Tokuriki et al., "Stability Effects of Mutations and Protein Evolvability," Curr Opin Structural Biol., vol. 19, (2009), pp. 596-604.
Urlaub and Chasin, "Isolation of Chinese hamster cell mutants deficient in dihydrofolate reductase activity," Proc. Natl. Acad. Sci. U.S.A. 77:4216-4220, Jul. 1980.
Wang et al., "The nuclear facto-kB RelA transcription factor is constitutively activated in human pancreatic adenocarcinoma cells," Clin. Cancer Res. 5(1):119-127, 1999.
Weintraub and Davis, "The myoD gene family: nodal point during specification of the muscle cell lineage," Science 251 (4995):761, Feb. 1991.
Wells, "Additivity of Mutational Effects in Proteins," Biochemistry, vol. 29, No. 37, (1990), pp. 8509-8517.
Yong et al., "Car T-Cell Therapy of Solid Tumors," Immunology and Cell Biology, vol. 95, (2017), pp. 356-363.
Zapata et al., "Engineering linear F(ab ')2 fragments for efficient production in *Escherichia coli* and enhanced antiproliferative activity," Protein Enz. 8(10):1057-1062, Oct. 1995.
Zhou, Binghan, et al. "Notch signaling pathway: architecture, disease, and therapeutics." Signal transduction and targeted therapy 7.1 (2022): 95.
Cromie et al., "Nanobodies and Their Use in GPCR Drug Discovery," Curr. Top. Med. Chem., vol. 15, (2016), pp. 2543-2557.
De Genst et al., "Antibody Repertoire Development in Camelids," Dev. and Comp. Immunol., vol. 30, (2006), pp. 187-198.
De Meyer et al., "Nanobody-Based Products as Research and Diagnostic Tools," Trends Biotechnol., vol. 32, (2014), pp. 263-270.
DiGiammarino et al., "Design and Generation of DVD-lg™ Molecules for Dual-Specific Targeting," Methods Mol. Biol., vol. 899, (2012), pp. 145-156.
Kovaleva et al., "Shark Variable New Antigen Receptor Biologics—A Novel Technology Platform for Therapeutic Drug Development," Expert. Opin. Biol. Ther., vol. 14, (2014), pp. 1527-1539.
Garber, "Bispecific Antibodies Rise Again," Nature Reviews Drug Discovery, vol. 13, (2014), pp. 799-801.
Jakob et al., "Structure Reveals Function of the Dual Variable Domain Immunoglobulin (DVD-lg™) Molecule," MABs, vol. 5, (2013), pp. 358-363.
Kijanka et al., "Nanobody-Based Cancer Therapy of Solid Tumors," Nanomedicine, vol. 10, (2015), pp. 161-174.
Krah et al., "Single Domain Antibodies for Biomedical Applications," Immunopharmacol. Immunotoxicol., vol. 38, (2016), pp. 1-22.
Mujic-Delic et al., "GPCR-Targeting Nanobodies: Attractive Research Tools, Diagnostics, and Therapeutics," Trends Pharmacol. Sci., vol. 35, (2014), pp. 247-255.
Muyldermans et al., "Recognition of Antigens by Single-Domain Antibody Fragments: The Superfluous Luxury of Paired Domains," Trends Biochem. Sci., vol. 26, (2001), pp. 230-235.
Muyldermans, "Nanobodies: Natural Single-Domain Antibodies," Ann. Rev. Biochem., vol. 82, (2013), pp. 775-797.
Muyldermans., "Single Domain Camel Antibodies: Current Status," Reviews in Molecular Biotechnology, vol. 74, (2001), pp. 277-302.
Navarro et al., "A Novel Destabilizing Domain based on a Small-Molecule Dependent Fluorophore," ACS Chem Biol., (2016) 11 (8) : 2101-2104.
Rahbarizadeh et a., "Nanobody: An Old Concept and New Vehicle for Immunotargeting," Immunol. Invest., vol. 40, (2011), pp. 299-338.
Rakhit et al., "Chemical Biology Strategies for Posttranslational Control of Protein Function," Chem Biol, 2014 21 (9) : 1238-1252.
Sakemura et al., "A Tet-On Inducible System for Controlling CD19-Chiimeric Antigen Receptor Expression upon Drug Administration," Cancer Immunol Res., (2016) 4 (8): 658-668.
Van Audenhove et al., "Nanobodies as Versatile Tools to Understand, Diagnose, Visualize and Treat Cancer," EBioMedicine, vol. 8, (2015), pp. 40-48.
Van Bockstaele et al., "The Development of Nanobodies for Therapeutic Applications," Curr. Opin. Investig. Drugs, vol. 10, (2009), pp. 1212-1224.
Vincke et al., "Introduction to Heavy Chain Antibodies and derived Nanobodies," Methods Mol. Biol., vol. 911, (2012), pp. 15-26.
Wesolowski et al., "Single Domain Antibodies: Promising Experimental and Therapeutic Tools in Infection and Immunity," Med., Microbiol. Immunol., vol. 198, (2009), pp. 157-174.
Wu et al., "Remote Control of Therapeutic T Cells Through a Small Molecule-Gated Chimeric Receptor," Science, (2015). 350 (6258) : aab4077.

* cited by examiner

Domain Architecture of Natural Human Notch Proteins and Engineered Synthetic Notch Proteins (SynNotch)

SEQUENCE LISTING

```
<160> NUMBER OF SEQ ID NOS: 35

<210> SEQ ID NO 1
<211> LENGTH: 22
<212> TYPE: PRT
```

-continued

<213> ORGANISM: Homo sapiens

<400> SEQUENCE: 1

Met Ala Leu Pro Val Thr Ala Leu Leu Leu Pro Leu Ala Leu Leu Leu
1               5                   10                  15

His Ala Ala Arg Pro Ser
            20

<210> SEQ ID NO 2
<211> LENGTH: 10
<212> TYPE: PRT
<213> ORGANISM: Artificial Sequence
<220> FEATURE:
<223> OTHER INFORMATION: Myc tag

<400> SEQUENCE: 2

Glu Gln Lys Leu Ile Ser Glu Glu Asp Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: GS linker

<400> SEQUENCE: 3

Gly Ser Ala Ala Ala Gly Gly Ser Gly Gly Ser Gly Gly Ser
1               5                   10

<210> SEQ ID NO 4
<211> LENGTH: 8
<212> TYPE: PRT
<213> ORGANISM: Artificial Sequence
<220> FEATURE:
<223> OTHER INFORMATION: GS linker

<400> SEQUENCE: 4

Gly Gly Gly Ser Gly Gly Gly Ser
1               5

<210> SEQ ID NO 5
<211> LENGTH: 638
<212> TYPE: PRT
<213> ORGANISM: Homo sapiens

<400> SEQUENCE: 5

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile

-continued

```
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
    370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Glu Ala Ala
    530                 535                 540
```

```
Leu Leu Pro Gln Val Phe Thr Ser Asp Thr Glu Ala Ser Ser Glu Ser
545                 550                 555                 560

Gly Leu His Thr Pro Ala Ser Gln Ala Thr Thr Leu His Val Pro Ser
                565                 570                 575

Gln Asp Pro Ala Gly Ile Gln His Leu Gln Pro Ala His Arg Leu Ser
            580                 585                 590

Ala Ser Pro Thr Val Ser Ser Ser Ser Leu Val Leu Tyr Gln Ser Ser
        595                 600                 605

Asp Ser Ser Asn Gly Gln Ser His Leu Leu Pro Ser Asn His Ser Val
    610                 615                 620

Ile Glu Thr Phe Ile Ser Thr Gln Met Ala Ser Ser Ser Gln
625                 630                 635


<210> SEQ ID NO 6
<211> LENGTH: 631
<212> TYPE: PRT
<213> ORGANISM: Homo sapiens

<400> SEQUENCE: 6

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
```

-continued

```
        275                 280                 285

Pro Pro Pro Gly Pro Gly Pro Gly Pro Ala Leu Pro Ala His Ser Ser
    290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
    370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Phe Thr
    530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
        595                 600                 605

His Leu Leu Pro Ser Asn His Ser Val Ile Glu Thr Phe Ile Ser Thr
    610                 615                 620

Gln Met Ala Ser Ser Ser Gln
625                 630


<210> SEQ ID NO 7
<211> LENGTH: 662
<212> TYPE: PRT
<213> ORGANISM: Homo sapiens

<400> SEQUENCE: 7

Met Val Ser Lys Leu Ser Gln Leu Gln Thr Glu Leu Leu Ala Ala Leu
1               5                   10                  15
```

-continued

```
Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
    370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
```

-continued

```
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Arg Ser
    530                 535                 540

Arg Pro Ala Gly Pro Pro Leu Ala Cys Asp Arg Ala Pro His Pro His
545                 550                 555                 560

Ile Pro Arg Ala Gln Glu Ala Ala Leu Leu Pro Gln Val Phe Thr Ser
                565                 570                 575

Asp Thr Glu Ala Ser Ser Glu Ser Gly Leu His Thr Pro Ala Ser Gln
            580                 585                 590

Ala Thr Thr Leu His Val Pro Ser Gln Asp Pro Ala Ser Ile Gln His
        595                 600                 605

Leu Gln Pro Ala His Arg Leu Ser Ala Ser Pro Thr Val Ser Ser Ser
    610                 615                 620

Ser Leu Val Leu Tyr Gln Ser Ser Asp Ser Ser Asn Gly Gln Ser His
625                 630                 635                 640

Leu Leu Pro Ser Asn His Ser Val Ile Glu Thr Phe Ile Ser Thr Gln
                645                 650                 655

Met Ala Ser Ser Ser Gln
            660


<210> SEQ ID NO 8
<211> LENGTH: 3438
<212> TYPE: DNA
<213> ORGANISM: Homo sapiens

<400> SEQUENCE: 8

ggggccctga ttcacgggcc gctggggcca gggttggggg ttgggggtgc ccacagggct      60

tggctagtgg ggttttgggg gggcagtggg tgcaaggagt ttggtttgtg tctgccggcc     120

ggcaggcaaa cgcaacccac gcggtggggg aggcggctag cgtggtggac ccgggccgcg     180

tggccctgtg gcagccgagc catggtttct aaactgagcc agctgcagac ggagctcctg     240

gcggccctgc tcgagtcagg gctgagcaaa gaggcactga tccaggcact gggtgagccg     300

gggccctacc tcctggctgg agaaggcccc ctggacaagg gggagtcctg cggcggcggt     360

cgaggggagc tggctgagct gcccaatggg ctgggggaga ctcggggctc cgaggacgag     420

acggacgacg atggggaaga cttcacgcca cccatcctca aagagctgga gaacctcagc     480

cctgaggagg cggcccacca gaaagccgtg gtggagaccc ttctgcagga ggacccgtgg     540

cgtgtggcga agatggtcaa gtcctacctg cagcagcaca acatcccaca gcgggaggtg     600

gtcgatacca ctggcctcaa ccagtcccac ctgtcccaac acctcaacaa gggcactccc     660

atgaagacgc agaagcgggc cgccctgtac acctggtacg tccgcaagca gcgagaggtg     720

gcgcagcagt tcacccatgc agggcaggga gggctgattg aagagcccac aggtgatgag     780

ctaccaacca agaaggggcg gaggaaccgt ttcaagtggg gcccagcatc ccagcagatc     840
```

-continued

```
ctgttccagg cctatgagag gcagaagaac cctagcaagg aggagcgaga gacgctagtg    900
gaggagtgca atagggcgga atgcatccag agaggggtgt ccccatcaca ggcacagggg    960
ctgggctcca acctcgtcac ggaggtgcgt gtctacaact ggtttgccaa ccggcgcaaa   1020
gaagaagcct tccggcacaa gctggccatg gacacgtaca gcgggccccc cccagggcca   1080
ggcccgggac ctgcgctgcc cgctcacagc tcccctggcc tgcctccacc tgccctctcc   1140
cccagtaagg tccacggtgt gcgctatgga cagcctgcga ccagtgagac tgcagaagta   1200
ccctcaagca gcggcggtcc cttagtgaca gtgtctacac ccctccacca agtgtccccc   1260
acgggcctgg agcccagcca cagcctgctg agtacagaag ccaagctggt ctcagcagct   1320
gggggccccc tccccctgt cagcaccctg acagcactgc acagcttgga gcagacatcc    1380
ccaggcctca accagcagcc ccagaacctc atcatggcct cacttcctgg ggtcatgacc   1440
atcgggcctg gtgagcctgc ctccctgggt cctacgttca ccaacacagg tgcctccacc   1500
ctggtcatcg gcctggcctc cacgcaggca cagagtgtgc cggtcatcaa cagcatgggc   1560
agcagcctga ccaccctgca gcccgtccag ttctcccagc cgctgcaccc ctcctaccag   1620
cagccgctca tgccacctgt gcagagccat gtgacccaga gccccttcat ggccaccatg   1680
gctcagctgc agagccccca cgccctctac agccacaagc ccgaggtggc ccagtacacc   1740
cacacgggcc tgctcccgca gactatgctc atcaccgaca ccaccaacct gagcgccctg   1800
gccagcctca cgcccaccaa gcaggaggct gctctgctcc cccaggtctt cacctcagac   1860
actgaggcct ccagtgagtc cgggcttcac acgccggcat ctcaggccac caccctccac   1920
gtccccagcc aggaccctgc cggcatccag cacctgcagc cggcccaccg gctcagcgcc   1980
agccccacag tgtcctccag cagcctggtg ctgtaccaga gctcagactc cagcaatggc   2040
cagagccacc tgctgccatc caaccacagc gtcatcgaga ccttcatctc cacccagatg   2100
gcctcttcct cccagtaacc acggcacctg ggccctgggg cctgtactgc ctgcttgggg   2160
ggtgatgagg gcagcagcca gccctgcctg gaggacctga gcctgccgag caaccgtggc   2220
ccttcctgga cagctgtgcc tcgctcccca ctctgctctg atgcatcaga aagggagggc   2280
tctgaggcgc cccaacccgt ggaggctgct cggggtgcac aggagggggt cgtggagagc   2340
taggagcaaa gcctgttcat ggcagatgta ggagggactg tcgctgcttc gtgggataca   2400
gtcttcttac ttggaactga agggggcggc ctatgacttg ggcacccccca gcctgggcct  2460
atggagagcc ctgggaccgc tacaccactc tggcagccac acttctcagg acacaggcct   2520
gtgtagctgt gacctgctga gctctgagag gccctggatc agcgtggcct tgttctgtca   2580
ccaatgtacc caccgggcca ctccttcctg ccccaactcc ttccagctag tgacccacat   2640
gccatttgta ctgaccccat cacctactca cacaggcatt tcctgggtgg ctactctgtg   2700
ccagagcctg gggctctaac gcctgagccc agggaggccg aagctaacag ggaaggcagg   2760
cagggctctc ctggcttccc atccccagcg attccctctc ccaggcccca tgacctccag   2820
ctttcctgta tttgttccca agagcatcat gcctctgagg ccagcctggc ctcctgcctc   2880
tactgggaag gctacttcgg ggctgggaag tcgtccttac tcctgtggga gcctcgcaac   2940
ccgtgccaag tccaggtcct ggtggggcag ctcctctgtc tcgagcgccc tgcagaccct   3000
gcccttgttt ggggcaggag tagctgagct cacaaggcag caaggcccga gcagctgagc   3060
agggccgggg aactggccaa gctgaggtgc ccaggagaag aaagaggtga ccccagggca   3120
caggagctac ctgtgtggac aggactaaca ctcagaagcc tgggggcctg gctggctgag   3180
```

-continued

```
ggcagttcgc agccaccctg aggagtctga ggtcctgagc actgccagga gggacaaagg   3240

agcctgtgaa cccaggacaa gcatggtccc acatccctgg gcctgctgct gagaacctgg   3300

ccttcagtgt accgcgtcta ccctgggatt caggaaaagg cctggggtga cccggcaccc   3360

cctgcagctt gtagccagcc ggggcgagtg gcacgtttat ttaactttta gtaaagtcaa   3420

ggagaaatgc ggtggaaa                                                 3438
```

<210> SEQ ID NO 9
<211> LENGTH: 3417
<212> TYPE: DNA
<213> ORGANISM: Homo sapiens

<400> SEQUENCE: 9

```
ggggccctga ttcacgggcc gctggggcca gggttggggg ttgggggtgc ccacagggct     60

tggctagtgg ggttttgggg gggcagtggg tgcaaggagt ttggtttgtg tctgccggcc    120

ggcaggcaaa cgcaacccac gcggtggggg aggcggctag cgtggtggac ccgggccgcg    180

tggccctgtg gcagccgagc catggtttct aaactgagcc agctgcagac ggagctcctg    240

gcggccctgc tcgagtcagg gctgagcaaa gaggcactga tccaggcact gggtgagccg    300

gggccctacc tcctggctgg agaaggcccc ctggacaagg gggagtcctg cggcggcggt    360

cgaggggagc tggctgagct gcccaatggg ctgggggaga ctcggggctc cgaggacgag    420

acggacgacg atggggaaga cttcacgcca cccatcctca aagagctgga gaacctcagc    480

cctgaggagg cggcccacca gaaagccgtg gtggagaccc ttctgcagga ggacccgtgg    540

cgtgtggcga agatggtcaa gtcctacctg cagcagcaca acatcccaca gcgggaggtg    600

gtcgatacca ctggcctcaa ccagtcccac ctgtcccaac acctcaacaa gggcactccc    660

atgaagacgc agaagcgggc cgccctgtac acctggtacg tccgcaagca gcgagaggtg    720

gcgcagcagt tcacccatgc agggcaggga gggctgattg aagagcccac aggtgatgag    780

ctaccaacca agaaggggcg gaggaaccgt ttcaagtggg gcccagcatc ccagcagatc    840

ctgttccagg cctatgagag gcagaagaac cctagcaagg aggagcgaga gacgctagtg    900

gaggagtgca atagggcgga atgcatccag agaggggtgt ccccatcaca ggcacagggg    960

ctgggctcca acctcgtcac ggaggtgcgt gtctacaact ggtttgccaa ccggcgcaaa   1020

gaagaagcct tccggcacaa gctggccatg gacacgtaca gcgggccccc cccagggcca   1080

ggcccgggac ctgcgctgcc cgctcacagc tcccctggcc tgcctccacc tgccctctcc   1140

cccagtaagg tccacggtgt gcgctatgga cagcctgcga ccagtgagac tgcagaagta   1200

ccctcaagca gcggcggtcc cttagtgaca gtgtctacac ccctccacca agtgtccccc   1260

acgggcctgg agcccagcca cagcctgctg agtacagaag ccaagctggt ctcagcagct   1320

gggggccccc tccccctgt cagcaccctg acagcactgc acagcttgga gcagacatcc    1380

ccaggcctca accagcagcc ccagaacctc atcatggcct cacttcctgg ggtcatgacc   1440

atcgggcctg gtgagcctgc ctccctgggt cctacgttca ccaacacagg tgcctccacc   1500

ctggtcatcg gcctggcctc cacgcaggca cagagtgtgc cggtcatcaa cagcatgggc   1560

agcagcctga ccaccctgca gcccgtccag ttctcccagc cgctgcaccc ctcctaccag   1620

cagccgctca tgccacctgt gcagagccat gtgacccaga gcccccttcat ggccaccatg  1680

gctcagctgc agagccccca cgccctctac agccacaagc ccgaggtggc ccagtacacc   1740

cacacgggcc tgctcccgca gactatgctc atcaccgaca ccaccaacct gagcgccctg   1800

gccagcctca cgcccaccaa gcaggtcttc acctcagaca ctgaggcctc cagtgagtcc   1860
```

```
gggcttcaca cgccggcatc tcaggccacc accctccacg tccccagcca ggaccctgcc   1920
ggcatccagc acctgcagcc ggcccaccgg ctcagcgcca gccccacagt gtcctccagc   1980
agcctggtgc tgtaccagag ctcagactcc agcaatggcc agagccacct gctgccatcc   2040
aaccacagcg tcatcgagac cttcatctcc acccagatgg cctcttcctc ccagtaacca   2100
cggcacctgg gccctggggc ctgtactgcc tgcttggggg gtgatgaggg cagcagccag   2160
ccctgcctgg aggacctgag cctgccgagc aaccgtggcc cttcctggac agctgtgcct   2220
cgctccccac tctgctctga tgcatcagaa agggagggct ctgaggcgcc ccaacccgtg   2280
gaggctgctc ggggtgcaca ggagggggtc gtggagagct aggagcaaag cctgttcatg   2340
gcagatgtag gagggactgt cgctgcttcg tgggatacag tcttcttact tggaactgaa   2400
gggggcggcc tatgacttgg gcacccccag cctgggccta tggagagccc tgggaccgct   2460
acaccactct ggcagccaca cttctcagga cacaggcctg tgtagctgtg acctgctgag   2520
ctctgagagg ccctggatca gcgtggcctt gttctgtcac caatgtaccc accgggccac   2580
tccttcctgc cccaactcct tccagctagt gacccacatg ccatttgtac tgaccccatc   2640
acctactcac acaggcattt cctgggtggc tactctgtgc cagagcctgg ggctctaacg   2700
cctgagccca gggaggccga agctaacagg gaaggcaggc agggctctcc tggcttccca   2760
tccccagcga ttccctctcc caggccccat gacctccagc tttcctgtat ttgttcccaa   2820
gagcatcatg cctctgaggc cagcctggcc tcctgcctct actgggaagg ctacttcggg   2880
gctgggaagt cgtccttact cctgtgggag cctcgcaacc cgtgccaagt ccaggtcctg   2940
gtggggcagc tcctctgtct cgagcgccct gcagaccctg cccttgtttg gggcaggagt   3000
agctgagctc acaaggcagc aaggcccgag cagctgagca gggccgggga actggccaag   3060
ctgaggtgcc caggagaaga aagaggtgac cccagggcac aggagctacc tgtgtggaca   3120
ggactaacac tcagaagcct gggggcctgg ctggctgagg gcagttcgca gccaccctga   3180
ggagtctgag gtcctgagca ctgccaggag ggacaaagga gcctgtgaac ccaggacaag   3240
catggtccca catccctggg cctgctgctg agaacctggc cttcagtgta ccgcgtctac   3300
cctgggattc aggaaaaggc ctggggtgac ccggcacccc ctgcagcttg tagccagccg   3360
gggcgagtgg cacgtttatt taacttttag taaagtcaag gagaaatgcg gtggaaa      3417
```

<210> SEQ ID NO 10
<211> LENGTH: 3563
<212> TYPE: DNA
<213> ORGANISM: Homo sapiens

<400> SEQUENCE: 10

```
ataaatatga accttggaga atttccccag ctccaatgta aacagaacag gcaggggccc     60
tgattcacgg gccgctgggg ccagggttgg gggttggggg tgcccacagg gcttggctag    120
tggggttttg ggggggcagt gggtgcaagg agtttggttt gtgtctgccg gccggcaggc    180
aaacgcaacc cacgcggtgg gggaggcggc tagcgtggtg gacccgggcc gcgtggccct    240
gtggcagccg agccatggtt tctaaactga gccagctgca gacggagctc ctggcggccc    300
tgctcgagtc agggctgagc aaagaggcac tgatccaggc actgggtgag ccggggccct    360
acctcctggc tggagaaggc cccctggaca agggggagtc ctgcggcggc ggtcgagggg    420
agctggctga gctgcccaat gggctggggg agactcgggg ctccgaggac gagacggacg    480
acgatgggga agacttcacg ccacccatcc tcaaagagct ggagaacctc agccctgagg    540
```

```
aggcggccca ccagaaagcc gtggtggaga cccttctgca ggaggacccg tggcgtgtgg    600
cgaagatggt caagtcctac ctgcagcagc acaacatccc acagcgggag gtggtcgata    660
ccactggcct caaccagtcc cacctgtccc aacacctcaa caagggcact cccatgaaga    720
cgcagaagcg ggccgccctg tacacctggt acgtccgcaa gcagcgagag gtggcgcagc    780
agttcaccca tgcagggcag ggagggctga ttgaagagcc cacaggtgat gagctaccaa    840
ccaagaaggg gcggaggaac cgtttcaagt ggggcccagc atcccagcag atcctgttcc    900
aggcctatga gaggcagaag aaccctagca aggaggagcg agagacgcta gtggaggagt    960
gcaatagggc ggaatgcatc cagagagggg tgtccccatc acaggcacag ggctgggct    1020
ccaacctcgt cacggaggtg cgtgtctaca actggtttgc caaccggcgc aaagaagaag   1080
ccttccggca caagctggcc atggacacgt acagcgggcc ccccccaggg ccaggcccgg   1140
gacctgcgct gcccgctcac agctcccctg gcctgcctcc acctgccctc tcccccagta   1200
aggtccacgg tgtgcgctat ggacagcctg cgaccagtga gactgcagaa gtaccctcaa   1260
gcagcggcgg tcccttagtg acagtgtcta caccctcca ccaagtgtcc cccacgggcc    1320
tggagcccag ccacagcctg ctgagtacag aagccaagct ggtctcagca gctgggggcc   1380
ccctccccc tgtcagcacc ctgacagcac tgcacagctt ggagcagaca tccccaggcc    1440
tcaaccagca gccccagaac ctcatcatgg cctcacttcc tggggtcatg accatcgggc   1500
ctggtgagcc tgcctccctg ggtcctacgt tcaccaacac aggtgcctcc accctggtca   1560
tcggcctggc ctccacgcag gcacagagtg tgccggtcat caacagcatg ggcagcagcc   1620
tgaccaccct gcagcccgtc cagttctccc agccgctgca cccctcctac cagcagccgc   1680
tcatgccacc tgtgcagagc catgtgaccc agagcccctt catggccacc atggctcagc   1740
tgcagagccc ccacgccctc tacagccaca agcccgaggt ggcccagtac acccacacgg   1800
gcctgctccc gcagactatg ctcatcaccg acaccaccaa cctgagcgcc ctggccagcc   1860
tcacgcccac caagcaggta aggtccaggc ctgctggccc tcccttggcc tgtgacagag   1920
cccctcaccc ccacatcccc cgggctcagg aggctgctct gctcccccag gtcttcacct   1980
cagacactga ggcctccagt gagtccgggc ttcacacgcc ggcatctcag gccaccaccc   2040
tccacgtccc cagccaggac cctgccagca tccagcacct gcagccggcc caccggctca   2100
gcgccagccc cacagtgtcc tccagcagcc tggtgctgta ccagagctca gactccagca   2160
atggccagag ccacctgctg ccatccaacc acagcgtcat cgagaccttc atctccaccc   2220
agatggcctc ttcctcccag taaccacggc acctgggccc tggggcctgt actgcctgct   2280
tggggggtga tgagggcagc agccagccct gcctggagga cctgagcctg ccgagcaacc   2340
gtggcccttc ctggacagct gtgcctcgct ccccactctg ctctgatgca tcagaaaggg   2400
agggctctga ggcgccccaa cccgtggagg ctgctcgggg tgcacaggag gggtcgtgg    2460
agagctagga gcaaagcctg ttcatggcag atgtaggagg gactgtcgct gcttcgtggg   2520
atacagtctt cttacttgga actgaagggg gcggcctatg acttgggcac ccccagcctg   2580
ggcctatgga gagccctggg accgctacac cactctggca gccacacttc tcaggacaca   2640
ggcctgtgta gctgtgacct gctgagctct gagaggccct ggatcagcgt ggccttgttc   2700
tgtcaccaat gtacccaccg ggccactcct tcctgcccca actccttcca gctagtgacc   2760
cacatgccat ttgtactgac cccatcacct actcacacag gcatttcctg ggtggctact   2820
ctgtgccaga gcctggggct ctaacgcctg agcccaggga ggccgaagct aacagggaag   2880
gcaggcaggg ctctcctggc ttcccatccc cagcgattcc ctctcccagg ccccatgacc   2940
```

tccagctttc ctgtatttgt tcccaagagc atcatgcctc tgaggccagc ctggcctcct 3000
gcctctactg ggaaggctac ttcggggctg ggaagtcgtc cttactcctg tgggagcctc 3060
gcaacccgtg ccaagtccag gtcctggtgg ggcagctcct ctgtctcgag cgccctgcag 3120
accctgccct tgtttggggc aggagtagct gagctcacaa ggcagcaagg cccgagcagc 3180
tgagcagggc cggggaactg gccaagctga ggtgcccagg agaagaaaga ggtgacccca 3240
gggcacagga gctacctgtg tggacaggac taacactcag aagcctgggg gcctggctgg 3300
ctgagggcag ttcgcagcca ccctgaggag tctgaggtcc tgagcactgc caggagggac 3360
aaaggagcct gtgaacccag gacaagcatg gtcccacatc cctgggcctg ctgctgagaa 3420
cctggccttc agtgtaccgc gtctaccctg ggattcagga aaaggcctgg ggtgacccgg 3480 cacccctgc agcttgtagc cagccggggc gagtggcacg tttatttaac ttttagtaaa 3540
gtcaaggaga aatgcggtgg aaa 3563

<210> SEQ ID NO 11
<211> LENGTH: 13
<212> TYPE: DNA
<213> ORGANISM: Artificial Sequence
<220> FEATURE:
<223> OTHER INFORMATION: Synthetic Sequence (HNF1-alpha binding sequence)
<220> FEATURE:
<221> NAME/KEY: misc_feature
<222> LOCATION: (7)..(7)
<223> OTHER INFORMATION: nucleotide at position 7 is any nucleotide

<400> SEQUENCE: 11
gttaatnatt aac 13

<210> SEQ ID NO 12
<211> LENGTH: 551
<212> TYPE: PRT
<213> ORGANISM: Homo sapiens

<400> SEQUENCE: 12

Met Asp Glu Leu Phe Pro Leu Ile Phe Pro Ala Glu Pro Ala Gln Ala
1 5 10 15

Ser Gly Pro Tyr Val Glu Ile Ile Glu Gln Pro Lys Gln Arg Gly Met
20 25 30

Arg Phe Arg Tyr Lys Cys Glu Gly Arg Ser Ala Gly Ser Ile Pro Gly
35 40 45

Glu Arg Ser Thr Asp Thr Thr Lys Thr His Pro Thr Ile Lys Ile Asn
50 55 60

Gly Tyr Thr Gly Pro Gly Thr Val Arg Ile Ser Leu Val Thr Lys Asp
65 70 75 80

Pro Pro His Arg Pro His Pro His Glu Leu Val Gly Lys Asp Cys Arg
85 90 95

Asp Gly Phe Tyr Glu Ala Glu Leu Cys Pro Asp Arg Cys Ile His Ser
100 105 110

Phe Gln Asn Leu Gly Ile Gln Cys Val Lys Lys Arg Asp Leu Glu Gln
115 120 125

Ala Ile Ser Gln Arg Ile Gln Thr Asn Asn Asn Pro Phe Gln Val Pro
130 135 140

Ile Glu Glu Gln Arg Gly Asp Tyr Asp Leu Asn Ala Val Arg Leu Cys
145 150 155 160

Phe Gln Val Thr Val Arg Asp Pro Ser Gly Arg Pro Leu Arg Leu Pro

-continued

```
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Pro Arg Arg Ile Ala Val Pro Ser Arg
                325                 330                 335

Ser Ser Ala Ser Val Pro Lys Pro Ala Pro Gln Pro Tyr Pro Phe Thr
            340                 345                 350

Ser Ser Leu Ser Thr Ile Asn Tyr Asp Glu Phe Pro Thr Met Val Phe
        355                 360                 365

Pro Ser Gly Gln Ile Ser Gln Ala Ser Ala Leu Ala Pro Ala Pro Pro
    370                 375                 380

Gln Val Leu Pro Gln Ala Pro Ala Pro Ala Pro Ala Pro Ala Met Val
385                 390                 395                 400

Ser Ala Leu Ala Gln Ala Pro Ala Pro Val Pro Val Leu Ala Pro Gly
                405                 410                 415

Pro Pro Gln Ala Val Ala Pro Pro Ala Pro Lys Pro Thr Gln Ala Gly
            420                 425                 430

Glu Gly Thr Leu Ser Glu Ala Leu Leu Gln Leu Gln Phe Asp Asp Glu
        435                 440                 445

Asp Leu Gly Ala Leu Leu Gly Asn Ser Thr Asp Pro Ala Val Phe Thr
    450                 455                 460

Asp Leu Ala Ser Val Asp Asn Ser Glu Phe Gln Gln Leu Leu Asn Gln
465                 470                 475                 480

Gly Ile Pro Val Ala Pro His Thr Thr Glu Pro Met Leu Met Glu Tyr
                485                 490                 495

Pro Glu Ala Ile Thr Arg Leu Val Thr Gly Ala Gln Arg Pro Pro Asp
            500                 505                 510

Pro Ala Pro Ala Pro Leu Gly Ala Pro Gly Leu Pro Asn Gly Leu Leu
        515                 520                 525

Ser Gly Asp Glu Asp Phe Ser Ser Ile Ala Asp Met Asp Phe Ser Ala
    530                 535                 540

Leu Leu Ser Gln Ile Ser Ser
545                 550
```

<210> SEQ ID NO 13
<211> LENGTH: 548
<212> TYPE: PRT
<213> ORGANISM: Homo sapiens

<400> SEQUENCE: 13

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Glu Glu
    130                 135                 140

Gln Arg Gly Asp Tyr Asp Leu Asn Ala Val Arg Leu Cys Phe Gln Val
145                 150                 155                 160

Thr Val Arg Asp Pro Ser Gly Arg Pro Leu Arg Leu Pro Pro Val Leu
                165                 170                 175

Ser His Pro Ile Phe Asp Asn Arg Ala Pro Asn Thr Ala Glu Leu Lys
            180                 185                 190

Ile Cys Arg Val Asn Arg Asn Ser Gly Ser Cys Leu Gly Gly Asp Glu
        195                 200                 205

Ile Phe Leu Leu Cys Asp Lys Val Gln Lys Glu Asp Ile Glu Val Tyr
    210                 215                 220

Phe Thr Gly Pro Gly Trp Glu Ala Arg Gly Ser Phe Ser Gln Ala Asp
225                 230                 235                 240

Val His Arg Gln Val Ala Ile Val Phe Arg Thr Pro Pro Tyr Ala Asp
                245                 250                 255

Pro Ser Leu Gln Ala Pro Val Arg Val Ser Met Gln Leu Arg Arg Pro
            260                 265                 270

Ser Asp Arg Glu Leu Ser Glu Pro Met Glu Phe Gln Tyr Leu Pro Asp
        275                 280                 285

Thr Asp Asp Arg His Arg Ile Glu Glu Lys Arg Lys Arg Thr Tyr Glu
    290                 295                 300

Thr Phe Lys Ser Ile Met Lys Lys Ser Pro Phe Ser Gly Pro Thr Asp
305                 310                 315                 320

Pro Arg Pro Pro Pro Arg Arg Ile Ala Val Pro Ser Arg Ser Ser Ala
                325                 330                 335

Ser Val Pro Lys Pro Ala Pro Gln Pro Tyr Pro Phe Thr Ser Ser Leu
            340                 345                 350

Ser Thr Ile Asn Tyr Asp Glu Phe Pro Thr Met Val Phe Pro Ser Gly
        355                 360                 365

Gln Ile Ser Gln Ala Ser Ala Leu Ala Pro Ala Pro Pro Gln Val Leu
    370                 375                 380

Pro Gln Ala Pro Ala Pro Ala Pro Ala Pro Ala Met Val Ser Ala Leu
385                 390                 395                 400

Ala Gln Ala Pro Ala Pro Val Pro Val Leu Ala Pro Gly Pro Pro Gln

-continued

```
                405                 410                 415

Ala Val Ala Pro Pro Ala Pro Lys Pro Thr Gln Ala Gly Glu Gly Thr
            420                 425                 430

Leu Ser Glu Ala Leu Leu Gln Leu Gln Phe Asp Asp Glu Asp Leu Gly
        435                 440                 445

Ala Leu Leu Gly Asn Ser Thr Asp Pro Ala Val Phe Thr Asp Leu Ala
    450                 455                 460

Ser Val Asp Asn Ser Glu Phe Gln Gln Leu Leu Asn Gln Gly Ile Pro
465                 470                 475                 480

Val Ala Pro His Thr Thr Glu Pro Met Leu Met Glu Tyr Pro Glu Ala
                485                 490                 495

Ile Thr Arg Leu Val Thr Gly Ala Gln Arg Pro Pro Asp Pro Ala Pro
            500                 505                 510

Ala Pro Leu Gly Ala Pro Gly Leu Pro Asn Gly Leu Leu Ser Gly Asp
        515                 520                 525

Glu Asp Phe Ser Ser Ile Ala Asp Met Asp Phe Ser Ala Leu Leu Ser
    530                 535                 540

Gln Ile Ser Ser
545


<210> SEQ ID NO 14
<211> LENGTH: 482
<212> TYPE: PRT
<213> ORGANISM: Homo sapiens

<400> SEQUENCE: 14

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220
```

-continued

```
Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Pro Arg Arg Ile Ala Val Pro Ser Arg
                325                 330                 335

Ser Ser Ala Ser Val Pro Lys Pro Ala Pro Gly Pro Pro Gln Ala Val
            340                 345                 350

Ala Pro Pro Ala Pro Lys Pro Thr Gln Ala Gly Glu Gly Thr Leu Ser
        355                 360                 365

Glu Ala Leu Leu Gln Leu Gln Phe Asp Asp Glu Asp Leu Gly Ala Leu
    370                 375                 380

Leu Gly Asn Ser Thr Asp Pro Ala Val Phe Thr Asp Leu Ala Ser Val
385                 390                 395                 400

Asp Asn Ser Glu Phe Gln Gln Leu Leu Asn Gln Gly Ile Pro Val Ala
                405                 410                 415

Pro His Thr Thr Glu Pro Met Leu Met Glu Tyr Pro Glu Ala Ile Thr
            420                 425                 430

Arg Leu Val Thr Gly Ala Gln Arg Pro Pro Asp Pro Ala Pro Ala Pro
        435                 440                 445

Leu Gly Ala Pro Gly Leu Pro Asn Gly Leu Leu Ser Gly Asp Glu Asp
    450                 455                 460

Phe Ser Ser Ile Ala Asp Met Asp Phe Ser Ala Leu Leu Ser Gln Ile
465                 470                 475                 480

Ser Ser


<210> SEQ ID NO 15
<211> LENGTH: 448
<212> TYPE: PRT
<213> ORGANISM: Homo sapiens

<400> SEQUENCE: 15

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110
```

-continued

```
Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Pro Arg Arg Ile Ala Val Pro Ser Arg
                325                 330                 335

Ser Ser Ala Ser Val Pro Lys Pro Ala Pro Gln Pro Tyr Pro Phe Thr
            340                 345                 350

Ser Ser Leu Ser Thr Ile Asn Tyr Asp Glu Phe Pro Thr Met Val Phe
        355                 360                 365

Pro Ser Gly Gln Ile Ser Gln Ala Ser Ala Leu Ala Pro Ala Pro Pro
    370                 375                 380

Gln Val Leu Pro Gln Ala Pro Ala Pro Ala Pro Ala Pro Ala Met Val
385                 390                 395                 400

Ser Ala Leu Ala Gln Arg Pro Pro Asp Pro Ala Pro Ala Pro Leu Gly
                405                 410                 415

Ala Pro Gly Leu Pro Asn Gly Leu Leu Ser Gly Asp Glu Asp Phe Ser
            420                 425                 430

Ser Ile Ala Asp Met Asp Phe Ser Ala Leu Leu Ser Gln Ile Ser Ser
        435                 440                 445


<210> SEQ ID NO 16
<211> LENGTH: 480
<212> TYPE: PRT
<213> ORGANISM: Homo sapiens

<400> SEQUENCE: 16

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45
```

-continued

```
Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Asp Asp Arg
    210                 215                 220

His Arg Ile Glu Glu Lys Arg Lys Arg Thr Tyr Glu Thr Phe Lys Ser
225                 230                 235                 240

Ile Met Lys Lys Ser Pro Phe Ser Gly Pro Thr Asp Pro Arg Pro Pro
                245                 250                 255

Pro Arg Arg Ile Ala Val Pro Ser Arg Ser Ser Ala Ser Val Pro Lys
            260                 265                 270

Pro Ala Pro Gln Pro Tyr Pro Phe Thr Ser Ser Leu Ser Thr Ile Asn
        275                 280                 285

Tyr Asp Glu Phe Pro Thr Met Val Phe Pro Ser Gly Gln Ile Ser Gln
    290                 295                 300

Ala Ser Ala Leu Ala Pro Ala Pro Pro Gln Val Leu Pro Gln Ala Pro
305                 310                 315                 320

Ala Pro Ala Pro Ala Pro Ala Met Val Ser Ala Leu Ala Gln Ala Pro
                325                 330                 335

Ala Pro Val Pro Val Leu Ala Pro Gly Pro Pro Gln Ala Val Ala Pro
            340                 345                 350

Pro Ala Pro Lys Pro Thr Gln Ala Gly Glu Gly Thr Leu Ser Glu Ala
        355                 360                 365

Leu Leu Gln Leu Gln Phe Asp Asp Glu Asp Leu Gly Ala Leu Leu Gly
    370                 375                 380

Asn Ser Thr Asp Pro Ala Val Phe Thr Asp Leu Ala Ser Val Asp Asn
385                 390                 395                 400

Ser Glu Phe Gln Gln Leu Leu Asn Gln Gly Ile Pro Val Ala Pro His
                405                 410                 415

Thr Thr Glu Pro Met Leu Met Glu Tyr Pro Glu Ala Ile Thr Arg Leu
            420                 425                 430

Val Thr Gly Ala Gln Arg Pro Pro Asp Pro Ala Pro Ala Pro Leu Gly
        435                 440                 445

Ala Pro Gly Leu Pro Asn Gly Leu Leu Ser Gly Asp Glu Asp Phe Ser
    450                 455                 460
```

Ser Ile Ala Asp Met Asp Phe Ser Ala Leu Leu Ser Gln Ile Ser Ser
465 470 475 480

<210> SEQ ID NO 17
<211> LENGTH: 445
<212> TYPE: PRT
<213> ORGANISM: Homo sapiens

<400> SEQUENCE: 17

Met Asp Glu Leu Phe Pro Leu Ile Phe Pro Ala Glu Pro Ala Gln Ala
1 5 10 15

Ser Gly Pro Tyr Val Glu Ile Ile Glu Gln Pro Lys Gln Arg Gly Met
20 25 30

Arg Phe Arg Tyr Lys Cys Glu Gly Arg Ser Ala Gly Ser Ile Pro Gly
35 40 45

Glu Arg Ser Thr Asp Thr Thr Lys Thr His Pro Thr Ile Lys Ile Asn
50 55 60

Gly Tyr Thr Gly Pro Gly Thr Val Arg Ile Ser Leu Val Thr Lys Asp
65 70 75 80

Pro Pro His Arg Pro His Pro His Glu Leu Val Gly Lys Asp Cys Arg
85 90 95

Asp Gly Phe Tyr Glu Ala Glu Leu Cys Pro Asp Arg Cys Ile His Ser
100 105 110

Phe Gln Asn Leu Gly Ile Gln Cys Val Lys Lys Arg Asp Leu Glu Gln
115 120 125

Ala Ile Ser Gln Arg Ile Gln Thr Asn Asn Asn Pro Phe Gln Val Pro
130 135 140

Ile Glu Glu Gln Arg Gly Asp Tyr Asp Leu Asn Ala Val Arg Leu Cys
145 150 155 160

Phe Gln Val Thr Val Arg Asp Pro Ser Gly Arg Pro Leu Arg Leu Pro
165 170 175

Pro Val Leu Ser His Pro Ile Phe Asp Asn His Asp Arg His Arg Ile
180 185 190

Glu Glu Lys Arg Lys Arg Thr Tyr Glu Thr Phe Lys Ser Ile Met Lys
195 200 205

Lys Ser Pro Phe Ser Gly Pro Thr Asp Pro Arg Pro Pro Pro Arg Arg
210 215 220

Ile Ala Val Pro Ser Arg Ser Ser Ala Ser Val Pro Lys Pro Ala Pro
225 230 235 240

Gln Pro Tyr Pro Phe Thr Ser Ser Leu Ser Thr Ile Asn Tyr Asp Glu
245 250 255

Phe Pro Thr Met Val Phe Pro Ser Gly Gln Ile Ser Gln Ala Ser Ala
260 265 270

Leu Ala Pro Ala Pro Pro Gln Val Leu Pro Gln Ala Pro Ala Pro Ala
275 280 285

Pro Ala Pro Ala Met Val Ser Ala Leu Ala Gln Ala Pro Ala Pro Val
290 295 300

Pro Val Leu Ala Pro Gly Pro Pro Gln Ala Val Ala Pro Pro Ala Pro
305 310 315 320

Lys Pro Thr Gln Ala Gly Glu Gly Thr Leu Ser Glu Ala Leu Leu Gln
325 330 335

Leu Gln Phe Asp Asp Glu Asp Leu Gly Ala Leu Leu Gly Asn Ser Thr
340 345 350

Asp Pro Ala Val Phe Thr Asp Leu Ala Ser Val Asp Asn Ser Glu Phe
355 360 365

-continued

```
Gln Gln Leu Leu Asn Gln Gly Ile Pro Val Ala Pro His Thr Thr Glu
    370                 375                 380

Pro Met Leu Met Glu Tyr Pro Glu Ala Ile Thr Arg Leu Val Thr Gly
385                 390                 395                 400

Ala Gln Arg Pro Pro Asp Pro Ala Pro Ala Pro Leu Gly Ala Pro Gly
                405                 410                 415

Leu Pro Asn Gly Leu Leu Ser Gly Asp Glu Asp Phe Ser Ser Ile Ala
            420                 425                 430

Asp Met Asp Phe Ser Ala Leu Leu Ser Gln Ile Ser Ser
        435                 440                 445


<210> SEQ ID NO 18
<211> LENGTH: 2595
<212> TYPE: DNA
<213> ORGANISM: Homo sapiens

<400> SEQUENCE: 18

agcgcgcagg cgcggccgga ttccgggcag tgacgcgacg gcgggccgcg cggcgcattt     60

ccgcctctgg cgaatggctc gtctgtagtg cacgccgcgg gcccagctgc gaccccggcc    120

ccgcccccgg gaccccggcc atggacgaac tgttcccccct catcttcccg gcagagccag    180

cccaggcctc tggcccctat gtggagatca ttgagcagcc caagcagcgg ggcatgcgct    240

tccgctacaa gtgcgagggg cgctccgcgg gcagcatccc aggcgagagg agcacagata    300

ccaccaagac ccaccccacc atcaagatca atggctacac aggaccaggg acagtgcgca    360

tctccctggt caccaaggac cctcctcacc ggcctcaccc ccacgagctt gtaggaaagg    420

actgccggga tggcttctat gaggctgagc tctgcccgga ccgctgcatc cacagtttcc    480

agaacctggg aatccagtgt gtgaagaagc gggacctgga gcaggctatc agtcagcgca    540

tccagaccaa caacaacccc ttccaagttc ctatagaaga gcagcgtggg gactacgacc    600

tgaatgctgt gcggctctgc ttccaggtga cagtgcggga cccatcaggc aggcccctcc    660

gcctgccgcc tgtcctttct catcccatct ttgacaatcg tgcccccaac actgccgagc    720

tcaagatctg ccgagtgaac cgaaactctg gcagctgcct cggtggggat gagatcttcc    780

tactgtgtga caaggtgcag aaagaggaca ttgaggtgta tttcacggga ccaggctggg    840

aggcccgagg ctccttttcg caagctgatg tgcaccgaca agtggccatt gtgttccgga    900

cccctcccta cgcagacccc agcctgcagg ctcctgtgcg tgtctccatg cagctgcggc    960

ggccttccga ccgggagctc agtgagccca tggaattcca gtacctgcca gatacagacg   1020

atcgtcaccg gattgaggag aaacgtaaaa ggacatatga gaccttcaag agcatcatga   1080

agaagagtcc tttcagcgga cccaccgacc cccggcctcc acctcgacgc attgctgtgc   1140

cttcccgcag ctcagcttct gtccccaagc cagcacccca gccctatccc tttacgtcat   1200

ccctgagcac catcaactat gatgagtttc ccaccatggt gtttccttct gggcagatca   1260

gccaggcctc ggccttggcc ccggcccctc cccaagtcct gccccaggct ccagcccctg   1320

cccctgctcc agccatggta tcagctctgg cccaggcccc agcccctgtc ccagtcctag   1380

ccccaggccc tcctcaggct gtggccccac ctgcccccaa gcccacccag gctggggaag   1440

gaacgctgtc agaggccctg ctgcagctgc agtttgatga tgaagacctg gggggccttgc   1500

ttggcaacag cacagaccca gctgtgttca cagacctggc atccgtcgac aactccgagt   1560

ttcagcagct gctgaaccag ggcatacctg tggcccccca cacaactgag cccatgctga   1620

tggagtaccc tgaggctata actcgcctag tgacaggggc ccagaggccc cccgacccag   1680
```

```
ctcctgctcc actgggggcc ccggggctcc ccaatggcct cctttcagga gatgaagact   1740
tctcctccat tgcggacatg gacttctcag ccctgctgag tcagatcagc tcctaagggg   1800
gtgacgcctg ccctccccag agcactgggt tgcaggggat tgaagccctc caaaagcact   1860
tacggattct ggtggggtgt gttccaactg cccccaactt tgtggatgtc ttccttggag   1920
gggggagcca tattttattc ttttattgtc agtatctgta tctctctctc tttttggagg   1980
tgcttaagca gaagcattaa cttctctgga aagggggagg ctggggaaac tcaaactttt   2040
cccctgtcct gatggtcagc tcccttctct gtagggaact ctggggtccc ccatccccat   2100
cctccagctt ctggtactct cctagagaca gaagcaggct ggaggtaagg cctttgagcc   2160
cacaaagcct tatcaagtgt cttccatcat ggattcatta cagcttaatc aaaataacgc   2220
cccagatacc agcccctgta tggcactggc attgtccctg tgcctaacac cagcgtttga   2280
ggggctggcc ttcctgccct acagaggtct ctgccggctc tttccttgct caaccatggc   2340
tgaaggaaac cagtgcaaca gcactggctc tctccaggat ccagaagggg tttggtctgg   2400
gacttccttg ctctccctct tctcaagtgc cttaatagta gggtaagttg ttaagagtgg   2460
gggagagcag gctggcagct ctccagtcag gaggcatagt ttttactgaa caatcaaagc   2520
acttggactc ttgctctttc tactctgaac taataaatct gttgccaagc tggctagaaa   2580
aaaaaaaaaa aaaaa                                                    2595
```

<210> SEQ ID NO 19
<211> LENGTH: 2586
<212> TYPE: DNA
<213> ORGANISM: Homo sapiens

<400> SEQUENCE: 19

```
agcgcgcagg cgcggccgga ttccgggcag tgacgcgacg gcgggccgcg cggcgcattt     60
ccgcctctgg cgaatggctc gtctgtagtg cacgccgcgg gcccagctgc gaccccggcc    120
ccgcccccgg gaccccggcc atggacgaac tgttccccct catcttcccg gcagagccag    180
cccaggcctc tggcccctat gtggagatca ttgagcagcc caagcagcgg ggcatgcgct    240
tccgctacaa gtgcgagggg cgctccgcgg gcagcatccc aggcgagagg agcacagata    300
ccaccaagac ccaccccacc atcaagatca atggctacac aggaccaggg acagtgcgca    360
tctccctggt caccaaggac cctcctcacc ggcctcaccc ccacgagctt gtaggaaagg    420
actgccggga tggcttctat gaggctgagc tctgcccgga ccgctgcatc cacagtttcc    480
agaacctggg aatccagtgt gtgaagaagc gggacctgga gcaggctatc agtcagcgca    540
tccagaccaa caacaacccc ttccaagaag agcagcgtgg ggactacgac ctgaatgctg    600
tgcggctctg cttccaggtg acagtgcggg acccatcagg caggcccctc cgcctgccgc    660
ctgtcctttc tcatcccatc tttgacaatc gtgcccccaa cactgccgag ctcaagatct    720
gccgagtgaa ccgaaactct ggcagctgcc tcggtgggga tgagatcttc ctactgtgtg    780
acaaggtgca gaaagaggac attgaggtgt atttcacggg accaggctgg gaggcccgag    840
gctccttttc gcaagctgat gtgcaccgac aagtggccat tgtgttccgg acccctccct    900
acgcagaccc cagcctgcag gctcctgtgc gtgtctccat gcagctgcgg cggccttccg    960
accgggagct cagtgagccc atggaattcc agtacctgcc agatacagac gatcgtcacc   1020
ggattgagga gaaacgtaaa aggacatatg agaccttcaa gagcatcatg aagaagagtc   1080
ctttcagcgg acccaccgac ccccggcctc cacctcgacg cattgctgtg ccttcccgca   1140
```

-continued gctcagcttc tgtccccaag ccagcacccc agccctatcc ctttacgtca tccctgagca 1200
ccatcaacta tgatgagttt cccaccatgg tgtttccttc tgggcagatc agccaggcct 1260
cggccttggc cccggcccct ccccaagtcc tgccccaggc tccagcccct gcccctgctc 1320
cagccatggt atcagctctg gcccaggccc cagcccctgt cccagtccta gccccaggcc 1380
ctcctcaggc tgtggcccca cctgccccca agcccaccca ggctggggaa ggaacgctgt 1440
cagaggccct gctgcagctg cagtttgatg atgaagacct gggggccttg cttggcaaca 1500
gcacagaccc agctgtgttc acagacctgg catccgtcga caactccgag tttcagcagc 1560
tgctgaacca gggcatacct gtggccccc acacaactga gcccatgctg atggagtacc 1620
ctgaggctat aactcgccta gtgacagggg cccagaggcc ccccgaccca gctcctgctc 1680 cactggggc cccggggctc cccaatggcc tcctttcagg agatgaagac ttctcctcca 1740
ttgcggacat ggacttctca gccctgctga gtcagatcag ctcctaaggg ggtgacgcct 1800
gccctcccca gagcactggg ttgcagggga ttgaagccct ccaaaagcac ttacggattc 1860
tggtggggtg tgttccaact gccccaact ttgtggatgt cttccttgga ggggggagcc 1920
atattttatt cttttattgt cagtatctgt atctctctct ctttttggag gtgcttaagc 1980
agaagcatta acttctctgg aaagggggga gctggggaaa ctcaaacttt tcccctgtcc 2040
tgatggtcag ctcccttctc tgtagggaac tctggggtcc cccatcccca tcctccagct 2100
tctggtactc tcctagagac agaagcaggc tggaggtaag gcctttgagc ccacaaagcc 2160
ttatcaagtg tcttccatca tggattcatt acagcttaat caaaataacg ccccagatac 2220
cagcccctgt atggcactgg cattgtccct gtgcctaaca ccagcgtttg aggggctggc 2280
cttcctgccc tacagaggtc tctgccggct ctttccttgc tcaaccatgg ctgaaggaaa 2340
ccagtgcaac agcactggct ctctccagga tccagaaggg gtttggtctg ggacttcctt 2400
gctctccctc ttctcaagtg ccttaatagt agggtaagtt gttaagagtg gggagagca 2460 ggctggcagc tctccagtca ggaggcatag tttttactga acaatcaaag cacttggact 2520
cttgctcttt ctactctgaa ctaataaatc tgttgccaag ctggctagaa aaaaaaaaaa 2580
aaaaaa 2586

<210> SEQ ID NO 20
<211> LENGTH: 2388
<212> TYPE: DNA
<213> ORGANISM: Homo sapiens

<400> SEQUENCE: 20
agcgcgcagg cgcggccgga ttccgggcag tgacgcgacg gcgggccgcg cggcgcattt 60
ccgcctctgg cgaatggctc gtctgtagtg cacgccgcgg gcccagctgc gaccccggcc 120 ccgccccgg gaccccggcc atggacgaac tgttcccct catcttcccg gcagagccag 180
cccaggcctc tggcccctat gtggagatca ttgagcagcc caagcagcgg ggcatgcgct 240
tccgctacaa gtgcgagggg cgctccgcgg gcagcatccc aggcgagagg agcacagata 300
ccaccaagac ccaccccacc atcaagatca atggctacac aggaccaggg acagtgcgca 360
tctccctggt caccaaggac cctcctcacc ggcctcaccc ccacgagctt gtaggaaagg 420
actgccggga tggcttctat gaggctgagc tctgcccgga ccgctgcatc cacagtttcc 480
agaacctggg aatccagtgt gtgaagaagc gggacctgga gcaggctatc agtcagcgca 540
tccagaccaa caacaacccc ttccaagttc ctatagaaga gcagcgtggg gactacgacc 600
tgaatgctgt gcggctctgc ttccaggtga cagtgcggga cccatcaggc aggcccctcc 660
gcctgccgcc tgtcctttct catcccatct ttgacaatcg tgcccccaac actgccgagc 720
tcaagatctg ccgagtgaac cgaaactctg gcagctgcct cggtggggat gagatcttcc 780
tactgtgtga caaggtgcag aaagaggaca ttgaggtgta tttcacggga ccaggctggg 840
aggcccgagg ctccttttcg caagctgatg tgcaccgaca agtggccatt gtgttccgga 900
cccctcccta cgcagacccc agcctgcagg ctcctgtgcg tgtctccatg cagctgcggc 960
ggccttccga ccgggagctc agtgagccca tggaattcca gtacctgcca gatacagacg 1020
atcgtcaccg gattgaggag aaacgtaaaa ggacatatga gaccttcaag agcatcatga 1080
agaagagtcc tttcagcgga cccaccgacc cccggcctcc acctcgacgc attgctgtgc 1140
cttcccgcag ctcagcttct gtccccaagc cagccccagg ccctcctcag gctgtggccc 1200
cacctgcccc caagcccacc caggctgggg aaggaacgct gtcagaggcc ctgctgcagc 1260
tgcagtttga tgatgaagac ctgggggcct tgcttggcaa cagcacagac ccagctgtgt 1320
tcacagacct ggcatccgtc gacaactccg agtttcagca gctgctgaac cagggcatac 1380
ctgtggcccc ccacacaact gagcccatgc tgatggagta ccctgaggct ataactcgcc 1440
tagtgacagg ggcccagagg ccccccgacc cagctcctgc tccactgggg gccccggggc 1500
tccccaatgg cctcctttca ggagatgaag acttctcctc cattgcggac atggacttct 1560
cagccctgct gagtcagatc agctcctaag gggtgacgc ctgccctccc cagagcactg 1620
ggttgcaggg gattgaagcc ctccaaaagc acttacggat tctggtgggg tgtgttccaa 1680
ctgcccccaa ctttgtggat gtcttccttg gagggggag ccatatttta ttcttttatt 1740
gtcagtatct gtatctctct ctctttttgg aggtgcttaa gcagaagcat taacttctct 1800
ggaaaggggg gagctgggga aactcaaact tttcccctgt cctgatggtc agctcccttc 1860
tctgtaggga actctggggt cccccatccc catcctccag cttctggtac tctcctagag 1920
acagaagcag gctggaggta aggcctttga gcccacaaag ccttatcaag tgtcttccat 1980
catggattca ttacagctta atcaaaataa cgccccagat accagcccct gtatggcact 2040
ggcattgtcc ctgtgcctaa caccagcgtt tgaggggctg gccttcctgc cctacagagg 2100
tctctgccgg ctctttcctt gctcaaccat ggctgaagga aaccagtgca acagcactgg 2160
ctctctccag gatccagaag ggtttggtc tgggacttcc ttgctctccc tcttctcaag 2220
tgccttaata gtagggtaag ttgttaagag tgggggagag caggctggca gctctccagt 2280
caggaggcat agtttttact gaacaatcaa agcacttgga ctcttgctct ttctactctg 2340
aactaataaa tctgttgcca agctggctag aaaaaaaaaa aaaaaaaa 2388

<210> SEQ ID NO 21
<211> LENGTH: 2286
<212> TYPE: DNA
<213> ORGANISM: Homo sapiens

<400> SEQUENCE: 21
agcgcgcagg cgcggccgga ttccgggcag tgacgcgacg gcgggccgcg cggcgcattt 60
ccgcctctgg cgaatggctc gtctgtagtg cacgccgcgg gcccagctgc gaccccggcc 120
ccgcccccgg gaccccggcc atggacgaac tgttccccct catcttcccg gcagagccag 180
cccaggcctc tggcccctat gtggagatca ttgagcagcc caagcagcgg ggcatgcgct 240
tccgctacaa gtgcgagggg cgctccgcgg gcagcatccc aggcgagagg agcacagata 300
ccaccaagac ccaccccacc atcaagatca atggctacac aggaccaggg acagtgcgca 360

-continued

```
tctccctggt caccaaggac cctcctcacc ggcctcaccc ccacgagctt gtaggaaagg    420

actgccggga tggcttctat gaggctgagc tctgcccgga ccgctgcatc cacagtttcc    480

agaacctggg aatccagtgt gtgaagaagc gggacctgga gcaggctatc agtcagcgca    540

tccagaccaa caacaacccc ttccaagttc ctatagaaga gcagcgtggg gactacgacc    600

tgaatgctgt gcggctctgc ttccaggtga cagtgcggga cccatcaggc aggcccctcc    660

gcctgccgcc tgtcctttct catcccatct ttgacaatcg tgcccccaac actgccgagc    720

tcaagatctg ccgagtgaac cgaaactctg gcagctgcct cggtggggat gagatcttcc    780

tactgtgtga caaggtgcag aaagaggaca ttgaggtgta tttcacggga ccaggctggg    840

aggcccgagg ctccttttcg caagctgatg tgcaccgaca agtggccatt gtgttccgga    900

cccctcccta cgcagacccc agcctgcagg ctcctgtgcg tgtctccatg cagctgcggc    960

ggccttccga ccgggagctc agtgagccca tggaattcca gtacctgcca gatacagacg   1020

atcgtcaccg gattgaggag aaacgtaaaa ggacatatga gaccttcaag agcatcatga   1080

agaagagtcc tttcagcgga cccaccgacc cccggcctcc acctcgacgc attgctgtgc   1140

cttcccgcag ctcagcttct gtccccaagc cagcacccca gccctatccc tttacgtcat   1200

ccctgagcac catcaactat gatgagtttc ccaccatggt gtttccttct gggcagatca   1260

gccaggcctc ggccttggcc ccggcccctc cccaagtcct gccccaggct ccagcccctg   1320

cccctgctcc agccatggta tcagctctgg cccagaggcc ccccgaccca gctcctgctc   1380

cactgggggc cccggggctc cccaatggcc tcctttcagg agatgaagac ttctcctcca   1440

ttgcggacat ggacttctca gccctgctga gtcagatcag ctcctaaggg ggtgacgcct   1500

gccctcccca gagcactggg ttgcagggga ttgaagccct ccaaaagcac ttacggattc   1560

tggtggggtg tgttccaact gcccccaact ttgtggatgt cttccttgga gggggggagcc  1620

atattttatt cttttattgt cagtatctgt atctctctct ctttttggag gtgcttaagc   1680

agaagcatta acttctctgg aaagggggga gctggggaaa ctcaaacttt tcccctgtcc   1740

tgatggtcag ctcccttctc tgtagggaac tctggggtcc cccatcccca tcctccagct   1800

tctggtactc tcctagagac agaagcaggc tggaggtaag gcctttgagc ccacaaagcc   1860

ttatcaagtg tcttccatca tggattcatt acagcttaat caaaataacg ccccagatac   1920

cagcccctgt atggcactgg cattgtccct gtgcctaaca ccagcgtttg aggggctggc   1980

cttcctgccc tacagaggtc tctgccggct ctttccttgc tcaaccatgg ctgaaggaaa   2040

ccagtgcaac agcactggct ctctccagga tccagaaggg gtttggtctg ggacttcctt   2100

gctctccctc ttctcaagtg ccttaatagt agggtaagtt gttaagagtg ggggagagca   2160

ggctggcagc tctccagtca ggaggcatag tttttactga acaatcaaag cacttggact   2220

cttgctcttt ctactctgaa ctaataaatc tgttgccaag ctggctagaa aaaaaaaaaa   2280

aaaaaa                                                              2286
```

```
<210> SEQ ID NO 22
<211> LENGTH: 2341
<212> TYPE: DNA
<213> ORGANISM: Homo sapiens

<400> SEQUENCE: 22

attccgggca gtgacgcgac ggcgggccgc gcggcgcatt tccgcctctg gcgaatggct     60

cgtctgtagt gcacgccgcg ggcccagctg cgaccccggc cccgcccccg ggaccccggc    120

catggacgaa ctgttccccc tcatcttccc ggcagagcca gcccaggcct ctggccccta    180
```

```
tgtggagatc attgagcagc ccaagcagcg gggcatgcgc ttccgctaca agtgcgaggg    240
gcgctccgcg ggcagcatcc caggcgagag gagcacagat accaccaaga cccaccccac    300
catcaagatc aatggctaca caggaccagg gacagtgcgc atctccctgg tcaccaagga    360
ccctcctcac cggcctcacc cccacgagct tgtaggaaag gactgccggg atggcttcta    420
tgaggctgag ctctgcccgg accgctgcat ccacagtttc cagaacctgg gaatccagtg    480
tgtgaagaag cgggacctgg agcaggctat cagtcagcgc atccagacca acaacaaccc    540
cttccaagtt cctatagaag agcagcgtgg ggactacgac ctgaatgctg tgcggctctg    600
cttccaggtg acagtgcggg acccatcagg caggcccctc cgcctgccgc ctgtcctttc    660
tcatcccatc tttgacaatc gtgcccccaa cactgccgag ctcaagatct gccgagtgaa    720
ccgaaactct ggcagctgcc tcggtgggga tgagatcttc ctactgtgtg acaaggtgca    780
gaaagacgat cgtcaccgga ttgaggagaa acgtaaaagg acatatgaga ccttcaagag    840
catcatgaag aagagtcctt tcagcggacc caccgacccc cggcctccac ctcgacgcat    900
tgctgtgcct tcccgcagct cagcttctgt ccccaagcca gcaccccagc cctatccctt    960
tacgtcatcc ctgagcacca tcaactatga tgagtttccc accatggtgt ttccttctgg   1020
gcagatcagc caggcctcgg ccttggcccc ggcccctccc caagtcctgc cccaggctcc   1080
agcccctgcc cctgctccag ccatggtatc agctctggcc caggccccag cccctgtccc   1140
agtcctagcc ccaggccctc ctcaggctgt ggccccacct gcccccaagc ccacccaggc   1200
tggggaagga acgctgtcag aggccctgct gcagctgcag tttgatgatg aagacctggg   1260
ggccttgctt ggcaacagca cagacccagc tgtgttcaca gacctggcat ccgtcgacaa   1320
ctccgagttt cagcagctgc tgaaccaggg catacctgtg gccccccaca caactgagcc   1380
catgctgatg gagtaccctg aggctataac tcgcctagtg acaggggccc agaggccccc   1440
cgacccagct cctgctccac tgggggcccc ggggctcccc aatggcctcc tttcaggaga   1500
tgaagacttc tcctccattg cggacatgga cttctcagcc ctgctgagtc agatcagctc   1560
ctaagggggt gacgcctgcc ctccccagag cactgggttg caggggattg aagccctcca   1620
aaagcactta cggattctgg tggggtgtgt tccaactgcc cccaactttg tggatgtctt   1680
ccttggaggg gggagccata ttttattctt ttattgtcag tatctgtatc tctctctctt   1740
tttggaggtg cttaagcaga agcattaact tctctggaaa ggggggagct ggggaaactc   1800
aaacttttcc cctgtcctga tggtcagctc ccttctctgt agggaactct ggggtccccc   1860
atccccatcc tccagcttct ggtactctcc tagagacaga agcaggctgg aggtaaggcc   1920
tttgagccca caaagcctta tcaagtgtct tccatcatgg attcattaca gcttaatcaa   1980
aataacgccc cagataccag cccctgtatg gcactggcat tgtccctgtg cctaacacca   2040
gcgtttgagg ggctggcctt cctgccctac agaggtctct gccggctctt tccttgctca   2100
accatggctg aaggaaacca gtgcaacagc actggctctc tccaggatcc agaaggggtt   2160
tggtctggga cttccttgct ctccctcttc tcaagtgcct taatagtagg gtaagttgtt   2220
aagagtgggg gagagcaggc tggcagctct ccagtcagga ggcatagttt ttactgaaca   2280
atcaaagcac ttggactctt gctctttcta ctctgaacta ataaatctgt tgccaagctg   2340
g                                                                   2341
```

<210> SEQ ID NO 23
<211> LENGTH: 2236
<212> TYPE: DNA

-continued

<213> ORGANISM: Homo sapiens

<400> SEQUENCE: 23

```
attccgggca gtgacgcgac ggcgggccgc gcggcgcatt tccgcctctg gcgaatggct     60
cgtctgtagt gcacgccgcg ggcccagctg cgaccccggc cccgcccccg ggaccccggc    120
catggacgaa ctgttccccc tcatcttccc ggcagagcca gcccaggcct ctggccccta    180
tgtggagatc attgagcagc ccaagcagcg gggcatgcgc ttccgctaca agtgcgaggg    240
gcgctccgcg ggcagcatcc caggcgagag gagcacagat accaccaaga cccaccccac    300
catcaagatc aatggctaca caggaccagg gacagtgcgc atctccctgg tcaccaagga    360
ccctcctcac cggcctcacc cccacgagct tgtaggaaag gactgccggg atggcttcta    420
tgaggctgag ctctgcccgg accgctgcat ccacagtttc cagaacctgg gaatccagtg    480
tgtgaagaag cgggacctgg agcaggctat cagtcagcgc atccagacca acaacaaccc    540
cttccaagtt cctatagaag agcagcgtgg ggactacgac ctgaatgctg tgcggctctg    600
cttccaggtg acagtgcggg acccatcagg caggcccctc cgcctgccgc ctgtcctttc    660
tcatcccatc tttgacaatc acgatcgtca ccggattgag gagaaacgta aaaggacata    720
tgagaccttc aagagcatca tgaagaagag tcctttcagc ggacccaccg acccccggcc    780
tccacctcga cgcattgctg tgccttcccg cagctcagct tctgtcccca agccagcacc    840
ccagccctat ccctttacgt catccctgag caccatcaac tatgatgagt ttcccaccat    900
ggtgtttcct tctgggcaga tcagccaggc ctcggccttg gccccggccc ctccccaagt    960
cctgccccag gctccagccc ctgcccctgc tccagccatg gtatcagctc tggcccaggc   1020
cccagcccct gtcccagtcc tagccccagg ccctcctcag gctgtggccc cacctgcccc   1080
caagcccacc caggctgggg aaggaacgct gtcagaggcc ctgctgcagc tgcagtttga   1140
tgatgaagac ctgggggcct tgcttggcaa cagcacagac ccagctgtgt tcacagacct   1200
ggcatccgtc gacaactccg agtttcagca gctgctgaac cagggcatac ctgtggcccc   1260
ccacacaact gagcccatgc tgatggagta ccctgaggct ataactcgcc tagtgacagg   1320
ggcccagagg ccccccgacc cagctcctgc tccactgggg gccccggggc tccccaatgg   1380
cctcctttca ggagatgaag acttctcctc cattgcggac atggacttct cagccctgct   1440
gagtcagatc agctcctaag gggtgacgc ctgccctccc cagagcactg ggttgcaggg   1500
gattgaagcc ctccaaaagc acttacggat tctggtgggg tgtgttccaa ctgcccccaa   1560
ctttgtggat gtcttccttg gaggggggag ccatatttta ttcttttatt gtcagtatct   1620
gtatctctct ctctttttgg aggtgcttaa gcagaagcat taacttctct ggaaaggggg   1680
gagctgggga aactcaaact tttcccctgt cctgatggtc agctcccttc tctgtaggga   1740
actctggggt cccccatccc catcctccag cttctggtac tctcctagag acagaagcag   1800
gctggaggta aggcctttga gcccacaaag ccttatcaag tgtcttccat catggattca   1860
ttacagctta atcaaaataa cgccccagat accagcccct gtatggcact ggcattgtcc   1920
ctgtgcctaa caccagcgtt tgaggggctg gccttcctgc cctacagagg tctctgccgg   1980
ctctttcctt gctcaaccat ggctgaagga aaccagtgca acagcactgg ctctctccag   2040
gatccagaag ggtttggtc tgggacttcc ttgctctccc tcttctcaag tgccttaata   2100
gtagggtaag ttgttaagag tgggggagag caggctggca gctctccagt caggaggcat   2160
agtttttact gaacaatcaa agcacttgga ctcttgctct ttctactctg aactaataaa   2220
tctgttgcca agctgg                                                   2236
```

<210> SEQ ID NO 24
<211> LENGTH: 2555
<212> TYPE: PRT
<213> ORGANISM: Homo sapiens

<400> SEQUENCE: 24

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
```

-continued

```
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800
```

-continued

```
Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                 1005

Cys Pro  Pro Gly Phe Thr Gly  Ser Tyr Cys Gln His  Asp Val Asn
    1010                 1015                 1020

Glu Cys  Asp Ser Gln Pro Cys  Leu His Gly Gly Thr  Cys Gln Asp
    1025                 1030                 1035

Gly Cys  Gly Ser Tyr Arg Cys  Thr Cys Pro Gln Gly  Tyr Thr Gly
    1040                 1045                 1050

Pro Asn  Cys Gln Asn Leu Val  His Trp Cys Asp Ser  Ser Pro Cys
    1055                 1060                 1065

Lys Asn  Gly Gly Lys Cys Trp  Gln Thr His Thr Gln  Tyr Arg Cys
    1070                 1075                 1080

Glu Cys  Pro Ser Gly Trp Thr  Gly Leu Tyr Cys Asp  Val Pro Ser
    1085                 1090                 1095

Val Ser  Cys Glu Val Ala Ala  Gln Arg Gln Gly Val  Asp Val Ala
    1100                 1105                 1110

Arg Leu  Cys Gln His Gly Gly  Leu Cys Val Asp Ala  Gly Asn Thr
    1115                 1120                 1125

His His  Cys Arg Cys Gln Ala  Gly Tyr Thr Gly Ser  Tyr Cys Glu
    1130                 1135                 1140

Asp Leu  Val Asp Glu Cys Ser  Pro Ser Pro Cys Gln  Asn Gly Ala
    1145                 1150                 1155

Thr Cys  Thr Asp Tyr Leu Gly  Gly Tyr Ser Cys Lys  Cys Val Ala
    1160                 1165                 1170

Gly Tyr  His Gly Val Asn Cys  Ser Glu Glu Ile Asp  Glu Cys Leu
    1175                 1180                 1185

Ser His  Pro Cys Gln Asn Gly  Gly Thr Cys Leu Asp  Leu Pro Asn
    1190                 1195                 1200
```

-continued

```
Thr Tyr  Lys Cys Ser Cys Pro  Arg Gly Thr Gln Gly  Val His Cys
    1205                 1210                 1215

Glu Ile  Asn Val Asp Asp Cys  Asn Pro Pro Val Asp  Pro Val Ser
    1220                 1225                 1230

Arg Ser  Pro Lys Cys Phe Asn  Asn Gly Thr Cys Val  Asp Gln Val
    1235                 1240                 1245

Gly Gly  Tyr Ser Cys Thr Cys  Pro Pro Gly Phe Val  Gly Glu Arg
    1250                 1255                 1260

Cys Glu  Gly Asp Val Asn Glu  Cys Leu Ser Asn Pro  Cys Asp Ala
    1265                 1270                 1275

Arg Gly  Thr Gln Asn Cys Val  Gln Arg Val Asn Asp  Phe His Cys
    1280                 1285                 1290

Glu Cys  Arg Ala Gly His Thr  Gly Arg Arg Cys Glu  Ser Val Ile
    1295                 1300                 1305

Asn Gly  Cys Lys Gly Lys Pro  Cys Lys Asn Gly Gly  Thr Cys Ala
    1310                 1315                 1320

Val Ala  Ser Asn Thr Ala Arg  Gly Phe Ile Cys Lys  Cys Pro Ala
    1325                 1330                 1335

Gly Phe  Glu Gly Ala Thr Cys  Glu Asn Asp Ala Arg  Thr Cys Gly
    1340                 1345                 1350

Ser Leu  Arg Cys Leu Asn Gly  Gly Thr Cys Ile Ser  Gly Pro Arg
    1355                 1360                 1365

Ser Pro  Thr Cys Leu Cys Leu  Gly Pro Phe Thr Gly  Pro Glu Cys
    1370                 1375                 1380

Gln Phe  Pro Ala Ser Ser Pro  Cys Leu Gly Gly Asn  Pro Cys Tyr
    1385                 1390                 1395

Asn Gln  Gly Thr Cys Glu Pro  Thr Ser Glu Ser Pro  Phe Tyr Arg
    1400                 1405                 1410

Cys Leu  Cys Pro Ala Lys Phe  Asn Gly Leu Leu Cys  His Ile Leu
    1415                 1420                 1425

Asp Tyr  Ser Phe Gly Gly Gly  Ala Gly Arg Asp Ile  Pro Pro Pro
    1430                 1435                 1440

Leu Ile  Glu Glu Ala Cys Glu  Leu Pro Glu Cys Gln  Glu Asp Ala
    1445                 1450                 1455

Gly Asn  Lys Val Cys Ser Leu  Gln Cys Asn Asn His  Ala Cys Gly
    1460                 1465                 1470

Trp Asp  Gly Gly Asp Cys Ser  Leu Asn Phe Asn Asp  Pro Trp Lys
    1475                 1480                 1485

Asn Cys  Thr Gln Ser Leu Gln  Cys Trp Lys Tyr Phe  Ser Asp Gly
    1490                 1495                 1500

His Cys  Asp Ser Gln Cys Asn  Ser Ala Gly Cys Leu  Phe Asp Gly
    1505                 1510                 1515

Phe Asp  Cys Gln Arg Ala Glu  Gly Gln Cys Asn Pro  Leu Tyr Asp
    1520                 1525                 1530

Gln Tyr  Cys Lys Asp His Phe  Ser Asp Gly His Cys  Asp Gln Gly
    1535                 1540                 1545

Cys Asn  Ser Ala Glu Cys Glu  Trp Asp Gly Leu Asp  Cys Ala Glu
    1550                 1555                 1560

His Val  Pro Glu Arg Leu Ala  Ala Gly Thr Leu Val  Val Val Val
    1565                 1570                 1575

Leu Met  Pro Pro Glu Gln Leu  Arg Asn Ser Ser Phe  His Phe Leu
    1580                 1585                 1590

Arg Glu  Leu Ser Arg Val Leu  His Thr Asn Val Val  Phe Lys Arg
```

```
    1595                1600                1605

Asp Ala  His Gly Gln Gln Met  Ile Phe Pro Tyr Tyr  Gly Arg Glu
    1610                1615                1620

Glu Glu  Leu Arg Lys His Pro  Ile Lys Arg Ala Ala  Glu Gly Trp
    1625                1630                1635

Ala Ala  Pro Asp Ala Leu Leu  Gly Gln Val Lys Ala  Ser Leu Leu
    1640                1645                1650

Pro Gly  Gly Ser Glu Gly Gly  Arg Arg Arg Arg Glu  Leu Asp Pro
    1655                1660                1665

Met Asp  Val Arg Gly Ser Ile  Val Tyr Leu Glu Ile  Asp Asn Arg
    1670                1675                1680

Gln Cys  Val Gln Ala Ser Ser  Gln Cys Phe Gln Ser  Ala Thr Asp
    1685                1690                1695

Val Ala  Ala Phe Leu Gly Ala  Leu Ala Ser Leu Gly  Ser Leu Asn
    1700                1705                1710

Ile Pro  Tyr Lys Ile Glu Ala  Val Gln Ser Glu Thr  Val Glu Pro
    1715                1720                1725

Pro Pro  Pro Ala Gln Leu His  Phe Met Tyr Val Ala  Ala Ala Ala
    1730                1735                1740

Phe Val  Leu Leu Phe Phe Val  Gly Cys Gly Val Leu  Leu Ser Arg
    1745                1750                1755

Lys Arg  Arg Arg Gln His Gly  Gln Leu Trp Phe Pro  Glu Gly Phe
    1760                1765                1770

Lys Val  Ser Glu Ala Ser Lys  Lys Lys Arg Arg Glu  Pro Leu Gly
    1775                1780                1785

Glu Asp  Ser Val Gly Leu Lys  Pro Leu Lys Asn Ala  Ser Asp Gly
    1790                1795                1800

Ala Leu  Met Asp Asp Asn Gln  Asn Glu Trp Gly Asp  Glu Asp Leu
    1805                1810                1815

Glu Thr  Lys Lys Phe Arg Phe  Glu Glu Pro Val Val  Leu Pro Asp
    1820                1825                1830

Leu Asp  Asp Gln Thr Asp His  Arg Gln Trp Thr Gln  Gln His Leu
    1835                1840                1845

Asp Ala  Ala Asp Leu Arg Met  Ser Ala Met Ala Pro  Thr Pro Pro
    1850                1855                1860

Gln Gly  Glu Val Asp Ala Asp  Cys Met Asp Val Asn  Val Arg Gly
    1865                1870                1875

Pro Asp  Gly Phe Thr Pro Leu  Met Ile Ala Ser Cys  Ser Gly Gly
    1880                1885                1890

Gly Leu  Glu Thr Gly Asn Ser  Glu Glu Glu Glu Asp  Ala Pro Ala
    1895                1900                1905

Val Ile  Ser Asp Phe Ile Tyr  Gln Gly Ala Ser Leu  His Asn Gln
    1910                1915                1920

Thr Asp  Arg Thr Gly Glu Thr  Ala Leu His Leu Ala  Ala Arg Tyr
    1925                1930                1935

Ser Arg  Ser Asp Ala Ala Lys  Arg Leu Leu Glu Ala  Ser Ala Asp
    1940                1945                1950

Ala Asn  Ile Gln Asp Asn Met  Gly Arg Thr Pro Leu  His Ala Ala
    1955                1960                1965

Val Ser  Ala Asp Ala Gln Gly  Val Phe Gln Ile Leu  Ile Arg Asn
    1970                1975                1980

Arg Ala  Thr Asp Leu Asp Ala  Arg Met His Asp Gly  Thr Thr Pro
    1985                1990                1995
```

Leu Ile Leu Ala Ala Arg Leu Ala Val Glu Gly Met Leu Glu Asp
2000 2005 2010

Leu Ile Asn Ser His Ala Asp Val Asn Ala Val Asp Asp Leu Gly
2015 2020 2025

Lys Ser Ala Leu His Trp Ala Ala Ala Val Asn Asn Val Asp Ala
2030 2035 2040

Ala Val Val Leu Leu Lys Asn Gly Ala Asn Lys Asp Met Gln Asn
2045 2050 2055

Asn Arg Glu Glu Thr Pro Leu Phe Leu Ala Ala Arg Glu Gly Ser
2060 2065 2070

Tyr Glu Thr Ala Lys Val Leu Leu Asp His Phe Ala Asn Arg Asp
2075 2080 2085

Ile Thr Asp His Met Asp Arg Leu Pro Arg Asp Ile Ala Gln Glu
2090 2095 2100

Arg Met His His Asp Ile Val Arg Leu Leu Asp Glu Tyr Asn Leu
2105 2110 2115

Val Arg Ser Pro Gln Leu His Gly Ala Pro Leu Gly Gly Thr Pro
2120 2125 2130

Thr Leu Ser Pro Pro Leu Cys Ser Pro Asn Gly Tyr Leu Gly Ser
2135 2140 2145

Leu Lys Pro Gly Val Gln Gly Lys Lys Val Arg Lys Pro Ser Ser
2150 2155 2160

Lys Gly Leu Ala Cys Gly Ser Lys Glu Ala Lys Asp Leu Lys Ala
2165 2170 2175

Arg Arg Lys Lys Ser Gln Asp Gly Lys Gly Cys Leu Leu Asp Ser
2180 2185 2190

Ser Gly Met Leu Ser Pro Val Asp Ser Leu Glu Ser Pro His Gly
2195 2200 2205

Tyr Leu Ser Asp Val Ala Ser Pro Pro Leu Leu Pro Ser Pro Phe
2210 2215 2220

Gln Gln Ser Pro Ser Val Pro Leu Asn His Leu Pro Gly Met Pro
2225 2230 2235

Asp Thr His Leu Gly Ile Gly His Leu Asn Val Ala Ala Lys Pro
2240 2245 2250

Glu Met Ala Ala Leu Gly Gly Gly Gly Arg Leu Ala Phe Glu Thr
2255 2260 2265

Gly Pro Pro Arg Leu Ser His Leu Pro Val Ala Ser Gly Thr Ser
2270 2275 2280

Thr Val Leu Gly Ser Ser Ser Gly Gly Ala Leu Asn Phe Thr Val
2285 2290 2295

Gly Gly Ser Thr Ser Leu Asn Gly Gln Cys Glu Trp Leu Ser Arg
2300 2305 2310

Leu Gln Ser Gly Met Val Pro Asn Gln Tyr Asn Pro Leu Arg Gly
2315 2320 2325

Ser Val Ala Pro Gly Pro Leu Ser Thr Gln Ala Pro Ser Leu Gln
2330 2335 2340

His Gly Met Val Gly Pro Leu His Ser Ser Leu Ala Ala Ser Ala
2345 2350 2355

Leu Ser Gln Met Met Ser Tyr Gln Gly Leu Pro Ser Thr Arg Leu
2360 2365 2370

Ala Thr Gln Pro His Leu Val Gln Thr Gln Gln Val Gln Pro Gln
2375 2380 2385

```
Asn Leu  Gln Met Gln Gln Gln  Asn Leu Gln Pro Ala  Asn Ile Gln
    2390                 2395                 2400

Gln Gln  Gln Ser Leu Gln Pro  Pro Pro Pro Pro Pro  Gln Pro His
    2405                 2410                 2415

Leu Gly  Val Ser Ser Ala Ala  Ser Gly His Leu Gly  Arg Ser Phe
    2420                 2425                 2430

Leu Ser  Gly Glu Pro Ser Gln  Ala Asp Val Gln Pro  Leu Gly Pro
    2435                 2440                 2445

Ser Ser  Leu Ala Val His Thr  Ile Leu Pro Gln Glu  Ser Pro Ala
    2450                 2455                 2460

Leu Pro  Thr Ser Leu Pro Ser  Ser Leu Val Pro Pro  Val Thr Ala
    2465                 2470                 2475

Ala Gln  Phe Leu Thr Pro Pro  Ser Gln His Ser Tyr  Ser Ser Pro
    2480                 2485                 2490

Val Asp  Asn Thr Pro Ser His  Gln Leu Gln Val Pro  Glu His Pro
    2495                 2500                 2505

Phe Leu  Thr Pro Ser Pro Glu  Ser Pro Asp Gln Trp  Ser Ser Ser
    2510                 2515                 2520

Ser Pro  His Ser Asn Val Ser  Asp Trp Ser Glu Gly  Val Ser Ser
    2525                 2530                 2535

Pro Pro  Thr Ser Met Gln Ser  Gln Ile Ala Arg Ile  Pro Glu Ala
    2540                 2545                 2550

Phe Lys
    2555
```

<210> SEQ ID NO 25
<211> LENGTH: 2471
<212> TYPE: PRT
<213> ORGANISM: Homo sapiens

<400> SEQUENCE: 25

```
Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190
```

-continued

```
Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605
```

-continued

```
Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly  Thr Cys Val Asp Gly  Ile Asn Ser
        995                 1000                 1005

Phe Ser  Cys Leu Cys Pro Val  Gly Phe Thr Gly Ser  Phe Cys Leu
    1010                 1015                 1020

His Glu  Ile Asn Glu Cys Ser  Ser His Pro Cys Leu  Asn Glu Gly
```

-continued

```
    1025                1030                1035

Thr Cys  Val Asp Gly Leu Gly  Thr Tyr Arg Cys Ser  Cys Pro Leu
    1040                1045                1050

Gly Tyr  Thr Gly Lys Asn Cys  Gln Thr Leu Val Asn  Leu Cys Ser
    1055                1060                1065

Arg Ser  Pro Cys Lys Asn Lys  Gly Thr Cys Val Gln  Lys Lys Ala
    1070                1075                1080

Glu Ser  Gln Cys Leu Cys Pro  Ser Gly Trp Ala Gly  Ala Tyr Cys
    1085                1090                1095

Asp Val  Pro Asn Val Ser Cys  Asp Ile Ala Ala Ser  Arg Arg Gly
    1100                1105                1110

Val Leu  Val Glu His Leu Cys  Gln His Ser Gly Val  Cys Ile Asn
    1115                1120                1125

Ala Gly  Asn Thr His Tyr Cys  Gln Cys Pro Leu Gly  Tyr Thr Gly
    1130                1135                1140

Ser Tyr  Cys Glu Glu Gln Leu  Asp Glu Cys Ala Ser  Asn Pro Cys
    1145                1150                1155

Gln His  Gly Ala Thr Cys Ser  Asp Phe Ile Gly Gly  Tyr Arg Cys
    1160                1165                1170

Glu Cys  Val Pro Gly Tyr Gln  Gly Val Asn Cys Glu  Tyr Glu Val
    1175                1180                1185

Asp Glu  Cys Gln Asn Gln Pro  Cys Gln Asn Gly Gly  Thr Cys Ile
    1190                1195                1200

Asp Leu  Val Asn His Phe Lys  Cys Ser Cys Pro Pro  Gly Thr Arg
    1205                1210                1215

Gly Leu  Leu Cys Glu Glu Asn  Ile Asp Asp Cys Ala  Arg Gly Pro
    1220                1225                1230

His Cys  Leu Asn Gly Gly Gln  Cys Met Asp Arg Ile  Gly Gly Tyr
    1235                1240                1245

Ser Cys  Arg Cys Leu Pro Gly  Phe Ala Gly Glu Arg  Cys Glu Gly
    1250                1255                1260

Asp Ile  Asn Glu Cys Leu Ser  Asn Pro Cys Ser Ser  Glu Gly Ser
    1265                1270                1275

Leu Asp  Cys Ile Gln Leu Thr  Asn Asp Tyr Leu Cys  Val Cys Arg
    1280                1285                1290

Ser Ala  Phe Thr Gly Arg His  Cys Glu Thr Phe Val  Asp Val Cys
    1295                1300                1305

Pro Gln  Met Pro Cys Leu Asn  Gly Gly Thr Cys Ala  Val Ala Ser
    1310                1315                1320

Asn Met  Pro Asp Gly Phe Ile  Cys Arg Cys Pro Pro  Gly Phe Ser
    1325                1330                1335

Gly Ala  Arg Cys Gln Ser Ser  Cys Gly Gln Val Lys  Cys Arg Lys
    1340                1345                1350

Gly Glu  Gln Cys Val His Thr  Ala Ser Gly Pro Arg  Cys Phe Cys
    1355                1360                1365

Pro Ser  Pro Arg Asp Cys Glu  Ser Gly Cys Ala Ser  Ser Pro Cys
    1370                1375                1380

Gln His  Gly Gly Ser Cys His  Pro Gln Arg Gln Pro  Pro Tyr Tyr
    1385                1390                1395

Ser Cys  Gln Cys Ala Pro Pro  Phe Ser Gly Ser Arg  Cys Glu Leu
    1400                1405                1410

Tyr Thr  Ala Pro Pro Ser Thr  Pro Pro Ala Thr Cys  Leu Ser Gln
    1415                1420                1425
```

-continued

```
Tyr Cys  Ala Asp Lys Ala Arg  Asp Gly Val Cys Asp  Glu Ala Cys
    1430                 1435                 1440

Asn Ser  His Ala Cys Gln Trp  Asp Gly Gly Asp Cys  Ser Leu Thr
    1445                 1450                 1455

Met Glu  Asn Pro Trp Ala Asn  Cys Ser Ser Pro Leu  Pro Cys Trp
    1460                 1465                 1470

Asp Tyr  Ile Asn Asn Gln Cys  Asp Glu Leu Cys Asn  Thr Val Glu
    1475                 1480                 1485

Cys Leu  Phe Asp Asn Phe Glu  Cys Gln Gly Asn Ser  Lys Thr Cys
    1490                 1495                 1500

Lys Tyr  Asp Lys Tyr Cys Ala  Asp His Phe Lys Asp  Asn His Cys
    1505                 1510                 1515

Asp Gln  Gly Cys Asn Ser Glu  Glu Cys Gly Trp Asp  Gly Leu Asp
    1520                 1525                 1530

Cys Ala  Ala Asp Gln Pro Glu  Asn Leu Ala Glu Gly  Thr Leu Val
    1535                 1540                 1545

Ile Val  Val Leu Met Pro Pro  Glu Gln Leu Leu Gln  Asp Ala Arg
    1550                 1555                 1560

Ser Phe  Leu Arg Ala Leu Gly  Thr Leu Leu His Thr  Asn Leu Arg
    1565                 1570                 1575

Ile Lys  Arg Asp Ser Gln Gly  Glu Leu Met Val Tyr  Pro Tyr Tyr
    1580                 1585                 1590

Gly Glu  Lys Ser Ala Ala Met  Lys Lys Gln Arg Met  Thr Arg Arg
    1595                 1600                 1605

Ser Leu  Pro Gly Glu Gln Glu  Gln Glu Val Ala Gly  Ser Lys Val
    1610                 1615                 1620

Phe Leu  Glu Ile Asp Asn Arg  Gln Cys Val Gln Asp  Ser Asp His
    1625                 1630                 1635

Cys Phe  Lys Asn Thr Asp Ala  Ala Ala Ala Leu Leu  Ala Ser His
    1640                 1645                 1650

Ala Ile  Gln Gly Thr Leu Ser  Tyr Pro Leu Val Ser  Val Val Ser
    1655                 1660                 1665

Glu Ser  Leu Thr Pro Glu Arg  Thr Gln Leu Leu Tyr  Leu Leu Ala
    1670                 1675                 1680

Val Ala  Val Val Ile Ile Leu  Phe Ile Ile Leu Leu  Gly Val Ile
    1685                 1690                 1695

Met Ala  Lys Arg Lys Arg Lys  His Gly Ser Leu Trp  Leu Pro Glu
    1700                 1705                 1710

Gly Phe  Thr Leu Arg Arg Asp  Ala Ser Asn His Lys  Arg Arg Glu
    1715                 1720                 1725

Pro Val  Gly Gln Asp Ala Val  Gly Leu Lys Asn Leu  Ser Val Gln
    1730                 1735                 1740

Val Ser  Glu Ala Asn Leu Ile  Gly Thr Gly Thr Ser  Glu His Trp
    1745                 1750                 1755

Val Asp  Asp Glu Gly Pro Gln  Pro Lys Lys Val Lys  Ala Glu Asp
    1760                 1765                 1770

Glu Ala  Leu Leu Ser Glu Glu  Asp Asp Pro Ile Asp  Arg Arg Pro
    1775                 1780                 1785

Trp Thr  Gln Gln His Leu Glu  Ala Ala Asp Ile Arg  Arg Thr Pro
    1790                 1795                 1800

Ser Leu  Ala Leu Thr Pro Pro  Gln Ala Glu Gln Glu  Val Asp Val
    1805                 1810                 1815
```

-continued

```
Leu Asp  Val Asn Val Arg Gly  Pro Asp Gly Cys Thr  Pro Leu Met
    1820                 1825                 1830

Leu Ala  Ser Leu Arg Gly Gly  Ser Ser Asp Leu Ser  Asp Glu Asp
    1835                 1840                 1845

Glu Asp  Ala Glu Asp Ser Ser  Ala Asn Ile Ile Thr  Asp Leu Val
    1850                 1855                 1860

Tyr Gln  Gly Ala Ser Leu Gln  Ala Gln Thr Asp Arg  Thr Gly Glu
    1865                 1870                 1875

Met Ala  Leu His Leu Ala Ala  Arg Tyr Ser Arg Ala  Asp Ala Ala
    1880                 1885                 1890

Lys Arg  Leu Leu Asp Ala Gly  Ala Asp Ala Asn Ala  Gln Asp Asn
    1895                 1900                 1905

Met Gly  Arg Cys Pro Leu His  Ala Ala Val Ala Ala  Asp Ala Gln
    1910                 1915                 1920

Gly Val  Phe Gln Ile Leu Ile  Arg Asn Arg Val Thr  Asp Leu Asp
    1925                 1930                 1935

Ala Arg  Met Asn Asp Gly Thr  Thr Pro Leu Ile Leu  Ala Ala Arg
    1940                 1945                 1950

Leu Ala  Val Glu Gly Met Val  Ala Glu Leu Ile Asn  Cys Gln Ala
    1955                 1960                 1965

Asp Val  Asn Ala Val Asp Asp  His Gly Lys Ser Ala  Leu His Trp
    1970                 1975                 1980

Ala Ala  Ala Val Asn Asn Val  Glu Ala Thr Leu Leu  Leu Leu Lys
    1985                 1990                 1995

Asn Gly  Ala Asn Arg Asp Met  Gln Asp Asn Lys Glu  Glu Thr Pro
    2000                 2005                 2010

Leu Phe  Leu Ala Ala Arg Glu  Gly Ser Tyr Glu Ala  Ala Lys Ile
    2015                 2020                 2025

Leu Leu  Asp His Phe Ala Asn  Arg Asp Ile Thr Asp  His Met Asp
    2030                 2035                 2040

Arg Leu  Pro Arg Asp Val Ala  Arg Asp Arg Met His  His Asp Ile
    2045                 2050                 2055

Val Arg  Leu Leu Asp Glu Tyr  Asn Val Thr Pro Ser  Pro Pro Gly
    2060                 2065                 2070

Thr Val  Leu Thr Ser Ala Leu  Ser Pro Val Ile Cys  Gly Pro Asn
    2075                 2080                 2085

Arg Ser  Phe Leu Ser Leu Lys  His Thr Pro Met Gly  Lys Lys Ser
    2090                 2095                 2100

Arg Arg  Pro Ser Ala Lys Ser  Thr Met Pro Thr Ser  Leu Pro Asn
    2105                 2110                 2115

Leu Ala  Lys Glu Ala Lys Asp  Ala Lys Gly Ser Arg  Arg Lys Lys
    2120                 2125                 2130

Ser Leu  Ser Glu Lys Val Gln  Leu Ser Glu Ser Ser  Val Thr Leu
    2135                 2140                 2145

Ser Pro  Val Asp Ser Leu Glu  Ser Pro His Thr Tyr  Val Ser Asp
    2150                 2155                 2160

Thr Thr  Ser Ser Pro Met Ile  Thr Ser Pro Gly Ile  Leu Gln Ala
    2165                 2170                 2175

Ser Pro  Asn Pro Met Leu Ala  Thr Ala Ala Pro Pro  Ala Pro Val
    2180                 2185                 2190

His Ala  Gln His Ala Leu Ser  Phe Ser Asn Leu His  Glu Met Gln
    2195                 2200                 2205

Pro Leu  Ala His Gly Ala Ser  Thr Val Leu Pro Ser  Val Ser Gln
```

-continued

```
    2210                2215                2220

Leu Leu  Ser His His His Ile  Val Ser Pro Gly Ser  Gly Ser Ala
    2225                2230                2235

Gly Ser  Leu Ser Arg Leu His  Pro Val Pro Val Pro  Ala Asp Trp
    2240                2245                2250

Met Asn  Arg Met Glu Val Asn  Glu Thr Gln Tyr Asn  Glu Met Phe
    2255                2260                2265

Gly Met  Val Leu Ala Pro Ala  Glu Gly Thr His Pro  Gly Ile Ala
    2270                2275                2280

Pro Gln  Ser Arg Pro Pro Glu  Gly Lys His Ile Thr  Thr Pro Arg
    2285                2290                2295

Glu Pro  Leu Pro Pro Ile Val  Thr Phe Gln Leu Ile  Pro Lys Gly
    2300                2305                2310

Ser Ile  Ala Gln Pro Ala Gly  Ala Pro Gln Pro Gln  Ser Thr Cys
    2315                2320                2325

Pro Pro  Ala Val Ala Gly Pro  Leu Pro Thr Met Tyr  Gln Ile Pro
    2330                2335                2340

Glu Met  Ala Arg Leu Pro Ser  Val Ala Phe Pro Thr  Ala Met Met
    2345                2350                2355

Pro Gln  Gln Asp Gly Gln Val  Ala Gln Thr Ile Leu  Pro Ala Tyr
    2360                2365                2370

His Pro  Phe Pro Ala Ser Val  Gly Lys Tyr Pro Thr  Pro Pro Ser
    2375                2380                2385

Gln His  Ser Tyr Ala Ser Ser  Asn Ala Ala Glu Arg  Thr Pro Ser
    2390                2395                2400

His Ser  Gly His Leu Gln Gly  Glu His Pro Tyr Leu  Thr Pro Ser
    2405                2410                2415

Pro Glu  Ser Pro Asp Gln Trp  Ser Ser Ser Ser Pro  His Ser Ala
    2420                2425                2430

Ser Asp  Trp Ser Asp Val Thr  Thr Ser Pro Thr Pro  Gly Gly Ala
    2435                2440                2445

Gly Gly  Gly Gln Arg Gly Pro  Gly Thr His Met Ser  Glu Pro Pro
    2450                2455                2460

His Asn  Asn Met Gln Val Tyr  Ala
    2465                2470


<210> SEQ ID NO 26
<211> LENGTH: 1235
<212> TYPE: PRT
<213> ORGANISM: Homo sapiens

<400> SEQUENCE: 26

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95
```

-continued

```
Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
```

```
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940
```

```
Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly  Thr Cys Val Asp Gly  Ile Asn Ser
        995                 1000                 1005

Phe Ser  Cys Leu Cys Pro Val  Gly Phe Thr Gly Ser  Phe Cys Leu
    1010                 1015                 1020

His Glu  Ile Asn Glu Cys Ser  Ser His Pro Cys Leu  Asn Glu Gly
    1025                 1030                 1035

Thr Cys  Val Asp Gly Leu Gly  Thr Tyr Arg Cys Ser  Cys Pro Leu
    1040                 1045                 1050

Gly Tyr  Thr Gly Lys Asn Cys  Gln Thr Leu Val Asn  Leu Cys Ser
    1055                 1060                 1065

Arg Ser  Pro Cys Lys Asn Lys  Gly Thr Cys Val Gln  Lys Lys Ala
    1070                 1075                 1080

Glu Ser  Gln Cys Leu Cys Pro  Ser Gly Trp Ala Gly  Ala Tyr Cys
    1085                 1090                 1095

Asp Val  Pro Asn Val Ser Cys  Asp Ile Ala Ala Ser  Arg Arg Gly
    1100                 1105                 1110

Val Leu  Val Glu His Leu Cys  Gln His Ser Gly Val  Cys Ile Asn
    1115                 1120                 1125

Ala Gly  Asn Thr His Tyr Cys  Gln Cys Pro Leu Gly  Tyr Thr Gly
    1130                 1135                 1140

Ser Tyr  Cys Glu Glu Gln Leu  Asp Glu Cys Ala Ser  Asn Pro Cys
    1145                 1150                 1155

Gln His  Gly Ala Thr Cys Ser  Asp Phe Ile Gly Gly  Tyr Arg Cys
    1160                 1165                 1170

Glu Cys  Val Pro Gly Tyr Gln  Gly Val Asn Cys Glu  Tyr Glu Val
    1175                 1180                 1185

Asp Glu  Cys Gln Asn Gln Pro  Cys Gln Asn Gly Gly  Thr Cys Ile
    1190                 1195                 1200

Asp Leu  Val Asn His Phe Lys  Cys Ser Cys Pro Pro  Gly Thr Arg
    1205                 1210                 1215

Gly Met  Lys Ser Ser Leu Ser  Ile Phe His Pro Gly  His Cys Leu
    1220                 1225                 1230

Lys Leu
    1235


<210> SEQ ID NO 27
<211> LENGTH: 2321
<212> TYPE: PRT
<213> ORGANISM: Homo sapiens

<400> SEQUENCE: 27

Met Gly Pro Gly Ala Arg Gly Arg Arg Arg Arg Arg Arg Pro Met Ser
1               5                   10                  15

Pro Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
```

```
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365

Asn Pro Val Asn Gly Arg Ala Ile Cys Thr Cys Pro Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480
```

-continued

```
Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895
```

-continued

```
Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu  Val Asp Trp Cys Ser  Arg Gln Pro
        995                 1000                 1005

Cys Gln  Asn Gly Gly Arg Cys  Val Gln Thr Gly Ala  Tyr Cys Leu
    1010                 1015                 1020

Cys Pro  Pro Gly Trp Ser Gly  Arg Leu Cys Asp Ile  Arg Ser Leu
    1025                 1030                 1035

Pro Cys  Arg Glu Ala Ala Ala  Gln Ile Gly Val Arg  Leu Glu Gln
    1040                 1045                 1050

Leu Cys  Gln Ala Gly Gly Gln  Cys Val Asp Glu Asp  Ser Ser His
    1055                 1060                 1065

Tyr Cys  Val Cys Pro Glu Gly  Arg Thr Gly Ser His  Cys Glu Gln
    1070                 1075                 1080

Glu Val  Asp Pro Cys Leu Ala  Gln Pro Cys Gln His  Gly Gly Thr
    1085                 1090                 1095

Cys Arg  Gly Tyr Met Gly Gly  Tyr Met Cys Glu Cys  Leu Pro Gly
    1100                 1105                 1110

Tyr Asn  Gly Asp Asn Cys Glu  Asp Asp Val Asp Glu  Cys Ala Ser
    1115                 1120                 1125

Gln Pro  Cys Gln His Gly Gly  Ser Cys Ile Asp Leu  Val Ala Arg
    1130                 1135                 1140

Tyr Leu  Cys Ser Cys Pro Pro  Gly Thr Leu Gly Val  Leu Cys Glu
    1145                 1150                 1155

Ile Asn  Glu Asp Asp Cys Gly  Pro Gly Pro Pro Leu  Asp Ser Gly
    1160                 1165                 1170

Pro Arg  Cys Leu His Asn Gly  Thr Cys Val Asp Leu  Val Gly Gly
    1175                 1180                 1185

Phe Arg  Cys Thr Cys Pro Pro  Gly Tyr Thr Gly Leu  Arg Cys Glu
    1190                 1195                 1200

Ala Asp  Ile Asn Glu Cys Arg  Ser Gly Ala Cys His  Ala Ala His
    1205                 1210                 1215

Thr Arg  Asp Cys Leu Gln Asp  Pro Gly Gly Gly Phe  Arg Cys Leu
    1220                 1225                 1230

Cys His  Ala Gly Phe Ser Gly  Pro Arg Cys Gln Thr  Val Leu Ser
    1235                 1240                 1245

Pro Cys  Glu Ser Gln Pro Cys  Gln His Gly Gly Gln  Cys Arg Pro
    1250                 1255                 1260

Ser Pro  Gly Pro Gly Gly Gly  Leu Thr Phe Thr Cys  His Cys Ala
    1265                 1270                 1275

Gln Pro  Phe Trp Gly Pro Arg  Cys Glu Arg Val Ala  Arg Ser Cys
    1280                 1285                 1290

Arg Glu  Leu Gln Cys Pro Val  Gly Val Pro Cys Gln  Gln Thr Pro
```

-continued

```
    1295                1300                1305

Arg Gly  Pro Arg Cys Ala Cys  Pro Pro Gly Leu Ser  Gly Pro Ser
    1310                1315                1320

Cys Arg  Ser Phe Pro Gly Ser  Pro Pro Gly Ala Ser  Asn Ala Ser
    1325                1330                1335

Cys Ala  Ala Ala Pro Cys Leu  His Gly Gly Ser Cys  Arg Pro Ala
    1340                1345                1350

Pro Leu  Ala Pro Phe Phe Arg  Cys Ala Cys Ala Gln  Gly Trp Thr
    1355                1360                1365

Gly Pro  Arg Cys Glu Ala Pro  Ala Ala Ala Pro Glu  Val Ser Glu
    1370                1375                1380

Glu Pro  Arg Cys Pro Arg Ala  Ala Cys Gln Ala Lys  Arg Gly Asp
    1385                1390                1395

Gln Arg  Cys Asp Arg Glu Cys  Asn Ser Pro Gly Cys  Gly Trp Asp
    1400                1405                1410

Gly Gly  Asp Cys Ser Leu Ser  Val Gly Asp Pro Trp  Arg Gln Cys
    1415                1420                1425

Glu Ala  Leu Gln Cys Trp Arg  Leu Phe Asn Asn Ser  Arg Cys Asp
    1430                1435                1440

Pro Ala  Cys Ser Ser Pro Ala  Cys Leu Tyr Asp Asn  Phe Asp Cys
    1445                1450                1455

His Ala  Gly Gly Arg Glu Arg  Thr Cys Asn Pro Val  Tyr Glu Lys
    1460                1465                1470

Tyr Cys  Ala Asp His Phe Ala  Asp Gly Arg Cys Asp  Gln Gly Cys
    1475                1480                1485

Asn Thr  Glu Glu Cys Gly Trp  Asp Gly Leu Asp Cys  Ala Ser Glu
    1490                1495                1500

Val Pro  Ala Leu Leu Ala Arg  Gly Val Leu Val Leu  Thr Val Leu
    1505                1510                1515

Leu Pro  Pro Glu Glu Leu Leu  Arg Ser Ser Ala Asp  Phe Leu Gln
    1520                1525                1530

Arg Leu  Ser Ala Ile Leu Arg  Thr Ser Leu Arg Phe  Arg Leu Asp
    1535                1540                1545

Ala His  Gly Gln Ala Met Val  Phe Pro Tyr His Arg  Pro Ser Pro
    1550                1555                1560

Gly Ser  Glu Pro Arg Ala Arg  Arg Glu Leu Ala Pro  Glu Val Ile
    1565                1570                1575

Gly Ser  Val Val Met Leu Glu  Ile Asp Asn Arg Leu  Cys Leu Gln
    1580                1585                1590

Ser Pro  Glu Asn Asp His Cys  Phe Pro Asp Ala Gln  Ser Ala Ala
    1595                1600                1605

Asp Tyr  Leu Gly Ala Leu Ser  Ala Val Glu Arg Leu  Asp Phe Pro
    1610                1615                1620

Tyr Pro  Leu Arg Asp Val Arg  Gly Glu Pro Leu Glu  Pro Pro Glu
    1625                1630                1635

Pro Ser  Val Pro Leu Leu Pro  Leu Leu Val Ala Gly  Ala Val Leu
    1640                1645                1650

Leu Leu  Val Ile Leu Val Leu  Gly Val Met Val Ala  Arg Arg Lys
    1655                1660                1665

Arg Glu  His Ser Thr Leu Trp  Phe Pro Glu Gly Phe  Ser Leu His
    1670                1675                1680

Lys Asp  Val Ala Ser Gly His  Lys Gly Arg Arg Glu  Pro Val Gly
    1685                1690                1695
```

```
Gln Asp  Ala Leu Gly Met Lys  Asn Met Ala Lys Gly  Glu Ser Leu
    1700                 1705                 1710

Met Gly  Glu Val Ala Thr Asp  Trp Met Asp Thr Glu  Cys Pro Glu
    1715                 1720                 1725

Ala Lys  Arg Leu Lys Val Glu  Glu Pro Gly Met Gly  Ala Glu Glu
    1730                 1735                 1740

Ala Val  Asp Cys Arg Gln Trp  Thr Gln His His Leu  Val Ala Ala
    1745                 1750                 1755

Asp Ile  Arg Val Ala Pro Ala  Met Ala Leu Thr Pro  Pro Gln Gly
    1760                 1765                 1770

Asp Ala  Asp Ala Asp Gly Met  Asp Val Asn Val Arg  Gly Pro Asp
    1775                 1780                 1785

Gly Phe  Thr Pro Leu Met Leu  Ala Ser Phe Cys Gly  Gly Ala Leu
    1790                 1795                 1800

Glu Pro  Met Pro Thr Glu Glu  Asp Glu Ala Asp Asp  Thr Ser Ala
    1805                 1810                 1815

Ser Ile  Ile Ser Asp Leu Ile  Cys Gln Gly Ala Gln  Leu Gly Ala
    1820                 1825                 1830

Arg Thr  Asp Arg Thr Gly Glu  Thr Ala Leu His Leu  Ala Ala Arg
    1835                 1840                 1845

Tyr Ala  Arg Ala Asp Ala Ala  Lys Arg Leu Leu Asp  Ala Gly Ala
    1850                 1855                 1860

Asp Thr  Asn Ala Gln Asp His  Ser Gly Arg Thr Pro  Leu His Thr
    1865                 1870                 1875

Ala Val  Thr Ala Asp Ala Gln  Gly Val Phe Gln Ile  Leu Ile Arg
    1880                 1885                 1890

Asn Arg  Ser Thr Asp Leu Asp  Ala Arg Met Ala Asp  Gly Ser Thr
    1895                 1900                 1905

Ala Leu  Ile Leu Ala Ala Arg  Leu Ala Val Glu Gly  Met Val Glu
    1910                 1915                 1920

Glu Leu  Ile Ala Ser His Ala  Asp Val Asn Ala Val  Asp Glu Leu
    1925                 1930                 1935

Gly Lys  Ser Ala Leu His Trp  Ala Ala Ala Val Asn  Asn Val Glu
    1940                 1945                 1950

Ala Thr  Leu Ala Leu Leu Lys  Asn Gly Ala Asn Lys  Asp Met Gln
    1955                 1960                 1965

Asp Ser  Lys Glu Glu Thr Pro  Leu Phe Leu Ala Ala  Arg Glu Gly
    1970                 1975                 1980

Ser Tyr  Glu Ala Ala Lys Leu  Leu Leu Asp His Phe  Ala Asn Arg
    1985                 1990                 1995

Glu Ile  Thr Asp His Leu Asp  Arg Leu Pro Arg Asp  Val Ala Gln
    2000                 2005                 2010

Glu Arg  Leu His Gln Asp Ile  Val Arg Leu Leu Asp  Gln Pro Ser
    2015                 2020                 2025

Gly Pro  Arg Ser Pro Pro Gly  Pro His Gly Leu Gly  Pro Leu Leu
    2030                 2035                 2040

Cys Pro  Pro Gly Ala Phe Leu  Pro Gly Leu Lys Ala  Ala Gln Ser
    2045                 2050                 2055

Gly Ser  Lys Lys Ser Arg Arg  Pro Pro Gly Lys Ala  Gly Leu Gly
    2060                 2065                 2070

Pro Gln  Gly Pro Arg Gly Arg  Gly Lys Lys Leu Thr  Leu Ala Cys
    2075                 2080                 2085
```

```
Pro Gly  Pro Leu Ala Asp Ser  Ser Val Thr Leu Ser  Pro Val Asp
    2090                 2095                 2100

Ser Leu  Asp Ser Pro Arg Pro  Phe Gly Gly Pro Pro  Ala Ser Pro
    2105                 2110                 2115

Gly Gly  Phe Pro Leu Glu Gly  Pro Tyr Ala Ala Ala  Thr Ala Thr
    2120                 2125                 2130

Ala Val  Ser Leu Ala Gln Leu  Gly Gly Pro Gly Arg  Ala Gly Leu
    2135                 2140                 2145

Gly Arg  Gln Pro Pro Gly Gly  Cys Val Leu Ser Leu  Gly Leu Leu
    2150                 2155                 2160

Asn Pro  Val Ala Val Pro Leu  Asp Trp Ala Arg Leu  Pro Pro Pro
    2165                 2170                 2175

Ala Pro  Pro Gly Pro Ser Phe  Leu Leu Pro Leu Ala  Pro Gly Pro
    2180                 2185                 2190

Gln Leu  Leu Asn Pro Gly Thr  Pro Val Ser Pro Gln  Glu Arg Pro
    2195                 2200                 2205

Pro Pro  Tyr Leu Ala Val Pro  Gly His Gly Glu Glu  Tyr Pro Ala
    2210                 2215                 2220

Ala Gly  Ala His Ser Ser Pro  Pro Lys Ala Arg Phe  Leu Arg Val
    2225                 2230                 2235

Pro Ser  Glu His Pro Tyr Leu  Thr Pro Ser Pro Glu  Ser Pro Glu
    2240                 2245                 2250

His Trp  Ala Ser Pro Ser Pro  Pro Ser Leu Ser Asp  Trp Ser Glu
    2255                 2260                 2265

Ser Thr  Pro Ser Pro Ala Thr  Ala Thr Gly Ala Met  Ala Thr Thr
    2270                 2275                 2280

Thr Gly  Ala Leu Pro Ala Gln  Pro Leu Pro Leu Ser  Val Pro Ser
    2285                 2290                 2295

Ser Leu  Ala Gln Ala Gln Thr  Gln Leu Gly Pro Gln  Pro Glu Val
    2300                 2305                 2310

Thr Pro  Lys Arg Gln Val Leu  Ala
    2315                 2320


<210> SEQ ID NO 28
<211> LENGTH: 2003
<212> TYPE: PRT
<213> ORGANISM: Homo sapiens

<400> SEQUENCE: 28

Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
        35                  40                  45

Gly Thr Cys Gln Cys Ala Pro Gly Phe Leu Gly Glu Thr Cys Gln Phe
    50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125
```

```
Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
    290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365

Thr Cys Ile Asp Arg Val Gly Ser Phe Ser Cys Leu Cys Pro Pro Gly
    370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
        435                 440                 445

Gly Gly Ser Cys Leu Asn Thr Pro Gly Ser Phe Asn Cys Leu Cys Pro
    450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
        515                 520                 525

His Asp Leu Leu Asn Gly Phe Gln Cys Ile Cys Leu Pro Gly Phe Ser
    530                 535                 540
```

-continued

```
Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
        595                 600                 605

Gly Ala Phe Phe Cys Leu Cys Pro Ser Gly Phe Thr Gly Gln Leu Cys
    610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
        675                 680                 685

Glu Ala Glu Leu Gly Gly Cys Ile Ser Ala Pro Cys Ala His Gly Gly
    690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Gly Tyr Tyr
            740                 745                 750

Cys Thr Cys Pro Pro Ser His Thr Gly Pro Gln Cys Gln Thr Ser Thr
        755                 760                 765

Asp Tyr Cys Val Ser Ala Pro Cys Phe Asn Gly Gly Thr Cys Val Asn
    770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
                805                 810                 815

Asn Arg Ala Thr Cys Gln Asp Ser Pro Gln Gly Pro Arg Cys Leu Cys
            820                 825                 830

Pro Thr Gly Tyr Thr Gly Gly Ser Cys Gln Thr Leu Met Asp Leu Cys
        835                 840                 845

Ala Gln Lys Pro Cys Pro Arg Asn Ser His Cys Leu Gln Thr Gly Pro
    850                 855                 860

Ser Phe His Cys Leu Cys Leu Gln Gly Trp Thr Gly Pro Leu Cys Asn
865                 870                 875                 880

Leu Pro Leu Ser Ser Cys Gln Lys Ala Ala Leu Ser Gln Gly Ile Asp
                885                 890                 895

Val Ser Ser Leu Cys His Asn Gly Gly Leu Cys Val Asp Ser Gly Pro
            900                 905                 910

Ser Tyr Phe Cys His Cys Pro Pro Gly Phe Gln Gly Ser Leu Cys Gln
        915                 920                 925

Asp His Val Asn Pro Cys Glu Ser Arg Pro Cys Gln Asn Gly Ala Thr
    930                 935                 940

Cys Met Ala Gln Pro Ser Gly Tyr Leu Cys Gln Cys Ala Pro Gly Tyr
945                 950                 955                 960

Asp Gly Gln Asn Cys Ser Lys Glu Leu Asp Ala Cys Gln Ser Gln Pro
```

-continued

```
                965                 970                 975

Cys His Asn His Gly Thr Cys Thr Pro Lys Pro Gly Gly Phe His Cys
            980                 985                 990

Ala Cys Pro Pro Gly Phe Val Gly  Leu Arg Cys Glu Gly  Asp Val Asp
        995                 1000                1005

Glu Cys  Leu Asp Gln Pro Cys  His Pro Thr Gly Thr  Ala Ala Cys
    1010                 1015                 1020

His Ser  Leu Ala Asn Ala Phe  Tyr Cys Gln Cys Leu  Pro Gly His
    1025                 1030                 1035

Thr Gly  Gln Trp Cys Glu Val  Glu Ile Asp Pro Cys  His Ser Gln
    1040                 1045                 1050

Pro Cys  Phe His Gly Gly Thr  Cys Glu Ala Thr Ala  Gly Ser Pro
    1055                 1060                 1065

Leu Gly  Phe Ile Cys His Cys  Pro Lys Gly Phe Glu  Gly Pro Thr
    1070                 1075                 1080

Cys Ser  His Arg Ala Pro Ser  Cys Gly Phe His His  Cys His His
    1085                 1090                 1095

Gly Gly  Leu Cys Leu Pro Ser  Pro Lys Pro Gly Phe  Pro Pro Arg
    1100                 1105                 1110

Cys Ala  Cys Leu Ser Gly Tyr  Gly Gly Pro Asp Cys  Leu Thr Pro
    1115                 1120                 1125

Pro Ala  Pro Lys Gly Cys Gly  Pro Pro Ser Pro Cys  Leu Tyr Asn
    1130                 1135                 1140

Gly Ser  Cys Ser Glu Thr Thr  Gly Leu Gly Gly Pro  Gly Phe Arg
    1145                 1150                 1155

Cys Ser  Cys Pro His Ser Ser  Pro Gly Pro Arg Cys  Gln Lys Pro
    1160                 1165                 1170

Gly Ala  Lys Gly Cys Glu Gly  Arg Ser Gly Asp Gly  Ala Cys Asp
    1175                 1180                 1185

Ala Gly  Cys Ser Gly Pro Gly  Gly Asn Trp Asp Gly  Gly Asp Cys
    1190                 1195                 1200

Ser Leu  Gly Val Pro Asp Pro  Trp Lys Gly Cys Pro  Ser His Ser
    1205                 1210                 1215

Arg Cys  Trp Leu Leu Phe Arg  Asp Gly Gln Cys His  Pro Gln Cys
    1220                 1225                 1230

Asp Ser  Glu Glu Cys Leu Phe  Asp Gly Tyr Asp Cys  Glu Thr Pro
    1235                 1240                 1245

Pro Ala  Cys Thr Pro Ala Tyr  Asp Gln Tyr Cys His  Asp His Phe
    1250                 1255                 1260

His Asn  Gly His Cys Glu Lys  Gly Cys Asn Thr Ala  Glu Cys Gly
    1265                 1270                 1275

Trp Asp  Gly Gly Asp Cys Arg  Pro Glu Asp Gly Asp  Pro Glu Trp
    1280                 1285                 1290

Gly Pro  Ser Leu Ala Leu Leu  Val Val Leu Ser Pro  Pro Ala Leu
    1295                 1300                 1305

Asp Gln  Gln Leu Phe Ala Leu  Ala Arg Val Leu Ser  Leu Thr Leu
    1310                 1315                 1320

Arg Val  Gly Leu Trp Val Arg  Lys Asp Arg Asp Gly  Arg Asp Met
    1325                 1330                 1335

Val Tyr  Pro Tyr Pro Gly Ala  Arg Ala Glu Glu Lys  Leu Gly Gly
    1340                 1345                 1350

Thr Arg  Asp Pro Thr Tyr Gln  Glu Arg Ala Ala Pro  Gln Thr Gln
    1355                 1360                 1365
```

```
Pro Leu  Gly Lys Glu Thr Asp  Ser Leu Ser Ala Gly  Phe Val Val
    1370                 1375                 1380

Val Met  Gly Val Asp Leu Ser  Arg Cys Gly Pro Asp  His Pro Ala
    1385                 1390                 1395

Ser Arg  Cys Pro Trp Asp Pro  Gly Leu Leu Leu Arg  Phe Leu Ala
    1400                 1405                 1410

Ala Met  Ala Ala Val Gly Ala  Leu Glu Pro Leu Leu  Pro Gly Pro
    1415                 1420                 1425

Leu Leu  Ala Val His Pro His  Ala Gly Thr Ala Pro  Pro Ala Asn
    1430                 1435                 1440

Gln Leu  Pro Trp Pro Val Leu  Cys Ser Pro Val Ala  Gly Val Ile
    1445                 1450                 1455

Leu Leu  Ala Leu Gly Ala Leu  Leu Val Leu Gln Leu  Ile Arg Arg
    1460                 1465                 1470

Arg Arg  Arg Glu His Gly Ala  Leu Trp Leu Pro Pro  Gly Phe Thr
    1475                 1480                 1485

Arg Arg  Pro Arg Thr Gln Ser  Ala Pro His Arg Arg  Arg Pro Pro
    1490                 1495                 1500

Leu Gly  Glu Asp Ser Ile Gly  Leu Lys Ala Leu Lys  Pro Lys Ala
    1505                 1510                 1515

Glu Val  Asp Glu Asp Gly Val  Val Met Cys Ser Gly  Pro Glu Glu
    1520                 1525                 1530

Gly Glu  Glu Val Gly Gln Ala  Glu Glu Thr Gly Pro  Pro Ser Thr
    1535                 1540                 1545

Cys Gln  Leu Trp Ser Leu Ser  Gly Gly Cys Gly Ala  Leu Pro Gln
    1550                 1555                 1560

Ala Ala  Met Leu Thr Pro Pro  Gln Glu Ser Glu Met  Glu Ala Pro
    1565                 1570                 1575

Asp Leu  Asp Thr Arg Gly Pro  Asp Gly Val Thr Pro  Leu Met Ser
    1580                 1585                 1590

Ala Val  Cys Cys Gly Glu Val  Gln Ser Gly Thr Phe  Gln Gly Ala
    1595                 1600                 1605

Trp Leu  Gly Cys Pro Glu Pro  Trp Glu Pro Leu Leu  Asp Gly Gly
    1610                 1615                 1620

Ala Cys  Pro Gln Ala His Thr  Val Gly Thr Gly Glu  Thr Pro Leu
    1625                 1630                 1635

His Leu  Ala Ala Arg Phe Ser  Arg Pro Thr Ala Ala  Arg Arg Leu
    1640                 1645                 1650

Leu Glu  Ala Gly Ala Asn Pro  Asn Gln Pro Asp Arg  Ala Gly Arg
    1655                 1660                 1665

Thr Pro  Leu His Ala Ala Val  Ala Ala Asp Ala Arg  Glu Val Cys
    1670                 1675                 1680

Gln Leu  Leu Leu Arg Ser Arg  Gln Thr Ala Val Asp  Ala Arg Thr
    1685                 1690                 1695

Glu Asp  Gly Thr Thr Pro Leu  Met Leu Ala Ala Arg  Leu Ala Val
    1700                 1705                 1710

Glu Asp  Leu Val Glu Glu Leu  Ile Ala Ala Gln Ala  Asp Val Gly
    1715                 1720                 1725

Ala Arg  Asp Lys Trp Gly Lys  Thr Ala Leu His Trp  Ala Ala Ala
    1730                 1735                 1740

Val Asn  Asn Ala Arg Ala Ala  Arg Ser Leu Leu Gln  Ala Gly Ala
    1745                 1750                 1755
```

```
Asp Lys  Asp Ala Gln Asp Asn  Arg Glu Gln Thr Pro  Leu Phe Leu
    1760                 1765                 1770

Ala Ala  Arg Glu Gly Ala Val  Glu Val Ala Gln Leu  Leu Leu Gly
    1775                 1780                 1785

Leu Gly  Ala Ala Arg Glu Leu  Arg Asp Gln Ala Gly  Leu Ala Pro
    1790                 1795                 1800

Ala Asp  Val Ala His Gln Arg  Asn His Trp Asp Leu  Leu Thr Leu
    1805                 1810                 1815

Leu Glu  Gly Ala Gly Pro Pro  Glu Ala Arg His Lys  Ala Thr Pro
    1820                 1825                 1830

Gly Arg  Glu Ala Gly Pro Phe  Pro Arg Ala Arg Thr  Val Ser Val
    1835                 1840                 1845

Ser Val  Pro Pro His Gly Gly  Gly Ala Leu Pro Arg  Cys Arg Thr
    1850                 1855                 1860

Leu Ser  Ala Gly Ala Gly Pro  Arg Gly Gly Gly Ala  Cys Leu Gln
    1865                 1870                 1875

Ala Arg  Thr Trp Ser Val Asp  Leu Ala Ala Arg Gly  Gly Gly Ala
    1880                 1885                 1890

Tyr Ser  His Cys Arg Ser Leu  Ser Gly Val Gly Ala  Gly Gly Gly
    1895                 1900                 1905

Pro Thr  Pro Arg Gly Arg Arg  Phe Ser Ala Gly Met  Arg Gly Pro
    1910                 1915                 1920

Arg Pro  Asn Pro Ala Ile Met  Arg Gly Arg Tyr Gly  Val Ala Ala
    1925                 1930                 1935

Gly Arg  Gly Gly Arg Val Ser  Thr Asp Asp Trp Pro  Cys Asp Trp
    1940                 1945                 1950

Val Ala  Leu Gly Ala Cys Gly  Ser Ala Ser Asn Ile  Pro Ile Pro
    1955                 1960                 1965

Pro Pro  Cys Leu Thr Pro Ser  Pro Glu Arg Gly Ser  Pro Gln Leu
    1970                 1975                 1980

Asp Cys  Gly Pro Pro Ala Leu  Gln Glu Met Pro Ile  Asn Gln Gly
    1985                 1990                 1995

Gly Glu  Gly Lys Lys
    2000
```

<210> SEQ ID NO 29
<211> LENGTH: 9322
<212> TYPE: DNA
<213> ORGANISM: Homo sapiens

<400> SEQUENCE: 29

```
atgccgccgc tcctggcgcc cctgctctgc ctggcgctgc tgcccgcgct cgccgcacga     60

ggcccgcgat gctcccagcc cggtgagacc tgcctgaatg gcgggaagtg tgaagcggcc    120

aatggcacgg aggcctgcgt ctgtggcggg gccttcgtgg gcccgcgatg ccaggacccc    180

aacccgtgcc tcagcacccc ctgcaagaac gccgggacat gccacgtggt ggaccgcaga    240

ggcgtggcag actatgcctg cagctgtgcc ctgggcttct ctgggcccct ctgcctgaca    300

cccctggaca atgcctgcct caccaacccc tgccgcaacg ggggcacctg cgacctgctc    360

acgctgacgg agtacaagtg ccgctgcccg cccggctggt cagggaaatc gtgccagcag    420

gctgacccgt gcgcctccaa cccctgcgcc aacggtggcc agtgcctgcc cttcgaggcc    480

tcctacatct gccactgccc acccagcttc catggcccca cctgccggca ggatgtcaac    540

gagtgtggcc agaagcccgg gctttgccgc cacggaggca cctgccacaa cgaggtcggc    600
```

-continued

```
tcctaccgct gcgtctgccg cgccacccac actggcccca actgcgagcg gccctacgtg    660
ccctgcagcc cctcgccctg ccagaacggg ggcacctgcc gccccacggg cgacgtcacc    720
cacgagtgtg cctgcctgcc aggcttcacc ggccagaact gtgaggaaaa tatcgacgat    780
tgtccaggaa acaactgcaa gaacgggggt gcctgtgtgg acggcgtgaa cacctacaac    840
tgccgctgcc cgccagagtg gacaggtcag tactgtaccg aggatgtgga cgagtgccag    900
ctgatgccaa atgcctgcca gaacggcggg acctgccaca acacccacgg tggctacaac    960
tgcgtgtgtg tcaacggctg gactggtgag gactgcagcg agaacattga tgactgtgcc   1020
agcgccgcct gcttccacgg cgccacctgc catgaccgtg tggcctcctt ctactgcgag   1080
tgtccccatg gccgcacagg tctgctgtgc cacctcaacg acgcatgcat cagcaacccc   1140
tgtaacgagg gctccaactg cgacaccaac cctgtcaatg gcaaggccat ctgcacctgc   1200
ccctcggggt acacgggccc ggcctgcagc caggacgtgg atgagtgctc gctgggtgcc   1260
aacccctgcg agcatgcggg caagtgcatc aacacgctgg gctccttcga gtgccagtgt   1320
ctgcagggct acacgggccc ccgatgcgag atcgacgtca acgagtgcgt ctcgaacccg   1380
tgccagaacg acgccacctg cctggaccag attggggagt tccagtgcat ctgcatgccc   1440
ggctacgagg gtgtgcactg cgaggtcaac acagacgagt gtgccagcag cccctgcctg   1500
cacaatggcc gctgcctgga caagatcaat gagttccagt gcgagtgccc cacgggcttc   1560
actgggcatc tgtgccagta cgatgtggac gagtgtgcca gcacccccctg caagaatggt   1620
gccaagtgcc tggacggacc caacacttac acctgtgtgt gcacggaagg gtacacgggg   1680
acgcactgcg aggtggacat cgatgagtgc gaccccgacc cctgccacta cggctcctgc   1740
aaggacggcg tcgccacctt cacctgcctc tgccgcccag gctacacggg ccaccactgc   1800
gagaccaaca tcaacgagtg ctccagccag ccctgccgcc acgggggcac ctgccaggac   1860
cgcgacaacg cctacctctg cttctgcctg aaggggacca caggacccaa ctgcgagatc   1920
aacctggatg actgtgccag cagcccctgc gactcgggca cctgtctgga caagatcgat   1980
ggctacgagt gtgcctgtga gccgggctac acagggagca tgtgtaacat caacatcgat   2040
gagtgtgcgg gcaacccctg ccacaacggg ggcacctgcg aggacggcat caatggcttc   2100
acctgccgct gccccgaggg ctaccacgac cccacctgcc tgtctgaggt caatgagtgc   2160
aacagcaacc cctgcgtcca cggggcctgc cgggacagcc tcaacgggta caagtgcgac   2220
tgtgaccctg ggtggagtgg gaccaactgt gacatcaaca acaatgagtg tgaatccaac   2280
ccttgtgtca acggcggcac ctgcaaagac atgaccagtg gctacgtgtg cacctgccgg   2340
gagggcttca gcggtcccaa ctgccagacc aacatcaacg agtgtgcgtc caacccatgt   2400
ctgaaccagg gcacgtgtat tgacgacgtt gccgggtaca agtgcaactg cctgctgccc   2460
tacacaggtg ccacgtgtga ggtggtgctg gccccgtgtg cccccagccc ctgcagaaac   2520
ggcggggagt gcaggcaatc cgaggactat gagagcttct cctgtgtctg ccccacgggc   2580
tggcaagggc agacctgtga ggtcgacatc aacgagtgcg ttctgagccc gtgccggcac   2640
ggcgcatcct gccagaacac ccacggcggc taccgctgcc actgccaggc cggctacagt   2700
gggcgcaact gcgagaccga catcgacgac tgccggccca acccgtgtca caacgggggc   2760
tcctgcacag acggcatcaa cacggccttc tgcgactgcc tgcccggctt ccggggcact   2820
ttctgtgagg aggacatcaa cgagtgtgcc agtgacccct gccgcaacgg ggccaactgc   2880
acggactgcg tggacagcta cacgtgcacc tgccccgcag gcttcagcgg gatccactgt   2940
gagaacaaca cgcctgactg cacagagagc tcctgcttca acggtggcac ctgcgtggac   3000
```

-continued ggcatcaact cgttcacctg cctgtgtcca cccggcttca cgggcagcta ctgccagcac 3060
gatgtcaatg agtgcgactc acagccctgc ctgcatggcg gcacctgtca ggacggctgc 3120
ggctcctaca ggtgcacctg cccccagggc tacactggcc ccaactgcca gaaccttgtg 3180
cactggtgtg actcctcgcc ctgcaagaac ggcggcaaat gctggcagac ccacacccag 3240
taccgctgcg agtgccccag cggctggacc ggcctttact gcgacgtgcc cagcgtgtcc 3300
tgtgaggtgg ctgcgcagcg acaaggtgtt gacgttgccc gcctgtgcca gcatggaggg 3360
ctctgtgtgg acgcgggcaa cacgcaccac tgccgctgcc aggcgggcta cacaggcagc 3420
tactgtgagg acctggtgga cgagtgctca cccagcccct gccagaacgg ggccacctgc 3480
acggactacc tgggcggcta ctcctgcaag tgcgtggccg gctaccacgg ggtgaactgc 3540
tctgaggaga tcgacgagtg cctctcccac ccctgccaga acgggggcac ctgcctcgac 3600
ctccccaaca cctacaagtg ctcctgccca cggggcactc agggtgtgca ctgtgagatc 3660
aacgtggacg actgcaatcc ccccgttgac cccgtgtccc ggagccccaa gtgctttaac 3720
aacggcacct gcgtggacca ggtgggcggc tacagctgca cctgcccgcc gggcttcgtg 3780
ggtgagcgct gtgagggga tgtcaacgag tgcctgtcca atccctgcga cgcccgtggc 3840
acccagaact gcgtgcagcg cgtcaatgac ttccactgcg agtgccgtgc tggtcacacc 3900
gggcgccgct gcgagtccgt catcaatggc tgcaaaggca agccctgcaa gaatgggggc 3960
acctgcgccg tggcctccaa caccgcccgc gggttcatct gcaagtgccc tgcgggcttc 4020
gagggcgcca cgtgtgagaa tgacgctcgt acctgcggca gcctgcgctg cctcaacggc 4080
ggcacatgca tctccggccc gcgcagcccc acctgcctgt gcctgggccc cttcacgggc 4140
cccgaatgcc agttcccggc cagcagcccc tgcctgggcg gcaacccctg ctacaaccag 4200
gggacctgtg agcccacatc cgagagcccc ttctaccgtt gcctgtgccc cgccaaattc 4260
aacgggctct tgtgccacat cctggactac agcttcgggg gtggggccgg gcgcgacatc 4320
cccccgccgc tgatcgagga ggcgtgcgag ctgcccgagt gccaggagga cgcgggcaac 4380
aaggtctgca gcctgcagtg caacaaccac gcgtgcggct gggacggcgg tgactgctcc 4440
ctcaacttca atgacccctg gaagaactgc acgcagtctc tgcagtgctg gaagtacttc 4500
agtgacggcc actgtgacag ccagtgcaac tcagccggct gcctcttcga cggctttgac 4560
tgccagcgtg cggaaggcca gtgcaacccc ctgtacgacc agtactgcaa ggaccacttc 4620
agcgacgggc actgcgacca gggctgcaac agcgcggagt gcgagtggga cgggctggac 4680
tgtgcggagc atgtacccga gaggctggcg gccggcacgc tggtggtggt ggtgctgatg 4740
ccgccggagc agctgcgcaa cagctccttc cacttcctgc gggagctcag ccgcgtgctg 4800
cacaccaacg tggtcttcaa gcgtgacgca cacggccagc agatgatctt cccctactac 4860
ggccgcgagg aggagctgcg caagcacccc atcaagcgtg ccgccgaggg ctgggccgca 4920
cctgacgccc tgctgggcca ggtgaaggcc tcgctgctcc ctggtggcag cgagggtggg 4980
cggcggcgga gggagctgga ccccatggac gtccgcggct ccatcgtcta cctggagatt 5040
gacaaccggc agtgtgtgca ggcctcctcg cagtgcttcc agagtgccac cgacgtggcc 5100
gcattcctgg gagcgctcgc ctcgctgggc agcctcaaca tcccctacaa gatcgaggcc 5160
gtgcagagtg agaccgtgga gccgcccccg ccggcgcagc tgcacttcat gtacgtggcg 5220
gcggccgcct ttgtgcttct gttcttcgtg ggctgcgggg tgctgctgtc ccgcaagcgc 5280
cggcggcagc atggccagct ctggttccct gagggcttca aagtgtctga ggccagcaag 5340

-continued

```
aagaagcggc gggagcccct cggcgaggac tccgtgggcc tcaagcccct gaagaacgct   5400
tcagacggtg ccctcatgga cgacaaccag aatgagtggg gggacgagga cctggagacc   5460
aagaagttcc ggttcgagga gcccgtggtt ctgcctgacc tggacgacca gacagaccac   5520
cggcagtgga ctcagcagca cctggatgcc gctgacctgc gcatgtctgc catggccccc   5580
acaccgcccc agggtgaggt tgacgccgac tgcatggacg tcaatgtccg cgggcctgat   5640
ggcttcaccc cgctcatgat cgcctcctgc agcgggggcg gcctggagac gggcaacagc   5700
gaggaagagg aggacgcgcc ggccgtcatc tccgacttca tctaccaggg cgccagcctg   5760
cacaaccaga cagaccgcac gggcgagacc gccttgcacc tggccgcccg ctactcacgc   5820
tctgatgccg ccaagcgcct gctggaggcc agcgcagatg ccaacatcca ggacaacatg   5880
ggccgcaccc cgctgcatgc ggctgtgtct gccgacgcac aaggtgtctt ccagatcctg   5940
atccggaacc gagccacaga cctggatgcc cgcatgcatg atggcacgac gccactgatc   6000
ctggctgccc gcctggccgt ggagggcatg ctggaggacc tcatcaactc acacgccgac   6060
gtcaacgccg tagatgacct gggcaagtcc gccctgcact gggccgccgc cgtgaacaat   6120
gtggatgccg cagttgtgct cctgaagaac ggggctaaca aagatatgca gaacaacagg   6180
gaggagacac ccctgtttct ggccgcccgg gagggcagct acgagaccgc caaggtgctg   6240
ctggaccact ttgccaaccg ggacatcacg gatcatatgg accgcctgcc gcgcgacatc   6300
gcacaggagc gcatgcatca cgacatcgtg aggctgctgg acgagtacaa cctggtgcgc   6360
agcccgcagc tgcacggagc ccgctggggg ggcacgccca ccctgtcgcc cccgctctgc   6420
tcgcccaacg gctacctggg cagcctcaag cccggcgtgc agggcaagaa ggtccgcaag   6480
cccagcagca aaggcctggc ctgtggaagc aaggaggcca aggacctcaa ggcacggagg   6540
aagaagtccc aggacggcaa gggctgcctg ctggacagct ccggcatgct ctcgcccgtg   6600
gactccctgg agtcacccca tggctacctg tcagacgtgg cctcgccgcc actgctgccc   6660
tccccgttcc agcagtctcc gtccgtgccc ctcaaccacc tgcctgggat gcccgacacc   6720
cacctgggca tcgggcacct gaacgtggcg gccaagcccg agatggcggc gctgggtggg   6780
ggcggccggc tggcctttga gactggccca cctcgtctct cccacctgcc tgtggcctct   6840
ggcaccagca ccgtcctggg ctccagcagc ggaggggccc tgaatttcac tgtgggcggg   6900
tccaccagtt tgaatggtca atgcgagtgg ctgtcccggc tgcagagcgg catggtgccg   6960
aaccaataca accctctgcg gggggagtgtg gcaccaggcc ccctgagcac acaggccccc   7020
tccctgcagc atggcatggt aggcccgctg cacagtagcc ttgctgccag cgccctgtcc   7080
cagatgatga gctaccaggg cctgcccagc acccggctgg ccacccagcc tcacctggtg   7140
cagacccagc aggtgcagcc acaaaactta cagatgcagc agcagaacct gcagccagca   7200
aacatccagc agcagcaaag cctgcagccg ccaccaccac caccacagcc gcaccttggc   7260
gtgagctcag cagccagcgg ccacctgggc cggagcttcc tgagtggaga gccgagccag   7320
gcagacgtgc agccactggg ccccagcagc ctggcggtgc acactattct gccccaggag   7380
agccccgccc tgcccacgtc gctgccatcc tcgctggtcc cacccgtgac cgcagcccag   7440
ttcctgacgc ccccctcgca gcacagctac tcctcgcctg tggacaacac ccccagccac   7500
cagctacagg tgcctgagca ccccttcctc accccgtccc ctgagtcccc tgaccagtgg   7560
tccagctcgt ccccgcattc caacgtctcc gactggtccg agggcgtctc cagccctccc   7620
accagcatgc agtcccagat cgcccgcatt ccggaggcct tcaagtaaac ggcgcgcccc   7680
acgagacccc ggcttccttt cccaagcctt cgggcgtctg tgtgcgctct gtggatgcca   7740
```

```
gggccgacca gaggagcctt tttaaaacac atgtttttat acaaaataag aacgaggatt   7800
ttaattttttt ttagtattta tttatgtact tttattttac acagaaacac tgccttttta   7860
tttatatgta ctgttttatc tggccccagg tagaaacttt tatctattct gagaaaacaa   7920
gcaagttctg agagccaggg ttttcctacg taggatgaaa agattcttct gtgtttataa   7980
aatataaaca aagattcatg atttataaat gccatttatt tattgattcc tttttcaaa   8040
atccaaaaag aaatgatgtt ggagaaggga agttgaacga gcatagtcca aaaagctcct   8100
ggggcgtcca ggccgcgccc tttccccgac gcccacccaa ccccaagcca gcccggccgc   8160
tccaccagca tcacctgcct gttaggagaa gctgcatcca gaggcaaacg gaggcaaagc   8220
tggctcacct tccgcacgcg gattaatttg catctgaaat aggaaacaag tgaaagcata   8280
tgggttagat gttgccatgt gttttagatg gtttcttgca agcatgcttg tgaaaatgtg   8340
ttctcggagt gtgtatgcca agagtgcacc catggtacca atcatgaatc tttgtttcag   8400
gttcagtatt atgtagttgt tcgttggtta tacaagttct tggtccctcc agaaccaccc   8460
cggcccccctg cccgttcttg aaatgtaggc atcatgcatg tcaaacatga gatgtgtgga   8520
ctgtggcact tgcctgggtc acacacggag gcatcctacc cttttctggg gaaagacact   8580
gcctgggctg accccggtgg cggccccagc acctcagcct gcacagtgtc ccccaggttc   8640
cgaagaagat gctccagcaa cacagcctgg gccccagctc gcgggacccg accccccgtg   8700
ggctcccgtg ttttgtagga gacttgccag agccgggcac attgagctgt gcaacgccgt   8760
gggctgcgtc ctttggtcct gtccccgcag ccctggcagg gggcatgcgg tcgggcaggg   8820
gctggaggga ggcgggggct gcccttgggc cacccctcct agtttgggag gagcagattt   8880
ttgcaatacc aagtatagcc tatggcagaa aaaatgtctg taaatatgtt tttaaaggtg   8940
gattttgttt aaaaaatctt aatgaatgag tctgttgtgt gtcatgccag tgagggacgt   9000
cagacttggc tcagctcggg gagccttagc cgcccatgca ctggggacgc tccgctgccg   9060
tgccgcctgc actcctcagg gcagcctccc ccggctctac gggggccgcg tggtgccatc   9120
cccaggggggc atgaccagat gcgtcccaag atgttgattt ttactgtgtt tttataaaata   9180
gagtgtagtt tacagaaaaa gactttaaaa gtgatctaca tgaggaactg tagatgatgt   9240
attttttttca tcttttttgt taactgattt gcaataaaaa tgatactgat ggtgatctgg   9300
cttccaaaaa aaaaaaaaaa aa                                             9322
```

<210> SEQ ID NO 30
<211> LENGTH: 11474
<212> TYPE: DNA
<213> ORGANISM: Homo sapiens

<400> SEQUENCE: 30

```
gcttgcggtg ggaggaggcg gctgaggcgg aaggacacac gaggctgctt cgttgcacac     60
ccgagaaagt ttcagccaaa cttcgggcgg cggctgaggc ggcggccgag gagcggcgga    120
ctcggggcgc ggggagtcga ggcatttgcg cctgggcttc ggagcgtagc gccagggcct    180
gagcctttga agcaggagga ggggaggaga gagtggggct cctctatcgg gaccccctcc    240
ccatgtggat ctgcccaggc ggcggcggcg gcggcggagg aggaggcgac cgagaagatg    300
cccgccctgc gccccgctct gctgtgggcg ctgctggcgc tctggctgtg ctgcgcggcc    360
cccgcgcatg cattgcagtg tcgagatggc tatgaaccct gtgtaaatga aggaatgtgt    420
gttacctacc acaatggcac aggatactgc aaatgtccag aaggcttctt gggggaatat    480
```

-continued

```
tgtcaacatc gagacccctg tgagaagaac cgctgccaga atggtgggac ttgtgtggcc    540
caggccatgc tggggaaagc cacgtgccga tgtgcctcag ggtttacagg agaggactgc    600
cagtactcaa catctcatcc atgctttgtg tctcgaccct gcctgaatgg cggcacatgc    660
catatgctca gccgggatac ctatgagtgc acctgtcaag tcgggtttac aggtaaggag    720
tgccaatgga cggatgcctg cctgtctcat ccctgtgcaa atggaagtac ctgtaccact    780
gtggccaacc agttctcctg caaatgcctc acaggcttca cagggcagaa atgtgagact    840
gatgtcaatg agtgtgacat tccaggacac tgccagcatg gtggcacctg cctcaacctg    900
cctggttcct accagtgcca gtgccctcag ggcttcacag gccagtactg tgacagcctg    960
tatgtgccct gtgcaccctc accttgtgtc aatggaggca cctgtcggca gactggtgac   1020
ttcacttttg agtgcaactg ccttccaggt tttgaaggga gcacctgtga gaggaatatt   1080
gatgactgcc ctaaccacag gtgtcagaat ggaggggttt gtgtggatgg ggtcaacact   1140
tacaactgcc gctgtccccc acaatggaca ggacagttct gcacagagga tgtggatgaa   1200
tgcctgctgc agcccaatgc ctgtcaaaat gggggcacct gtgccaaccg caatggaggc   1260
tatggctgtg tatgtgtcaa cggctggagt ggagatgact gcagtgagaa cattgatgat   1320
tgtgccttcg cctcctgtac tccaggctcc acctgcatcg accgtgtggc ctccttctct   1380
tgcatgtgcc cagaggggaa ggcaggtctc ctgtgtcatc tggatgatgc atgcatcagc   1440
aatccttgcc acaagggggc actgtgtgac accaaccccc taaatgggca atatatttgc   1500
acctgcccac aaggctacaa agggggctgac tgcacagaag atgtggatga atgtgccatg   1560
gccaatagca atccttgtga gcatgcagga aaatgtgtga acacggatgg cgccttccac   1620
tgtgagtgtc tgaagggtta tgcaggacct cgttgtgaga tggacatcaa tgagtgccat   1680
tcagacccct gccagaatga tgctacctgt ctggataaga ttggaggctt cacatgtctg   1740
tgcatgccag gtttcaaagg tgtgcattgt gaattagaaa taaatgaatg tcagagcaac   1800
ccttgtgtga acaatgggca gtgtgtggat aaagtcaatc gtttccagtg cctgtgtcct   1860
cctggtttca ctgggccagt ttgccagatt gatattgatg actgttccag tactccgtgt   1920
ctgaatgggg caaagtgtat cgatcacccg aatggctatg aatgccagtg tgccacaggt   1980
ttcactggtg tgttgtgtga ggagaacatt gacaactgtg accccgatcc ttgccaccat   2040
ggtcagtgtc aggatggtat tgattcctac acctgcatct gcaatcccgg gtacatgggc   2100
gccatctgca gtgaccagat tgatgaatgt tacagcagcc cttgcctgaa cgatggtcgc   2160
tgcattgacc tggtcaatgg ctaccagtgc aactgccagc caggcacgtc aggggttaat   2220
tgtgaaatta attttgatga ctgtgcaagt aacccttgta tccatggaat ctgtatggat   2280
ggcattaatc gctacagttg tgtctgctca ccaggattca cagggcagag atgtaacatt   2340
gacattgatg agtgtgcctc caatccctgt cgcaagggtg caacatgtat caacggtgtg   2400
aatggtttcc gctgtatatg ccccgaggga ccccatcacc ccagctgcta ctcacaggtg   2460
aacgaatgcc tgagcaatcc ctgcatccat ggaaactgta ctggaggtct cagtggatat   2520
aagtgtctct gtgatgcagg ctgggttggc atcaactgtg aagtggacaa aaatgaatgc   2580
ctttcgaatc catgccagaa tggaggaact tgtgacaatc tggtgaatgg atacaggtgt   2640
acttgcaaga agggctttaa aggctataac tgccaggtga atattgatga atgtgcctca   2700
aatccatgcc tgaaccaagg aacctgcttt gatgacataa gtggctacac ttgccactgt   2760
gtgctgccat acacaggcaa gaattgtcag acagtattgg ctccctgttc cccaaaccct   2820
tgtgagaatg ctgctgtttg caaagagtca ccaaattttg agagttatac ttgcttgtgt   2880
```

gctcctggct ggcaaggtca gcggtgtacc attgacattg acgagtgtat ctccaagccc 2940
tgcatgaacc atggtctctg ccataacacc cagggcagct acatgtgtga atgtccacca 3000
ggcttcagtg gtatggactg tgaggaggac attgatgact gccttgccaa tccttgccag 3060
aatggaggtt cctgtatgga tggagtgaat actttctcct gcctctgcct tccgggtttc 3120
actggggata agtgccagac agacatgaat gagtgtctga gtgaaccctg taagaatgga 3180
gggacctgct ctgactacgt caacagttac acttgcaagt gccaggcagg atttgatgga 3240
gtccattgtg agaacaacat caatgagtgc actgagagct cctgtttcaa tggtggcaca 3300
tgtgttgatg ggattaactc cttctcttgc ttgtgccctg tgggtttcac tggatccttc 3360
tgcctccatg agatcaatga atgcagctct catccatgcc tgaatgaggg aacgtgtgtt 3420
gatggcctgg gtacctaccg ctgcagctgc cccctgggct acactgggaa aaactgtcag 3480
accctggtga atctctgcag tcggtctcca tgtaaaaaca aaggtacttg cgttcagaaa 3540
aaagcagagt cccagtgcct atgtccatct ggatgggctg gtgcctattg tgacgtgccc 3600
aatgtctctt gtgacatagc agcctccagg agaggtgtgc ttgttgaaca cttgtgccag 3660
cactcaggtg tctgcatcaa tgctggcaac acgcattact gtcagtgccc cctgggctat 3720
actgggagct actgtgagga gcaactcgat gagtgtgcgt ccaacccctg ccagcacggg 3780
gcaacatgca gtgacttcat tggtggatac agatgcgagt gtgtcccagg ctatcagggt 3840
gtcaactgtg agtatgaagt ggatgagtgc cagaatcagc cctgccagaa tggaggcacc 3900
tgtattgacc ttgtgaacca tttcaagtgc tcttgcccac caggcactcg gggcctactc 3960
tgtgaagaga acattgatga ctgtgcccgg ggtccccatt gccttaatgg tggtcagtgc 4020
atggatagga ttggaggcta cagttgtcgc tgcttgcctg gctttgctgg ggagcgttgt 4080
gagggagaca tcaacgagtg cctctccaac ccctgcagct ctgagggcag cctggactgt 4140
atacagctca ccaatgacta cctgtgtgtt tgccgtagtg cctttactgg ccggcactgt 4200
gaaaccttcg tcgatgtgtg tccccagatg ccctgcctga atggagggac ttgtgctgtg 4260
gccagtaaca tgcctgatgg tttcatttgc cgttgtcccc cgggattttc cggggcaagg 4320
tgccagagca gctgtggaca agtgaaatgt aggaaggggg agcagtgtgt gcacaccgcc 4380
tctggacccc gctgcttctg ccccagtccc cgggactgcg agtcaggctg tgccagtagc 4440
ccctgccagc acgggggcag ctgccaccct cagcgccagc ctccttatta ctcctgccag 4500
tgtgccccac cattctcggg tagccgctgt gaactctaca cggcaccccc cagcacccct 4560
cctgccacct gtctgagcca gtattgtgcc gacaaagctc gggatggcgt ctgtgatgag 4620
gcctgcaaca gccatgcctg ccagtgggat gggggtgact gttctctcac catggagaac 4680
ccctgggcca actgctcctc cccacttccc tgctgggatt atatcaacaa ccagtgtgat 4740
gagctgtgca acacggtcga gtgcctgttt gacaactttg aatgccaggg gaacagcaag 4800
acatgcaagt atgacaaata ctgtgcagac cacttcaaag acaaccactg tgaccagggg 4860
tgcaacagtg aggagtgtgg ttgggatggg ctggactgtg ctgctgacca acctgagaac 4920
ctggcagaag gtaccctggt tattgtggta ttgatgccac ctgaacaact gctccaggat 4980
gctcgcagct tcttgcgggc actgggtacc ctgctccaca ccaacctgcg cattaagcgg 5040
gactcccagg gggaactcat ggtgtacccc tattatggtg agaagtcagc tgctatgaag 5100
aaacagagga tgacacgcag atcccttcct ggtgaacaag aacaggaggt ggctggctct 5160
aaagtctttc tggaaattga caaccgccag tgtgttcaag actcagacca ctgcttcaag 5220
aacacggatg cagcagcagc tctcctggcc tctcacgcca tacaggggac cctgtcatac 5280
cctcttgtgt ctgtcgtcag tgaatccctg actccagaac gcactcagct cctctatctc 5340
cttgctgttg ctgttgtcat cattctgttt attattctgc tgggggtaat catggcaaaa 5400
cgaaagcgta agcatggctc tctctggctg cctgaaggtt tcactcttcg ccgagatgca 5460
agcaatcaca agcgtcgtga gccagtggga caggatgctg tggggctgaa aaatctctca 5520
gtgcaagtct cagaagctaa cctaattggt actggaacaa gtgaacactg ggtcgatgat 5580
gaagggcccc agccaaagaa agtaaaggct gaagatgagg ccttactctc agaagaagat 5640
gaccccattg atcgacggcc atggacacag cagcaccttg aagctgcaga catccgtagg 5700
acaccatcgc tggctctcac ccctcctcag gcagagcagg aggtggatgt gttagatgtg 5760
aatgtccgtg gcccagatgg ctgcacccca ttgatgttgg cttctctccg aggaggcagc 5820
tcagatttga gtgatgaaga tgaagatgca gaggactctt ctgctaacat catcacagac 5880
ttggtctacc agggtgccag cctccaggcc cagacagacc ggactggtga gatggccctg 5940
caccttgcag cccgctactc acgggctgat gctgccaagc gtctcctgga tgcaggtgca 6000
gatgccaatg cccaggacaa catgggccgc tgtccactcc atgctgcagt ggcagctgat 6060
gcccaaggtg tcttccagat tctgattcgc aaccgagtaa ctgatctaga tgccaggatg 6120
aatgatggta ctacacccct gatcctggct gcccgcctgg ctgtggaggg aatggtggca 6180
gaactgatca actgccaagc ggatgtgaat gcagtggatg accatggaaa atctgctctt 6240
cactgggcag ctgctgtcaa taatgtggag gcaactcttt tgttgttgaa aaatggggcc 6300
aaccgagaca tgcaggacaa caaggaagag acacctctgt ttcttgctgc ccgggagggg 6360
agctatgaag cagccaagat cctgttagac catttttgcca atcgagacat cacagaccat 6420
atggatcgtc ttccccggga tgtggctcgg gatcgcatgc accatgacat tgtgcgcctt 6480
ctggatgaat acaatgtgac cccaagccct ccaggcaccg tgttgacttc tgctctctca 6540
cctgtcatct gtgggcccaa cagatctttc ctcagcctga agcacacccc aatgggcaag 6600
aagtctagac ggcccagtgc caagagtacc atgcctacta gcctccctaa ccttgccaag 6660
gaggcaaagg atgccaaggg tagtaggagg aagaagtctc tgagtgagaa ggtccaactg 6720
tctgagagtt cagtaacttt atcccctgtt gattccctag aatctcctca cacgtatgtt 6780
tccgacacca catcctctcc aatgattaca tcccctggga tcttacaggc ctcacccaac 6840
cctatgttgg ccactgccgc ccctcctgcc ccagtccatg cccagcatgc actatctttt 6900
tctaaccttc atgaaatgca gcctttggca catggggcca gcactgtgct tccctcagtg 6960
agccagttgc tatcccacca ccacattgtg tctccaggca gtggcagtgc tggaagcttg 7020
agtaggctcc atccagtccc agtcccagca gattggatga accgcatgga ggtgaatgag 7080
acccagtaca atgagatgtt tggtatggtc ctggctccag ctgagggcac ccatcctggc 7140
atagctcccc agagcaggcc acctgaaggg aagcacataa ccaccccctcg ggagcccttg 7200
ccccccattg tgactttcca gctcatccct aaaggcagta ttgcccaacc agcgggggct 7260
ccccagcctc agtccacctg ccctccagct gttgcgggcc ccctgcccac catgtaccag 7320
attccagaaa tggcccgttt gcccagtgtg gctttcccca ctgccatgat gccccagcag 7380
gacgggcagg tagctcagac cattctccca gcctatcatc ctttcccagc ctctgtgggc 7440
aagtacccca cacccccttc acagcacagt tatgcttcct caaatgctgc tgagcgaaca 7500
cccagtcaca gtggtcacct ccagggtgag catccctacc tgacaccatc cccagagtct 7560
cctgaccagt ggtcaagttc atcacccccac tctgcttctg actggtcaga tgtgaccacc 7620
agccctaccc ctgggggtgc tggaggaggt cagcggggac ctgggacaca catgtctgag 7680
ccaccacaca acaacatgca ggtttatgcg tgagagagtc cacctccagt gtagagacat 7740
aactgacttt tgtaaatgct gctgaggaac aaatgaaggt catccgggag agaaatgaag 7800
aaatctctgg agccagcttc tagaggtagg aaagagaaga tgttcttatt cagataatgc 7860
aagagaagca attcgtcagt ttcactgggt atctgcaagg cttattgatt attctaatct 7920
aataagacaa gtttgtggaa atgcaagatg aatacaagcc ttgggtccat gtttactctc 7980
ttctatttgg agaataagat ggatgcttat tgaagcccag acattcttgc agcttggact 8040
gcattttaag ccctgcaggc ttctgccata tccatgagaa gattctacac tagcgtcctg 8100
ttgggaatta tgccctggaa ttctgcctga attgacctac gcatctcctc ctccttggac 8160
attcttttgt cttcatttgg tgcttttggt tttgcacctc tccgtgattg tagccctacc 8220
agcatgttat agggcaagac ctttgtgctt ttgatcattc tggcccatga aagcaacttt 8280
ggtctccttt cccctcctgt cttcccggta tcccttggag tctcacaagg tttactttgg 8340
tatggttctc agcacaaacc tttcaagtat gttgtttctt tggaaaatgg acatactgta 8400
ttgtgttctc ctgcatatat cattcctgga gagagaaggg gagaagaata cttttcttca 8460
acaaattttg ggggcaggag atcccttcaa gaggctgcac cttaattttt cttgtctgtg 8520
tgcaggtctt catataaact ttaccaggaa gaagggtgtg agtttgttgt ttttctgtgt 8580
atgggcctgg tcagtgtaaa gttttatcct tgatagtcta gttactatga ccctccccac 8640
ttttttaaaa ccagaaaaag gtttggaatg ttggaatgac caagagacaa gttaactcgt 8700
gcaagagcca gttacccacc cacaggtccc cctacttcct gccaagcatt ccattgactg 8760
cctgtatgga acacatttgt cccagatctg agcattctag gcctgtttca ctcactcacc 8820
cagcatatga aactagtctt aactgttgag cctttccttt catatccaca gaagacactg 8880
tctcaaatgt tgtacccttg ccatttagga ctgaactttc cttagcccaa gggacccagt 8940
gacagttgtc ttccgtttgt cagatgatca gtctctactg attatcttgc tgcttaaagg 9000
cctgctcacc aatctttctt tcacaccgtg tggtccgtgt tactggtata cccagtatgt 9060
tctcactgaa gacatggact ttatatgttc aagtgcagga attggaaagt tggacttgtt 9120
ttctatgatc caaaacagcc ctataagaag gttggaaaag gaggaactat atagcagcct 9180
ttgctatttt ctgctaccat ttcttttcct ctgaagcggc catgacattc cctttggcaa 9240
ctaacgtaga aactcaacag aacattttcc tttcctagag tcacctttta gatgataatg 9300
gacaactata gacttgctca ttgttcagac tgattgcccc tcacctgaat ccactctctg 9360
tattcatgct cttggcaatt tctttgactt tcttttaagg gcagaagcat tttagttaat 9420
tgtagataaa gaatagtttt cttcctcttc tccttgggcc agttaataat tggtccatgg 9480
ctacactgca acttccgtcc agtgctgtga tgcccatgac acctgcaaaa taagttctgc 9540
ctgggcattt tgtagatatt aacaggtgaa ttcccgactc ttttggtttg aatgacagtt 9600
ctcattcctt ctatggctgc aagtatgcat cagtgcttcc cacttacctg atttgtctgt 9660
cggtggcccc atatggaaac cctgcgtgtc tgttggcata atagtttaca aatggttttt 9720
tcagtcctat ccaaatttat tgaaccaaca aaaataatta cttctgccct gagataagca 9780
gattaagttt gttcattctc tgctttattc tctccatgtg gcaacattct gtcagcctct 9840
ttcatagtgt gcaaacattt tatcattcta aatggtgact ctctgccctt ggacccattt 9900
attattcaca gatggggaga acctatctgc atggacctct gtggaccaca gcgtacctgc 9960

```
ccctttctgc cctcctgctc cagccccact tctgaaagta tcagctactg atccagccac  10020

tggatatttt atatcctccc ttttccttaa gcacaatgtc agaccaaatt gcttgtttct  10080

ttttcttgga ctactttaat ttggatcctt tgggtttgga gaaagggaat gtgaaagctg  10140

tcattacaga caacaggttt cagtgatgag gaggacaaca ctgcctttca aactttttac  10200

tgatctctta gattttaaga actcttgaat tgtgtggtat ctaataaaag ggaaggtaag  10260

atggataatc actttctcat ttgggttctg aattggagac tcagttttta tgagacacat  10320

cttttatgcc atgtatagat cctcccctgc tatttttggt ttatttttat tgttataaat  10380

gctttctttc tttgactcct cttctgcctg cctttgggga taggtttttt tgtttgttta  10440

tttgcttcct ctgttttgtt ttaagcatca ttttcttatg tgaggtgggg aagggaaagg  10500

tatgagggaa agagagtctg agaattaaaa tattttagta taagcaattg gctgtgatgc  10560

tcaaatccat tgcatcctct tattgaattt gccaatttgt aatttttgca taataaagaa  10620

ccaaaggtgt aatgttttgt tgagaggtgg tttagggatt ttggccctaa ccaatacatt  10680

gaatgtatga tgactatttg ggaggacaca tttatgtacc cagaggcccc cactaataag  10740

tggtactatg gttacttcct tgtgtacatt tctcttaaaa gtgatattat atctgtttgt  10800

atgagaaacc cagtaaccaa taaaatgacc gcatattcct gactaaacgt agtaaggaaa  10860

atgcacactt tgtttttact tttccgtttc attctaaagg tagttaagat gaaatttata  10920

tgaaagcatt tttatcacaa aataaaaaag gtttgccaag ctcagtggtg ttgtattttt  10980

tattttccaa tactgcatcc atggcctggc agtgttacct catgatgtca taatttgctg  11040

agagagcaaa ttttcttttc tttctgaatc ccacaaagcc tagcaccaaa cttctttttt  11100

tcttccttta attagatcat aaataaatga tcctggggaa aaagcatctg tcaaatagga  11160

aacatcacaa aactgagcac tcttctgtgc actagccata gctggtgaca aacagatggt  11220

tgctcaggga caaggtgcct tccaatggaa atgcgaagta gttgctatag caagaattgg  11280

gaactgggat ataagtcata atattaatta tgctgttatg taaatgattg gtttgtaaca  11340

ttccttaagt gaaatttgtg tagaacttaa tatacaggat tataaaataa tattttgtgt  11400

ataaatttgt tataagttca cattcataca tttatttata aagtcagtga gatatttgaa  11460

catgaaaaaa aaaa                                                    11474
```

<210> SEQ ID NO 31
<211> LENGTH: 4326
<212> TYPE: DNA
<213> ORGANISM: Homo sapiens

<400> SEQUENCE: 31

```
gcttgcggtg ggaggaggcg gctgaggcgg aaggacacac gaggctgctt cgttgcacac     60

ccgagaaagt ttcagccaaa cttcgggcgg cggctgaggc ggcggccgag gagcggcgga    120

ctcggggcgc ggggagtcga ggcatttgcg cctgggcttc ggagcgtagc gccagggcct    180

gagcctttga agcaggagga ggggaggaga gagtggggct cctctatcgg gaccccctcc    240

ccatgtggat ctgcccaggc ggcggcggcg gcggcggagg aggaggcgac cgagaagatg    300

cccgccctgc gccccgctct gctgtgggcg ctgctggcgc tctggctgtg ctgcgcggcc    360

cccgcgcatg cattgcagtg tcgagatggc tatgaaccct gtgtaaatga aggaatgtgt    420

gttacctacc acaatggcac aggatactgc aaatgtccag aaggcttctt gggggaatat    480

tgtcaacatc gagacccctg tgagaagaac cgctgccaga atggtgggac ttgtgtggcc    540

caggccatgc tggggaaagc cacgtgccga tgtgcctcag ggtttacagg agaggactgc    600
```

-continued cagtactcaa catctcatcc atgctttgtg tctcgaccct gcctgaatgg cggcacatgc 660
catatgctca gccgggatac ctatgagtgc acctgtcaag tcgggtttac aggtaaggag 720
tgccaatgga cggatgcctg cctgtctcat ccctgtgcaa atggaagtac ctgtaccact 780
gtggccaacc agttctcctg caaatgcctc acaggcttca cagggcagaa atgtgagact 840
gatgtcaatg agtgtgacat tccaggacac tgccagcatg gtggcacctg cctcaacctg 900
cctggttcct accagtgcca gtgccctcag ggcttcacag gccagtactg tgacagcctg 960
tatgtgccct gtgcaccctc accttgtgtc aatggaggca cctgtcggca gactggtgac 1020
ttcacttttg agtgcaactg ccttccaggt tttgaaggga gcacctgtga gaggaatatt 1080
gatgactgcc ctaaccacag gtgtcagaat ggaggggttt gtgtggatgg ggtcaacact 1140
tacaactgcc gctgtccccc acaatggaca ggacagttct gcacagagga tgtggatgaa 1200
tgcctgctgc agcccaatgc ctgtcaaaat gggggcacct gtgccaaccg caatggaggc 1260
tatggctgtg tatgtgtcaa cggctggagt ggagatgact gcagtgagaa cattgatgat 1320
tgtgccttcg cctcctgtac tccaggctcc acctgcatcg accgtgtggc ctccttctct 1380
tgcatgtgcc cagaggggaa ggcaggtctc ctgtgtcatc tggatgatgc atgcatcagc 1440
aatccttgcc acaaggggc actgtgtgac accaaccccc taaatgggca atatatttgc 1500
acctgcccac aaggctacaa aggggctgac tgcacagaag atgtggatga atgtgccatg 1560
gccaatagca atccttgtga gcatgcagga aaatgtgtga acacggatgg cgccttccac 1620
tgtgagtgtc tgaagggtta tgcaggacct cgttgtgaga tggacatcaa tgagtgccat 1680
tcagacccct gccagaatga tgctacctgt ctggataaga ttggaggctt cacatgtctg 1740
tgcatgccag gtttcaaagg tgtgcattgt gaattagaaa taaatgaatg tcagagcaac 1800
ccttgtgtga acaatgggca gtgtgtggat aaagtcaatc gtttccagtg cctgtgtcct 1860
cctggtttca ctgggccagt ttgccagatt gatattgatg actgttccag tactccgtgt 1920
ctgaatgggg caaagtgtat cgatcacccg aatggctatg aatgccagtg tgccacaggt 1980
ttcactggtg tgttgtgtga ggagaacatt gacaactgtg accccgatcc ttgccaccat 2040
ggtcagtgtc aggatggtat tgattcctac acctgcatct gcaatcccgg gtacatgggc 2100
gccatctgca gtgaccagat tgatgaatgt tacagcagcc cttgcctgaa cgatggtcgc 2160
tgcattgacc tggtcaatgg ctaccagtgc aactgccagc caggcacgtc aggggttaat 2220
tgtgaaatta attttgatga ctgtgcaagt aacccttgta tccatggaat ctgtatggat 2280
ggcattaatc gctacagttg tgtctgctca ccaggattca cagggcagag atgtaacatt 2340
gacattgatg agtgtgcctc caatccctgt cgcaagggtg caacatgtat caacggtgtg 2400
aatggtttcc gctgtatatg ccccgaggga ccccatcacc ccagctgcta ctcacaggtg 2460
aacgaatgcc tgagcaatcc ctgcatccat ggaaactgta ctggaggtct cagtggatat 2520
aagtgtctct gtgatgcagg ctgggttggc atcaactgtg aagtggacaa aaatgaatgc 2580
ctttcgaatc catgccagaa tggaggaact tgtgacaatc tggtgaatgg atacaggtgt 2640
acttgcaaga agggctttaa aggctataac tgccaggtga atattgatga atgtgcctca 2700
aatccatgcc tgaaccaagg aacctgcttt gatgacataa gtggctacac ttgccactgt 2760
gtgctgccat acacaggcaa gaattgtcag acagtattgg ctccctgttc cccaaaccct 2820
tgtgagaatg ctgctgtttg caaagagtca ccaaattttg agagttatac ttgcttgtgt 2880
gctcctggct ggcaaggtca gcggtgtacc attgacattg acgagtgtat ctccaagccc 2940
tgcatgaacc atggtctctg ccataacacc cagggcagct acatgtgtga atgtccacca 3000
ggcttcagtg gtatggactg tgaggaggac attgatgact gccttgccaa tccttgccag 3060
aatggaggtt cctgtatgga tggagtgaat actttctcct gcctctgcct tccgggtttc 3120
actggggata agtgccagac agacatgaat gagtgtctga gtgaaccctg taagaatgga 3180
gggacctgct ctgactacgt caacagttac acttgcaagt gccaggcagg atttgatgga 3240
gtccattgtg agaacaacat caatgagtgc actgagagct cctgtttcaa tggtggcaca 3300
tgtgttgatg ggattaactc cttctcttgc ttgtgccctg tgggtttcac tggatccttc 3360
tgcctccatg agatcaatga atgcagctct catccatgcc tgaatgaggg aacgtgtgtt 3420
gatggcctgg gtacctaccg ctgcagctgc cccctgggct acactgggaa aaactgtcag 3480
accctggtga atctctgcag tcggtctcca tgtaaaaaca aaggtacttg cgttcagaaa 3540
aaagcagagt cccagtgcct atgtccatct ggatgggctg gtgcctattg tgacgtgccc 3600
aatgtctctt gtgacatagc agcctccagg agaggtgtgc ttgttgaaca cttgtgccag 3660
cactcaggtg tctgcatcaa tgctggcaac acgcattact gtcagtgccc cctgggctat 3720
actgggagct actgtgagga gcaactcgat gagtgtgcgt ccaacccctg ccagcacggg 3780
gcaacatgca gtgacttcat tggtggatac agatgcgagt gtgtcccagg ctatcagggt 3840
gtcaactgtg agtatgaagt ggatgagtgc cagaatcagc cctgccagaa tggaggcacc 3900
tgtattgacc ttgtgaacca tttcaagtgc tcttgcccac caggcactcg ggtatgaaa 3960 tcatccttat ccattttcca tccagggcat tgtcttaagt tataaatcca ttcttagtgt 4020
tcaggggatt ttataaaatt aaagatagga agactagctt cattccaagc atttagttct 4080
acatcctagt aattcaagcc attttattct cccatctctt gctagctctg atgttgtggt 4140
ttatgttgtc agttttatct ggttgtttgg catcttgata ttccatgaaa cacagaatat 4200
ggaagggata caacattagc ataacattaa aaaattagcc tggtcagtaa gatttcttgt 4260
tgcttcacag aaaagcaact aatggcctct aaaataaaca atttacattt aaaaaaaaaa 4320
aaaaaa 4326

<210> SEQ ID NO 32
<211> LENGTH: 8089
<212> TYPE: DNA
<213> ORGANISM: Homo sapiens

<400> SEQUENCE: 32
gcggcgcgga ggctggcccg ggacgcgccc ggagcccagg gaaggaggga ggaggggagg 60
gtcgcggccg gccgccatgg ggccgggggc ccgtggccgc cgccgccgcc gtcgcccgat 120
gtcgccgcca ccgccaccgc cacccgtgcg ggcgctgccc ctgctgctgc tgctagcggg 180
gccgggggct gcagcccccc cttgcctgga cggaagcccg tgtgcaaatg gaggtcgttg 240
cacccagctg ccctcccggg aggctgcctg cctgtgcccg cctggctggg tgggtgagcg 300
gtgtcagctg gaggacccct gtcactcagg cccctgtgct ggccgtggtg tctgccagag 360
ttcagtggtg gctggcaccg cccgattctc atgccggtgc ccccgtggct tccgaggccc 420
tgactgctcc ctgccagatc cctgcctcag cagcccttgt gcccacggtg cccgctgctc 480
agtggggccc gatggacgct tcctctgctc ctgcccacct ggctaccagg gccgcagctg 540
ccgaagcgac gtggatgagt gccgggtggg tgagccctgc cgccatggtg gcacctgcct 600
caacacacct ggctccttcc gctgccagtg tccagctggc tacacagggc cactatgtga 660
gaaccccgcg gtgccctgtg caccctcacc atgccgtaac gggggcacct gcaggcagag 720

```
tggcgacctc acttacgact gtgcctgtct tcctgggttt gagggtcaga attgtgaagt    780
gaacgtggac gactgtccag gacaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct tcaacacgct    960
gggtggccac agctgcgtgt gtgtcaatgg ctggacaggc gagagctgca gtcagaatat   1020
cgatgactgt gccacagccg tgtgcttcca tggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca aatccggtga acggccgggc   1200
catttgcacc tgtcctcccg gcttcacggg tggggcatgt gaccaggatg tggacgagtg   1260
ctctatcggc gccaacccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg gacattgacg agtgtcagag   1500
tagcccctgt gtcaacggtg ggtctgcaa ggaccgagtc aatggcttca gctgcacctg   1560
cccctcgggc ttcagcggct ccacgtgtca gctggacgtg gacgaatgcg ccagcacgcc   1620
ctgcaggaat ggcgccaaat gcgtggacca gcccgatggc tacgagtgcc gctgtgccga   1680
gggctttgag ggcacgctgt gtgatcgcaa cgtggacgac tgctcccctg acccatgcca   1740
ccatggtcgc tgcgtggatg gcatcgccag cttctcatgt gcctgtgctc ctggctacac   1800
gggcacacgc tgcgagagcc aggtggacga atgccgcagc cagccctgcc gccatggcgg   1860
caaatgccta gacctggtgg acaagtacct ctgccgctgc ccttctggga ccacaggtgt   1920
gaactgcgaa gtgaacattg acgactgtgc cagcaacccc tgcacctttg gagtctgccg   1980
tgatggcatc aaccgctacg actgtgtctg ccaacctggc ttcacagggc cccttttgtaa   2040
cgtggagatc aatgagtgtg cttccagccc atgcggcgag ggaggttcct gtgtggatgg   2100
ggaaaatggc ttccgctgcc tctgcccgcc tggctccttg cccccactct gcctcccccc   2160
gagccatccc tgtgcccatg agccctgcag tcacggcatc tgctatgatg cacctggcgg   2220
gttccgctgt gtgtgtgagc ctggctggag tggcccccgc tgcagccaga gcctggcccg   2280
agacgcctgt gagtcccagc cgtgcagggc cggtgggaca tgcagcagcg atggaatggg   2340
tttccactgc acctgcccgc ctggtgtcca gggacgtcag tgtgaactcc tctcccccctg   2400
caccccgaac ccctgtgagc atgggggccg ctgcgagtct gcccctggcc agctgcctgt   2460
ctgctcctgc ccccagggct ggcaaggccc acgatgccag caggatgtgg acgagtgtgc   2520
tggccccgca ccctgtggcc ctcatggtat ctgcaccaac ctggcaggga gtttcagctg   2580
cacctgccat ggagggtaca ctggcccttc ctgcgatcag gacatcaatg actgtgaccc   2640
caacccatgc ctgaacggtg gctcgtgcca agacggcgtg ggctcctttt cctgctcctg   2700
cctccctggt ttcgccggcc cacgatgcgc ccgcgatgtg gatgagtgcc tgagcaaccc   2760
ctgcggcccg ggcacctgta ccgaccacgt ggcctccttc acctgcacct gcccgccagg   2820
ctacggaggc ttccactgcg aacaggacct gcccgactgc agccccagct cctgcttcaa   2880
tggcgggacc tgtgtggacg gcgtgaactc gttcagctgc ctgtgccgtc ccggctacac   2940
aggagcccac tgccaacatg aggcagaccc ctgcctctcg cggccctgcc tacacggggg   3000
cgtctgcagc gccgcccacc ctggcttccg ctgcacctgc ctcgagagct tcacgggccc   3060
```

gcagtgccag acgctggtgg attggtgcag ccgccagcct tgtcaaaacg ggggtcgctg 3120
cgtccagact ggggcctatt gcctttgtcc ccctggatgg agcggacgcc tctgtgacat 3180
ccgaagcttg ccctgcaggg aggccgcagc ccagatcggg gtgcggctgg agcagctgtg 3240
tcaggcgggt gggcagtgtg tggatgaaga cagctcccac tactgcgtgt gcccagaggg 3300
ccgtactggt agccactgtg agcaggaggt ggacccctgc ttggcccagc cctgccagca 3360
tggggggacc tgccgtggct atatgggggg ctacatgtgt gagtgtcttc ctggctacaa 3420
tggtgataac tgtgaggacg acgtggacga gtgtgcctcc cagccctgcc agcacggggg 3480
ttcatgcatt gacctcgtgg cccgctatct ctgctcctgt cccccaggaa cgctgggggt 3540
gctctgcgag attaatgagg atgactgcgg cccaggccca ccgctggact cagggccccg 3600
gtgcctacac aatggcacct gcgtggacct ggtgggtggt ttccgctgca cctgtccccc 3660
aggatacact ggtttgcgct gcgaggcaga catcaatgag tgtcgctcag gtgcctgcca 3720
cgcggcacac acccgggact gcctgcagga cccaggcgga ggtttccgtt gcctttgtca 3780
tgctggcttc tcaggtcctc gctgtcagac tgtcctgtct ccctgcgagt cccagccatg 3840
ccagcatgga ggccagtgcc gtcctagccc gggtcctggg ggtgggctga ccttcacctg 3900
tcactgtgcc cagccgttct ggggtccgcg ttgcgagcgg gtggcgcgct cctgccggga 3960
gctgcagtgc ccggtgggcg tcccatgcca gcagacgccc cgcgggccgc gctgcgcctg 4020
ccccccaggg ttgtcgggac cctcctgccg cagcttcccg gggtcgccgc cgggggccag 4080
caacgccagc tgcgcggccg ccccctgtct ccacgggggc tcctgccgcc ccgcgccgct 4140
cgcgcccttc ttccgctgcg cttgcgcgca gggctggacc gggccgcgct gcgaggcgcc 4200
cgccgcggca cccgaggtct cggaggagcc gcggtgcccg cgcgccgcct gccaggccaa 4260
gcgcggggac cagcgctgcg accgcgagtg caacagccca ggctgcggct gggacggcgg 4320
cgactgctcg ctgagcgtgg gcgacccctg gcggcaatgc gaggcgctgc agtgctggcg 4380
cctcttcaac aacagccgct gcgaccccgc ctgcagctcg cccgcctgcc tctacgacaa 4440
cttcgactgc cacgccggtg gccgcgagcg cacttgcaac ccggtgtacg agaagtactg 4500
cgccgaccac tttgccgacg gccgctgcga ccagggctgc aacacggagg agtgcggctg 4560
ggatgggctg gattgtgcca gcgaggtgcc ggccctgctg gcccgcggcg tgctggtgct 4620
cacagtgctg ctgccgccag aggagctact gcgttccagc gccgactttc tgcagcggct 4680
cagcgccatc ctgcgcacct cgctgcgctt ccgcctggac gcgcacggcc aggccatggt 4740
cttcccttac caccggccta gtcctggctc cgaaccccgg gcccgtcggg agctggcccc 4800
cgaggtgatc ggctcggtag taatgctgga gattgacaac cggctctgcc tgcagtcgcc 4860
tgagaatgat cactgcttcc ccgatgccca gagcgccgct gactacctgg gagcgttgtc 4920
agcggtggag cgcctggact tcccgtaccc actgcgggac gtgcgggggg agccgctgga 4980
gcctccagaa cccagcgtcc cgctgctgcc actgctagtg gcgggcgctg tcttgctgct 5040
ggtcattctc gtcctgggtg tcatggtggc ccggcgcaag cgcgagcaca gcaccctctg 5100
gttccctgag ggcttctcac tgcacaagga cgtggcctct ggtcacaagg gccggcggga 5160
acccgtgggc caggacgcgc tgggcatgaa gaacatggcc aagggtgaga gcctgatggg 5220
ggaggtggcc acagactgga tggacacaga gtgcccagag gccaagcggc taaaggtaga 5280
ggagccaggc atgggggctg aggaggctgt ggattgccgt cagtggactc aacaccatct 5340
ggttgctgct gacatccgcg tggcaccagc catggcactg acaccaccac agggcgacgc 5400
agatgctgat ggcatggatg tcaatgtgcg tggcccagat ggcttcaccc cgctaatgct 5460

```
ggcttccttc tgtggggggg ctctggagcc aatgccaact gaagaggatg aggcagatga   5520
cacatcagct agcatcatct ccgacctgat ctgccagggg gctcagcttg gggcacggac   5580
tgaccgtact ggcgagactg ctttgcacct ggctgcccgt tatgcccgtg ctgatgcagc   5640
caagcggctg ctggatgctg gggcagacac caatgcccag gaccactcag gccgcactcc   5700
cctgcacaca gctgtcacag ccgatgccca gggtgtcttc cagattctca tccgaaaccg   5760
ctctacagac ttggatgccc gcatggcaga tggctcaacg gcactgatcc tggcggcccg   5820
cctggcagta gagggcatgg tggaagagct catcgccagc catgctgatg tcaatgctgt   5880
ggatgagctt gggaaatcag ccttacactg ggctgcggct gtgaacaacg tggaagccac   5940
tttggccctg ctcaaaaatg gagccaataa ggacatgcag gatagcaagg aggagacccc   6000
cctattcctg gccgcccgcg agggcagcta tgaggctgcc aagctgctgt tggaccactt   6060
tgccaaccgt gagatcaccg accacctgga caggctgccg cgggacgtag cccaggagag   6120
actgcaccag gacatcgtgc gcttgctgga tcaacccagt gggccccgca gcccccccgg   6180
tccccacggc ctggggcctc tgctctgtcc tccaggggcc ttcctccctg gcctcaaagc   6240
ggcacagtcg gggtccaaga agagcaggag gccccccggg aaggcggggc tggggccgca   6300
ggggccccgg gggcggggca agaagctgac gctggcctgc ccgggccccc tggctgacag   6360
ctcggtcacg ctgtcgcccg tggactcgct ggactccccg cggcctttcg gtgggccccc   6420
tgcttcccct ggtggcttcc cccttgaggg gccctatgca gctgccactg ccactgcagt   6480
gtctctggca cagcttggtg gcccaggccg ggcgggtcta gggcgccagc cccctggagg   6540
atgtgtactc agcctgggcc tgctgaaccc tgtggctgtg cccctcgatt gggcccggct   6600
gcccccacct gcccctccag gcccctcgtt cctgctgcca ctggcgccgg gaccccagct   6660
gctcaaccca gggacccccg tctccccgca ggagcggccc ccgccttacc tggcagtccc   6720
aggacatggc gaggagtacc cggcggctgg ggcacacagc agccccccaa aggcccgctt   6780
cctgcgggtt cccagtgagc acccttacct gaccccatcc cccgaatccc ctgagcactg   6840
ggccagcccc tcacctccct ccctctcaga ctggtccgaa tccacgccta gcccagccac   6900
tgccactggg gccatggcca ccaccactgg ggcactgcct gcccagccac ttcccttgtc   6960
tgttcccagc tcccttgctc aggcccagac ccagctgggg ccccagccgg aagttacccc   7020
caagaggcaa gtgttggcct gagacgctcg tcagttctta gatcttgggg gcctaaagag   7080
acccccgtcc tgcctccttt ctttctctgt ctcttccttc cttttagtct tttcatcct    7140
cttctctttc caccaaccct cctgcatcct tgccttgcag cgtgaccgag ataggtcatc   7200
agcccagggc ttcagtcttc ctttatttat aatgggtggg ggctaccacc caccctctca   7260
gtcttgtgaa gagtctggga cctccttctt ccccacttct ctcttccctc attcctttct   7320
ctctccttct ggcctctcat ttccttacac tctgacatga atgaattatt attattttta   7380
tttttctttt ttttttttaca ttttgtatag aaacaaattc atttaaacaa acttattatt   7440
attatttttt acaaaatata tatatggaga tgctccctcc ccctgtgaac cccccagtgc   7500
ccccgtgggg ctgagtctgt gggcccattc ggccaagctg gattctgtgt acctagtaca   7560
caggcatgac tgggatcccg tgtaccgagt acacgaccca ggtatgtacc aagtaggcac   7620
ccttgggcgc acccactggg gccaggggtc gggggagtgt tgggagcctc ctccccaccc   7680
cacctccctc acttcactgc attccagatg ggacatgttc catagccttg ctggggaagg   7740
gcccactgcc aactccctct gccccagccc caccccttggc catctccctt tgggaactag   7800
```

-continued

```
ggggctgctg gtgggaaatg ggagccaggg cagatgtatg cattcctttg tgtccctgta   7860

aatgtgggac tacaagaaga ggagctgcct gagtggtact ttctcttcct ggtaatcctc   7920

tggcccagcc tcatggcaga atagaggtat ttttaggcta tttttgtaat atggcttctg   7980

gtcaaaatcc ctgtgtagct gaattcccaa gccctgcatt gtacagcccc ccactcccct   8040

caccacctaa taaaggaata gttaacactc aaaaaaaaaa aaaaaaaaa              8089
```

<210> SEQ ID NO 33
<211> LENGTH: 6762
<212> TYPE: DNA
<213> ORGANISM: Homo sapiens

<400> SEQUENCE: 33

```
agacgtgagg cttgcagcag gccgaggagg aagaagaggg gcagtgggag cagaggaggt     60

ggctcctgcc ccagtgagag ctctgagggt ccctgcctga agagggacag ggaccggggc    120

ttggagaagg ggctgtggaa tgcagccccc ttcactgctg ctgctgctgc tgctgctgct    180

gctgctatgt gtctcagtgg tcagacccag agggctgctg tgtgggagtt tcccagaacc    240

ctgtgccaat ggaggcacct gcctgagcct gtctctggga caagggacct gccagtgtgc    300

ccctggcttc ctgggtgaga cgtgccagtt tcctgacccc tgccagaacg cccagctctg    360

ccaaaatgga ggcagctgcc aagccctgct tcccgctccc ctagggctcc ccagctctcc    420

ctctccattg acacccagct tcttgtgcac ttgcctccct ggcttcactg gtgagagatg    480

ccaggccaag cttgaagacc cttgtcctcc ctccttctgt tccaaaaggg gccgctgcca    540

catccaggcc tcgggccgcc cacagtgctc ctgcatgcct ggatggacag gtgagcagtg    600

ccagcttcgg gacttctgtt cagccaaccc atgtgttaat ggaggggtgt gtctggccac    660

atacccccag atccagtgcc actgcccacc gggcttcgag ggccatgcct gtgaacgtga    720

tgtcaacgag tgcttccagg acccaggacc ctgccccaaa ggcacctcct gccataacac    780

cctgggctcc ttccagtgcc tctgccctgt ggggcaggag ggtccacgtt gtgagctgcg    840

ggcaggaccc tgccctccta ggggctgttc gaatgggggc acctgccagc tgatgccaga    900

gaaagactcc acctttcacc tctgcctctg tcccccaggt ttcataggcc cagactgtga    960

ggtgaatcca gacaactgtg tcagccacca gtgtcagaat gggggcactt gccaggatgg   1020

gctggacacc tacacctgcc tctgcccaga aacctggaca ggctgggact gctccgaaga   1080

tgtggatgag tgtgagaccc agggtccccc tcactgcaga aacgggggca cctgccagaa   1140

ctctgctggt agctttcact gcgtgtgtgt gagtggctgg ggcggcacaa gctgtgagga   1200

gaacctggat gactgtattg ctgccacctg tgccccggga tccacctgca ttgaccgggt   1260

gggctctttc tcctgcctct gcccacctgg acgcacagga ctcctgtgcc acttggaaga   1320

catgtgtctg agccagccgt gccatgggga tgcccaatgc agcaccaacc ccctcacagg   1380

ctccacactc tgcctgtgtc agcctggcta ttcggggccc acctgccacc aggacctgga   1440

cgagtgtctg atggcccagc aaggcccaag tccctgtgaa catggcggtt cctgcctcaa   1500

cactcctggc tccttcaact gcctctgtcc acctggctac acaggctccc gttgtgaggc   1560

tgatcacaat gagtgcctct cccagccctg ccacccagga agcacctgtc tggacctact   1620

tgccaccttc cactgcctct gcccgccagg cttagaaggg cagctctgtg aggtggagac   1680

caacgagtgt gcctcagctc cctgcctgaa ccacgcggat tgccatgacc tgctcaacgg   1740

cttccagtgc atctgcctgc ctggattctc cggcacccga tgtgaggagg atatcgatga   1800

gtgcagaagc tctccctgtg ccaatggtgg gcagtgccag gaccagcctg gagccttcca   1860
```

-continued

```
ctgcaagtgt ctcccaggct ttgaagggcc acgctgtcaa acagaggtgg atgagtgcct   1920
gagtgaccca tgtcccgttg gagccagctg ccttgatctt ccaggagcct tcttttgcct   1980
ctgcccctct ggtttcacag gccagctctg tgaggttccc ctgtgtgctc ccaacctgtg   2040
ccagcccaag cagatatgta aggaccagaa agacaaggcc aactgcctct gtcctgatgg   2100
aagccctggc tgtgccccac ctgaggacaa ctgcacctgc caccacgggc actgccagag   2160
atcctcatgt gtgtgtgacg tgggttggac ggggccagag tgtgaggcag agctaggggg   2220
ctgcatctct gcaccctgtg cccatggggg gacctgctac ccccagccct ctggctacaa   2280
ctgcacctgc cctacaggct acacaggacc cacctgtagt gaggagatga cagcttgtca   2340
ctcagggcca tgtctcaatg gcggctcctg caaccctagc cctggaggct actactgcac   2400
ctgccctcca agccacacag ggccccagtg ccaaaccagc actgactact gtgtgtctgc   2460
cccgtgcttc aatgggggta cctgtgtgaa caggcctggc accttctcct gcctctgtgc   2520
catgggcttc cagggcccgc gctgtgaggg aaagctccgc cccagctgtg cagacagccc   2580
ctgtaggaat agggcaacct gccaggacag ccctcagggt ccccgctgcc tctgccccac   2640
tggctacacc ggaggcagct gccagactct gatggactta tgtgcccaga agccctgccc   2700
acgcaattcc cactgcctcc agactgggcc ctccttccac tgcttgtgcc tccagggatg   2760
gaccgggcct ctctgcaacc ttccactgtc ctcctgccag aaggctgcac tgagccaagg   2820
catagacgtc tcttcccttt gccacaatgg aggcctctgt gtcgacagcg gcccctccta   2880
tttctgccac tgcccccctg gattccaagg cagcctgtgc caggatcacg tgaacccatg   2940
tgagtccagg ccttgccaga acggggccac ctgcatggcc cagcccagtg ggtatctctg   3000
ccagtgtgcc ccaggctacg atggacagaa ctgctcaaag gaactcgatg cttgtcagtc   3060
ccaaccctgt cacaaccatg gaacctgtac tcccaaacct ggaggattcc actgtgcctg   3120
ccctccaggc tttgtggggc tacgctgtga gggagacgtg gacgagtgtc tggaccagcc   3180
ctgccacccc acaggcactg cagcctgcca ctctctggcc aatgccttct actgccagtg   3240
tctgcctgga cacacaggcc agtggtgtga ggtggagata gacccctgcc acagccaacc   3300
ctgctttcat ggagggacct gtgaggccac agcaggatca cccctgggtt tcatctgcca   3360
ctgccccaag ggttttgaag gccccacctg cagccacagg gccccttcct gcggcttcca   3420
tcactgccac cacggaggcc tgtgtctgcc ctcccctaag ccaggcttcc caccacgctg   3480
tgcctgcctc agtggctatg gggtcctga ctgcctgacc ccaccagctc ctaaaggctg   3540
tggccctccc tccccatgcc tatacaatgg cagctgctca gagaccacgg gcttgggggg   3600
cccaggcttt cgatgctcct gccctcacag ctctccaggg ccccggtgtc agaaacccgg   3660
agccaagggg tgtgagggca gaagtggaga tggggcctgc gatgctggct gcagtggccc   3720
gggaggaaac tgggatggag gggactgctc tctgggagtc ccagacccct ggaagggctg   3780
cccctcccac tctcggtgct ggcttctctt ccgggacggg cagtgccacc cacagtgtga   3840
ctctgaagag tgtctgtttg atggctacga ctgtgagacc cctccagcct gcactccagc   3900
ctatgaccag tactgccatg atcacttcca caacgggcac tgtgagaaag gctgcaacac   3960
tgcagagtgt ggctgggatg gaggtgactg caggcctgaa gatggggacc cagagtgggg   4020
gccctccctg gccctgctgg tggtactgag ccccccagcc ctagaccagc agctgtttgc   4080
cctggcccgg gtgctgtccc tgactctgag ggtaggactc tgggtaagga aggatcgtga   4140
tggcagggac atggtgtacc cctatcctgg ggcccgggct gaagaaaagc taggaggaac   4200
```

-continued

```
tcgggacccc acctatcagg agagagcagc ccctcaaacg cagcccctgg gcaaggagac   4260
cgactccctc agtgctgggt ttgtggtggt catgggtgtg gatttgtccc gctgtggccc   4320
tgaccacccg gcatcccgct gtccctggga ccctgggctt ctactccgct tccttgctgc   4380
gatggctgca gtgggagccc tggagcccct gctgcctgga ccactgctgg ctgtccaccc   4440
tcatgcaggg accgcacccc ctgccaacca gcttccctgg cctgtgctgt gctccccagt   4500
ggccggggtg attctcctgg ccctaggggc tcttctcgtc ctccagctca tccggcgtcg   4560
acgccgagag catggagctc tctggctgcc ccctggtttc actcgacggc ctcggactca   4620
gtcagctccc caccgacgcc ggcccccact aggcgaggac agcattggtc tcaaggcact   4680
gaagccaaag gcagaagttg atgaggatgg agttgtgatg tgctcaggcc ctgaggaggg   4740
agaggaggtg ggccaggctg aagaaacagg cccaccctcc acgtgccagc tctggtctct   4800
gagtggtggc tgtggggcgc tccctcaggc agccatgcta actcctcccc aggaatctga   4860
gatggaagcc cctgacctgg acacccgtgg acctgatggg gtgacacccc tgatgtcagc   4920
agtttgctgt ggggaagtac agtccgggac cttccaaggg gcatggttgg gatgtcctga   4980
gccctgggaa cctctgctgg atggaggggc ctgtccccag gctcacaccg tgggcactgg   5040
ggagaccccc ctgcacctgg ctgcccgatt ctcccggcca accgctgccc gccgcctcct   5100
tgaggctgga gccaacccca accagccaga ccgggcaggg cgcacacccc ttcatgctgc   5160
tgtggctgct gatgctcggg aggtctgcca gcttctgctc cgtagcagac aaactgcagt   5220
ggacgctcgc acagaggacg ggaccacacc cttgatgctg gctgccaggc tggcggtgga   5280
agacctggtt gaagaactga ttgcagccca agcagacgtg gggggccagag ataaatgggg   5340
gaaaactgcg ctgcactggg ctgctgccgt gaacaacgcc cgagccgccc gctcgcttct   5400
ccaggccgga gccgataaag atgcccagga caacagggag cagacgccgc tattcctggc   5460
ggcgcgggaa ggagcggtgg aagtagccca gctactgctg gggctggggg cagcccgaga   5520
gctgcgggac caggctgggc tagcgccggc ggacgtcgct caccaacgta accactggga   5580
tctgctgacg ctgctggaag ggctgggcc accagaggcc cgtcacaaag ccacgccggg   5640
ccgcgaggct gggcccttcc cgcgcgcacg gacggtgtca gtaagcgtgc ccccgcatgg   5700
gggcggggct ctgccgcgct gccggacgct gtcagccgga gcaggccctc gtgggggcgg   5760
agcttgtctg caggctcgga cttggtccgt agacttggct gcgcgggggg gcggggccta   5820
ttctcattgc cggagcctct cgggagtagg agcaggagga ggcccgaccc ctcgcggccg   5880
taggttttct gcaggcatgc gcgggcctcg gcccaaccct gcgataatgc gaggaagata   5940
cggagtggct gccgggcgcg gaggcagggt ctcaacggat gactggccct gtgattgggt   6000
ggccctggga gcttgcggtt ctgcctccaa cattccgatc ccgcctcctt gccttactcc   6060
gtccccggag cggggatcac ctcaacttga ctgtggtccc ccagccctcc aagaaatgcc   6120
cataaaccaa ggaggagagg gtaaaaaata gaagaataca tggtagggag gaattccaaa   6180
aatgattacc cattaaaagg caggctggaa ggccttcctg gttttaagat ggatccccca   6240
aaatgaaggg ttgtgagttt agtttctctc ctaaaatgaa tgtatgccca ccagagcaga   6300
catcttccac gtggagaagc tgcagctctg gaaagagggt ttaagatgct aggatgaggc   6360
aggcccagtc ctcctccaga aaataagaca ggccacagga gggcagagtg gagtggaaat   6420
acccctaagt tggaaccaag aattgcaggc atatgggatg taagatgttc tttcctatat   6480
atggtttcca aagggtgccc ctatgatcca ttgtccccac tgcccacaaa tggctgacaa   6540
atatttattg ggcacctact atgtgccagg cactgtgtag gtgctgaaaa gtggccaagg   6600
```

-continued

```
gccaccccg ctgatgactc cttgcattcc ctcccctcac aacaaagaac tccactgtgg   6660

ggatgaagcg cttcttctag ccactgctat cgctatttaa gaaccctaaa tctgtcaccc   6720

ataataaagc tgatttgaag tgttaaaaaa aaaaaaaaaa aa                      6762


<210> SEQ ID NO 34
<211> LENGTH: 200
<212> TYPE: DNA
<213> ORGANISM: Artificial Sequence
<220> FEATURE:
<223> OTHER INFORMATION: CMV promoter

<400> SEQUENCE: 34

atcgatgtta ataattaaca tatatgttaa tcattaacta tatagttaat tattaaccgc     60

tatgttaatg attaacacta gttaggcgtg tacggtggga ggcctatata agcagagctc    120

gtttagtgaa ccgtcagatc gcctggagac gccatccacg ctgttttgac ctccatagaa    180

gacaccggga ccgatccagc                                                200


<210> SEQ ID NO 35
<211> LENGTH: 9
<212> TYPE: DNA
<213> ORGANISM: Artificial Sequence
<220> FEATURE:
<223> OTHER INFORMATION: Kozak sequence

<400> SEQUENCE: 35

gccgccacc                                                              9
```

METHODS AND COMPOSITIONS FOR REDUCING THE IMMUNOGENICITY OF CHIMERIC NOTCH RECEPTORS

CROSS-REFERENCE TO RELATED APPLICATIONS

This application is a divisional application under 35 U.S.C. § 121 of U.S. application Ser. No. 16/010,805 filed on Jun. 18, 2018. U.S. application Ser. No. 16/010,805 claims priority to U.S. Provisional Patent Application Ser. No. 62/603,993, filed Jun. 19, 2017, and U.S. Provisional Application Ser. No. 62/556,765, filed on Sep. 11, 2017. The entire contents of these applications are hereby incorporated by reference in their entireties.

STATEMENT REGARDING SEQUENCE LISTING

The Sequence Listing associated with this application is provided in text format in lieu of paper copy, and is hereby incorporated by reference into the specification. The name of the text file containing the Sequence Listing is "356829_ST25.txt." The text file is 218,000 bytes, was created on Jul. 25, 2022, and is being submitted electronically via EFS-Web.

TECHNICAL FIELD

The present invention relates to molecular biology, and particularly to methods and compositions for reducing the immunogenicity of certain receptors useful for controlling selective gene expression in cells of the monocyte/macrophage lineage, and applications thereof.

BACKGROUND

An important problem which limits the development of gene therapy in humans is the regulation of therapeutic gene expression, such that gene expression or the vehicle used to realize expression, does not give rise to enhanced immunogenicity resulting in host rejection. One way to realize gene expression is described in U.S. Pat. No. 9,670,281, and Roybal et al., *Cell, Feb.* 11, 2016. There is described activation of gene expression using chimeric Notch receptors.

Notch receptors are single pass transmembrane proteins that mediate cell-cell contact signaling and play a central role in development and other aspects of cell-to-cell communication between two contacting cells, in which one contacting cell has the Notch receptor, and the other contacting cell is a cell that exhibits a ligand on its surface which binds to the corresponding Notch receptor. The engagement of native Notch and Delta, it's native ligand, leads to two-step proteolysis of the Notch receptor that ultimately causes the release of the intracellular portion of the receptor from the membrane into the cytoplasm, where it moves to the nucleus. There the released domain alters cell behavior by functioning as a transcriptional regulator. Notch receptors are involved in and are required for a variety of cellular functions during development and are critical for the function of numerous cell-types across species.

Described in U.S. Pat. No. 9,670,281 are chimeric Notch receptors which show that the Notch expressing cell can have one or more different binding moieties on the cell surface, for example, scFVs, nanobodies, single chain T-cell receptors, to name a few, that recognize a ligand associated with a cell ultimately causing the release of the intracellular, transcriptional regulatory portion of the receptor from the membrane into the cytoplasm resulting in transcriptional regulation. Engineered cells bearing chimeric Notch receptors that encounter their specific target antigen will then be cleaved such that their cytosolic fragment is free to translocate into the cell nucleus to regulate the transcription of any open reading frame (ORF) under the control of a synthetic promoter. The ORF expressed could be a cytokine to locally induce and recruit immune activity to the location of target antigen detection. Further, the ORF expressed could be a chimeric antigen T-cell receptor (CAR-T) that targets a separate, distinct target antigen for target cell killing, only after the priming target antigen detected by the chimeric Notch receptor has been detected. This enables highly-specific combinatorial antigen pattern recognition to allow greater discrimination between diseased or cancerous cells and healthy cells. This could greatly enable the application of engineered CAR-T cells to safely target a wider range of tumors with less side-effects on healthy tissue.

To date, the transcriptional machinery used in chimeric Notch constructs has been GAL4-VP16. Since the DNA-binding fragment, GAL4, is of yeast origin, and VP16, a highly acidic portion of the herpes simplex virus protein, GAL4-VP16 is highly immunogenic, and thus limits the use of chimeric Notch receptors for treating human disease.

Another major obstacle in the efficacy of many immunotherapy-based approaches for solid tumors, including cell therapy, is delivery of drugs or activation of immune cells in the solid tumor. Cells of the monocyte/macrophage lineage make up a major component of immune cells that infiltrate into solid tumors (Long et al., *Oncoimmunology* 2:e26860, 2013 doi:10.4161/onci26860). Because these cell types are actively recruited and retained in the solid tumor they could be an important cell type for the delivery of gene therapy.

The genetic engineering of macrophages with clinically approved vectors such has HIV-1-based lentivirus has been difficult due to the inhibition of HIV-1 infection in macrophages. Hrecka et al. ("Vpx relieves the inhibition of HIV-1 infection of macrophages mediated by the SAMHD1 protein," *Nature* 474(7353):658-661, 2011) demonstrated that the addition of the viron associated Vpx accessory proteins found in HIV-2 and simian immunodeficiency viruses relieves the inhibition of HIV-1 infection of macrophages through the degradation of a macrophage restriction factor SAMHD1. Subsequently, it has been demonstrated by the monocyte-derived macrophages can be efficiently transduced with Vpx+ lentivirus encoding for the production cytokines from macrophages aimed at modulating the tumor microenvironment (Moyes et al., *Human Gene Therapy* 28(2):200-215, 2017).

SUMMARY OF THE INVENTION

The present invention relates to methods and compositions for reducing the immunogenicity of chimeric Notch receptors. The Notch receptors described herein can be genetically engineered in cells of the monocyte/macrophage lineage.

Another embodiment of the invention relates to methods and compositions for reducing the immunogenicity of chimeric Notch receptors by humanizing transcription factors useful for controlling gene expression delivered to tissues by chimeric Notch receptors.

In yet another embodiment of the invention are methods and compositions for reducing the immunogenicity of chimeric Notch receptors by humanizing transcription factors used to express genes in cells that contain the chimeric Notch receptors wherein such transcription factors comprise a transcription factor from the family of Hepatocyte Nuclear Factor transcription factors.

The invention also relates to the use of the DNA binding domains (DBD) of HNF1 transcription factors, such as HNF1 alpha and vHNF1 beta, for generating chimeric transcription factors with reduced immunogenicity, useful for delivery of transgenes with chimeric Notch receptors to tissues preferably not expressing endogenous HNF1 or vHNF1. US Patent Application No. 200301096678.

A further embodiment of the invention is a human HNF1 DNA binding domain that is used in conjunction with a human transcriptional activator (TAD) or repressor domain, and optionally a human regulatory domain.

A further embodiment of the invention is a human HNF1 DNA binding domain that is used in conjunction with a human transcriptional activator domain (TAD) derived from the WWTR1 (TAZ) protein.

A further embodiment of the invention is a human HNF1 DNA binding domain that is used in conjunction with a human transcriptional activator domain (TAD) derived from the CREB3(LZIP) protein.

A further embodiment of the invention is a human HNF1 DNA binding domain that is used in conjunction with a human transcriptional activator domain (TAD) derived from the NF-κB system factor, p65 (RelA).

The present invention also relates to nucleic acid molecules and proteins useful for regulating the expression of genes in eukaryotic cells and organisms using chimeric Notch receptors having low immunogenicity.

The present invention further provides low immunogenicity chimeric Notch receptor polypeptides, nucleic acids comprising nucleotide sequences encoding the chimeric Notch receptor polypeptides, and host cells genetically modified with the nucleic acids wherein the low immunogenicity is realized by using transcription factor comprising a human HNF1 DNA binding domain in conjunction with a human transcriptional activator domain (TAD) derived from the NF-κB system factor, p65 (RelA).

In one specific embodiment of the invention, the humanized chimeric notch receptor is comprised of the following sequences, 5' to 3':

- Human CD8a signal peptide 1-22 (NP_001139345 amino acids 1-22, (MALPVTALLLPLALLLHAARPS) (SEQ ID NO: 1))—directs protein expression to the cell surface.
- Myc-tag (EQKLISEEDL) (SEQ ID NO: 2)—peptide tag for antibody labelling of surface-expressed synthetic receptor. A Myc antibody: Cell Signaling Techology, Myc-Tag (9B11) Mouse mAb (Alexa Fluor®647 Conjugate; Catalogue No. 2233.
- Anti-Human B cell (CD19) Antibody, clone FMC63.
- Human Notch3 core (gi|134244285|NP_000426.2 amino acids 1374-1738) comprising the three NLR domains, the transmembrane domain, and a short cytosolic fragment including the native Nuclear Localization Sequence (NLS) of human Notch3.
- GS flexible Linker (GSAAAGGSGGSGGS) (SEQ ID NO: 3).
- Human HNF1alpha (gi|807201167|NP_001293108.1 amino acids 1-283) comprising the dimerization and DNA-Binding Domain (DBD) of *Homo sapiens* hepatocyte nuclear factor 1-alpha isoform 1.
- GS flexible Linker (GGGSGGGS) (SEQ ID NO: 4).
- Human Rel-A (p65) (gi|223468676|NP_068810.3 amino acids 1-551) comprising the transactivation domain of transcription factor p65 isoform 1 [*Homo sapiens*].

Also provided herein is a method of treating disease, including cancer, in a subject (e.g., a human) that includes administering to the subject a mammalian cell comprising a humanized chimeric Notch receptor. In some embodiments, the mammalian cell can be a monocyte/macrophage cell.

Other features and advantages of the invention will be apparent from the following Detailed Description of the Invention, and from the claims. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
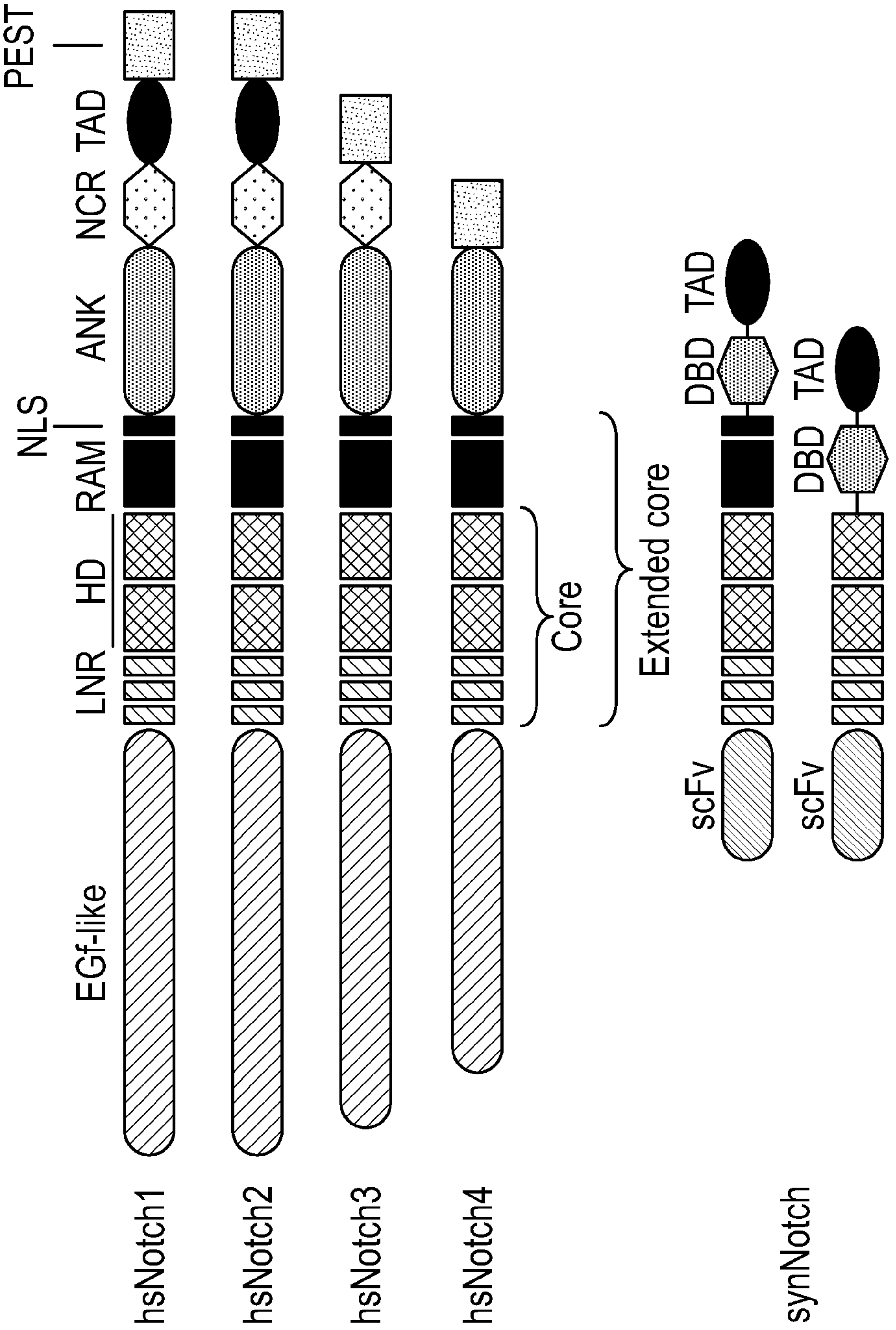
FIG. 1. Schematic of synthetic Notch receptor and the constituent domains comprising it.

Incorporation by reference: All publications mentioned herein, including patents, patent application publications, and scientific papers, are incorporated by reference in their entirety.

DETAILED DESCRIPTION OF THE INVENTION

Definitions

"Chimeric Notch polypeptide" also referred to as "Chimeric Notch receptor polypeptide," or "chimeric Notch" or "synNotch" is described in U.S. Pat. No. 9,670,281, and comprises, from N-terminal to C-terminal and in covalent linkage: a) an extracellular domain comprising a first member of a specific binding pair; b) wherein the Notch receptor polypeptide has a length of from 50 amino acids to 1000 amino acids, and comprises one or more ligand-inducible proteolytic cleavage sites; and c) an intracellular domain, wherein the first member of the specific binding pair is heterologous to the Notch receptor polypeptide, and wherein binding of the first member of the specific binding pair to a second member of the specific binding pair induces cleavage of the Notch receptor polypeptide at the one or more ligand-inducible proteolytic cleavage sites, thereby releasing the intracellular domain. In some cases, the Notch receptor polypeptide has a length of from 300 amino acids to 400 amino acids.

Further, the "chimeric Notch receptor polypeptide" comprises a linker interposed between the extracellular domain and the Notch receptor polypeptide. In some cases, the intracellular domain is a transcriptional activator. In some cases, the intracellular domain is a transcriptional repressor. In some cases, the first member of the specific binding pair comprises an antibody-based recognition scaffold. In some cases, the first member of the specific binding pair comprises an antibody. In some cases, where the first member of the specific binding pair is an antibody, the antibody specifically binds a tumor-specific antigen, a disease-associated antigen, or an extracellular matrix component. In some cases, where the first member of the specific binding pair is an antibody, the antibody specifically binds a cell surface antigen, a soluble antigen, or an antigen immobilized on an insoluble substrate. In some cases, where the first member of the specific binding pair is an antibody, the antibody is a single-chain Fv. In some cases, the first member of the specific binding pair is a nanobody, a single-domain antibody, a diabody, a triabody, or a minibody. In some cases, the first member of the specific binding pair is a non-antibody-based recognition scaffold. In some cases, where the first member of the specific binding pair is a non-antibody-based recognition scaffold, the non-antibody-based recognition scaffold is an avimer, a DARPin, an adnectin, an avimer, an affibody, an anticalin, or an affilin. In some cases, the first member of the specific binding pair is an antigen. In some cases, where the first member of the specific binding pair is an antigen, the antigen is an endogenous antigen. In some cases, where the first member of the specific binding pair is an antigen, the antigen is an exogenous antigen. In some cases, the first member of the specific binding pair is a ligand for a receptor. In some cases, the first member of the specific binding pair is a receptor. In some cases, the first member of the specific binding pair is a cellular adhesion molecule (e.g., all or a portion of an extracellular region of a cellular adhesion molecule).

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space.

"GFP" or green fluorescent protein (GFP), is a commonly used reporter of gene expression. Arun et al., *J. Pharmacol. Toxicol. Methods* 51(1):1-23, 2005.

By "HNF1 binding site" is intended any specific binding site for any of the known forms of HNF. HNF1 (also called LF-B1 or HNF1alpha) is a 628 aa long protein DNA binding protein that has been implicated as a major determinant of hepatocyte-specific transcription of several genes (Frain, *Cell* 59, 145-157, 1990).

In some embodiments, the DNA binding domain of human origin is a DNA-binding domain of a HNF1 transcription factor (e.g., any of the HNF1 transcription factors described herein or known in the art) and the transactivation domain is a human RelA protein or a portion thereof.

In some embodiments, the amino acid sequence of HNF1alpha is NCBI Nos. NP_001293108.1, NP_000536.5, or XP_005253988.1. In some embodiments, the amino acid sequence of the transcriptional regulator of the humanized chimeric Notch receptor comprises hepatocyte nuclear factor 1-alpha isoform 1 (NP_001293108.1), hepatocyte nuclear factor 1-alpha isoform 1 (NP_000536.5), or hepatocyte nuclear factor 1-alpha isoform X1 (XP_005253988.1), or a portion thereof. In some embodiments, the amino acid sequence of the transcriptional regulator of the humanized Notch receptor comprises all or a portion of SEQ ID NO: 5, SEQ ID NO: 6, or SEQ ID NO: 7.

As used herein, a "portion" of a polypeptide or protein refers at least 10 amino acids of the reference sequence, e.g., 10 to 200, 25 to 300, 50 to 400, 100 to 500, 200 to 600, 300 to 700, 400 to 800, 500 to 900, or 600 to 1000 or more amino acids of the reference sequence. In some embodiments, the portion of a polypeptide or protein is functional. In some embodiments, the transcriptional regulator is or comprises the dimerization and DNA-Binding Domain (DBD) of hepatocyte nuclear factor 1-alpha isoform 1 (NP_001293108.1), hepatocyte nuclear factor 1-alpha isoform 1 (NP_000536.5), or hepatocyte nuclear factor 1-alpha isoform X1 (XP_005253988.1). In some embodiments, the amino acid sequence of the transcriptional regulator of the humanized Notch receptor is amino acids is or comprises the dimerization and DNA-Binding Domain (DBD) of SEQ ID NO: 5, SEQ ID NO: 6, or SEQ ID NO:7. In some embodiments, the amino acid sequence of the transcriptional regulator of the humanized Notch receptor is or comprises amino acids 1-283 of SEQ ID NO: 5.

Human hepatocyte nuclear factor 1-alpha isoform 1 NP_001293108.1

(SEQ ID NO: 5)

MVSKLSQLQTELLAALLESGLSKEALIQALGEPGPYLLAGEGPLDKGESC

GGGRGELAELPNGLGETRGSEDETDDDGEDFTPPILKELENLSPEEAAHQ

KAVVETLLQEDPWRVAKMVKSYLQQHNIPQREVVDTTGLNQSHLSQHLNK

GTPMKTQKRAALYTWYVRKQREVAQQFTHAGQGGLIEEPTGDELPTKKGR

RNRFKWGPASQQILFQAYERQKNPSKEERETLVEECNRAECIQRGVSPSQ

AQGLGSNLVTEVRVYNWFANRRKEEAFRHKLAMDTYSGPPPGPGPGPALP

AHSSPGLPPPALSPSKVHGVRYGQPATSETAEVPSSSGGPLVTVSTPLHQ

VSPTGLEPSHSLLSTEAKLVSAAGGPLPPVSTLTALHSLEQTSPGLNQQP

QNLIMASLPGVMTIGPGEPASLGPTFTNTGASTLVIGLASTQAQSVPVIN

SMGSSLTTLQPVQFSQPLHPSYQQPLMPPVQSHVTQSPFMATMAQLQSPH

ALYSHKPEVAQYTHTGLLPQTMLITDTTNLSALASLTPTKQEAALLPQVF

TSDTEASSESGLHTPASQATTLHVPSQDPAGIQHLQPAHRLSASPTVSSS

SLVLYQSSDSSNGQSHLLPSNHSVIETFISTQMASSSQ

Human hepatocyte nuclear factor 1-alpha isoform 2 NP_000536.5

(SEQ ID NO: 6)

MVSKLSQLQTELLAALLESGLSKEALIQALGEPGPYLLAGEGPLDKGESC

GGGRGELAELPNGLGETRGSEDETDDDGEDFTPPILKELENLSPEEAAHQ

KAVVETLLQEDPWRVAKMVKSYLQQHNIPQREVVDTTGLNQSHLSQHLNK

GTPMKTQKRAALYTWYVRKQREVAQQFTHAGQGGLIEEPTGDELPTKKGR

RNRFKWGPASQQILFQAYERQKNPSKEERETLVEECNRAECIQRGVSPSQ

AQGLGSNLVTEVRVYNWFANRRKEEAFRHKLAMDTYSGPPPGPGPGPALP

AHSSPGLPPPALSPSKVHGVRYGQPATSETAEVPSSSGGPLVTVSTPLHQ

VSPTGLEPSHSLLSTEAKLVSAAGGPLPPVSTLTALHSLEQTSPGLNQQP

QNLIMASLPGVMTIGPGEPASLGPTFTNTGASTLVIGLASTQAQSVPVIN

SMGSSLTTLQPVQFSQPLHPSYQQPLMPPVQSHVTQSPFMATMAQLQSPH

ALYSHKPEVAQYTHTGLLPQTMLITDTTNLSALASLTPTKQVFTSDTEAS

SESGLHTPASQATTLHVPSQDPAGIQHLQPAHRLSASPTVSSSSLVLYQS

SDSSNGQSHLLPSNHSVIETFISTQMASSSQ

Human hepatocyte nuclear factor 1-alpha isoform X1 (predicted) XP_005253988.1

(SEQ ID NO: 7)

MVSKLSQLQTELLAALLESGLSKEALIQALGEPGPYLLAGEGPLDKGESC

GGGRGELAELPNGLGETRGSEDETDDDGEDFTPPILKELENLSPEEAAHQ

KAVVETLLQEDPWRVAKMVKSYLQQHNIPQREVVDTTGLNQSHLSQHLNK

GTPMKTQKRAALYTWYVRKQREVAQQFTHAGQGGLIEEPTGDELPTKKGR

RNRFKWGPASQQILFQAYERQKNPSKEERETLVEECNRAECIQRGVSPSQ

AQGLGSNLVTEVRVYNWFANRRKEEAFRHKLAMDTYSGPPPGPGPGPALP

AHSSPGLPPPALSPSKVHGVRYGQPATSETAEVPSSSGGPLVTVSTPLHQ

VSPTGLEPSHSLLSTEAKLVSAAGGPLPPVSTLTALHSLEQTSPGLNQQP

QNLIMASLPGVMTIGPGEPASLGPTFTNTGASTLVIGLASTQAQSVPVIN

SMGSSLTTLQPVQFSQPLHPSYQQPLMPPVQSHVTQSPFMATMAQLQSPH

-continued

ALYSHKPEVAQYTHTGLLPQTMLITDTTNLSALASLTPTKQVRSRPAGPP

LACDRAPHPHIPRAQEAALLPQVFTSDTEASSESGLHTPASQATTLHVPS

QDPASIQHLQPAHRLSASPTVSSSSLVLYQSSDSSNGQSHLLPSNHSVIE

TFISTQMASSSQ

In some embodiments, the amino acid sequence of HNF1alpha or the portion thereof, as described herein, is at least 80% identical to a corresponding amino acid sequence in SEQ ID NO: 5, SEQ ID NO: 6, or SEQ ID NO: 7. In some embodiments, the amino acid sequence of HNF1alpha or portion thereof is 80%, 81%, 82%, 83%, 84%, 85%, 86%, 87%, 88%, 89%, 90%, 91%, 92%, 93%, 94%, 95%, 96%, 97%, 98%, or 99% identical to a corresponding amino acid sequence in SEQ ID NO: 5, SEQ ID NO: 6, or SEQ ID NO: 7. In some embodiments, the amino acid sequence of HNF1alpha or the portion thereof, as described herein, can vary from the corresponding amino acid sequence in SEQ ID NO: 5, SEQ ID NO: 6, or SEQ ID NO: 7 by 1 amino acid, 2 amino acids, 3 amino acids, 4 amino acids, 5 amino acids, 6 amino acids, 7 amino acids, 8 amino acids, 9 amino acids, or 10 or more amino acids.

In some embodiments, the mRNA sequence of HFN1alpha is NCBI No. NM_001306179.1, NM_00545.6, or XM_005253931.3. In some embodiments, the mRNA sequence of HFN1alpha is SEQ ID NO: 8, SEQ ID NO: 9, or SEQ ID NO: 10.

Human HNF1 homeobox A (HNF1A), transcript variant 1, mRNA NM_001306179.1

(SEQ ID NO: 8)

GGGGCCCTGATTCACGGGCCGCTGGGGCCAGGGTTGGGGGTTGGGGGTGC

CCACAGGGCTTGGCTAGTGGGGTTTTGGGGGGGCAGTGGGTGCAAGGAGT

TTGGTTTGTGTCTGCCGGCCGGCAGGCAAACGCAACCCACGCGGTGGGGG

AGGCGGCTAGCGTGGTGGACCCGGGCCGCGTGGCCCTGTGGCAGCCGAGC

CATGGTTTCTAAACTGAGCCAGCTGCAGACGGAGCTCCTGGCGGCCCTGC

TCGAGTCAGGGCTGAGCAAAGAGGCACTGATCCAGGCACTGGGTGAGCCG

GGGCCCTACCTCCTGGCTGGAGAAGGCCCCCTGGACAAGGGGGAGTCCTG

CGGCGGCGGTCGAGGGGAGCTGGCTGAGCTGCCCAATGGGCTGGGGGAGA

CTCGGGGCTCCGAGGACGAGACGGACGACGATGGGGAAGACTTCACGCCA

CCCATCCTCAAAGAGCTGGAGAACCTCAGCCCTGAGGAGGCGGCCCACCA

GAAAGCCGTGGTGGAGACCCTTCTGCAGGAGGACCCGTGGCGTGTGGCGA

AGATGGTCAAGTCCTACCTGCAGCAGCACAACATCCCACAGCGGGAGGTG

GTCGATACCACTGGCCTCAACCAGTCCCACCTGTCCCAACACCTCAACAA

GGGCACTCCCATGAAGACGCAGAAGCGGGCCGCCCTGTACACCTGGTACG

TCCGCAAGCAGCGAGAGGTGGCGCAGCAGTTCACCCATGCAGGGCAGGGA

GGGCTGATTGAAGAGCCCACAGGTGATGAGCTACCAACCAAGAAGGGGCG

GAGGAACCGTTTCAAGTGGGGCCCAGCATCCCAGCAGATCCTGTTCCAGG

CCTATGAGAGGCAGAAGAACCCTAGCAAGGAGGAGCGAGAGACGCTAGTG

GAGGAGTGCAATAGGGCGGAATGCATCCAGAGAGGGGTGTCCCCATCACA

GGCACAGGGGCTGGGCTCCAACCTCGTCACGGAGGTGCGTGTCTACAACT

GGTTTGCCAACCGGCGCAAAGAAGAAGCCTTCCGGCACAAGCTGGCCATG

-continued

GACACGTACAGCGGGCCCCCCCCAGGGCCAGGCCCGGGACCTGCGCTGCC

CGCTCACAGCTCCCCTGGCCTGCCTCCACCTGCCCTCTCCCCCAGTAAGG

TCCACGGTGTGCGCTATGGACAGCCTGCGACCAGTGAGACTGCAGAAGTA

CCCTCAAGCAGCGGCGGTCCCTTAGTGACAGTGTCTACACCCCTCCACCA

AGTGTCCCCCACGGGCCTGGAGCCCAGCCACAGCCTGCTGAGTACAGAAG

CCAAGCTGGTCTCAGCAGCTGGGGGCCCCCTCCCCCCTGTCAGCACCCTG

ACAGCACTGCACAGCTTGGAGCAGACATCCCCAGGCCTCAACCAGCAGCC

CCAGAACCTCATCATGGCCTCACTTCCTGGGGTCATGACCATCGGGCCTG

GTGAGCCTGCCTCCCTGGGTCCTACGTTCACCAACACAGGTGCCTCCACC

CTGGTCATCGGCCTGGCCTCCACGCAGGCACAGAGTGTGCCGGTCATCAA

CAGCATGGGCAGCAGCCTGACCACCCTGCAGCCCGTCCAGTTCTCCCAGC

CGCTGCACCCCTCCTACCAGCAGCCGCTCATGCCACCTGTGCAGAGCCAT

GTGACCCAGAGCCCCTTCATGGCCACCATGGCTCAGCTGCAGAGCCCCCA

CGCCCTCTACAGCCACAAGCCCGAGGTGGCCCAGTACACCCACACGGGCC

TGCTCCCGCAGACTATGCTCATCACCGACACCACCAACCTGAGCGCCCTG

GCCAGCCTCACGCCCACCAAGCAGGAGGCTGCTCTGCTCCCCCAGGTCTT

CACCTCAGACACTGAGGCCTCCAGTGAGTCCGGGCTTCACACGCCGGCAT

CTCAGGCCACCACCCTCCACGTCCCCAGCCAGGACCCTGCCGGCATCCAG

CACCTGCAGCCGGCCCACCGGCTCAGCGCCAGCCCCACAGTGTCCTCCAG

CAGCCTGGTGCTGTACCAGAGCTCAGACTCCAGCAATGGCCAGAGCCACC

TGCTGCCATCCAACCACAGCGTCATCGAGACCTTCATCTCCACCCAGATG

GCCTCTTCCTCCCAGTAACCACGGCACCTGGGCCCTGGGGCCTGTACTGC

CTGCTTGGGGGGTGATGAGGGCAGCAGCCAGCCCTGCCTGGAGGACCTGA

GCCTGCCGAGCAACCGTGGCCCTTCCTGGACAGCTGTGCCTCGCTCCCCA

CTCTGCTCTGATGCATCAGAAAGGGAGGGCTCTGAGGCGCCCCAACCCGT

GGAGGCTGCTCGGGGTGCACAGGAGGGGGTCGTGGAGAGCTAGGAGCAAA

GCCTGTTCATGGCAGATGTAGGAGGGACTGTCGCTGCTTCGTGGGATACA

GTCTTCTTACTTGGAACTGAAGGGGGCGGCCTATGACTTGGGCACCCCCA

GCCTGGGCCTATGGAGAGCCCTGGGACCGCTACACCACTCTGGCAGCCAC

ACTTCTCAGGACACAGGCCTGTGTAGCTGTGACCTGCTGAGCTCTGAGAG

GCCCTGGATCAGCGTGGCCTTGTTCTGTCACCAATGTACCCACCGGGCCA

CTCCTTCCTGCCCCAACTCCTTCCAGCTAGTGACCCACATGCCATTTGTA

CTGACCCCATCACCTACTCACACAGGCATTTCCTGGGTGGCTACTCTGTG

CCAGAGCCTGGGGCTCTAACGCCTGAGCCCAGGGAGGCCGAAGCTAACAG

GGAAGGCAGGCAGGGCTCTCCTGGCTTCCCATCCCCAGCGATTCCCTCTC

CCAGGCCCCATGACCTCCAGCTTTCCTGTATTTGTTCCCAAGAGCATCAT

GCCTCTGAGGCCAGCCTGGCCTCCTGCCTCTACTGGGAAGGCTACTTCGG

GGCTGGGAAGTCGTCCTTACTCCTGTGGGAGCCTCGCAACCCGTGCCAAG

TCCAGGTCCTGGTGGGGCAGCTCCTCTGTCTCGAGCGCCCTGCAGACCCT

GCCCTTGTTTGGGGCAGGAGTAGCTGAGCTCACAAGGCAGCAAGGCCCGA

-continued

GCAGCTGAGCAGGGCCGGGGAACTGGCCAAGCTGAGGTGCCCAGGAGAAG

AAAGAGGTGACCCCAGGGCACAGGAGCTACCTGTGTGGACAGGACTAACA

CTCAGAAGCCTGGGGGCCTGGCTGGCTGAGGGCAGTTCGCAGCCACCCTG

AGGAGTCTGAGGTCCTGAGCACTGCCAGGAGGGACAAAGGAGCCTGTGAA

CCCAGGACAAGCATGGTCCCACATCCCTGGGCCTGCTGCTGAGAACCTGG

CCTTCAGTGTACCGCGTCTACCCTGGGATTCAGGAAAAGGCCTGGGGTGA

CCCGGCACCCCCTGCAGCTTGTAGCCAGCCGGGGCGAGTGGCACGTTTAT

TTAACTTTTAGTAAAGTCAAGGAGAAATGCGGTGGAAA

Human HNF1 homeobox A (HNF1A), transcript variant 2, mRNA NM_000545.6

(SEQ ID NO: 9)

GGGGCCCTGATTCACGGGCCGCTGGGGCCAGGGTTGGGGGTTGGGGGTGC

CCACAGGGCTTGGCTAGTGGGGTTTTGGGGGGGCAGTGGGTGCAAGGAGT

TTGGTTTGTGTCTGCCGGCCGGCAGGCAAACGCAACCCACGCGGTGGGGG

AGGCGGCTAGCGTGGTGGACCCGGGCCGCGTGGCCCTGTGGCAGCCGAGC

CATGGTTTCTAAACTGAGCCAGCTGCAGACGGAGCTCCTGGCGGCCCTGC

TCGAGTCAGGGCTGAGCAAAGAGGCACTGATCCAGGCACTGGGTGAGCCG

GGGCCCTACCTCCTGGCTGGAGAAGGCCCCCTGGACAAGGGGGAGTCCTG

CGGCGGCGGTCGAGGGGAGCTGGCTGAGCTGCCCAATGGGCTGGGGGAGA

CTCGGGGCTCCGAGGACGAGACGGACGACGATGGGGAAGACTTCACGCCA

CCCATCCTCAAAGAGCTGGAGAACCTCAGCCCTGAGGAGGCGGCCCACCA

GAAAGCCGTGGTGGAGACCCTTCTGCAGGAGGACCCGTGGCGTGTGGCGA

AGATGGTCAAGTCCTACCTGCAGCAGCACAACATCCCACAGCGGGAGGTG

GTCGATACCACTGGCCTCAACCAGTCCCACCTGTCCCAACACCTCAACAA

GGGCACTCCCATGAAGACGCAGAAGCGGGCCGCCCTGTACACCTGGTACG

TCCGCAAGCAGCGAGAGGTGGCGCAGCAGTTCACCCATGCAGGGCAGGGA

GGGCTGATTGAAGAGCCCACAGGTGATGAGCTACCAACCAAGAAGGGGCG

GAGGAACCGTTTCAAGTGGGGCCCAGCATCCCAGCAGATCCTGTTCCAGG

CCTATGAGAGGCAGAAGAACCCTAGCAAGGAGGAGCGAGAGACGCTAGTG

GAGGAGTGCAATAGGGCGGAATGCATCCAGAGAGGGGTGTCCCCATCACA

GGCACAGGGGCTGGGCTCCAACCTCGTCACGGAGGTGCGTGTCTACAACT

GGTTTGCCAACCGGCGCAAAGAAGAAGCCTTCCGGCACAAGCTGGCCATG

GACACGTACAGCGGGCCCCCCCCAGGGCCAGGCCCGGGACCTGCGCTGCC

CGCTCACAGCTCCCCTGGCCTGCCTCCACCTGCCCTCTCCCCCAGTAAGG

TCCACGGTGTGCGCTATGGACAGCCTGCGACCAGTGAGACTGCAGAAGTA

CCCTCAAGCAGCGGCGGTCCCTTAGTGACAGTGTCTACACCCCTCCACCA

AGTGTCCCCCACGGGCCTGGAGCCCAGCCACAGCCTGCTGAGTACAGAAG

CCAAGCTGGTCTCAGCAGCTGGGGGCCCCCTCCCCCCTGTCAGCACCCTG

ACAGCACTGCACAGCTTGGAGCAGACATCCCCAGGCCTCAACCAGCAGCC

CCAGAACCTCATCATGGCCTCACTTCCTGGGGTCATGACCATCGGGCCTG

GTGAGCCTGCCTCCCTGGGTCCTACGTTCACCAACACAGGTGCCTCCACC

CTGGTCATCGGCCTGGCCTCCACGCAGGCACAGAGTGTGCCGGTCATCAA

-continued

CAGCATGGGCAGCAGCCTGACCACCCTGCAGCCCGTCCAGTTCTCCCAGC

CGCTGCACCCCTCCTACCAGCAGCCGCTCATGCCACCTGTGCAGAGCCAT

GTGACCCAGAGCCCCTTCATGGCCACCATGGCTCAGCTGCAGAGCCCCCA

CGCCCTCTACAGCCACAAGCCCGAGGTGGCCCAGTACACCCCACACGGGC

TGCTCCCGCAGACTATGCTCATCACCGACACCACCAACCTGAGCGCCCTG

GCCAGCCTCACGCCCACCAAGCAGGTCTTCACCTCAGACACTGAGGCCTC

CAGTGAGTCCGGGCTTCACACGCCGGCATCTCAGGCCACCACCCTCCACG

TCCCCAGCCAGGACCCTGCCGGCATCCAGCACCTGCAGCCGGCCCACCGG

CTCAGCGCCAGCCCCACAGTGTCCTCCAGCAGCCTGGTGCTGTACCAGAG

CTCAGACTCCAGCAATGGCCAGAGCCACCTGCTGCCATCCAACCACAGCG

TCATCGAGACCTTCATCTCCACCCAGATGGCCTCTTCCTCCCAGTAACCA

CGGCACCTGGGCCCTGGGGCCTGTACTGCCTGCTTGGGGGGTGATGAGGG

CAGCAGCCAGCCCTGCCTGGAGGACCTGAGCCTGCCGAGCAACCGTGGCC

CTTCCTGGACAGCTGTGCCTCGCTCCCCACTCTGCTCTGATGCATCAGAA

AGGGAGGGCTCTGAGGCGCCCCAACCCGTGGAGGCTGCTCGGGGTGCACA

GGAGGGGGTCGTGGAGAGCTAGGAGCAAAGCCTGTTCATGGCAGATGTAG

GAGGGACTGTCGCTGCTTCGTGGGATACAGTCTTCTTACTTGGAACTGAA

GGGGGCGGCCTATGACTTGGGCACCCCCAGCCTGGGCCTATGGAGAGCCC

TGGGACCGCTACACCACTCTGGCAGCCACACTTCTCAGGACACAGGCCTG

TGTAGCTGTGACCTGCTGAGCTCTGAGAGGCCCTGGATCAGCGTGGCCTT

GTTCTGTCACCAATGTACCCACCGGGCCACTCCTTCCTGCCCCAACTCCT

TCCAGCTAGTGACCCACATGCCATTTGTACTGACCCCATCACCTACTCAC

ACAGGCATTTCCTGGGTGGCTACTCTGTGCCAGAGCCTGGGGCTCTAACG

CCTGAGCCCAGGGAGGCCGAAGCTAACAGGGAAGGCAGGCAGGGCTCTCC

TGGCTTCCCATCCCCAGCGATTCCCTCTCCCAGGCCCCATGACCTCCAGC

TTTCCTGTATTTGTTCCCAAGAGCATCATGCCTCTGAGGCCAGCCTGGCC

TCCTGCCTCTACTGGGAAGGCTACTTCGGGGCTGGGAAGTCGTCCTTACT

CCTGTGGGAGCCTCGCAACCCGTGCCAAGTCCAGGTCCTGGTGGGGCAGC

TCCTCTGTCTCGAGCGCCCTGCAGACCCTGCCCTTGTTTGGGGCAGGAGT

AGCTGAGCTCACAAGGCAGCAAGGCCCGAGCAGCTGAGCAGGGCCGGGGA

ACTGGCCAAGCTGAGGTGCCCAGGAGAAGAAAGAGGTGACCCCAGGGCAC

AGGAGCTACCTGTGTGGACAGGACTAACACTCAGAAGCCTGGGGGCCTGG

CTGGCTGAGGGCAGTTCGCAGCCACCCTGAGGAGTCTGAGGTCCTGAGCA

CTGCCAGGAGGGACAAAGGAGCCTGTGAACCCAGGACAAGCATGGTCCCA

CATCCCTGGGCCTGCTGCTGAGAACCTGGCCTTCAGTGTACCGCGTCTAC

CCTGGGATTCAGGAAAAGGCCTGGGGTGACCCGGCACCCCCTGCAGCTTG

TAGCCAGCCGGGGCGAGTGGCACGTTTATTTAACTTTTAGTAAAGTCAAG

GAGAAATGCGGTGGAAA

-continued

Human HNF1 homeobox A (HNF1A), transcript variant X1, mRNA XM_005253931.3

(SEQ ID NO: 10)

ATAAATATGAACCTTGGAGAATTTCCCGAGCTCCAATGTAAACAGAACAG

GGAGGGGCCCTGATTCACGGGCCGCTGGGGCCAGGGTTGGGGGTTGGGGG

TGCCCACAGGGCTTGGCTAGTGGGGTTTTGGGGGGGCAGTGGGTGCAAGG

AGTTTGGTTTGTGTCTGCCGGCCGGCAGGCAAACGCAACCCACGCGGTGG

GGGAGGCGGCTAGCGTGGTGGACCCGGGCCGCGTGGCCCTGTGGCAGCCG

AGCCATGGTTTCTAAACTGAGCCAGCTGCAGACGGAGCTCCTGGCGGCCC

TGCTCGAGTCAGGGCTGAGCAAAGAGGCACTGATCCAGGCACTGGGTGAG

CCGGGGCCCTACCTCCTGGCTGGAGAAGGCCCCCTGGACAAGGGGGAGTC

CTGCGGCGGCGGTCGAGGGGAGCTGGCTGAGCTGCCCAATGGGCTGGGGG

AGACTCGGGGCTCCGAGGACGAGACGGACGACGATGGGGAAGACTTCACG

CCACCCATCCTCAAAGAGCTGGAGAACCTCAGCCCTGAGGAGGCGGCCCA

CCAGAAAGCCGTGGTGGAGACCCTTCTGCAGGAGGACCCGTGGCGTGTGG

CGAAGATGGTCAAGTCCTACCTGCAGCAGCACAACATCCCACAGCGGGAG

GTGGTCGATACCACTGGCCTCAACCAGTCCCACCTGTCCCAACACCTCAA

CAAGGGCACTCCCATGAAGACGCAGAAGCGGGCCGCCCTGTACACCTGGT

ACGTCCGCAAGCAGCGAGAGGTGGCGCAGCAGTTCACCCATGCAGGGCAG

GGAGGGCTGATTGAAGAGCCCACAGGTGATGAGCTACCAACCAAGAAGGG

GCGGAGGAACCGTTTCAAGTGGGGCCCAGCATCCCAGCAGATCCTGTTCC

AAGGCCTATGAGAGGCAGAGAACCCTAGCAAGGAGGAGCGAGAGACGCTA

GTGGAGGAGTGCAATAGGGCGGAATGCATCCAGAGAGGGGTGTCCCCATC

ACAGGCACAGGGGCTGGGCTCCAACCTCGTCACGGAGGTGCGTGTCTACA

ACTGGTTTGCCAACCGGCGCAAAGAAGAAGCCTTCCGGCACAAGCTGGCC

ATGGACACGTACAGCGGGCCCCCCCCAGGGCCAGGCCCGGGACCTGCGCT

GCCCGCTCACAGCTCCCCTGGCCTGCCTCCACCTGCCCTCTCCCCCAGTA

AGGTCCACGGTGTGCGCTATGGACAGCCTGCGACCAGTGAGACTGCAGAA

GTACCCTCAAGCAGCGGCGGTCCCTTAGTGACAGTGTCTACACCCCTCCA

CCAAGTGTCCCCCACGGGCCTGGAGCCCAGCCACAGCCTGCTGAGTACAG

AAGCCAAGCTGGTCTCAGCAGCTGGGGGCCCCCTCCCCCCTGTCAGCACC

CTGACAGCACTGCACAGCTTGGAGCAGACATCCCCAGGCCTCAACCAGCA

GCCCCAGAACCTCATCATGGCCTCACTTCCTGGGGTCATGACCATCGGGC

CTGGTGAGCCTGCCTCCCTGGGTCCTACGTTCACCAACACAGGTGCCTCC

ACCCTGGTCATCGGCCTGGCCTCCACGCAGGCACAGAGTGTGCCGGTCAT

CAACAGCATGGGCAGCAGCCTGACCACCCTGCAGCCCGTCCAGTTCTCCC

AGCCGCTGCACCCCTCCTACCAGCAGCCGCTCATGCCACCTGTGCAGAGC

CATGTGACCCAGAGCCCCTTCATGGCCACCATGGCTCAGCTGCAGAGCCC

CCACGCCCTCTACAGCCACAAGCCCGAGGTGGCCCAGTACACCCCACACGG

GCCTGCTCCCGCAGACTATGCTCATCACCGACACCACCAACCTGAGCGCC

CTGGCCAGCCTCACGCCCACCAAGCAGGTAAGGTCCAGGCCTGCTGGCCC

TCCCTTGGCCTGTGACAGAGCCCCTCACCCCCACATCCCCCGGGCTCAGG

-continued

AGGCTGCTCTGCTCCCCCAGGTCTTCACCTCAGACACTGAGGCCTCCAGT

GAGTCCGGGCTTCACACGCCGGCATCTCAGGCCACCACCCTCCACGTCCC

CAGCCAGGACCCTGCCAGCATCCAGCACCTGCAGCCGGCCCACCGGCTCA

GCGCCAGCCCCACAGTGTCCTCCAGCAGCCTGGTGCTGTACCAGAGCTCA

GACTCCAGCAATGGCCAGAGCCACCTGCTGCCATCCAACCACAGCGTCAT

CGAGACCTTCATCTCCACCCAGATGGCCTCTTCCTCCCAGTAACCACGGC

ACCTGGGCCCTGGGGCCTGTACTGCCTGCTTGGGGGGTGATGAGGGCAGC

AGCCAGCCCTGCCTGGAGGACCTGAGCCTGCCGAGCAACCGTGGCCCTTC

CTGGACAGCTGTGCCTCGCTCCCCACTCTGCTCTGATGCATCAGAAAGGG

AGGGCTCTGAGGCGCCCCAACCCGTGGAGGCTGCTCGGGGTGCACAGGAG

GGGGTCGTGGAGAGCTAGGAGCAAAGCCTGTTCATGGCAGATGTAGGAGG

GACTGTCGCTGCTTCGTGGGATACAGTCTTCTTACTTGGAACTGAAGGGG

GCGGCCTATGACTTGGGCACCCCCAGCCTGGGCCTATGGAGAGCCCTGGG

ACCGCTACACCACTCTGGCAGCCACACTTCTCAGGACACAGGCCTGTGTA

GCTGTGACCTGCTGAGCTCTGAGAGGCCCTGGATCAGCGTGGCCTTGTTC

TGTCACCAATGTACCCACCGGGCCACTCCTTCCTGCCCCAACTCCTTCCA

GCTAGTGAGCCACATGCCATTTGTACTGAGCCCATCACCTACTCACACAG

GCATTTCCTGGGTGGCTACTCTGTGCCAGAGCCTGGGGCTCTAACGCCTG

AGCCCAGGGAGGCCGAAGCTAACAGGGAAGGCAGGCAGGGCTCTCCTGGC

TTCCCATCCCCAGCGATTCCCTCTCCCAGGCCCCATGACCTCCAGCTTTC

CTGTATTTGTTCCCAAGAGCATCATGCCTCTGAGGCCAGCCTGGCCTCCT

GCCTCTACTGGGAAGGCTACTTCGGGGCTGGGAAGTCGTCCTTACTCCTG

TGGGAGCCTCGCAACCCGTGCCAAGTCCAGGTCCTGGTGGGGCAGCTCCT

CTGTCTCGAGCGCCCTGCAGACCCTGCCCTTGTTTGGGGCAGGAGTAGCT

GAGCTCACAAGGCAGCAAGGCCCGAGCAGCTGAGCAGGGCCGGGGAACTG

GCCAAGCTGAGGTGCCCAGGAGAAGAAAGAGGTGACCCCAGGGCACAGGA

GCTACCTGTGTGGACAGGACTAACACTCAGAAGCCTGGGGGCCTGGCTGG

CTGAGGGCAGTTCGCAGCCACCCTGAGGAGTCTGAGGTCCTGAGCACTGC

CAGGAGGGACAAAGGAGCCTGTGAACCCAGGACAAGCATGGTCCCACATC

CCTGGGCCTGCTGCTGAGAACCTGGCCTTCAGTGTACCGCGTCTACCCTG

GGATTCAGGAAAAGGCCTGGGGTGACCCGGCACCCCCTGCAGCTTGTAGC

CAGCCGGGGCGAGTGGCACGTTTATTTAACTTTTAGTAAAGTCAAGGAGA

AATGCGGTGGAAA

In some embodiments, the HNF1alpha binds to the inverted palindrome 5-GTTAATNATTAAC-3 (SEQ ID NO: 11).

In some embodiments, the nucleic acid sequence encoding HNF1alpha, as described herein, is at least 80% identical to the sequence of SEQ ID NO: 8, SEQ ID NO: 9, or SEQ ID NO: 10. In some embodiments, the nucleic acid sequence encoding HNF1alpha is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 8, SEQ ID NO: 9, or SEQ ID NO: 10. In some embodiments, the nucleic acid nucleotide sequence encoding HNF1alpha, as described herein, can vary from the sequence of SEQ ID NO: 8, SEQ ID NO: 9, or SEQ ID NO: 10 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

In some embodiments, the amino acid sequence of Rel-A (p65) is NCBI No. NP_068810.3, NP_001138610.1, NP_001230913.1, NP_001230914.1, XP_011543508.1, or XP_011543509.1. In some embodiments, the amino acid sequence of Rel-A (p65) is or comprises all or a portion of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of the transactivation domain of the humanized chimeric Notch receptor comprises all or a portion of transcription factor p65 isoform 1 (NP_068810.3), transcription factor p65 isoform 2 (NP_001138610.1), transcription factor p65 isoform 3 (NP_001230913.1), transcription factor p65 isoform 4 (NP_001230914.1), transcription factor p65 isoform X1 (XP_011543508.1), or transcription factor p65 isoform X2 (XP_011543509.1). In some embodiments, the amino acid sequence of the transactivation domain of the humanized Notch receptor comprises all or a portion of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of the transactivation domain of the humanized Notch receptor is or comprises amino acids 1-551 of SEQ ID NO: 12.

Human transcription factor p65 isoform 1
NP_068810.3

(SEQ ID NO: 12)

MDELFPLIFPAEPAQASGPYVEIIEQPKQRGMRFRYKCEGRSAGSIPGE

RSTDTTKTHPTIKINGYTGPGTVRISLVTKDPPHRPHPHELVGKDCRDG

FYEAELCPDRCIHSFQNLGIQCVKKRDLEQAISQRIQTNNNPFQVPIEE

QRGDYDLNAVRLCFQVTVRDPSGRPLRLPPVLSHPIFDNRAPNTAELKI

CRVNRNSGSCLGGDEIFLLCDKVQKEDIEVYFTGPGWEARGSFSQADVH

RQVAIVFRTPPYADPSLQAPVRVSMQLRRPSDRELSEPMEFQYLPDTDD

RHRIEEKRKRTYETFKSIMKKSPESGPTDPRPPPRRIAVPSRSSASVPK

PAPQPYPFTSSLSTINYDEFPTMVFPSGQISQASALAPAPPQVLPQAPA

PAPAPAMVSALAQAPAPVPVLAPGPPQAVAPPAPKPTQAGEGTLSEALL

QLQFDDEDLGALLGNSTDPAVFTDLASVDNSEFQQLLNQGIPVAPHTTE

PMLMEYPEAITRLVTGAQRPPDPAPAPLGAPGLPNGLLSGDEDFSSIAD

MDFSALLSQISS

Human transcription factor p65 isoform 2
NP_001138610.1

(SEQ ID NO: 13)

MDELFPLIFPAEPAQASGPYVEIIEQPKQRGMRFRYKCEGRSAGSIPGE

RSTDTTKTHPTIKINGYTGPGTVRISLVTKDPPHRPHPHELVGKDCRDG

FYEAELCPDRCIHSFQNLGIQCVKKRDLEQAISQRIQTNNNPFQEEQRG

DYDLNAVRLCFQVTVRDPSGRPLRLPPVLSHPIFDNRAPNTAELKICRV

NRNSGSCLGGDEIFLLCDKVQKEDIEVYFTGPGWEARGSFSQADVHRQV

AIVFRTPPYADPSLQAPVRVSMQLRRPSDRELSEPMEFQYLPDTDDRHR

IEEKRKRTYETFKSIMKKSPFSGPTDPRPPPRRIAVPSRSSASVPKPAP

QPYPFTSSLSTINYDEFPTMVFPSGQISQASALAPAPPQVLPQAPAPAP

-continued

APAMVSALAQAPAPVPVLAPGPPQAVAPPAPKPTQAGEGTLSEALLQLQ

FDDEDLGALLGNSTDPAVFTDLASVDNSEFQQLLNQGIPVAPHTTEPML

MEYPEAITRLVTGAQRPPDPAPAPLGAPGLPNGLLSGDEDFSSIADMDF

SALLSQISS

Human transcription factor p65 isoform 3
NP_001230913.1
(SEQ ID NO: 14)

MDELFPLIFPAEPAQASGPYVEIIEQPKQRGMRFRYKCEGRSAGSIPGE

RSTDTTKTHPTIKINGYTGPGTVRISLVTKDPPHRPHPHELVGKDCRDG

FYEAELCPDRCIHSFQNLGIQCVKKRDLEQAISQRIQTNNNPFQVPIEE

QRGDYDLNAVRLCFQVTVRDPSGRPLRLPPVLSHPIFDNRAPNTAELKI

CRVNRNSGSCLGGDEIFLLCDKVQKEDIEVYFTGPGWEARGSFSQADVH

RQVAIVFRTPPYADPSLQAPVRVSMQLRRPSDRELSEPMEFQYLPDTDD

RHRIEEKRKRTYETFKSIMKKSPESGPTDPRPPPRRIAVPSRSSASVPK

PAPGPPQAVAPPAPKPTQAGEGTLSEALLQLQFDDEDLGALLGNSTDPA

VFTDLASVDNSEFQQLLNQGIPVAPHTTEPMLMEYPEAITRLVTGAQRP

PDPAPAPLGAPGLPNGLLSGDEDFSSIADMDFSALLSQISS

Human transcription factor p65 isoform 4
NP_001230914.1
(SEQ ID NO: 15)

MDELFPLIFPAEPAQASGPYVEIIEQPKQRGMRFRYKCEGRSAGSIPGE

RSTDTTKTHPTIKINGYTGPGTVRISLVTKDPPHRPHPHELVGKDCRDG

FYEAELCPDRCIHSFQNLGIQCVKKRDLEQAISQRIQTNNNPFQVPIEE

QRGDYDLNAVRLCFQVTVRDPSGRPLRLPPVLSHPIFDNRAPNTAELKI

CRVNRNSGSCLGGDEIFLLCDKVQKEDIEVYFTGPGWEARGSFSQADVH

RQVAIVFRTPPYADPSLQAPVRVSMQLRRPSDRELSEPMEFQYLPDTDD

RHRIEEKRKRTYETFKSIMKKSPESGPTDPRPPPRRIAVPSRSSASVPK

PAPQPYPFTSSLSTINYDEFPTMVFPSGQISQASALAPAPPQVLPQAPA

PAPAPAMVSALAQRPPDPAPAPLGAPGLPNGLLSGDEDFSSIADMDFSA

LLSQISS

Human transcription factor p65 isoform X1
XP_011543508.1
(SEQ ID NO: 16)

MDELFPLIFPAEPAQASGPYVEIIEQPKQRGMRFRYKCEGRSAGSIPGE

RSTDTTKTHPTIKINGYTGPGTVRISLVTKDPPHRPHPHELVGKDCRDG

FYEAELCPDRCIHSFQNLGIQCVKKRDLEQAISQRIQTNNNPFQVPIEE

QRGDYDLNAVRLCFQVTVRDPSGRPLRLPPVLSHPIFDNRAPNTAELKI

-continued

CRVNRNSGSCLGGDEIFLLCDKVQKDDRHRIEEKRKRTYETFKSIMKKS

PFSGPTDPRPPPRRIAVPSRSSASVPKPAPQPYPFTSSLSTINYDEFPT

MVFPSGQISQASALAPAPPQVLPQAPAPAPAPAMVSALAQAPAPVPVLA

PGPPQAVAPPAPKPTQAGEGTLSEALLQLQFDDEDLGALLGNSTDPAVF

TDLASVDNSEFQQLLNQGIPVAPHTTEPMLMEYPEAITRLVTGAQRPPD

PAPAPLGAPGLPNGLLSGDEDFSSIADMDFSALLSQISS

Human transcription factor p65 isoform X2
XP_011543509.1
(SEQ ID NO: 17)

MDELFPLIFPAEPAQASGPYVEIIEQPKQRGMRFRYKCEGRSAGSIPGE

RSTDTTKTHPTIKINGYTGPGTVRISLVTKDPPHRPHPHELVGKDCRDG

FYEAELCPDRCIHSFQNLGIQCVKKRDLEQAISQRIQTNNNPFQVPIEE

QRGDYDLNAVRLCFQVTVRDPSGRPLRLPPVLSHPIFDNHDRHRIEEKR

KRTYETFKSIMKKSPFSGPTDPRPPPRRIAVPSRSSASVPKPAPQPYPF

TSSLSTINYDEFPTMVFPSGQISQASALAPAPPQVLPQAPAPAPAPAMV

SALAQAPAPVPVLAPGPPQAVAPPAPKPTQAGEGTLSEALLQLQFDDED

LGALLGNSTDPAVFTDLASVDNSEFQQLLNQGIPVAPHTTEPMLMEYPE

AITRLVTGAQRPPDPAPAPLGAPGLPNGLLSGDEDFSSIADMDFSALLS

QISS

In some embodiments, the amino acid sequence of Rel-A (p65), as described herein, is at least 80% identical to the amino acid sequence of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of Rel-A (p65) is 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of Rel-A (p65), as described herein, can vary from the amino acid sequence of SEQ ID NO: 12, SEQ ID NO: 13, SEQ ID NO: 14, SEQ ID NO: 15, SEQ ID NO: 16, or SEQ ID NO: 17 by 1 amino acid, 2 amino acids, 3 amino acids, 4 amino acids, 5 amino acids, 6 amino acids, 7 amino acids, 8 amino acids, 9 amino acids, or 10 or more amino acids.

In some embodiments, the nucleic acid sequence encoding Rel-A (p65) is provided by NCBI No. NM_021975.3, NM_001145138.1, NM_001243984.1, NM_001243985.1, XM_011545206.1, or XM_011545207.1. In some embodiments, the nucleic acid sequence encoding Rel-A (p65) is or comprises SEQ ID NO: 18, SEQ ID NO: 19, SEQ ID NO: 20, SEQ ID NO: 21, SEQ ID NO: 22, or SEQ ID NO: 23.

Human RELA proto-oncogene, NF-kB subunit (RELA), transcript variant 1, mRNA NM_021975.3
(SEQ ID NO: 18)

AGCGCGCAGGCGCGGCCGGATTCCGGGCAGTGACGCGACGGCGGGCCGCGCGGCGCATTTCCGCCTCTGGCGAATGGCTCGTCTGTAGTGC

ACGCCGCGGGCCCAGCTGCGACCCCGGCCCCGCCCCCGGGACCCCGGCCATGGACGAACTGTTCCCCCTCATCTTCCCGGCAGAGCCAGCC

CAGGCCTCTGGCCCCTATGTGGAGATCATTGAGCAGCCCAAGCAGCGGGGCATGCGCTTCCGCTACAAGTGCGAGGGGCGCTCCGCGGGCA

GCATCCCAGGCGAGAGGAGCACAGATACCACCAAGACCCACCCCACCATCAAGATCAATGGCTACACAGGACCAGGGACAGTGCGCATCTC

CCTGGTCACCAAGGACCCTCCTCACCGGCCTCACCCCCACGAGCTTGTAGGAAAGGACTGCCGGGATGGCTTCTATGAGGCTGAGCTCTGC

-continued

CCGGACCGCTGCATCCACAGTTTCCAGAACCTGGGAATCCAGTGTGTGAAGAAGCGGGACCTGGAGCAGGCTATCAGTCAGCGCATCCAGA

CCAACAACAACCCCTTCCAAGTTCCTATAGAAGAGCAGCGTGGGGACTACGACCTGAATGCTGTGCGGCTCTGCTTCCAGGTGACAGTGCG

GGACCCATCAGGCAGGCCCCTCCGCCTGCCGCCTGTCCTTTCTCATCCCATCTTTGACAATCGTGCCCCCAACACTGCCGAGCTCAAGATC

TGCCGAGTGAACCGAAACTCTGGCAGCTGCCTCGGTGGGGATGAGATCTTCCTACTGTGTGACAAGGTGCAGAAAGAGGACATTGAGGTGT

ATTTCACGGGACCAGGCTGGGAGGCCCGAGGCTCCTTTTCGCAAGCTGATGTGCACCGACAAGTGGCCATTGTGTTCCGGACCCCTCCCTA

CGCAGACCCCAGCCTGCAGGCTCCTGTGCGTGTCTCCATGCAGCTGCGGCGGCCTTCCGACCGGGAGCTCAGTGAGCCCATGGAATTCCAG

TACCTGCCAGATACAGACGATCGTCACCGGATTGAGGAGAAACGTAAAAGGAGATATGAGACCTTCAAGAGCATCATGAAGAAGAGTCCTT

TCAGCGGACCCACCGACCCCCGGCCTCCACCTCGACGCATTGCTGTGCCTTCCCGCAGCTCAGCTTCTGTCCCCAAGCCAGCACCCCAGCC

CTATCCCTTTACGTCATCCCTGAGCACCATCAACTATGATGAGTTTCCCACCATGGTGTTTCCTTCTGGGCAGATCAGCCAGGCCTCGGCC

TTGGCCCCGGCCCCTCCCCAAGTCCTGCCCCAGGCTCCAGCCCCTGCCCCTGCTCCAGCCATGGTATCAGCTCTGGCCCAGGCCCCAGCCC

CTGTCCCAGTCCTAGCCCCAGGCCCTCCTCAGGCTGTGGCCCCACCTGCCCCCAAGCCCACCCAGGCTGGGGAAGGAACGCTGTCAGAGGC

CCTGCTGCAGCTGCAGTTTGATGATGAAGACCTGGGGGCCTTGCTTGGCAACAGCACAGACCCAGCTGTGTTCACAGACCTGGCATCCGTC

GACAACTCCGAGTTTCAGCAGCTGCTGAACCAGGGCATACCTGTGGCCCCCCACACAACTGAGCCCATGCTGATGGAGTACCCTGAGGCTA

TAACTCGCCTAGTGACAGGGGCCCAGAGGCCCCCCGACCCAGCTCCTGCTCCACTGGGGGCCCCGGGGCTCCCCAATGGCCTCCTTTCAGG

AGATGAAGACTTCTCCTCCATTGCGGACATGGACTTCTCAGCCCTGCTGAGTCAGATCAGCTCCTAAGGGGGTGACGCCTGCCCTCCCCAG

AGCACTGGGTTGCAGGGGATTGAAGCCCTCCAAAAGCACTTACGGATTCTGGTGGGGTGTGTTCCAACTGCCCCCAACTTTGTGGATGTCT

TCCTTGGAGGGGGGAGCCATATTTTATTCTTTTATTGTCAGTATCTGTATCTCTCTCTCTTTTTGGAGGTGCTTAAGCAGAAGCATTAACT

TCTCTGGAAAGGGGGGAGCTGGGGAAACTCAAACTTTTCCCCTGTCCTGATGGTCAGCTCCCTTCTCTGTAGGGAACTCTGGGGTCCCCCA

TCCCCATCCTCCAGCTTCTGGTACTCTCCTAGAGACAGAAGCAGGCTGGAGGTAAGGCCTTTGAGCCCACAAAGCCTTATCAAGTGTCTTC

CATCATGGATTCATTACAGCTTAATCAAAATAACGCCCCAGATACCAGCCCCTGTATGGCACTGGCATTGTCCCTGTGCCTAACACCAGCG

TTTGAGGGGCTGGCCTTCCTGCCCTACAGAGGTCTCTGCCGGCTCTTTCCTTGCTCAACCATGGCTGAAGGAAACCAGTGCAACAGCACTG

GCTCTCTCCAGGATCCAGAAGGGGTTTGGTCTGGGACTTCCTTGCTCTCCCTCTTCTCAAGTGCCTTAATAGTAGGGTAAGTTGTTAAGAG

TGGGGGAGAGCAGGCTGGCAGCTCTCCAGTCAGGAGGCATAGTTTTTACTGAACAATCAAAGCACTTGGACTCTTGCTCTTTCTACTCTGA

ACTAATAAATCTGTTGCCAAGCTGGCTAGAAAAAAAAAAAAAAAAAA

Human RELA proto-oncogene, NF-kB subunit (RELA), transcript variant 2, mRNA NM_001145138.1
(SEQ ID NO: 19)

AGCGCGCAGGCGCGGCCGGATTCCGGGCAGTGACGCGACGGCGGGCCGCGCGGCGCATTTCCGCCTCTGGCGAATGGCTCGTCTGTAGTGC

ACGCCGCGGGCCCAGCTGCGACCCCGGCCCCGCCCCCGGGACCCCGGCCATGGACGAACTGTTCCCCCTCATCTTCCCGGCAGAGCCAGCC

CAGGCCTCTGGCCCCTATGTGGAGATCATTGAGCAGCCCAAGCAGCGGGGCATGCGCTTCCGCTACAAGTGCGAGGGGCGCTCCGCGGGCA

GCATCCCAGGCGAGAGGAGCACAGATACCACCAAGACCCACCCCACCATCAAGATCAATGGCTACACAGGACCAGGGACAGTGCGCATCTC

CCTGGTCACCAAGGACCCTCCTCACCGGCCTCACCCCCACGAGCTTGTAGGAAAGGACTGCCGGGATGGCTTCTATGAGGCTGAGCTCTGC

CCGGACCGCTGCATCCACAGTTTCCAGAACCTGGGAATCCAGTGTGTGAAGAAGCGGGACCTGGAGCAGGCTATCAGTCAGCGCATCCAGA

CCAACAACAACCCCTTCCAAGAAGAGCAGCGTGGGGACTACGACCTGAATGCTGTGCGGCTCTGCTTCCAGGTGACAGTGCGGGACCCATC

AGGCAGGCCCCTCCGCCTGCCGCCTGTCCTTTCTCATCCCATCTTTGACAATCGTGCCCCCAACACTGCCGAGCTCAAGATCTGCCGAGTG

AACCGAAACTCTGGCAGCTGCCTCGGTGGGGATGAGATCTTCCTACTGTGTGACAAGGTGCAGAAAGAGGACATTGAGGTGTATTTCACGG

GACCAGGCTGGGAGGCCCGAGGCTCCTTTTCGCAAGCTGATGTGCACCGACAAGTGGCCATTGTGTTCCGGACCCCTCCCTACGCAGACCC

CAGCCTGCAGGCTCCTGTGCGTGTCTCCATGCAGCTGCGGCGGCCTTCCGACCGGGAGCTCAGTGAGCCCATGGAATTCCAGTACCTGCCA

GATACAGACGATCGTCACCGGATTGAGGAGAAACGTAAAAGGACATATGAGACCTTCAAGAGCATCATGAAGAAGAGTCCTTTCAGCGGAC

CCACCGACCCCCGGCCTCCACCTCGACGCATTGCTGTGCCTTCCCGCAGCTCAGCTTCTGTCCCCAAGCCAGCACCCCAGCCCTATCCCTT

TACGTCATCCCTGAGCACCATCAACTATGATGAGTTTCCCACCATGGTGTTTCCTTCTGGGCAGATCAGCCAGGCCTCGGCCTTGGCCCCG

GCCCCTCCCCAAGTCCTGCCCCAGGCTCCAGCCCCTGCCCCTGCTCCAGCCATGGTATCAGCTCTGGCCCAGGCCCCAGCCCCTGTCCCAG

TCCTAGCCCCAGGCCCTCCTCAGGCTGTGGCCCCACCTGCCCCCAAGCCCACCCAGGCTGGGGAAGGAACGCTGTCAGAGGCCCTGCTGCA

-continued

GCTGCAGTTTGATGATGAAGACCTGGGGGCCTTGCTTGGCAACAGCACAGACCCAGCTGTGTTCACAGACCTGGCATCCGTCGACAACTCC

GAGTTTCAGCAGCTGCTGAACCAGGGCATACCTGTGGCCCCCCACACAACTGAGCCCATGCTGATGGAGTACCCTGAGGCTATAACTCGCC

TAGTGACAGGGGCCCAGAGGCCCCCCGACCCAGCTCCTGCTCCACTGGGGGCCCCGGGGCTCCCCAATGGCCTCCTTTCAGGAGATGAAGA

CTTCTCCTCCATTGCGGACATGGACTTCTCAGCCCTGCTGAGTCAGATCAGCTCCTAAGGGGGTGACGCCTGCCCTCCCCAGAGCACTGGG

TTGCAGGGGATTGAAGCCCTCCAAAAGCACTTACGGATTCTGGTGGGGTGTGTTCCAACTGCCCCCAACTTTGTGGATGTCTTCCTTGGAG

GGGGGAGCCATATTTTATTCTTTTATTGTCAGTATCTGTATCTCTCTCTCTTTTTGGAGGTGCTTAAGCAGAAGCATTAACTTCTCTGGAA

AGGGGGGAGCTGGGGAAACTCAAACTTTTCCCCTGTCCTGATGGTCAGCTCCCTTCTCTGTAGGGAACTCTGGGGTCCCCCATCCCCATCC

TCCAGCTTCTGGTACTCTCCTAGAGACAGAAGCAGGCTGGAGGTAAGGCCTTTGAGCCCACAAAGCCTTATCAAGTGTCTTCCATCATGGA

TTCATTACAGCTTAATCAAAATAACGCCCCAGATACCAGCCCCTGTATGGCACTGGCATTGTCCCTGTGCCTAACACCAGCGTTTGAGGGG

CTGGCCTTCCTGCCCTACAGAGGTCTCTGCCGGCTCTTTCCTTGCTCAACCATGGCTGAAGGAAACCAGTGCAACAGCACTGGCTCTCTCC

AGGATCCAGAAGGGGTTTGGTCTGGGACTTCCTTGCTCTCCCTCTTCTCAAGTGCCTTAATAGTAGGGTAAGTTGTTAAGAGTGGGGGAGA

GCAGGCTGGCAGCTCTCCAGTCAGGAGGCATAGTTTTTACTGAACAATCAAAGCACTTGGACTCTTGCTCTTTCTACTCTGAACTAATAAA

TCTGTTGCCAAGCTGGCTAGAAAAAAAAAAAAAAAAAA

Human RELA proto-oncogene, NF-kB subunit (RELA), transcript variant 3, mRNA NM_001243984.1
(SEQ ID NO: 20)

AGCGCGCAGGCGCGGCCGGATTCCGGGCAGTGACGCGACGGCGGGCCGCGCGGCGCATTTCCGCCTCTGGCGAATGGCTCGTCTGTAGTGC

ACGCCGCGGGCCCAGCTGCGACCCCGGCCCCGCCCCCGGGACCCCGGCCATGGACGAACTGTTCCCCCTCATCTTCCCGGCAGAGCCAGCC

CAGGCCTCTGGCCCCTATGTGGAGATCATTGAGCAGCCCAAGCAGCGGGGCATGCGCTTCCGCTACAAGTGCGAGGGGCGCTCCGCGGGCA

GCATCCCAGGCGAGAGGAGCACAGATACCACCAAGACCCACCCCACCATCAAGATCAATGGCTACACAGGACCAGGGACAGTGCGCATCTC

CCTGGTCACCAAGGACCCTCCTCACCGGCCTCACCCCCACGAGCTTGTAGGAAAGGACTGCCGGGATGGCTTCTATGAGGCTGAGCTCTGC

CCGGACCGCTGCATCCACAGTTTCCAGAACCTGGGAATCCAGTGTGTGAAGAAGCGGGACCTGGAGCAGGCTATCAGTCAGCGCATCCAGA

CCAACAACAACCCCTTCCAAGTTCCTATAGAAGAGCAGCGTGGGGACTACGACCTGAATGCTGTGCGGCTCTGCTTCCAGGTGACAGTGCG

GGACCCATCAGGCAGGCCCCTCCGCCTGCCGCCTGTCCTTTCTCATCCCATCTTTGACAATCGTGCCCCCAACACTGCCGAGCTCAAGATC

TGCCGAGTGAACCGAAACTCTGGCAGCTGCCTCGGTGGGGATGAGATCTTCCTACTGTGTGACAAGGTGCAGAAAGAGGACATTGAGGTGT

ATTTCACGGGACCAGGCTGGGAGGCCCGAGGCTCCTTTTCGCAAGCTGATGTGCACCGACAAGTGGCCATTGTGTTCCGGACCCCTCCCTA

CGCAGACCCCAGCCTGCAGGCTCCTGTGCGTGTCTCCATGCAGCTGCGGCGGCCTTCCGACCGGGAGCTCAGTGAGCCCATGGAATTCCAG

TACCTGCCAGATACAGACGATCGTCACCGGATTGAGGAGAAACGTAAAAGGAGATATGAGACCTTCAAGAGCATCATGAAGAAGAGTCCTT

TCAGCGGACCCACCGACCCCCGGCCTCCACCTCGACGCATTGCTGTGCCTTCCCGCAGCTCAGCTTCTGTCCCCAAGCCAGCCCCAGGCCC

TCCTCAGGCTGTGGCCCCACCTGCCCCCAAGCCCACCCAGGCTGGGGAAGGAACGCTGTCAGAGGCCCTGCTGCAGCTGCAGTTTGATGAT

GAAGACCTGGGGGCCTTGCTTGGCAACAGCACAGACCCAGCTGTGTTCACAGACCTGGCATCCGTCGACAACTCCGAGTTTCAGCAGCTGC

TGAACCAGGGCATACCTGTGGCCCCCCACACAACTGAGCCCATGCTGATGGAGTACCCTGAGGCTATAACTCGCCTAGTGACAGGGGCCCA

GAGGCCCCCCGACCCAGCTCCTGCTCCACTGGGGGCCCCGGGGCTCCCCAATGGCCTCCTTTCAGGAGATGAAGACTTCTCCTCCATTGCG

GACATGGACTTCTCAGCCCTGCTGAGTCAGATCAGCTCCTAAGGGGGTGACGCCTGCCCTCCCCAGAGCACTGGGTTGCAGGGGATTGAAG

CCCTCCAAAAGCACTTACGGATTCTGGTGGGGTGTGTTCCAACTGCCCCCAACTTTGTGGATGTCTTCCTTGGAGGGGGGAGCCATATTTT

ATTCTTTTATTGTCAGTATCTGTATCTCTCTCTCTTTTTGGAGGTGCTTAAGCAGAAGCATTAACTTCTCTGGAAAGGGGGGAGCTGGGGA

AACTCAAACTTTTCCCCTGTCCTGATGGTCAGCTCCCTTCTCTGTAGGGAACTCTGGGGTCCCCCATCCCCATCCTCCAGCTTCTGGTACT

CTCCTAGAGACAGAAGCAGGCTGGAGGTAAGGCCTTTGAGCCCACAAAGCCTTATCAAGTGTCTTCCATCATGGATTCATTACAGCTTAAT

CAAAATAACGCCCCAGATACCAGCCCCTGTATGGCACTGGCATTGTCCCTGTGCCTAACACCAGCGTTTGAGGGGCTGGCCTTCCTGCCCT

ACAGAGGTCTCTGCCGGCTCTTTCCTTGCTCAACCATGGCTGAAGGAAACCAGTGCAACAGCACTGGCTCTCTCCAGGATCCAGAAGGGGT

-continued

TTGGTCTGGGACTTCCTTGCTCTCCCTCTTCTCAAGTGCCTTAATAGTAGGGTAAGTTGTTAAGAGTGGGGGAGAGCAGGCTGGCAGCTCT
CCAGTCAGGAGGCATAGTTTTTACTGAACAATCAAAGCACTTGGACTCTTGCTCTTTCTACTCTGAACTAATAAATCTGTTGCCAAGCTGG
CTAGAAAAAAAAAAAAAAAAAA

Human RELA proto-oncogene, NF-kB subunit (RELA), transcript variant 4, mRNA NM_001243985.1 (SEQ ID NO: 21)

AGCGCGCAGGCGCGGCCGGATTCCGGGCAGTGACGCGACGGCGGGCCGCGCGGCGCATTTCCGCCTCTGGCGAATGGCTCGTCTGTAGTGC
ACGCCGCGGGCCCAGCTGCGACCCCGGCCCCGCCCCCGGGACCCCGGCCATGGACGAACTGTTCCCCCTCATCTTCCCGGCAGAGCCAGCC
CAGGCCTCTGGCCCCTATGTGGAGATCATTGAGCAGCCCAAGCAGCGGGGCATGCGCTTCCGCTACAAGTGCGAGGGGCGCTCCGCGGGCA
GCATCCCAGGCGAGAGGAGCACAGATACCACCAAGACCCACCCCACCATCAAGATCAATGGCTACACAGGACCAGGGACAGTGCGCATCTC
CCTGGTCACCAAGGACCCTCCTCACCGGCCTCACCCCCACGAGCTTGTAGGAAAGGACTGCCGGGATGGCTTCTATGAGGCTGAGCTCTGC
CCGGACCGCTGCATCCACAGTTTCCAGAACCTGGGAATCCAGTGTGTGAAGAAGCGGGACCTGGAGCAGGCTATCAGTCAGCGCATCCAGA
CCAACAACAACCCCTTCCAAGTTCCTATAGAAGAGCAGCGTGGGGACTACGACCTGAATGCTGTGCGGCTCTGCTTCCAGGTGACAGTGCG
GGACCCATCAGGCAGGCCCCTCCGCCTGCCGCCTGTCCTTTCTCATCCCATCTTTGACAATCGTGCCCCCAACACTGCCGAGCTCAAGATC
TGCCGAGTGAACCGAAACTCTGGCAGCTGCCTCGGTGGGGATGAGATCTTCCTACTGTGTGACAAGGTGCAGAAAGAGGACATTGAGGTGT
ATTTCACGGGACCAGGCTGGGAGGCCCGAGGCTCCTTTTCGCAAGCTGATGTGCACCGACAAGTGGCCATTGTGTTCCGGACCCCTCCCTA
CGCAGACCCCAGCCTGCAGGCTCCTGTGCGTGTCTCCATGCAGCTGCGGCGGCCTTCCGACCGGGAGCTCAGTGAGCCCATGGAATTCCAG
TACCTGCCAGATACAGACGATCGTCACCGGATTGAGGAGAAACGTAAAAGGAGATATGAGACCTTCAAGAGCATCATGAAGAAGAGTCCTT
TCAGCGGACCCACCGACCCCCGGCCTCCACCTCGACGCATTGCTGTGCCTTCCCGCAGCTCAGCTTCTGTCCCCAAGCCAGCACCCCAGCC
CTATCCCTTTACGTCATCCCTGAGCACCATCAACTATGATGAGTTTCCCACCATGGTGTTTCCTTCTGGGCAGATCAGCCAGGCCTCGGCC
TTGGCCCCGGCCCCTCCCCAAGTCCTGCCCCAGGCTCCAGCCCCTGCCCCTGCTCCAGCCATGGTATCAGCTCTGGCCCAGAGGCCCCCCG
ACCCAGCTCCTGCTCCACTGGGGGCCCCGGGGCTCCCCAATGGCCTCCTTTCAGGAGATGAAGACTTCTCCTCCATTGCGGACATGGACTT
CTCAGCCCTGCTGAGTCAGATCAGCTCCTAAGGGGGTGACGCCTGCCCTCCCCAGAGCACTGGGTTGCAGGGGATTGAAGCCCTCCAAAAG
CACTTACGGATTCTGGTGGGGTGTGTTCCAACTGCCCCCAACTTTGTGGATGTCTTCCTTGGAGGGGGGAGCCATATTTTATTCTTTTATT
GTCAGTATCTGTATCTCTCTCTCTTTTTGGAGGTGCTTAAGCAGAAGCATTAACTTCTCTGGAAAGGGGGGAGCTGGGGAAACTCAAACTT
TTCCCCTGTCCTGATGGTCAGCTCCCTTCTCTGTAGGGAACTCTGGGGTCCCCCATCCCCATCCTCCAGCTTCTGGTACTCTCCTAGAGAC
AGAAGCAGGCTGGAGGTAAGGCCTTTGAGCCCACAAAGCCTTATCAAGTGTCTTCCATCATGGATTCATTACAGCTTAATCAAAATAACGC
CCCAGATACCAGCCCCTGTATGGCACTGGCATTGTCCCTGTGCCTAACACCAGCGTTTGAGGGGCTGGCCTTCCTGCCCTACAGAGGTCTC
TGCCGGCTCTTTCCTTGCTCAACCATGGCTGAAGGAAACCAGTGCAACAGCACTGGCTCTCTCCAGGATCCAGAAGGGGTTTGGTCTGGGA
CTTCCTTGCTCTCCCTCTTCTCAAGTGCCTTAATAGTAGGGTAAGTTGTTAAGAGTGGGGGAGAGCAGGCTGGCAGCTCTCCAGTCAGGAG
GCATAGTTTTTACTGAACAATCAAAGCACTTGGACTCTTGCTCTTTCTACTCTGAACTAATAAATCTGTTGCCAAGCTGGCTAGAAAAAAA
AAAAAAAAAAA

Human RELA proto-oncogene, NF-kB subunit (RELA), transcript variant X1, mRNA XM_011545206.1 (SEQ ID NO: 22)

ATTCCGGGCAGTGACGCGACGGCGGGCCGCGCGGCGCATTTCCGCCTCTGGCGAATGGCTCGTCTGTAGTGCACGCCGCGGGCCCAGCTGC
GACCCCGGCCCCGCCCCCGGGACCCCGGCCATGGACGAACTGTTCCCCCTCATCTTCCCGGCAGAGCCAGCCCAGGCCTCTGGCCCCTATG
TGGAGATCATTGAGCAGCCCAAGCAGCGGGGCATGCGCTTCCGCTACAAGTGCGAGGGGCGCTCCGCGGGCAGCATCCCAGGCGAGAGGAG
CACAGATACCACCAAGACCCACCCCACCATCAAGATCAATGGCTACACAGGACCAGGGACAGTGCGCATCTCCCTGGTCACCAAGGACCCT
CCTCACCGGCCTCACCCCCACGAGCTTGTAGGAAAGGACTGCCGGGATGGCTTCTATGAGGCTGAGCTCTGCCCGGACCGCTGCATCCACA
GTTTCCAGAACCTGGGAATCCAGTGTGTGAAGAAGCGGGACCTGGAGCAGGCTATCAGTCAGCGCATCCAGACCAACAACAACCCCTTCCA
AGTTCCTATAGAAGAGCAGCGTGGGGACTACGACCTGAATGCTGTGCGGCTCTGCTTCCAGGTGACAGTGCGGGACCCATCAGGCAGGCCC
CTCCGCCTGCCGCCTGTCCTTTCTCATCCCATCTTTGACAATCGTGCCCCCAACACTGCCGAGCTCAAGATCTGCCGAGTGAACCGAAACT
CTGGCAGCTGCCTCGGTGGGGATGAGATCTTCCTACTGTGTGAGAAGGTGCAGAAAGACGATCGTCACCGGATTGAGGAGAAACGTAAAAG

-continued

GAGATATGAGACCTTCAAGAGCATCATGAAGAAGAGTCCTTTCAGCGGACCCACCGACCCCCGGCCTCCACCTCGACGCATTGCTGTGCCT

TCCCGCAGCTCAGCTTCTGTCCCCAAGCCAGCACCCCAGCCCTATCCCTTTACGTCATCCCTGAGCACCATCAACTATGATGAGTTTCCCA

CCATGGTGTTTCCTTCTGGGCAGATCAGCCAGGCCTCGGCCTTGGCCCCGGCCCCTCCCCAAGTCCTGCCCCAGGCTCCAGCCCCTGCCCC

TGCTCCAGCCATGGTATCAGCTCTGGCCCAGGCCCCAGCCCCTGTCCCAGTCCTAGCCCCAGGCCCTCCTCAGGCTGTGGCCCCACCTGCC

CCCAAGCCCACCCAGGCTGGGGAAGGAACGCTGTCAGAGGCCCTGCTGCAGCTGCAGTTTGATGATGAAGACCTGGGGGCCTTGCTTGGCA

ACAGCACAGACCCAGCTGTGTTCACAGACCTGGCATCCGTCGACAACTCCGAGTTTCAGCAGCTGCTGAACCAGGGCATACCTGTGGCCCC

CCACACAACTGAGCCCATGCTGATGGAGTACCCTGAGGCTATAACTCGCCTAGTGACAGGGGCCCAGAGGCCCCCCGACCCAGCTCCTGCT

CCACTGGGGGCCCCGGGGCTCCCCAATGGCCTCCTTTCAGGAGATGAAGACTTCTCCTCCATTGCGGACATGGACTTCTCAGCCCTGCTGA

GTCAGATCAGCTCCTAAGGGGGTGACGCCTGCCCTCCCCAGAGCACTGGGTTGCAGGGGATTGAAGCCCTCCAAAAGCACTTACGGATTCT

GGTGGGGTGTGTTCCAACTGCCCCCAACTTTGTGGATGTCTTCCTTGGAGGGGGGAGCCATATTTTATTCTTTTATTGTCAGTATCTGTAT

CTCTCTCTCTTTTTGGAGGTGCTTAAGCAGAAGCATTAACTTCTCTGGAAAGGGGGGAGCTGGGGAAACTCAAACTTTTCCCCTGTCCTGA

TGGTCAGCTCCCTTCTCTGTAGGGAACTCTGGGGTCCCCCATCCCCATCCTCCAGCTTCTGGTACTCTCCTAGAGACAGAAGCAGGCTGGA

GGTAAGGCCTTTGAGCCCACAAAGCCTTATCAAGTGTCTTCCATCATGGATTCATTACAGCTTAATCAAAATAACGCCCCAGATACCAGCC

CCTGTATGGCACTGGCATTGTCCCTGTGCCTAACACCAGCGTTTGAGGGGCTGGCCTTCCTGCCCTACAGAGGTCTCTGCCGGCTCTTTCC

TTGCTCAACCATGGCTGAAGGAAACCAGTGCAACAGCACTGGCTCTCTCCAGGATCCAGAAGGGGTTTGGTCTGGGACTTCCTTGCTCTCC

CTCTTCTCAAGTGCCTTAATAGTAGGGTAAGTTGTTAAGAGTGGGGGAGAGCAGGCTGGCAGCTCTCCAGTCAGGAGGCATAGTTTTTACT

GAACAATCAAAGCACTTGGACTCTTGCTCTTTCTACTCTGAACTAATAAATCTGTTGCCAAGCTGG

Human RELA proto-oncogene, NF-kB subunit (RELA), transcript variant X2, mRNA XM_011545207.1 (SEQ ID NO: 23)

ATTCCGGGCAGTGACGCGACGGCGGGCCGCGCGGCGCATTTCCGCCTCTGGCGAATGGCTCGTCTGTAGTGCACGCCGCGGGCCCAGCTGC

GACCCCGGCCCCGCCCCCGGGACCCCGGCCATGGACGAACTGTTCCCCCTCATCTTCCCGGCAGAGCCAGCCCAGGCCTCTGGCCCCTATG

TGGAGATCATTGAGCAGCCCAAGCAGCGGGGCATGCGCTTCCGCTACAAGTGCGAGGGGCGCTCCGCGGGCAGCATCCCAGGCGAGAGGAG

CACAGATACCACCAAGACCCACCCCACCATCAAGATCAATGGCTACACAGGACCAGGGACAGTGCGCATCTCCCTGGTCACCAAGGACCCT

CCTCACCGGCCTCACCCCCACGAGCTTGTAGGAAAGGACTGCCGGGATGGCTTCTATGAGGCTGAGCTCTGCCCGGACCGCTGCATCCACA

GTTTCCAGAACCTGGGAATCCAGTGTGTGAAGAAGCGGGACCTGGAGCAGGCTATCAGTCAGCGCATCCAGACCAACAACAACCCCTTCCA

AGTTCCTATAGAAGAGCAGCGTGGGGACTACGACCTGAATGCTGTGCGGCTCTGCTTCCAGGTGACAGTGCGGGACCCATCAGGCAGGCCC

CTCCGCCTGCCGCCTGTCCTTTCTCATCCCATCTTTGACAATCACGATCGTCACCGGATTGAGGAGAAACGTAAAAGGACATATGAGACCT

TCAAGAGCATCATGAAGAAGAGTCCTTTCAGCGGACCCACCGACCCCCGGCCTCCACCTCGACGCATTGCTGTGCCTTCCCGCAGCTCAGC

TTCTGTCCCCAAGCCAGCACCCCAGCCCTATCCCTTTACGTCATCCCTGAGCACCATCAACTATGATGAGTTTCCCACCATGGTGTTTCCT

TCTGGGCAGATCAGCCAGGCCTCGGCCTTGGCCCCGGCCCCTCCCCAAGTCCTGCCCCAGGCTCCAGCCCCTGCCCCTGCTCCAGCCATGG

TATCAGCTCTGGCCCAGGCCCCAGCCCCTGTCCCAGTCCTAGCCCCAGGCCCTCCTCAGGCTGTGGCCCCACCTGCCCCCAAGCCCACCCA

GGCTGGGGAAGGAACGCTGTCAGAGGCCCTGCTGCAGCTGCAGTTTGATGATGAAGACCTGGGGGCCTTGCTTGGCAACAGCACAGACCCA

GCTGTGTTCACAGACCTGGCATCCGTCGACAACTCCGAGTTTCAGCAGCTGCTGAACCAGGGCATACCTGTGGCCCCCCACACAACTGAGC

CCATGCTGATGGAGTACCCTGAGGCTATAACTCGCCTAGTGACAGGGGCCCAGAGGCCCCCCGACCCAGCTCCTGCTCCACTGGGGGCCCC

GGGGCTCCCCAATGGCCTCCTTTCAGGAGATGAAGACTTCTCCTCCATTGCGGACATGGACTTCTCAGCCCTGCTGAGTCAGATCAGCTCC

TAAGGGGGTGACGCCTGCCCTCCCCAGAGCACTGGGTTGCAGGGGATTGAAGCCCTCCAAAAGCACTTACGGATTCTGGTGGGGTGTGTTC

CAACTGCCCCCAACTTTGTGGATGTCTTCCTTGGAGGGGGGAGCCATATTTTATTCTTTTATTGTCAGTATCTGTATCTCTCTCTCTTTTT

GGAGGTGCTTAAGCAGAAGCATTAACTTCTCTGGAAAGGGGGGAGCTGGGGAAACTCAAACTTTTCCCCTGTCCTGATGGTCAGCTCCCTT

CTCTGTAGGGAACTCTGGGGTCCCCCATCCCCATCCTCCAGCTTCTGGTACTCTCCTAGAGACAGAAGCAGGCTGGAGGTAAGGCCTTTGA

GCCCACAAAGCCTTATCAAGTGTCTTCCATCATGGATTCATTACAGCTTAATCAAAATAACGCCCCAGATACCAGCCCCTGTATGGCACTG

GCATTGTCCCTGTGCCTAACACCAGCGTTTGAGGGGCTGGCCTTCCTGCCCTACAGAGGTCTCTGCCGGCTCTTTCCTTGCTCAACCATGG

CTGAAGGAAACCAGTGCAACAGCACTGGCTCTCTCCAGGATCCAGAAGGGGTTTGGTCTGGGACTTCCTTGCTCTCCCTCTTCTCAAGTGC

-continued

CTTAATAGTAGGGTAAGTTGTTAAGAGTGGGGGAGAGCAGGCTGGCAGCTCTCCAGTCAGGAGGCATAGTTTTTACTGAACAATCAAAGCA

CTTGGACTCTTGCTCTTTCTACTCTGAACTAATAAATCTGTTGCCAAGCTGG

In some embodiments, the nucleic acid sequence encoding Rel-A (p65), as described herein, is at least 80% identical to the sequence of SEQ ID NO: 18, SEQ ID NO: 19, SEQ ID NO: 20. SEQ ID NO: 21, SEQ ID NO: 22, or SEQ ID NO: 23. In some embodiments, the nucleic acid sequence encoding Rel-A (p65) is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 18, SEQ ID NO: 19, SEQ ID NO: 20, SEQ ID NO: 21, SEQ ID NO: 22, or SEQ ID NO: 23. In some embodiments, the nucleic acid encoding Rel-A (p65), as described herein, can vary from the sequence of SEQ ID NO: 18, SEQ ID NO: 19, SEQ ID NO: 20, SEQ ID NO: 21, SEQ ID NO: 22, or SEQ ID NO: 23 by 1, 2, 3,4, 5, 6,7, 8, 9, 10, 11, 12, 13, 14, 15, 16, 17, 18, 19, 20, 21, 22, 23, 24, 25, 26, 27, 28, 29, or 30 or more nucleotides.

"Linkers" are short amino acid sequences created in nature to separate multiple domains in a single protein, and, generally, can be classified into three groups: flexible, rigid and cleavable. Chen, X., et al., 2013, Adv. Drug Deliv. Rev., 65, 1357-1369. Linkers can be natural or synthetic. A number of linkers are employed to realize the subject invention including "flexible linkers." The latter are rich in glycine. Klein et al., Protein Engineering, Design & Selection Vol. 27, No. 10, pp. 325-330, 2014; Priyanka et al., Protein Sci., 2013 February; 22(2): 153-167.

In some embodiments, the linker is a synthetic linker. A synthetic linker can have a length of from about 10 amino acids to about 200 amino acids, e.g., from 10 to 25 amino acids, from 25 to 50 amino acids, from 50 to 75 amino acids, from 75 to 100 amino acids, from 100 to 125 amino acids, from 125 to 150 amino acids, from 150 to 175 amino acids, or from 175 to 200 amino acids. A synthetic linker can have a length of from 10 to 30 amino acids, e.g., 10, 11, 12, 13, 14, 15, 16, 17, 18, 19, 20, 21, 22, 23, 24, 25, 26, 27, 28, 29, or 30 amino acids. A synthetic linker can have a length of from 30 to 50 amino acids, e.g., from 30 to 35 amino acids, from 35 to 40 amino acids, from 40 to 45 amino acids, or from 45 to 50 amino acids.

In some embodiments, the linker is a flexible linker. In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences. In some embodiments, the linker is GSAAAGGSGGSGGS (SEQ ID NO: 3). In some embodiments, the linker is GGGSGGGS (SEQ ID NO: 4).

"Native or natural Notch" is meant to encompass all known forms of Notch receptors. In humans, 4 forms of Notch are known. Joanna Pancewicz: BMC Cancer 11(1): 502. November 2011. The human Notch family includes four receptors and five ligands.

In some embodiments, the chimeric Notch receptor polypeptide contains all or a portion of human Notch1, Notch2, Notch3, or Notch4. In some embodiments, the chimeric Notch receptor polypeptide contains all or a portion of SEQ ID NO: 24, SEQ ID NO: 25, SEQ ID NO: 26, SEQ ID NO: 27, or SEQ ID NO: 28. In some embodiments, a "portion" of Notch comprises the three NLR domains, the transmembrane domain, and a short cytosolic fragment including the native Nuclear Localization Sequence (NLS) of Notch.

Human neurogenic locus notch homolog protein 1 preprotein NP_060087.3
(SEQ ID NO: 24)

MPPLLAPLLCLALLPALAARGPRCSQPGETCLNGGKCEAANGTEACVCGGAFVGPRCQDPNPCLSTPCKNAGTCHVVDRRG

VADYACSCALGFSGPLCLTPLDNACLTNPCRNGGTCDLLTLTEYKCRCPPGWSGKSCQQADPCASNPCANGGQCLPFEASY

ICHCPPSFHGPTCRQDVNECGQKPGLCRHGGTCHNEVGSYRCVCRATHTGPNCERPYVPCSPSPCQNGGTCRPTGDVTHEC

ACLPGFTGQNCEENIDDCPGNNCKNGGACVDGVNTYNCRCPPEWTGQYCTEDVDECQLMPNACQNGGTCHNTHGGYNCVCV

NGWTGEDCSENIDDCASAACFHGATCHDRVASFYCECPHGRTGLLCHLNDACISNPCNEGSNCDTNPVNGKAICTCPSGYT

GPACSQDVDECSLGANPCEHAGKCINTLGSFECQCLQGYTGPRCEIDVNECVSNPCQNDATCLDQIGEFQCICMPGYEGVH

CEVNTDECASSPCLHNGRCLDKINEFQCECPTGFTGHLCQYDVDECASTPCKNGAKCLDGPNTYTCVCTEGYTGTHCEVDI

DECDPDPCHYGSCKDGVATFTCLCRPGYTGHHCETNINECSSQPCRHGGTCQDRDNAYLCFCLKGTTGPNCEINLDDCASS

PCDSGTCLDKIDGYECACEPGYTGSMCNINIDECAGNPCHNGGTCEDGINGFTCRCPEGYHDPTCLSEVNECNSNPCVHGA

CRDSLNGYKCDCDPGWSGTNCDINNNECESNPCVNGGTCKDMTSGYVCTCREGFSGPNCQTNINECASNPCLNQGTCIDDV

AGYKCNCLLPYTGATCEVVLAPCAPSPCRNGGECRQSEDYESFSCVCPTGWQGQTCEVDINECVLSPCRHGASCQNTHGGY

RCHCQAGYSGRNCETDIDDCRPNPCHNGGSCTDGINTAFCDCLPGFRGTFCEEDINECASDPCRNGANCTDCVDSYTCTCP

AGFSGIHCENNTPDCTESSCFNGGTCVDGINSFTCLCPPGFTGSYCQHDVNECDSQPCLHGGTCQDGCGSYRCTCPQGYTG

PNCQNLVHWCDSSPCKNGGKCWQTHTQYRCECPSGWTGLYCDVPSVSCEVAAQRQGVDVARLCQHGGLCVDAGNTHHCRCQ

-continued

AGYTGSYCEDLVDECSPSPCQNGATCTDYLGGYSCKCVAGYHGVNCSEEIDECLSHPCQNGGTCLDLPNTYKCSCPRGTQG

VHCEINVDDCNPPVDPVSRSPKCFNNGTCVDQVGGYSCTCPPGFVGERCEGDVNECLSNPCDARGTQNCVQRVNDFHCECR

AGHTGRRCESVINGCKGKPCKNGGTCAVASNTARGFICKCPAGFEGATCENDARTCGSLRCLNGGTCISGPRSPTCLCLGP

FTGPECQFPASSPCLGGNPCYNQGTCEPTSESPFYRCLCPAKFNGLLCHILDYSFGGGAGRDIPPPLIEEACELPECQEDA

GNKVCSLQCNNHACGWDGGDCSLNFNDPWKNCTQSLQCWKYFSDGHCDSQCNSAGCLFDGFDCQRAEGQCNPLYDQYCKDH

FSDGHCDQGCNSAECEWDGLDCAEHVPERLAAGTLVVVVLMPPEQLRNSSFHFLRELSRVLHTNVVFKRDAHGQQMIFPYY

GREEELRKHPIKRAAEGWAAPDALLGQVKASLLPGGSEGGRRRRELDPMDVRGSIVYLEIDNRQCVQASSQCFQSATDVAA

FLGALASLGSLNIPYKIEAVQSETVEPPPPAQLHFMYVAAAAFVLLFFVGCGVLLSRKRRRQHGQLWFPEGFKVSEASKKK

RREPLGEDSVGLKPLKNASDGALMDDNQNEWGDEDLETKKFRFEEPVVLPDLDDQTDHRQWTQQHLDAADLRMSAMAPTPP

QGEVDADCMDVNVRGPDGFTPLMIASCSGGGLETGNSEEEEDAPAVISDFIYQGASLHNQTDRTGETALHLAARYSRSDAA

KRLLEASADANIQDNMGRTPLHAAVSADAQGVFQILIRNRATDLDARMHDGTTPLILAARLAVEGMLEDLINSHADVNAVD

DLGKSALHWAAAVNNVDAAVVLLKNGANKDMQNNREETPLFLAAREGSYETAKVLLDHFANRDITDHMDRLPRDIAQERMH

HDIVRLLDEYNLVRSPQLHGAPLGGTPTLSPPLCSPNGYLGSLKPGVQGKKVRKPSSKGLACGSKEAKDLKARRKKSQDGK

GCLLDSSGMLSPVDSLESPHGYLSDVASPPLLPSPFQQSPSVPLNHLPGMPDTHLGIGHLNVAAKPEMAALGGGGRLAFET

GPPRLSHLPVASGTSTVLGSSSGGALNFTVGGSTSLNGQCEWLSRLQSGMVPNQYNPLRGSVAPGPLSTQAPSLQHGMVGP

LHSSLAASALSQMMSYQGLPSTRLATQPHLVQTQQVQPQNLQMQQQNLQPANIQQQQSLQPPPPPPQPHLGVSSAASGHLG

RSFLSGEPSQADVQPLGPSSLAVHTILPQESPALPTSLPSSLVPPVTAAQFLTPPSQHSYSSPVDNTPSHQLQVPEHPFLT

PSPESPDQWSSSSPHSNVSDWSEGVSSPPTSMQSQIARIPEAFK

Human neurogenic locus notch homolog protein 2 isoform 1 preprotein NP_077719.2 (SEQ ID NO: 25)

MPALRPALLWALLALWLCCAAPAHALQCRDGYEPCVNEGMCVTYHNGTGYCKCPEGFLGEYCQHRDPCEKNRCQNGGTCVA

QAMLGKATCRCASGFTGEDCQYSTSHPCFVSRPCLNGGTCHMLSRDTYECTCQVGFTGKECQWTDACLSHPCANGSTCTTV

ANQFSCKCLTGFTGQKCETDVNECDIPGHCQHGGTCLNLPGSYQCQCPQGETGQYCDSLYVPCAPSPCVNGGTCRQTGDFT

FECNCLPGFEGSTCERNIDDCPNHRCQNGGVCVDGVNTYNCRCPPQWTGQFCTEDVDECLLQPNACQNGGTCANRNGGYGC

VCVNGWSGDDCSENIDDCAFASCTPGSTCIDRVASFSCMCPEGKAGLLCHLDDACISNPCHKGALCDTNPLNGQYICTCPQ

GYKGADCTEDVDECAMANSNPCEHAGKCVNTDGAFHCECLKGYAGPRCEMDINECHSDPCQNDATCLDKIGGFTCLCMPGF

KGVHCELEINECQSNPCVNNGQCVDKVNRFQCLCPPGFTGPVCQIDIDDCSSTPCLNGAKCIDHPNGYECQCATGFTGVLC

EENIDNCDPDPCHHGQCQDGIDSYTCICNPGYMGAICSDQIDECYSSPCLNDGRCIDLVNGYQCNCQPGTSGVNCEINFDD

CASNPCIHGICMDGINRYSCVCSPGFTGQRCNIDIDECASNPCRKGATCINGVNGFRCICPEGPHHPSCYSQVNECLSNPC

IHGNCTGGLSGYKCLCDAGWVGINCEVDKNECLSNPCQNGGTCDNLVNGYRCTCKKGFKGYNCQVNIDECASNPCLNQGTC

FDDISGYTCHCVLPYTGKNCQTVLAPCSPNPCENAAVCKESPNFESYTCLCAPGWQGQRCTIDIDECISKPCMNHGLCHNT

QGSYMCECPPGFSGMDCEEDIDDCLANPCQNGGSCMDGVNTFSCLCLPGFTGDKCQTDMNECLSEPCKNGGTCSDYVNSYT

CKCQAGFDGVHCENNINECTESSCFNGGTCVDGINSFSCLCPVGFTGSFCLHEINECSSHPCLNEGTCVDGLGTYRCSCPL

GYTGKNCQTLVNLCSRSPCKNKGTCVQKKAESQCLCPSGWAGAYCDVPNVSCDIAASRRGVLVEHLCQHSGVCINAGNTHY

CQCPLGYTGSYCEEQLDECASNPCQHGATCSDFIGGYRCECVPGYQGVNCEYEVDECQNQPCQNGGTCIDLVNHFKCSCPP

GTRGLLCEENIDDCARGPHCLNGGQCMDRIGGYSCRCLPGFAGERCEGDINECLSNPCSSEGSLDCIQLTNDYLCVCRSAF

TGRHCETFVDVCPQMPCLNGGTCAVASNMPDGFICRCPPGFSGARCQSSCGQVKCRKGEQCVHTASGPRCFCPSPRDCESG

CASSPCQHGGSCHPQRQPPYYSCQCAPPFSGSRCELYTAPPSTPPATCLSQYCADKARDGVCDEACNSHACQWDGGDCSLT

MENPWANCSSPLPCWDYINNQCDELCNTVECLFDNFECQGNSKTCKYDKYCADHFKDNHCDQGCNSEECGWDGLDCAADQP

ENLAEGTLVIVVLMPPEQLLQDARSFLRALGTLLHTNLRIKRDSQGELMVYPYYGEKSAAMKKQRMTRRSLPGEQEQEVAG

SKVFLEIDNRQCVQDSDHCFKNTDAAAALLASHAIQGTLSYPLVSVVSESLTPERTQLLYLLAVAVVIILFIILLGVIMAK

-continued

RKRKHGSLWLPEGFTLRRDASNHKRREPVGQDAVGLKNLSVQVSEANLIGTGTSEHWVDDEGPQPKKVKAEDEALLSEEDD

PIDRRPWTQQHLEAADIRRTPSLALTPPQAEQEVDVLDVNVRGPDGCTPLMLASLRGGSSDLSDEDEDAEDSSANIITDLV

YQGASLQAQTDRTGEMALHLAARYSRADAAKRLLDAGADANAQDNMGRCPLHAAVAADAQGVFQILIRNRVTDLDARMNDG

TTPLILAARLAVEGMVAELINCQADVNAVDDHGKSALHWAAAVNNVEATLLLLKNGANRDMQDNKEETPLFLAAREGSYEA

AKILLDHFANRDITDHMDRLPRDVARDRMHHDIVRLLDEYNVTPSPPGTVLTSALSPVICGPNRSFLSLKHTPMGKKSRRP

SAKSTMPTSLPNLAKEAKDAKGSRRKKSLSEKVQLSESSVTLSPVDSLESPHTYVSDTTSSPMITSPGILQASPNPMLATA

APPAPVHAQHALSFSNLHEMQPLAHGASTVLPSVSQLLSHHHIVSPGSGSAGSLSRLHPVPVPADWMNRMEVNETQYNEMF

GMVLAPAEGTHPGIAPQSRPPEGKHITTPREPLPPIVTFQLIPKGSIAQPAGAPQPQSTCPPAVAGPLPTMYQIPEMARLP

SVAFPTAMMPQQDGQVAQTILPAYHPFPASVGKYPTPPSQHSYASSNAAERTPSHSGHLQGEHPYLTPSPESPDQWSSSSP

HSASDWSDVTTSPTPGGAGGGQRGPGTHMSEPPHNNMQVYA

Human neurogenic locus notch homolog protein 2 isoform 2 precursor NP_001186930.1
(SEQ ID NO: 26)

MPALRPALLWALLALWLCCAAPAHALQCRDGYEPCVNEGMCVTYHNGTGYCKCPEGFLGEYCQHRDPCEKNRCQNGGTCVA

QAMLGKATCRCASGFTGEDCQYSTSHPCFVSRPCLNGGTCHMLSRDTYECTCQVGFTGKECQWTDACLSHPCANGSTCTTV

ANQFSCKCLTGFTGQKCETDVNECDIPGHCQHGGTCLNLPGSYQCQCPQGFTGQYCDSLYVPCAPSPCVNGGTCRQTGDFT

FECNCLPGFEGSTCERNIDDCPNHRCQNGGVCVDGVNTYNCRCPPQWTGQFCTEDVDECLLQPNACQNGGTCANRNGGYGC

VCVNGWSGDDCSENIDDCAFASCTPGSTCIDRVASFSCMCPEGKAGLLCHLDDACISNPCHKGALCDTNPLNGQYICTCPQ

GYKGADCTEDVDECAMANSNPCEHAGKCVNTDGAFHCECLKGYAGPRCEMDINECHSDPCQNDATCLDKIGGFTCLCMPGF

KGVHCELEINECQSNPCVNNGQCVDKVNRFQCLCPPGFTGPVCQIDIDDCSSTPCLNGAKCIDHPNGYECQCATGFTGVLC

EENIDNCDPDPCHHGQCQDGIDSYTCICNPGYMGAICSDQIDECYSSPCLNDGRCIDLVNGYQCNCQPGTSGVNCEINFDD

CASNPCIHGICMDGINRYSCVCSPGFTGQRCNIDIDECASNPCRKGATCINGVNGFRCICPEGPHHPSCYSQVNECLSNPC

IHGNCTGGLSGYKCLCDAGWVGINCEVDKNECLSNPCQNGGTCDNLVNGYRCTCKKGFKGYNCQVNIDECASNPCLNQGTC

FDDISGYTCHCVLPYTGKNCQTVLAPCSPNPCENAAVCKESPNFESYTCLCAPGWQGQRCTIDIDECISKPCMNHGLCHNT

AGSYMCECPPGFSGMDCEEDIDDCLANPCQNGGSCMDGVNTFSCLCLPGFTGDKCQTDMNECLSEPCKNGGTCSDYVNSYT

CKCQAGFDGVHCENNINECTESSCFNGGTCVDGINSFSCLCPVGFTGSFCLHEINECSSHPCLNEGTCVDGLGTYRCSCPL

GYTGKNCQTLVNLCSRSPCKNKGTCVQKKAESQCLCPSGWAGAYCDVPNVSCDIAASRRGVLVEHLCQHSGVCINAGNTHY

CQCPLGYTGSYCEEQLDECASNPCQHGATCSDFIGGYRCECVPGYQGVNCEYEVDECQNQPCQNGGTCIDLVNHFKCSCPP

GTRGMKSSLSIFHPGHCLKL

Human neurogenic locus notch homolog protein 3 precursor NP_000426.2
(SEQ ID NO: 27)

MGPGARGRRRRRRPMSPPPPPPPVRALPLLLLLAGPGAAAPPCLDGSPCANGGRCTQLPSREAACLCPPGWVGERCQLEDP

CHSGPCAGRGVCQSSVVAGTARFSCRCPRGFRGPDCSLPDPCLSSPCAHGARCSVGPDGRFLCSCPPGYQGRSCRSDVDEC

RVGEPCRHGGTCLNTPGSFRCQCPAGYTGPLCENPAVPCAPSPCRNGGTCRQSGDLTYDCACLPGFEGQNCEVNVDDCPGH

RCLNGGTCVDGVNTYNCQCPPEWTGQFCTEDVDECQLQPNACHNGGTCFNTLGGHSCVCVNGWTGESCSQNIDDCATAVCF

HGATCHDRVASFYCACPMGKTGLLCHLDDACVSNPCHEDAICDTNPVNGRAICTCPPGFTGGACDQDVDECSIGANPCEHL

GRCVNTQGSFLCQCGRGYTGPRCETDVNECLSGPCRNQATCLDRIGQFTCICMAGFTGTYCEVDIDECQSSPCVNGGVCKD

RVNGFSCTCPSGFSGSTCQLDVDECASTPCRNGAKCVDQPDGYECRCAEGFEGTLCDRNVDDCSPDPCHHGRCVDGIASFS

VACAPGYTGTRCESQVDECRSQPCRHGGKCLDLVDKYLCRCPSGTTGVNCEVNIDDCASNPCTFGVCRDGINRYDCVCQPG

FTGPLCNVEINECASSPCGEGGSCVDGENGFRCLCPPGSLPPLCLPPSHPCAHEPCSHGICYDAPGGFRCVCEPGWSGPRC

SQSLARDACESQPCRAGGTCSSDGMGFHCTCPPGVQGRQCELLSPCTPNPCEHGGRCESAPGQLPVCSCPQGWQGPRCQQD

VDECAGPAPCGPHGICTNLAGSFSCTCHGGYTGPSCDQDINDCDPNPCLNGGSCQDGVGSFSCSCLPGFAGPRCARDVDEC

LSNPCGPGTCTDHVASFTCTCPPGYGGFHCEQDLPDCSPSSCFNGGTCVDGVNSFSCLCRPGYTGAHCQHEADPCLSRPCL

HGGVCSAAHPGFRCTCLESFTGPQCQTLVDWCSRQPCQNGGRCVQTGAYCLCPPGWSGRLCDIRSLPCREAAAQIGVRLEQ

-continued

LCQAGGQCVDEDSSHYCVCPEGRTGSHCEQEVDPCLAQPCQHGGTCRGYMGGYMCECLPGYNGDNCEDDVDECASQPCQHG

GSCIDLVARYLCSCPPGTLGVLCEINEDDCGPGPPLDSGPRCLHNGTCVDLVGGFRCTCPPGYTGLRCEADINECRSGACH

AAHTRDCLQDPGGGFRCLCHAGFSGPRCQTVLSPCESQPCQHGGQCRPSPGPGGGLTFTCHCAQPFWGPRCERVARSCREL

QCPVGVPCQQTPRGPRCACPPGLSGPSCRSFPGSPPGASNASCAAAPCLHGGSCRPAPLAPFFRCACAQGWTGPRCEAPAA

APEVSEEPRCPRAACQAKRGDQRCDRECNSPGCGWDGGDCSLSVGDPWRQCEALQCWRLFNNSRCDPACSSPACLYDNFDC

HAGGRERTCNPVYEKYCADHFADGRCDQGCNTEECGWDGLDCASEVPALLARGVLVLTVLLPPEELLRSSADFLQRLSAIL

RTSLRFRLDAHGQAMVFPYHRPSPGSEPRARRELAPEVIGSVVMLEIDNRLCLQSPENDHCFPDAQSAADYLGALSAVERL

DFPYPLRDVRGEPLEPPEPSVPLLPLLVAGAVLLLVILVLGVMVARRKREHSTLWFPEGFSLHKDVASGHKGRREPVGQDA

LGMKNMAKGESLMGEVATDWMDTECPEAKRLKVEEPGMGAEEAVDCRQWTQHHLVAADIRVAPAMALTPPQGDADADGMDV

NVRGPDGFTPLMLASFCGGALEPMPTEEDEADDTSASIISDLICQGAQLGARTDRTGETALHLAARYARADAAKRLLDAGA

DTNAQDHSGRTPLHTAVTADAQGVFQILIRNRSTDLDARMADGSTALILAARLAVEGMVEELIASHADVNAVDELGKSALH

WAAAVNNVEATLALLKNGANKDMQDSKEETPLFLAAREGSYEAAKLLLDHEANREITDHLDRLPRDVAQERLHQDIVRLLD

QPSGPRSPPGPHGLGPLLCPPGAFLPGLKAAQSGSKKSRRPPGKAGLGPQGPRGRGKKLTLACPGPLADSSVTLSPVDSLD

SPRPFGGPPASPGGFPLEGPYAAATATAVSLAQLGGPGRAGLGRQPPGGCVLSLGLLNPVAVPLDWARLPPPAPPGPSFLL

PLAPGPQLLNPGTPVSPQERPPPYLAVPGHGEEYPAAGAHSSPPKARFLRVPSEHPYLTPSPESPEHWASPSPPSLSDWSE

STPSPATATGAMATTTGALPAQPLPLSVPSSLAQAQTQLGPQPEVTPKRQVLA

Human neurogenic locus notch homolog protein 4 preprotein NP_004548.3
(SEQ ID NO: 28)

MQPPSLLLLLLLLLLLCVSVVRPRGLLCGSFPEPCANGGTCLSLSLGQGTCQCAPGFLGETCQFPDPCQNAQLCQNGGSCQ

ALLPAPLGLPSSPSPLTPSFLCTCLPGFTGERCQAKLEDPCPPSFCSKRGRCHIQASGRPQCSCMPGWTGEQCQLRDFCSA

NPCVNGGVCLATYPQIQCHCPPGFEGHACERDVNECFQDPGPCPKGTSCHNTLGSFQCLCPVGQEGPRCELRAGPCPPRGC

SNGGTCQLMPEKDSTFHLCLCPPGFIGPDCEVNPDNCVSHQCQNGGTCQDGLDTYTCLCPETWTGWDCSEDVDECETQGPP

HCRNGGTCQNSAGSFHCVCVSGWGGTSCEENLDDCIAATCAPGSTCIDRVGSFSCLCPPGRTGLLCHLEDMCLSQPCHGDA

QCSTNPLTGSTLCLCQPGYSGPTCHQDLDECLMAQQGPSPCEHGGSCLNTPGSFNCLCPPGYTGSRCEADHNECLSQPCHP

GSTCLDLLATFHCLCPPGLEGQLCEVETNECASAPCLNHADCHDLLNGFQCICLPGFSGTRCEEDIDECRSSPCANGGQCQ

DQPGAFHCKCLPGFEGPRCQTEVDECLSDPCPVGASCLDLPGAFFCLCPSGFTGQLCEVPLCAPNLCQPKQICKDQKDKAN

CLCPDGSPGCAPPEDNCTCHHGHCQRSSCVCDVGWTGPECEAELGGCISAPCAHGGTCYPQPSGYNCTCPTGYTGPTCSEE

MTACHSGPCLNGGSCNPSPGGYYCTCPPSHTGPQCQTSTDYCVSAPCFNGGTCVNRPGTFSCLCAMGFQGPRCEGKLRPSC

ADSPCRNRATCQDSPQGPRCLCPTGYTGGSCQTLMDLCAQKPCPRNSHCLQTGPSFHCLCLQGWTGPLCNLPLSSCQKAAL

SQGIDVSSLCHNGGLCVDSGPSYFCHCPPGFQGSLCQDHVNPCESRPCQNGATCMAQPSGYLCQCAPGYDGQNCSKELDAC

QSQPCHNHGTCTPKPGGFHCACPPGFVGLRCEGDVDECLDQPCHPTGTAACHSLANAFYCQCLPGHTGQWCEVEIDPCHSQ

PCFHGGTCEATAGSPLGFICHCPKGFEGPTCSHRAPSCGFHHCHHGGLCLPSPKPGFPPRCACLSGYGGPDCLTPPAPKGC

GPPSPCLYNGSCSETTGLGGPGFRCSCPHSSPGPRCQKPGAKGCEGRSGDGACDAGCSGPGGNWDGGDCSLGVPDPWKGCP

SHSRCWLLFRDGQCHPQCDSEECLFDGYDCETPPACTPAYDQYCHDHFHNGHCEKGCNTAECGWDGGDCRPEDGDPEWGPS

LALLVVLSPPALDQQLFALARVLSLTLRVGLWVRKDRDGRDMVYPYPGARAEEKLGGTRDPTYQERAAPQTQPLGKETDSL

SAGFVVVMGVDLSRCGPDHPASRCPWDPGLLLRFLAAMAAVGALEPLLPGPLLAVHPHAGTAPPANQLPWPVLCSPVAGVI

LLALGALLVLQLIRRRRREHGALWLPPGFTRRPRTQSAPHRRRPPLGEDSIGLKALKPKAEVDEDGVVMCSGPEEGEEVGQ

AEETGPPSTCQLWSLSGGCGALPQAAMLTPPQESEMEAPDLDTRGPDGVTPLMSAVCCGEVQSGTFQGAWLGCPEPWEPLL

DGGACPQAHTVGTGETPLHLAARFSRPTAARRLLEAGANPNQPDRAGRTPLHAAVAADAREVCQLLLRSRQTAVDARTEDG

TTPLMLAARLAVEDLVEELIAAQADVGARDKWGKTALHWAAAVNNARAARSLLQAGADKDAQDNREQTPLFLAAREGAVEV

AQLLLGLGAARELRDQAGLAPADVAHQRNHWDLLTLLEGAGPPEARHKATPGREAGPFPRARTVSVSVPPHGGGALPRCRT

-continued

LSAGAGPRGGGACLQARTWSVDLAARGGGAYSHCRSLSGVGAGGGPTPRGRRFSAGMRGPRPNPAIMRGRYGVAAGRGGRV

STDDWPCDWVALGACGSASNIPIPPPCLTPSPERGSPQLDCGPPALQEMPINQGGEGKK

In some embodiments, the Notch core of the chimeric Notch receptor polypeptide contains a portion of SEQ ID NO: 24, SEQ ID NO: 25, SEQ ID NO: 26, SEQ ID NO: 27, or SEQ ID NO: 28. In some embodiments, the chimeric Notch receptor polypeptide contains 50 to 1000 amino acids of SEQ ID NO: 24, SEQ ID NO: 25, SEQ ID NO: 26, SEQ ID NO: 27, or SEQ ID NO: 28. In some embodiments, the chimeric Notch receptor polypeptide contains 50 to 900 amino acids, 100 to 800 amino acids, 200 to 700 amino acids, 300 to 600 amino acids, 400 to 500 amino acids of SEQ ID NO: 24, SEQ ID NO: 25, SEQ ID NO: 26, SEQ ID NO: 27, or SEQ ID NO: 28. In some embodiments, the chimeric Notch receptor polypeptide contains amino acids 1374 to 1734 of SEQ ID NO: 27.

In some embodiments, the amino acid sequence of Notch, as described herein, is at least 80% identical to a corresponding amino acid sequence in SEQ ID NO: 24, SEQ ID NO: 25, SEQ ID NO: 26, SEQ ID NO: 27, or SEQ ID NO: 28. In some embodiments, the amino acid sequence of Notch is 80%, 81%, 82%, 83%, 84%, 85%, 86%, 87%, 88%, 89%, 90%, 91%, 92%, 93%, 94%, 95%, 96%, 97%, 98%, or 99% identical to a corresponding amino acid sequence in SEQ ID NO: 24, SEQ ID NO: 25, SEQ ID NO: 26, SEQ ID NO: 27, or SEQ ID NO: 28. In some embodiments, the amino acid sequence of Notch, as described herein, can vary from the amino acid sequence of SEQ ID NO: 24, SEQ ID NO: 25, SEQ ID NO: 26, SEQ ID NO: 27, or SEQ ID NO: 28 by 1 to 50 amino acids, e.g., 1, 2, 3, 4, 5, 6,7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 amino acids.

In some embodiments, the mRNA sequence of Notch, as described herein, is SEQ ID NO: 29, SEQ ID NO: 30, SEQ ID NO: 31, SEQ ID NO: 32, or SEQ ID NO: 33.

Human notch 1 (NOTCH1) mRNA NM_017617.4

(SEQ ID NO: 29)

ATGCCGCCGCTCCTGGCGCCCCTGCTCTGCCTGGCGCTGCTGCCCGCGCTCGCCGCACGAGGCCCGCGATGCTCCCAGCCCGGTGAGA

CCTGCCTGAATGGCGGGAAGTGTGAAGCGGCCAATGGCACGGAGGCCTGCGTCTGTGGCGGGGCCTTCGTGGGCCCGCGATGCCAGGA

CCCCAACCCGTGCCTCAGCACCCCCTGCAAGAACGCCGGGACATGCCACGTGGTGGACCGCAGAGGCGTGGCAGACTATGCCTGCAGC

TGTGCCCTGGGCTTCTCTGGGCCCCTCTGCCTGACACCCCTGGACAATGCCTGCCTCACCAACCCCTGCCGCAACGGGGGCACCTGCG

ACCTGCTCACGCTGACGGAGTACAAGTGCCGCTGCCCGCCCGGCTGGTCAGGGAAATCGTGCCAGCAGGCTGACCCGTGCGCCTCCAA

CCCCTGCGCCAACGGTGGCCAGTGCCTGCCCTTCGAGGCCTCCTACATCTGCCACTGCCCACCCAGCTTCCATGGCCCCACCTGCCGG

CAGGATGTCAACGAGTGTGGCCAGAAGCCCGGGCTTTGCCGCCACGGAGGCACCTGCCACAACGAGGTCGGCTCCTACCGCTGCGTCT

GCCGCGCCACCCACACTGGCCCCAACTGCGAGCGGCCCTACGTGCCCTGCAGCCCCTCGCCCTGCCAGAACGGGGGCACCTGCCGCCC

CACGGGCGACGTCACCCACGAGTGTGCCTGCCTGCCAGGCTTCACCGGCCAGAACTGTGAGGAAAATATCGACGATTGTCCAGGAAAC

AACTGCAAGAACGGGGGTGCCTGTGTGGACGGCGTGAACACCTACAACTGCCGCTGCCCGCCAGAGTGGACAGGTCAGTACTGTACCG

AGGATGTGGACGAGTGCCAGCTGATGCCAAATGCCTGCCAGAACGGCGGGACCTGCCACAACACCCACGGTGGCTACAACTGCGTGTG

TGTCAACGGCTGGACTGGTGAGGACTGCAGCGAGAACATTGATGACTGTGCCAGCGCCGCCTGCTTCCACGGCGCCACCTGCCATGAC

CGTGTGGCCTCCTTCTACTGCGAGTGTCCCCATGGCCGCACAGGTCTGCTGTGCCACCTCAACGACGCATGCATCAGCAACCCCTGTA

ACGAGGGCTCCAACTGCGACACCAACCCTGTCAATGGCAAGGCCATCTGCACCTGCCCCTCGGGGTACACGGGCCCGGCCTGCAGCCA

GGACGTGGATGAGTGCTCGCTGGGTGCCAACCCCTGCGAGCATGCGGGCAAGTGCATCAACACGCTGGGCTCCTTCGAGTGCCAGTGT

CTGCAGGGCTACACGGGCCCCCGATGCGAGATCGACGTCAACGAGTGCGTCTCGAACCCGTGCCAGAACGACGCCACCTGCCTGGACC

AGATTGGGGAGTTCCAGTGCATCTGCATGCCCGGCTACGAGGGTGTGCACTGCGAGGTCAACACAGACGAGTGTGCCAGCAGCCCCTG

CCTGCACAATGGCCGCTGCCTGGACAAGATCAATGAGTTCCAGTGCGAGTGCCCCACGGGCTTCACTGGGCATCTGTGCCAGTACGAT

GTGGACGAGTGTGCCAGCACCCCCTGCAAGAATGGTGCCAAGTGCCTGGACGGACCCAACACTTACACCTGTGTGTGCACGGAAGGGT

ACACGGGGACGCACTGCGAGGTGGACATCGATGAGTGCGACCCCGACCCCTGCCACTACGGCTCCTGCAAGGACGGCGTCGCCACCTT

CACCTGCCTCTGCCGCCCAGGCTACACGGGCCACCACTGCGAGACCAACATCAACGAGTGCTCCAGCCAGCCCTGCCGCCACGGGGGC

ACCTGCCAGGACCGCGACAACGCCTACCTCTGCTTCTGCCTGAAGGGGACCACAGGACCCAACTGCGAGATCAACCTGGATGACTGTG

CCAGCAGCCCCTGCGACTCGGGCACCTGTCTGGACAAGATCGATGGCTACGAGTGTGCCTGTGAGCCGGGCTACACAGGGAGCATGTG

TAACATCAACATCGATGAGTGTGCGGGCAACCCCTGCCACAACGGGGGCACCTGCGAGGACGGCATCAATGGCTTCACCTGCCGCTGC

CCCGAGGGCTACCACGACCCCACCTGCCTGTCTGAGGTCAATGAGTGCAACAGCAACCCCTGCGTCCACGGGGCCTGCCGGGACAGCC

TCAACGGGTACAAGTGCGACTGTGACCCTGGGTGGAGTGGGACCAACTGTGACATCAACAACAATGAGTGTGAATCCAACCCTTGTGT

-continued

CAACGGCGGCACCTGCAAAGACATGACCAGTGGCTACGTGTGCACCTGCCGGGAGGGCTTCAGCGGTCCCAACTGCCAGACCAACATC

AACGAGTGTGCGTCCAACCCATGTCTGAACCAGGGCACGTGTATTGACGACGTTGCCGGGTACAAGTGCAACTGCCTGCTGCCCTACA

CAGGTGCCACGTGTGAGGTGGTGCTGGCCCCGTGTGCCCCCAGCCCCTGCAGAAACGGCGGGGAGTGCAGGCAATCCGAGGACTATGA

GAGCTTCTCCTGTGTCTGCCCCACGGGCTGGCAAGGGCAGACCTGTGAGGTCGACATCAACGAGTGCGTTCTGAGCCCGTGCCGGCAC

GGCGCATCCTGCCAGAACACCCACGGCGGCTACCGCTGCCACTGCCAGGCCGGCTACAGTGGGCGCAACTGCGAGACCGACATCGACG

ACTGCCGGCCCAACCCGTGTCACAACGGGGGCTCCTGCACAGACGGCATCAACACGGCCTTCTGCGACTGCCTGCCCGGCTTCCGGGG

CACTTTCTGTGAGGAGGACATCAACGAGTGTGCCAGTGACCCCTGCCGCAACGGGGCCAACTGCACGGACTGCGTGGACAGCTACACG

TGCACCTGCCCCGCAGGCTTCAGCGGGATCCACTGTGAGAACAACACGCCTGACTGCACAGAGAGCTCCTGCTTCAACGGTGGCACCT

GCGTGGACGGCATCAACTCGTTCACCTGCCTGTGTCCACCCGGCTTCACGGGCAGCTACTGCCAGCACGATGTCAATGAGTGCGACTC

ACAGCCCTGCCTGCATGGCGGCACCTGTCAGGACGGCTGCGGCTCCTACAGGTGCACCTGCCCCCAGGGCTACACTGGCCCCAACTGC

CAGAACCTTGTGCACTGGTGTGACTCCTCGCCCTGCAAGAACGGCGGCAAATGCTGGCAGACCCACACCCAGTACCGCTGCGAGTGCC

CCAGCGGCTGGACCGGCCTTTACTGCGACGTGCCCAGCGTGTCCTGTGAGGTGGCTGCGCAGCGACAAGGTGTTGACGTTGCCCGCCT

GTGCCAGCATGGAGGGCTCTGTGTGGACGCGGGCAACACGCACCACTGCCGCTGCCAGGCGGGCTACACAGGCAGCTACTGTGAGGAC

CTGGTGGACGAGTGCTCACCCAGCCCCTGCCAGAACGGGGCCACCTGCACGGACTACCTGGGCGGCTACTCCTGCAAGTGCGTGGCCG

GCTACCACGGGGTGAACTGCTCTGAGGAGATCGACGAGTGCCTCTCCCACCCCTGCCAGAACGGGGGCACCTGCCTCGACCTCCCCAA

CACCTACAAGTGCTCCTGCCCACGGGGCACTCAGGGTGTGCACTGTGAGATCAACGTGGACGACTGCAATCCCCCCGTTGACCCCGTG

TCCCGGAGCCCCAAGTGCTTTAACAACGGCACCTGCGTGGACCAGGTGGGCGGCTACAGCTGCACCTGCCCGCCGGGCTTCGTGGGTG

AGCGCTGTGAGGGGGATGTCAACGAGTGCCTGTCCAATCCCTGCGACGCCCGTGGCACCCAGAACTGCGTGCAGCGCGTCAATGACTT

CCACTGCGAGTGCCGTGCTGGTCACACCGGGCGCCGCTGCGAGTCCGTCATCAATGGCTGCAAAGGCAAGCCCTGCAAGAATGGGGGC

ACCTGCGCCGTGGCCTCCAACACCGCCCGCGGGTTCATCTGCAAGTGCCCTGCGGGCTTCGAGGGCGCCACGTGTGAGAATGACGCTC

GTACCTGCGGCAGCCTGCGCTGCCTCAACGGCGGCACATGCATCTCCGGCCCGCGCAGCCCCACCTGCCTGTGCCTGGGCCCCTTCAC

GGGCCCCGAATGCCAGTTCCCGGCCAGCAGCCCCTGCCTGGGCGGCAACCCCTGCTACAACCAGGGGACCTGTGAGCCCACATCCGAG

AGCCCCTTCTACCGTTGCCTGTGCCCCGCCAAATTCAACGGGCTCTTGTGCCACATCCTGGACTACAGCTTCGGGGGTGGGGCCGGGC

GCGACATCCCCCCGCCGCTGATCGAGGAGGCGTGCGAGCTGCCCGAGTGCCAGGAGGACGCGGGCAACAAGGTCTGCAGCCTGCAGTG

CAACAACCACGCGTGCGGCTGGGACGGCGGTGACTGCTCCCTCAACTTCAATGACCCCTGGAAGAACTGCACGCAGTCTCTGCAGTGC

TGGAAGTACTTCAGTGACGGCCACTGTGACAGCCAGTGCAACTCAGCCGGCTGCCTCTTCGACGGCTTTGACTGCCAGCGTGCGGAAG

GCCAGTGCAACCCCCTGTACGACCAGTACTGCAAGGACCACTTCAGCGACGGGCACTGCGACCAGGGCTGCAACAGCGCGGAGTGCGA

GTGGGACGGGCTGGACTGTGCGGAGCATGTACCCGAGAGGCTGGCGGCCGGCACGCTGGTGGTGGTGGTGCTGATGCCGCCGGAGCAG

CTGCGCAACAGCTCCTTCCACTTCCTGCGGGAGCTCAGCCGCGTGCTGCACACCAACGTGGTCTTCAAGCGTGACGCACACGGCCAGC

AGATGATCTTCCCCTACTACGGCCGCGAGGAGGAGCTGCGCAAGCACCCCATCAAGCGTGCCGCCGAGGGCTGGGCCGCACCTGACGC

CCTGCTGGGCCAGGTGAAGGCCTCGCTGCTCCCTGGTGGCAGCGAGGGTGGGCGGCGGCGGAGGGAGCTGGACCCCATGGACGTCCGC

GGCTCCATCGTCTACCTGGAGATTGACAACCGGCAGTGTGTGCAGGCCTCCTCGCAGTGCTTCCAGAGTGCCACCGACGTGGCCGCAT

TCCTGGGAGCGCTCGCCTCGCTGGGCAGCCTCAACATCCCCTACAAGATCGAGGCCGTGCAGAGTGAGACCGTGGAGCCGCCCCCGCC

GGCGCAGCTGCACTTCATGTACGTGGCGGCGGCCGCCTTTGTGCTTCTGTTCTTCGTGGGCTGCGGGGTGCTGCTGTCCCGCAAGCGC

CGGCGGCAGCATGGCCAGCTCTGGTTCCCTGAGGGCTTCAAAGTGTCTGAGGCCAGCAAGAAGAAGCGGCGGGAGCCCCTCGGCGAGG

ACTCCGTGGGCCTCAAGCCCCTGAAGAACGCTTCAGACGGTGCCCTCATGGACGACAACCAGAATGAGTGGGGGGACGAGGACCTGGA

GACCAAGAAGTTCCGGTTCGAGGAGCCCGTGGTTCTGCCTGACCTGGACGACCAGACAGACCACCGGCAGTGGACTCAGCAGCACCTG

GATGCCGCTGACCTGCGCATGTCTGCCATGGCCCCCACACCGCCCCAGGGTGAGGTTGACGCCGACTGCATGGACGTCAATGTCCGCG

GGCCTGATGGCTTCACCCCGCTCATGATCGCCTCCTGCAGCGGGGGCGGCCTGGAGACGGGCAACAGCGAGGAAGAGGAGGACGCGCC

GGCCGTCATCTCCGACTTCATCTACCAGGGCGCCAGCCTGCACAACCAGACAGACCGCACGGGCGAGACCGCCTTGCACCTGGCCGCC

-continued

CGCTACTCACGCTCTGATGCCGCCAAGCGCCTGCTGGAGGCCAGCGCAGATGCCAACATCCAGGACAACATGGGCCGCACCCCGCTGC

ATGCGGCTGTGTCTGCCGACGCACAAGGTGTCTTCCAGATCCTGATCCGGAACCGAGCCACAGACCTGGATGCCCGCATGCATGATGG

CACGACGCCACTGATCCTGGCTGCCCGCCTGGCCGTGGAGGGCATGCTGGAGGACCTCATCAACTCACACGCCGACGTCAACGCCGTA

GATGACCTGGGCAAGTCCGCCCTGCACTGGGCCGCCGCCGTGAACAATGTGGATGCCGCAGTTGTGCTCCTGAAGAACGGGGCTAACA

AAGATATGCAGAACAACAGGGAGGAGACACCCCTGTTTCTGGCCGCCCGGGAGGGCAGCTACGAGACCGCCAAGGTGCTGCTGGACCA

CTTTGCCAACCGGGACATCACGGATCATATGGACCGCCTGCCGCGCGACATCGCACAGGAGCGCATGCATCACGACATCGTGAGGCTG

CTGGACGAGTACAACCTGGTGCGCAGCCCGCAGCTGCACGGAGCCCCGCTGGGGGGCACGCCCACCCTGTCGCCCCCGCTCTGCTCGC

CCAACGGCTACCTGGGCAGCCTCAAGCCCGGCGTGCAGGGCAAGAAGGTCCGCAAGCCCAGCAGCAAAGGCCTGGCCTGTGGAAGCAA

GGAGGCCAAGGACCTCAAGGCACGGAGGAAGAAGTCCCAGGACGGCAAGGGCTGCCTGCTGGACAGCTCCGGCATGCTCTCGCCCGTG

GACTCCCTGGAGTCACCCCATGGCTACCTGTCAGACGTGGCCTCGCCGCCACTGCTGCCCTCCCCGTTCCAGCAGTCTCCGTCCGTGC

CCCTCAACCACCTGCCTGGGATGCCCGACACCCACCTGGGCATCGGGCACCTGAACGTGGCGGCCAAGCCCGAGATGGCGGCGCTGGG

TGGGGGCGGCCGGCTGGCCTTTGAGACTGGCCCACCTCGTCTCTCCCACCTGCCTGTGGCCTCTGGCACCAGCACCGTCCTGGGCTCC

AGCAGCGGAGGGGCCCTGAATTTCACTGTGGGCGGGTCCACCAGTTTGAATGGTCAATGCGAGTGGCTGTCCCGGCTGCAGAGCGGCA

TGGTGCCGAACCAATACAACCCTCTGCGGGGGAGTGTGGCACCAGGCCCCCTGAGCACACAGGCCCCCTCCCTGCAGCATGGCATGGT

AGGCCCGCTGCACAGTAGCCTTGCTGCCAGCGCCCTGTCCCAGATGATGAGCTACCAGGGCCTGCCCAGCACCCGGCTGGCCACCCAG

CCTCACCTGGTGCAGACCCAGCAGGTGCAGCCACAAAACTTACAGATGCAGCAGCAGAACCTGCAGCCAGCAAACATCCAGCAGCAGC

AAAGCCTGCAGCCGCCACCACCACCACCACAGCCGCACCTTGGCGTGAGCTCAGCAGCCAGCGGCCACCTGGGCCGGAGCTTCCTGAG

TGGAGAGCCGAGCCAGGCAGACGTGCAGCCACTGGGCCCCAGCAGCCTGGCGGTGCACACTATTCTGCCCCAGGAGAGCCCCGCCCTG

CCCACGTCGCTGCCATCCTCGCTGGTCCCACCCGTGACCGCAGCCCAGTTCCTGACGCCCCCCTCGCAGCACAGCTACTCCTCGCCTG

TGGACAACACCCCCAGCCACCAGCTACAGGTGCCTGAGCACCCCTTCCTCACCCCGTCCCCTGAGTCCCCTGACCAGTGGTCCAGCTC

GTCCCCGCATTCCAACGTCTCCGACTGGTCCGAGGGCGTCTCCAGCCCTCCCACCAGCATGCAGTCCCAGATCGCCCGCATTCCGGAG

GCCTTCAAGTAAACGGCGCGCCCCACGAGACCCCGGCTTCCTTTCCCAAGCCTTCGGGCGTCTGTGTGCGCTCTGTGGATGCCAGGGC

CGACCAGAGGAGCCTTTTTAAAACACATGTTTTTATACAAAATAAGAACGAGGATTTTAATTTTTTTTAGTATTTATTTATGTACTTT

TATTTTACACAGAAACACTGCCTTTTTATTTATATGTACTGTTTTATCTGGCCCGAGGTAGAAACTTTTATCTATTCTGAGAAAACAA

GCAAGTTCTGAGAGCGAGGGTTTTCCTAGGTAGGATGAAAAGATTCTTCTGTGTTTATAAAATATAAACAAAGATTCATGATTTATAA

ATGCCATTTATTTATTGATTCCTTTTTTCAAAATCCAAAAAGAAATGATGTTGGAGAAGGGAAGTTGAACGAGCATAGTCCAAAAAGC

TCCTGGGGCGTCCAGGCCGCGCCCTTTCCCCGACGCCCACCCAACCCCAAGCCAGCCCGGCCGCTCCACCAGCATCACCTGCCTGTTA

GGAGAAGCTGCATCCAGAGGCAAACGGAGGCAAAGCTGGCTCACCTTCCGCACGCGGATTAATTTGCATCTGAAATAGGAAACAAGTG

AAAGCATATGGGTTAGATGTTGCCATGTGTTTTAGATGGTTTCTTGCAAGCATGCTTGTGAAAATGTGTTCTCGGAGTGTGTATGCCA

AGAGTGCACCCATGGTACCAATCATGAATCTTTGTTTCAGGTTCAGTATTATGTAGTTGTTCGTTGGTTATACAAGTTCTTGGTCCCT

CCAGAACCACCCCGGCCCCCTGCCCGTTCTTGAAATGTAGGCATCATGCATGTCAAACATGAGATGTGTGGACTGTGGCACTTGCCTG

GGTCACACACGGAGGCATCCTACCCTTTTCTGGGGAAAGACACTGCCTGGGCTGACCCCGGTGGCGGCCCCAGCACCTCAGCCTGCAC

AGTGTCCCCCAGGTTCCGAAGAAGATGCTCCAGCAACACAGCCTGGGCCCCAGCTCGCGGGACCCGACCCCCCGTGGGCTCCCGTGTT

TTGTAGGAGACTTGCCAGAGCCGGGCACATTGAGCTGTGCAACGCCGTGGGCTGCGTCCTTTGGTCCTGTCCCCGCAGCCCTGGCAGG

GGGCATGCGGTCGGGCAGGGGCTGGAGGGAGGCGGGGGCTGCCCTTGGGCCACCCCTCCTAGTTTGGGAGGAGCAGATTTTTGCAATA

CCAAGTATAGCCTATGGCAGAAAAAATGTCTGTAAATATGTTTTTAAAGGTGGATTTTGTTTAAAAAATCTTAATGAATGAGTCTGTT

GTGTGTCATGCCAGTGAGGGACGTCAGACTTGGCTCAGCTCGGGGAGCCTTAGCCGCCCATGCACTGGGGACGCTCCGCTGCCGTGCC

GCCTGCACTCCTCAGGGCAGCCTCCCCCGGCTCTACGGGGGCCGCGTGGTGCCATCCCCAGGGGGCATGACCAGATGCGTCCCAAGAT

GTTGATTTTTACTGTGTTTTATAAAATAGAGTGTAGTTTACAGAAAAAGACTTTAAAAGTGATCTAGATGAGGAACTGTAGATGATGT

ATTTTTTTCATCTTTTTTGTTAACTGATTTGCAATAAAAATGATACTGATGGTGATCTGGCTTCCAAAAAAAAAAAAAAAA

-continued

Human notch 2 (NOTCH2), transcript variant 1, mRNA NM_024408.3

(SEQ ID NO: 30)

GCTTGCGGTGGGAGGAGGCGGCTGAGGCGGAAGGACACACGAGGCTGCTTCGTTGCACACCCGAGAAAGTTTCAGCCAAACTTCGGGC

GGCGGCTGAGGCGGCGGCCGAGGAGCGGCGGACTCGGGGCGCGGGGAGTCGAGGCATTTGCGCCTGGGCTTCGGAGCGTAGCGCCAGG

GCCTGAGCCTTTGAAGCAGGAGGAGGGGAGGAGAGAGTGGGGCTCCTCTATCGGGACCCCCTCCCCATGTGGATCTGCCCAGGCGGCG

GCGGCGGCGGCGGAGGAGGAGGCGACCGAGAAGATGCCCGCCCTGCGCCCCGCTCTGCTGTGGGCGCTGCTGGCGCTCTGGCTGTGCT

GCGCGGCCCCCGCGCATGCATTGCAGTGTCGAGATGGCTATGAACCCTGTGTAAATGAAGGAATGTGTGTTACCTACCACAATGGCAC

AGGATACTGCAAATGTCCAGAAGGCTTCTTGGGGGAATATTGTCAACATCGAGACCCCTGTGAGAAGAACCGCTGCCAGAATGGTGGG

ACTTGTGTGGCCCAGGCCATGCTGGGGAAAGCCACGTGCCGATGTGCCTCAGGGTTTACAGGAGAGGACTGCCAGTACTCAACATCTC

ATCCATGCTTTGTGTCTCGACCCTGCCTGAATGGCGGCACATGCCATATGCTCAGCCGGGATACCTATGAGTGCACCTGTCAAGTCGG

GTTTACAGGTAAGGAGTGCCAATGGACGGATGCCTGCCTGTCTCATCCCTGTGCAAATGGAAGTACCTGTACCACTGTGGCCAACCAG

TTCTCCTGCAAATGCCTCACAGGCTTCACAGGGCAGAAATGTGAGACTGATGTCAATGAGTGTGACATTCCAGGACACTGCCAGCATG

GTGGCACCTGCCTCAACCTGCCTGGTTCCTACCAGTGCCAGTGCCCTCAGGGCTTCACAGGCCAGTACTGTGACAGCCTGTATGTGCC

CTGTGCACCCTCACCTTGTGTCAATGGAGGCACCTGTCGGCAGACTGGTGACTTCACTTTTGAGTGCAACTGCCTTCCAGGTTTTGAA

GGGAGCACCTGTGAGAGGAATATTGATGACTGCCCTAACCACAGGTGTCAGAATGGAGGGGTTTGTGTGGATGGGGTCAACACTTACA

ACTGCCGCTGTCCCCCACAATGGACAGGACAGTTCTGCACAGAGGATGTGGATGAATGCCTGCTGCAGCCCAATGCCTGTCAAAATGG

GGGCACCTGTGCCAACCGCAATGGAGGCTATGGCTGTGTATGTGTCAACGGCTGGAGTGGAGATGACTGCAGTGAGAACATTGATGAT

TGTGCCTTCGCCTCCTGTACTCCAGGCTCCACCTGCATCGACCGTGTGGCCTCCTTCTCTTGCATGTGCCCAGAGGGGAAGGCAGGTC

TCCTGTGTCATCTGGATGATGCATGCATCAGCAATCCTTGCCACAAGGGGGCACTGTGTGACACCAACCCCCTAAATGGGCAATATAT

TTGCACCTGCCCACAAGGCTACAAAGGGGCTGACTGCACAGAAGATGTGGATGAATGTGCCATGGCCAATAGCAATCCTTGTGAGCAT

GCAGGAAAATGTGTGAACACGGATGGCGCCTTCCACTGTGAGTGTCTGAAGGGTTATGCAGGACCTCGTTGTGAGATGGACATCAATG

AGTGCCATTCAGACCCCTGCCAGAATGATGCTACCTGTCTGGATAAGATTGGAGGCTTCACATGTCTGTGCATGCCAGGTTTCAAAGG

TGTGCATTGTGAATTAGAAATAAATGAATGTCAGAGCAACCCTTGTGTGAACAATGGGCAGTGTGTGGATAAAGTCAATCGTTTCCAG

TGCCTGTGTCCTCCTGGTTTCACTGGGCCAGTTTGCCAGATTGATATTGATGACTGTTCCAGTACTCCGTGTCTGAATGGGGCAAAGT

GTATCGATCACCCGAATGGCTATGAATGCCAGTGTGCCACAGGTTTCACTGGTGTGTTGTGTGAGGAGAACATTGACAACTGTGACCC

CGATCCTTGCCACCATGGTCAGTGTCAGGATGGTATTGATTCCTACACCTGCATCTGCAATCCCGGGTACATGGGCGCCATCTGCAGT

GACCAGATTGATGAATGTTACAGCAGCCCTTGCCTGAACGATGGTCGCTGCATTGACCTGGTCAATGGCTACCAGTGCAACTGCCAGC

CAGGCACGTCAGGGGTTAATTGTGAAATTAATTTTGATGACTGTGCAAGTAACCCTTGTATCCATGGAATCTGTATGGATGGCATTAA

TCGCTACAGTTGTGTCTGCTCACCAGGATTCACAGGGCAGAGATGTAACATTGACATTGATGAGTGTGCCTCCAATCCCTGTCGCAAG

GGTGCAACATGTATCAACGGTGTGAATGGTTTCCGCTGTATATGCCCCGAGGGACCCCATCACCCCAGCTGCTACTCACAGGTGAACG

AATGCCTGAGCAATCCCTGCATCCATGGAAACTGTACTGGAGGTCTCAGTGGATATAAGTGTCTCTGTGATGCAGGCTGGGTTGGCAT

CAACTGTGAAGTGGACAAAAATGAATGCCTTTCGAATCCATGCCAGAATGGAGGAACTTGTGACAATCTGGTGAATGGATACAGGTGT

ACTTGCAAGAAGGGCTTTAAAGGCTATAACTGCCAGGTGAATATTGATGAATGTGCCTCAAATCCATGCCTGAACCAAGGAACCTGCT

TTGATGACATAAGTGGCTACACTTGCCACTGTGTGCTGCCATACACAGGCAAGAATTGTCAGACAGTATTGGCTCCCTGTTCCCCAAA

CCCTTGTGAGAATGCTGCTGTTTGCAAAGAGTCACCAAATTTTGAGAGTTATACTTGCTTGTGTGCTCCTGGCTGGCAAGGTCAGCGG

TGTACCATTGACATTGACGAGTGTATCTCCAAGCCCTGCATGAACCATGGTCTCTGCCATAACACCCAGGGCAGCTACATGTGTGAAT

GTCCACCAGGCTTCAGTGGTATGGACTGTGAGGAGGACATTGATGACTGCCTTGCCAATCCTTGCCAGAATGGAGGTTCCTGTATGGA

TGGAGTGAATACTTTCTCCTGCCTCTGCCTTCCGGGTTTCACTGGGGATAAGTGCCAGACAGACATGAATGAGTGTCTGAGTGAACCC

TGTAAGAATGGAGGGAGCTGCTCTGACTACGTCAACAGTTACACTTGCAAGTGCCAGGCAGGATTTGATGGAGTCCATTGTGAGAACA

ACATCAATGAGTGCACTGAGAGCTCCTGTTTCAATGGTGGCACATGTGTTGATGGGATTAACTCCTTCTCTTGCTTGTGCCCTGTGGG

TTTCACTGGATCCTTCTGCCTCCATGAGATCAATGAATGCAGCTCTCATCCATGCCTGAATGAGGGAACGTGTGTTGATGGCCTGGGT

-continued

ACCTACCGCTGCAGCTGCCCCCTGGGCTACACTGGGAAAAACTGTCAGACCCTGGTGAATCTCTGCAGTCGGTCTCCATGTAAAAACA

AAGGTACTTGCGTTCAGAAAAAAGCAGAGTCCCAGTGCCTATGTCCATCTGGATGGGCTGGTGCCTATTGTGACGTGCCCAATGTCTC

TTGTGACATAGCAGCCTCCAGGAGAGGTGTGCTTGTTGAACACTTGTGCCAGCACTCAGGTGTCTGCATCAATGCTGGCAACACGCAT

TACTGTCAGTGCCCCCTGGGCTATACTGGGAGCTACTGTGAGGAGCAACTCGATGAGTGTGCGTCCAACCCCTGCCAGCACGGGGCAA

CATGCAGTGACTTCATTGGTGGATACAGATGCGAGTGTGTCCCAGGCTATCAGGGTGTCAACTGTGAGTATGAAGTGGATGAGTGCCA

GAATCAGCCCTGCCAGAATGGAGGCACCTGTATTGACCTTGTGAACCATTTCAAGTGCTCTTGCCCACCAGGCACTCGGGGCCTACTC

TGTGAAGAGAACATTGATGACTGTGCCCGGGGTCCCCATTGCCTTAATGGTGGTCAGTGCATGGATAGGATTGGAGGCTACAGTTGTC

GCTGCTTGCCTGGCTTTGCTGGGGAGCGTTGTGAGGGAGACATCAACGAGTGCCTCTCCAACCCCTGCAGCTCTGAGGGCAGCCTGGA

CTGTATACAGCTCACCAATGACTACCTGTGTGTTTGCCGTAGTGCCTTTACTGGCCGGCACTGTGAAACCTTCGTCGATGTGTGTCCC

CAGATGCCCTGCCTGAATGGAGGGACTTGTGCTGTGGCCAGTAACATGCCTGATGGTTTCATTTGCCGTTGTCCCCCGGGATTTTCCG

GGGCAAGGTGCCAGAGCAGCTGTGGACAAGTGAAATGTAGGAAGGGGGAGCAGTGTGTGCACACCGCCTCTGGACCCCGCTGCTTCTG

CCCCAGTCCCCGGGACTGCGAGTCAGGCTGTGCCAGTAGCCCCTGCCAGCACGGGGGCAGCTGCCACCCTCAGCGCCAGCCTCCTTAT

TACTCCTGCCAGTGTGCCCCACCATTCTCGGGTAGCCGCTGTGAACTCTACACGGCACCCCCCAGCACCCCTCCTGCCACCTGTCTGA

GCCAGTATTGTGCCGACAAAGCTCGGGATGGCGTCTGTGATGAGGCCTGCAACAGCCATGCCTGCCAGTGGGATGGGGGTGACTGTTC

TCTCACCATGGAGAACCCCTGGGCCAACTGCTCCTCCCCACTTCCCTGCTGGGATTATATCAACAACCAGTGTGATGAGCTGTGCAAC

ACGGTCGAGTGCCTGTTTGACAACTTTGAATGCCAGGGGAACAGCAAGACATGCAAGTATGAGAAATACTGTGCAGACCACTTCAAAG

ACAACCACTGTGAGGAGGGGTGCAACAGTGAGGAGTGTGGTTGGGATGGGCTGGACTGTGCTGCTGACCAACCTGAGAACCTGGCAGA

AGGTACCCTGGTTATTGTGGTATTGATGCCACCTGAACAACTGCTCCAGGATGCTCGCAGCTTCTTGCGGGCACTGGGTACCCTGCTC

CACACCAACCTGCGCATTAAGCGGGACTCCCAGGGGGAACTCATGGTGTACCCCTATTATGGTGAGAAGTCAGCTGCTATGAAGAAAC

AGAGGATGACACGCAGATCCCTTCCTGGTGAACAAGAACAGGAGGTGGCTGGCTCTAAAGTCTTTCTGGAAATTGACAACCGCCAGTG

TGTTCAAGACTCAGACCACTGCTTCAAGAACACGGATGCAGCAGCAGCTCTCCTGGCCTCTCACGCCATACAGGGGACCCTGTCATAC

CCTCTTGTGTCTGTCGTCAGTGAATCCCTGACTCCAGAACGCACTCAGCTCCTCTATCTCCTTGCTGTTGCTGTTGTCATCATTCTGT

TTATTATTCTGCTGGGGGTAATCATGGCAAAACGAAAGCGTAAGCATGGCTCTCTCTGGCTGCCTGAAGGTTTCACTCTTCGCCGAGA

TGCAAGCAATCACAAGCGTCGTGAGCCAGTGGGACAGGATGCTGTGGGGCTGAAAAATCTCTCAGTGCAAGTCTCAGAAGCTAACCTA

ATTGGTACTGGAACAAGTGAACACTGGGTCGATGATGAAGGGCCCCAGCCAAAGAAAGTAAAGGCTGAAGATGAGGCCTTACTCTCAG

AAGAAGATGACCCCATTGATCGACGGCCATGGACACAGCAGCACCTTGAAGCTGCAGACATCCGTAGGACACCATCGCTGGCTCTCAC

CCCTCCTCAGGCAGAGCAGGAGGTGGATGTGTTAGATGTGAATGTCCGTGGCCCAGATGGCTGCACCCCATTGATGTTGGCTTCTCTC

CGAGGAGGCAGCTCAGATTTGAGTGATGAAGATGAAGATGCAGAGGACTCTTCTGCTAACATCATCACAGACTTGGTCTACCAGGGTG

CCAGCCTCCAGGCCCAGACAGACCGGACTGGTGAGATGGCCCTGCACCTTGCAGCCCGCTACTCACGGGCTGATGCTGCCAAGCGTCT

CCTGGATGCAGGTGCAGATGCCAATGCCCAGGACAACATGGGCCGCTGTCCACTCCATGCTGCAGTGGCAGCTGATGCCCAAGGTGTC

TTCCAGATTCTGATTCGCAACCGAGTAACTGATCTAGATGCCAGGATGAATGATGGTACTACACCCCTGATCCTGGCTGCCCGCCTGG

CTGTGGAGGGAATGGTGGCAGAACTGATCAACTGCCAAGCGGATGTGAATGCAGTGGATGACCATGGAAAATCTGCTCTTCACTGGGC

AGCTGCTGTCAATAATGTGGAGGCAACTCTTTTGTTGTTGAAAAATGGGGCCAACCGAGACATGCAGGACAACAAGGAAGAGACACCT

CTGTTTCTTGCTGCCCGGGAGGGGAGCTATGAAGCAGCCAAGATCCTGTTAGACCATTTTGCCAATCGAGACATCACAGACCATATGG

ATCGTCTTCCCCGGGATGTGGCTCGGGATCGCATGCACCATGACATTGTGCGCCTTCTGGATGAATACAATGTGACCCCAAGCCCTCC

AGGCACCGTGTTGACTTCTGCTCTCTCACCTGTCATCTGTGGGCCCAACAGATCTTTCCTCAGCCTGAAGCACACCCCAATGGGCAAG

AAGTCTAGACGGCCCAGTGCCAAGAGTACCATGCCTACTAGCCTCCCTAACCTTGCCAAGGAGGCAAAGGATGCCAAGGGTAGTAGGA

GGAAGAAGTCTCTGAGTGAGAAGGTCCAACTGTCTGAGAGTTCAGTAACTTTATCCCCTGTTGATTCCCTAGAATCTCCTCACACGTA

TGTTTCCGACACCACATCCTCTCCAATGATTACATCCCCTGGGATCTTACAGGCCTCACCCAACCCTATGTTGGCCACTGCCGCCCCT

CCTGCCCCAGTCCATGCCCAGCATGCACTATCTTTTTCTAACCTTCATGAAATGCAGCCTTTGGCACATGGGGCCAGCACTGTGCTTC

-continued

CCTCAGTGAGCCAGTTGCTATCCCACCACCACATTGTGTCTCCAGGCAGTGGCAGTGCTGGAAGCTTGAGTAGGCTCCATCCAGTCCC

AGTCCCAGCAGATTGGATGAACCGCATGGAGGTGAATGAGACCCAGTACAATGAGATGTTTGGTATGGTCCTGGCTCCAGCTGAGGGC

ACCCATCCTGGCATAGCTCCCCAGAGCAGGCCACCTGAAGGGAAGCACATAACCACCCCTCGGGAGCCCTTGCCCCCCATTGTGACTT

TCCAGCTCATCCCTAAAGGCAGTATTGCCCAACCAGCGGGGGCTCCCCAGCCTCAGTCCACCTGCCCTCCAGCTGTTGCGGGCCCCCT

GCCCACCATGTACCAGATTCCAGAAATGGCCCGTTTGCCCAGTGTGGCTTTCCCCACTGCCATGATGCCCCAGCAGGACGGGCAGGTA

GCTCAGACCATTCTCCCAGCCTATCATCCTTTCCCAGCCTCTGTGGGCAAGTACCCCACACCCCCTTCACAGCACAGTTATGCTTCCT

CAAATGCTGCTGAGCGAACACCCAGTCACAGTGGTCACCTCCAGGGTGAGCATCCCTACCTGACACCATCCCCAGAGTCTCCTGACCA

GTGGTCAAGTTCATCACCCCACTCTGCTTCTGACTGGTCAGATGTGACCACCAGCCCTACCCCTGGGGGTGCTGGAGGAGGTCAGCGG

GGACCTGGGACACACATGTCTGAGCCACCACACAACAACATGCAGGTTTATGCGTGAGAGAGTCCACCTCCAGTGTAGAGACATAACT

GACTTTTGTAAATGCTGCTGAGGAACAAATGAAGGTCATCCGGGAGAGAAATGAAGAAATCTCTGGAGCCAGCTTCTAGAGGTAGGAA

AGAGAAGATGTTCTTATTCAGATAATGCAAGAGAAGCAATTCGTCAGTTTCACTGGGTATCTGCAAGGCTTATTGATTATTCTAATCT

AATAAGACAAGTTTGTGGAAATGCAAGATGAATACAAGCCTTGGGTCCATGTTTACTCTCTTCTATTTGGAGAATAAGATGGATGCTT

ATTGAAGCCCAGACATTCTTGCAGCTTGGACTGCATTTTAAGCCCTGCAGGCTTCTGCCATATCCATGAGAAGATTCTACACTAGCGT

CCTGTTGGGAATTATGCCCTGGAATTCTGCCTGAATTGACCTACGCATCTCCTCCTCCTTGGACATTCTTTTGTCTTCATTTGGTGCT

TTTGGTTTTGCACCTCTCCGTGATTGTAGCCCTACCAGCATGTTATAGGGCAAGACCTTTGTGCTTTTGATCATTCTGGCCCATGAAA

GCAACTTTGGTCTCCTTTCCCCTCCTGTCTTCCCGGTATCCCTTGGAGTCTCACAAGGTTTACTTTGGTATGGTTCTCAGCACAAACC

TTTCAAGTATGTTGTTTCTTTGGAAAATGGACATACTGTATTGTGTTCTCCTGCATATATCATTCCTGGAGAGAGAAGGGGAGAAGAA

TACTTTTCTTCAACAAATTTTGGGGGCAGGAGATCCCTTCAAGAGGCTGCACCTTAATTTTTCTTGTCTGTGTGCAGGTCTTCATATA

AACTTTACCAGGAAGAAGGGTGTGAGTTTGTTGTTTTTCTGTGTATGGGCCTGGTCAGTGTAAAGTTTTATCCTTGATAGTCTAGTTA

CTATGACCCTCCCCACTTTTTTAAAACCAGAAAAAGGTTTGGAATGTTGGAATGAGCAAGAGACAAGTTAACTCGTGCAAGAGCCAGT

TACCCACCCACAGGTCCCCCTACTTCCTGCCAAGCATTCCATTGACTGCCTGTATGGAACACATTTGTCCCAGATCTGAGCATTCTAG

GCCTGTTTCACTCACTCACCCAGCATATGAAACTAGTCTTAACTGTTGAGCCTTTCCTTTCATATCCACAGAAGACACTGTCTCAAAT

GTTGTACCCTTGCCATTTAGGACTGAACTTTCCTTAGCCCAAGGGACCCAGTGACAGTTGTCTTCCGTTTGTCAGATGATCAGTCTCT

ACTGATTATCTTGCTGCTTAAAGGCCTGCTCACCAATCTTTCTTTCACACCGTGTGGTCCGTGTTACTGGTATACCCAGTATGTTCTC

ACTGAAGACATGGACTTTATATGTTCAAGTGCAGGAATTGGAAAGTTGGACTTGTTTTCTATGATCCAAAACAGCCCTATAAGAAGGT

TGGAAAAGGAGGAACTATATAGCAGCCTTTGCTATTTTCTGCTACCATTTCTTTTCCTCTGAAGCGGCCATGACATTCCCTTTGGCAA

CTAACGTAGAAACTCAACAGAACATTTTCCTTTCCTAGAGTCACCTTTTAGATGATAATGGAGAACTATAGACTTGCTCATTGTTCAG

ACTGATTGCCCCTCACCTGAATCCACTCTCTGTATTCATGCTCTTGGCAATTTCTTTGACTTTCTTTTAAGGGCAGAAGCATTTTAGT

TAATTGTAGATAAAGAATAGTTTTCTTCCTCTTCTCCTTGGGCCAGTTAATAATTGGTCCATGGCTACACTGCAACTTCCGTCCAGTG

CTGTGATGCCCATGACACCTGCAAAATAAGTTCTGCCTGGGCATTTTGTAGATATTAACAGGTGAATTCCCGACTCTTTTGGTTTGAA

TGACAGTTCTCATTCCTTCTATGGCTGCAAGTATGCATCAGTGCTTCCCACTTACCTGATTTGTCTGTCGGTGGCCCCATATGGAAAC

CCTGCGTGTCTGTTGGCATAATAGTTTACAAATGGTTTTTTGAGTCCTATCCAAATTTATTGAACCAACAAAAATAATTACTTCTGCC

CTGAGATAAGCAGATTAAGTTTGTTCATTCTCTGCTTTATTCTCTCCATGTGGCAACATTCTGTCAGCCTCTTTCATAGTGTGCAAAC

ATTTTATCATTCTAAATGGTGACTCTCTGCCCTTGGACCCATTTATTATTCACAGATGGGGAGAACCTATCTGCATGGACCTCTGTGG

ACCACAGCGTACCTGCCCCTTTCTGCCCTCCTGCTCCAGCCCCACTTCTGAAAGTATCAGCTACTGATCCAGCCACTGGATATTTTAT

ATCCTCCCTTTTCCTTAAGCACAATGTCAGACCAAATTGCTTGTTTCTTTTTCTTGGACTACTTTAATTTGGATCCTTTGGGTTTGGA

GAAAGGGAATGTGAAAGCTGTCATTACAGACAACAGGTTTCAGTGATGAGGAGGACAACACTGCCTTTCAAACTTTTTAGTGATCTCT

TAGATTTTAAGAACTCTTGAATTGTGTGGTATCTAATAAAAGGGAAGGTAAGATGGATAATCACTTTCTCATTTGGGTTCTGAATTGG

AGACTCAGTTTTTATGAGACACATCTTTTATGCCATGTATAGATCCTCCCCTGCTATTTTTGGTTTATTTTTATTGTTATAAATGCTT

TCTTTCTTTGACTCCTCTTCTGCCTGCCTTTGGGGATAGGTTTTTTTGTTTGTTTATTTGCTTCCTCTGTTTTGTTTTAAGCATCATT

TTCTTATGTGAGGTGGGGAAGGGAAAGGTATGAGGGAAAGAGAGTCTGAGAATTAAAATATTTTAGTATAAGCAATTGGCTGTGATGC

-continued

TCAAATCCATTGCATCCTCTTATTGAATTTGCCAATTTGTAATTTTTGCATAATAAAGAACCAAAGGTGTAATGTTTTGTTGAGAGGT

GGTTTAGGGATTTTGGCCCTAACCAATACATTGAATGTATGATGACTATTTGGGAGGACACATTTATGTACCCAGAGGCCCCCACTAA

TAAGTGGTACTATGGTTACTTCCTTGTGTACATTTCTCTTAAAAGTGATATTATATCTGTTTGTATGAGAAACCCAGTAACCAATAAA

ATGACCGCATATTCCTGACTAAACGTAGTAAGGAAAATGCACACTTTGTTTTTACTTTTCCGTTTCATTCTAAAGGTAGTTAAGATGA

AATTTATATGAAAGCATTTTTATCACAAAATAAAAAAGGTTTGCCAAGCTCAGTGGTGTTGTATTTTTTATTTTCCAATACTGCATCC

ATGGCCTGGCAGTGTTACCTCATGATGTCATAATTTGCTGAGAGAGCAAATTTTCTTTTCTTTCTGAATCCCACAAAGCCTAGCACCA

AACTTCTTTTTTTCTTCCTTTAATTAGATCATAAATAAATGATCCTGGGGAAAAAGCATCTGTCAAATAGGAAACATCACAAAACTGA

GCACTCTTCTGTGCACTAGCCATAGCTGGTGACAAACAGATGGTTGCTCAGGGACAAGGTGCCTTCCAATGGAAATGCGAAGTAGTTG

CTATAGCAAGAATTGGGAACTGGGATATAAGTCATAATATTAATTATGCTGTTATGTAAATGATTGGTTTGTAACATTCCTTAAGTGA

AATTTGTGTAGAACTTAATATACAGGATTATAAAATAATATTTTGTGTATAAATTTGTTATAAGTTCACATTCATACATTTATTTATA

AAGTCAGTGAGATATTTGAACATGAAAAAAAAAA

Human notch 2 (NOTCH2), transcript variant 2, mRNA NM_001200001.1

(SEQ ID NO: 31)

GCTTGCGGTGGGAGGAGGCGGCTGAGGCGGAAGGACACACGAGGCTGCTTCGTTGCACACCCGAGAAAGTTTCAGCCAAACTTCGGGC

GGCGGCTGAGGCGGCGGCCGAGGAGCGGCGGACTCGGGGCGCGGGGAGTCGAGGCATTTGCGCCTGGGCTTCGGAGCGTAGCGCCAGG

GCCTGAGCCTTTGAAGCAGGAGGAGGGGAGGAGAGAGTGGGGCTCCTCTATCGGGACCCCCTCCCCATGTGGATCTGCCCAGGCGGCG

GCGGCGGCGGCGGAGGAGGAGGCGACCGAGAAGATGCCCGCCCTGCGCCCCGCTCTGCTGTGGGCGCTGCTGGCGCTCTGGCTGTGCT

GCGCGGCCCCCGCGCATGCATTGCAGTGTCGAGATGGCTATGAACCCTGTGTAAATGAAGGAATGTGTGTTACCTACCACAATGGCAC

AGGATACTGCAAATGTCCAGAAGGCTTCTTGGGGGAATATTGTCAACATCGAGACCCCTGTGAGAAGAACCGCTGCCAGAATGGTGGG

ACTTGTGTGGCCCAGGCCATGCTGGGGAAAGCCACGTGCCGATGTGCCTCAGGGTTTACAGGAGAGGACTGCCAGTACTCAACATCTC

ATCCATGCTTTGTGTCTCGACCCTGCCTGAATGGCGGCACATGCCATATGCTCAGCCGGGATACCTATGAGTGCACCTGTCAAGTCGG

GTTTACAGGTAAGGAGTGCCAATGGACGGATGCCTGCCTGTCTCATCCCTGTGCAAATGGAAGTACCTGTACCACTGTGGCCAACCAG

TTCTCCTGCAAATGCCTCACAGGCTTCACAGGGCAGAAATGTGAGACTGATGTCAATGAGTGTGACATTCCAGGACACTGCCAGCATG

GTGGCACCTGCCTCAACCTGCCTGGTTCCTACCAGTGCCAGTGCCCTCAGGGCTTCACAGGCCAGTACTGTGACAGCCTGTATGTGCC

CTGTGCACCCTCACCTTGTGTCAATGGAGGCACCTGTCGGCAGACTGGTGACTTCACTTTTGAGTGCAACTGCCTTCCAGGTTTTGAA

GGGAGCACCTGTGAGAGGAATATTGATGACTGCCCTAACCACAGGTGTCAGAATGGAGGGGTTTGTGTGGATGGGGTCAACACTTACA

ACTGCCGCTGTCCCCCACAATGGACAGGACAGTTCTGCACAGAGGATGTGGATGAATGCCTGCTGCAGCCCAATGCCTGTCAAAATGG

GGGCACCTGTGCCAACCGCAATGGAGGCTATGGCTGTGTATGTGTCAACGGCTGGAGTGGAGATGACTGCAGTGAGAACATTGATGAT

TGTGCCTTCGCCTCCTGTACTCCAGGCTCCACCTGCATCGACCGTGTGGCCTCCTTCTCTTGCATGTGCCCAGAGGGGAAGGCAGGTC

TCCTGTGTCATCTGGATGATGCATGCATCAGCAATCCTTGCCACAAGGGGGCACTGTGTGACACCAACCCCCTAAATGGGCAATATAT

TTGCACCTGCCCACAAGGCTACAAAGGGGCTGACTGCACAGAAGATGTGGATGAATGTGCCATGGCCAATAGCAATCCTTGTGAGCAT

GCAGGAAAATGTGTGAACACGGATGGCGCCTTCCACTGTGAGTGTCTGAAGGGTTATGCAGGACCTCGTTGTGAGATGGACATCAATG

AGTGCCATTCAGACCCCTGCCAGAATGATGCTACCTGTCTGGATAAGATTGGAGGCTTCACATGTCTGTGCATGCCAGGTTTCAAAGG

TGTGCATTGTGAATTAGAAATAAATGAATGTCAGAGCAACCCTTGTGTGAACAATGGGCAGTGTGTGGATAAAGTCAATCGTTTCCAG

TGCCTGTGTCCTCCTGGTTTCACTGGGCCAGTTTGCCAGATTGATATTGATGACTGTTCCAGTACTCCGTGTCTGAATGGGGCAAAGT

GTATCGATCACCCGAATGGCTATGAATGCCAGTGTGCCACAGGTTTCACTGGTGTGTTGTGTGAGGAGAACATTGACAACTGTGACCC

CGATCCTTGCCACCATGGTCAGTGTCAGGATGGTATTGATTCCTACACCTGCATCTGCAATCCCGGGTACATGGGCGCCATCTGCAGT

GACCAGATTGATGAATGTTACAGCAGCCCTTGCCTGAACGATGGTCGCTGCATTGACCTGGTCAATGGCTACCAGTGCAACTGCCAGC

CAGGCACGTCAGGGGTTAATTGTGAAATTAATTTTGATGACTGTGCAAGTAACCCTTGTATCCATGGAATCTGTATGGATGGCATTAA

TCGCTACAGTTGTGTCTGCTCACCAGGATTCACAGGGCAGAGATGTAACATTGACATTGATGAGTGTGCCTCCAATCCCTGTCGCAAG

GGTGCAACATGTATCAACGGTGTGAATGGTTTCCGCTGTATATGCCCCGAGGGACCCCATCACCCCAGCTGCTACTCACAGGTGAACG

-continued

AATGCCTGAGCAATCCCTGCATCCATGGAAACTGTACTGGAGGTCTCAGTGGATATAAGTGTCTCTGTGATGCAGGCTGGGTTGGCAT

CAACTGTGAAGTGGACAAAAATGAATGCCTTTCGAATCCATGCCAGAATGGAGGAACTTGTGACAATCTGGTGAATGGATACAGGTGT

ACTTGCAAGAAGGGCTTTAAAGGCTATAACTGCCAGGTGAATATTGATGAATGTGCCTCAAATCCATGCCTGAACCAAGGAACCTGCT

TTGATGACATAAGTGGCTACACTTGCCACTGTGTGCTGCCATACACAGGCAAGAATTGTCAGACAGTATTGGCTCCCTGTTCCCCAAA

CCCTTGTGAGAATGCTGCTGTTTGCAAAGAGTCACCAAATTTTGAGAGTTATACTTGCTTGTGTGCTCCTGGCTGGCAAGGTCAGCGG

TGTACCATTGACATTGACGAGTGTATCTCCAAGCCCTGCATGAACCATGGTCTCTGCCATAACACCCAGGGCAGCTACATGTGTGAAT

GTCCACCAGGCTTCAGTGGTATGGACTGTGAGGAGGACATTGATGACTGCCTTGCCAATCCTTGCCAGAATGGAGGTTCCTGTATGGA

TGGAGTGAATACTTTCTCCTGCCTCTGCCTTCCGGGTTTCACTGGGGATAAGTGCCAGACAGACATGAATGAGTGTCTGAGTGAACCC

TGTAAGAATGGAGGGAGCTGCTCTGACTACGTCAACAGTTACACTTGCAAGTGCCAGGCAGGATTTGATGGAGTCCATTGTGAGAACA

ACATCAATGAGTGCACTGAGAGCTCCTGTTTCAATGGTGGCACATGTGTTGATGGGATTAACTCCTTCTCTTGCTTGTGCCCTGTGGG

TTTCACTGGATCCTTCTGCCTCCATGAGATCAATGAATGCAGCTCTCATCCATGCCTGAATGAGGGAACGTGTGTTGATGGCCTGGGT

ACCTACCGCTGCAGCTGCCCCCTGGGCTACACTGGGAAAAACTGTCAGACCCTGGTGAATCTCTGCAGTCGGTCTCCATGTAAAAACA

AAGGTACTTGCGTTCAGAAAAAAGCAGAGTCCCAGTGCCTATGTCCATCTGGATGGGCTGGTGCCTATTGTGACGTGCCCAATGTCTC

TTGTGACATAGCAGCCTCCAGGAGAGGTGTGCTTGTTGAACACTTGTGCCAGCACTCAGGTGTCTGCATCAATGCTGGCAACACGCAT

TACTGTCAGTGCCCCCTGGGCTATACTGGGAGCTACTGTGAGGAGCAACTCGATGAGTGTGCGTCCAACCCCTGCCAGCACGGGGCAA

CATGCAGTGACTTCATTGGTGGATACAGATGCGAGTGTGTCCCAGGCTATCAGGGTGTCAACTGTGAGTATGAAGTGGATGAGTGCCA

GAATCAGCCCTGCCAGAATGGAGGCACCTGTATTGACCTTGTGAACCATTTCAAGTGCTCTTGCCCACCAGGCACTCGGGGTATGAAA

TCATCCTTATCCATTTTCCATCCAGGGCATTGTCTTAAGTTATAAATCCATTCTTAGTGTTCAGGGGATTTTATAAAATTAAAGATAG

GAAGACTAGCTTCATTCCAAGCATTTAGTTCTACATCCTAGTAATTCAAGCCATTTTATTCTCCCATCTCTTGCTAGCTCTGATGTTG

TGGTTTATGTTGTCAGTTTTATCTGGTTGTTTGGCATCTTGATATTCCATGAAACACAGAATATGGAAGGGATACAACATTAGCATAA

CATTAAAAAATTAGCCTGGTCAGTAAGATTTCTTGTTGCTTCACAGAAAAGCAACTAATGGCCTCTAAAATAAACAATTTACATTTAA

AAAAAAAAAAAAAA

Human notch 3 (NOTCH3), mRNA NM_000435.2

(SEQ ID NO: 32)

GCGGCGCGGAGGCTGGCCCGGGACGCGCCCGGAGCCCAGGGAAGGAGGGAGGAGGGGAGGGTCGCGGCCGGCCGCCATGGGGCCGGGG

GCCCGTGGCCGCCGCCGCCGCCGTCGCCCGATGTCGCCGCCACCGCCACCGCCACCCGTGCGGGCGCTGCCCCTGCTGCTGCTGCTAG

CGGGGCCGGGGGCTGCAGCCCCCCCTTGCCTGGACGGAAGCCCGTGTGCAAATGGAGGTCGTTGCACCCAGCTGCCCTCCCGGGAGGC

TGCCTGCCTGTGCCCGCCTGGCTGGGTGGGTGAGCGGTGTCAGCTGGAGGACCCCTGTCACTCAGGCCCCTGTGCTGGCCGTGGTGTC

TGCCAGAGTTCAGTGGTGGCTGGCACCGCCCGATTCTCATGCCGGTGCCCCCGTGGCTTCCGAGGCCCTGACTGCTCCCTGCCAGATC

CCTGCCTCAGCAGCCCTTGTGCCCACGGTGCCCGCTGCTCAGTGGGGCCCGATGGACGCTTCCTCTGCTCCTGCCCACCTGGCTACCA

GGGCCGCAGCTGCCGAAGCGACGTGGATGAGTGCCGGGTGGGTGAGCCCTGCCGCCATGGTGGCACCTGCCTCAACACACCTGGCTCC

TTCCGCTGCCAGTGTCCAGCTGGCTACACAGGGCCACTATGTGAGAACCCCGCGGTGCCCTGTGCACCCTCACCATGCCGTAACGGGG

GCACCTGCAGGCAGAGTGGCGACCTCACTTACGACTGTGCCTGTCTTCCTGGGTTTGAGGGTCAGAATTGTGAAGTGAACGTGGACGA

CTGTCCAGGACACCGATGTCTCAATGGGGGGACATGCGTGGATGGCGTCAACACCTATAACTGCCAGTGCCCTCCTGAGTGGACAGGC

CAGTTCTGCACGGAGGACGTGGATGAGTGTCAGCTGCAGCCCAACGCCTGCCACAATGGGGGTACCTGCTTCAACACGCTGGGTGGCC

ACAGCTGCGTGTGTGTCAATGGCTGGACAGGCGAGAGCTGCAGTCAGAATATCGATGACTGTGCCACAGCCGTGTGCTTCCATGGGGC

CACCTGCCATGACCGCGTGGCTTCTTTCTACTGTGCCTGCCCCATGGGCAAGACTGGCCTCCTGTGTCACCTGGATGACGCCTGTGTC

AGCAACCCCTGCCACGAGGATGCTATCTGTGACACAAATCCGGTGAACGGCCGGGCCATTTGCACCTGTCCTCCCGGCTTCACGGGTG

GGGCATGTGACCAGGATGTGGACGAGTGCTCTATCGGCGCCAACCCCTGCGAGCACTTGGGCAGGTGCGTGAACACGCAGGGCTCCTT

CCTGTGCCAGTGCGGTCGTGGCTACACTGGACCTCGCTGTGAGACCGATGTCAACGAGTGTCTGTCGGGGCCCTGCCGAAACCAGGCC

ACGTGCCTCGACCGCATAGGCCAGTTCACCTGTATCTGTATGGCAGGCTTCACAGGAACCTATTGCGAGGTGGACATTGACGAGTGTC

AGAGTAGCCCCTGTGTCAACGGTGGGGTCTGCAAGGACCGAGTCAATGGCTTCAGCTGCACCTGCCCCTCGGGCTTCAGCGGCTCCAC

-continued

GTGTCAGCTGGACGTGGACGAATGCGCCAGCACGCCCTGCAGGAATGGCGCCAAATGCGTGGACCAGCCCGATGGCTACGAGTGCCGC

TGTGCCGAGGGCTTTGAGGGCACGCTGTGTGATCGCAACGTGGACGACTGCTCCCCTGACCCATGCCACCATGGTCGCTGCGTGGATG

GCATCGCCAGCTTCTCATGTGCCTGTGCTCCTGGCTACACGGGCACACGCTGCGAGAGCCAGGTGGACGAATGCCGCAGCCAGCCCTG

CCGCCATGGCGGCAAATGCCTAGACCTGGTGGACAAGTACCTCTGCCGCTGCCCTTCTGGGACCACAGGTGTGAACTGCGAAGTGAAC

ATTGACGACTGTGCCAGCAACCCCTGCACCTTTGGAGTCTGCCGTGATGGCATCAACCGCTACGACTGTGTCTGCCAACCTGGCTTCA

CAGGGCCCCTTTGTAACGTGGAGATCAATGAGTGTGCTTCCAGCCCATGCGGCGAGGGAGGTTCCTGTGTGGATGGGGAAAATGGCTT

CCGCTGCCTCTGCCCGCCTGGCTCCTTGCCCCCACTCTGCCTCCCCCCGAGCCATCCCTGTGCCCATGAGCCCTGCAGTCACGGCATC

TGCTATGATGCACCTGGCGGGTTCCGCTGTGTGTGTGAGCCTGGCTGGAGTGGCCCCCGCTGCAGCCAGAGCCTGGCCCGAGACGCCT

GTGAGTCCCAGCCGTGCAGGGCCGGTGGGACATGCAGCAGCGATGGAATGGGTTTCCACTGCACCTGCCCGCCTGGTGTCCAGGGACG

TCAGTGTGAACTCCTCTCCCCCTGCACCCCGAACCCCTGTGAGCATGGGGGCCGCTGCGAGTCTGCCCCTGGCCAGCTGCCTGTCTGC

TCCTGCCCCCAGGGCTGGCAAGGCCCACGATGCCAGCAGGATGTGGACGAGTGTGCTGGCCCCGCACCCTGTGGCCCTCATGGTATCT

GCACCAACCTGGCAGGGAGTTTCAGCTGCACCTGCCATGGAGGGTACACTGGCCCTTCCTGCGATCAGGACATCAATGACTGTGACCC

CAACCCATGCCTGAACGGTGGCTCGTGCCAAGACGGCGTGGGCTCCTTTTCCTGCTCCTGCCTCCCTGGTTTCGCCGGCCCACGATGC

GCCCGCGATGTGGATGAGTGCCTGAGCAACCCCTGCGGCCCGGGCACCTGTACCGACCACGTGGCCTCCTTCACCTGCACCTGCCCGC

CAGGCTACGGAGGCTTCCACTGCGAACAGGACCTGCCCGACTGCAGCCCCAGCTCCTGCTTCAATGGCGGGACCTGTGTGGACGGCGT

GAACTCGTTCAGCTGCCTGTGCCGTCCCGGCTACACAGGAGCCCACTGCCAACATGAGGCAGACCCCTGCCTCTCGCGGCCCTGCCTA

CACGGGGGCGTCTGCAGCGCCGCCCACCCTGGCTTCCGCTGCACCTGCCTCGAGAGCTTCACGGGCCCGCAGTGCCAGACGCTGGTGG

ATTGGTGCAGCCGCCAGCCTTGTCAAAACGGGGGTCGCTGCGTCCAGACTGGGGCCTATTGCCTTTGTCCCCCTGGATGGAGCGGACG

CCTCTGTGACATCCGAAGCTTGCCCTGCAGGGAGGCCGCAGCCCAGATCGGGGTGCGGCTGGAGCAGCTGTGTCAGGCGGGTGGGCAG

TGTGTGGATGAAGACAGCTCCCACTACTGCGTGTGCCCAGAGGGCCGTACTGGTAGCCACTGTGAGCAGGAGGTGGACCCCTGCTTGG

CCCAGCCCTGCCAGCATGGGGGGACCTGCCGTGGCTATATGGGGGGCTACATGTGTGAGTGTCTTCCTGGCTACAATGGTGATAACTG

TGAGGACGACGTGGACGAGTGTGCCTCCCAGCCCTGCCAGCACGGGGGTTCATGCATTGACCTCGTGGCCCGCTATCTCTGCTCCTGT

CCCCCAGGAACGCTGGGGGTGCTCTGCGAGATTAATGAGGATGACTGCGGCCCAGGCCCACCGCTGGACTCAGGGCCCCGGTGCCTAC

ACAATGGCACCTGCGTGGACCTGGTGGGTGGTTTCCGCTGCACCTGTCCCCCAGGATACACTGGTTTGCGCTGCGAGGCAGACATCAA

TGAGTGTCGCTCAGGTGCCTGCCACGCGGCACACACCCGGGACTGCCTGCAGGACCCAGGCGGAGGTTTCCGTTGCCTTTGTCATGCT

GGCTTCTCAGGTCCTCGCTGTCAGACTGTCCTGTCTCCCTGCGAGTCCCAGCCATGCCAGCATGGAGGCCAGTGCCGTCCTAGCCCGG

GTCCTGGGGGTGGGCTGACCTTCACCTGTCACTGTGCCCAGCCGTTCTGGGGTCCGCGTTGCGAGCGGGTGGCGCGCTCCTGCCGGGA

GCTGCAGTGCCCGGTGGGCGTCCCATGCCAGCAGACGCCCCGCGGGCCGCGCTGCGCCTGCCCCCCAGGGTTGTCGGGACCCTCCTGC

CGCAGCTTCCCGGGGTCGCCGCCGGGGGCCAGCAACGCCAGCTGCGCGGCCGCCCCCTGTCTCCACGGGGGCTCCTGCCGCCCCGCGC

CGCTCGCGCCCTTCTTCCGCTGCGCTTGCGCGCAGGGCTGGACCGGGCCGCGCTGCGAGGCGCCCGCCGCGGCACCCGAGGTCTCGGA

GGAGCCGCGGTGCCCGCGCGCCGCCTGCCAGGCCAAGCGCGGGGACCAGCGCTGCGACCGCGAGTGCAACAGCCCAGGCTGCGGCTGG

GACGGCGGCGACTGCTCGCTGAGCGTGGGCGACCCCTGGCGGCAATGCGAGGCGCTGCAGTGCTGGCGCCTCTTCAACAACAGCCGCT

GCGACCCCGCCTGCAGCTCGCCCGCCTGCCTCTACGACAACTTCGACTGCCACGCCGGTGGCCGCGAGCGCACTTGCAACCCGGTGTA

CGAGAAGTACTGCGCCGACCACTTTGCCGACGGCCGCTGCGACCAGGGCTGCAACACGGAGGAGTGCGGCTGGGATGGGCTGGATTGT

GCCAGCGAGGTGCCGGCCCTGCTGGCCCGCGGCGTGCTGGTGCTCACAGTGCTGCTGCCGCCAGAGGAGCTACTGCGTTCCAGCGCCG

ACTTTCTGCAGCGGCTCAGCGCCATCCTGCGCACCTCGCTGCGCTTCCGCCTGGACGCGCACGGCCAGGCCATGGTCTTCCCTTACCA

CCGGCCTAGTCCTGGCTCCGAACCCCGGGCCCGTCGGGAGCTGGCCCCCGAGGTGATCGGCTCGGTAGTAATGCTGGAGATTGACAAC

CGGCTCTGCCTGCAGTCGCCTGAGAATGATCACTGCTTCCCCGATGCCCAGAGCGCCGCTGACTACCTGGGAGCGTTGTCAGCGGTGG

AGCGCCTGGACTTCCCGTACCCACTGCGGGACGTGCGGGGGGAGCCGCTGGAGCCTCCAGAACCCAGCGTCCCGCTGCTGCCACTGCT

AGTGGCGGGCGCTGTCTTGCTGCTGGTCATTCTCGTCCTGGGTGTCATGGTGGCCCGGCGCAAGCGCGAGCACAGCACCCTCTGGTTC

-continued

CCTGAGGGCTTCTCACTGCACAAGGACGTGGCCTCTGGTCACAAGGGCCGGCGGGAACCCGTGGGCCAGGACGCGCTGGGCATGAAGA

ACATGGCCAAGGGTGAGAGCCTGATGGGGGAGGTGGCCACAGACTGGATGGACACAGAGTGCCCAGAGGCCAAGCGGCTAAAGGTAGA

GGAGCCAGGCATGGGGGCTGAGGAGGCTGTGGATTGCCGTCAGTGGACTCAACACCATCTGGTTGCTGCTGACATCCGCGTGGCACCA

GCCATGGCACTGACACCACCACAGGGCGACGCAGATGCTGATGGCATGGATGTCAATGTGCGTGGCCCAGATGGCTTCACCCCGCTAA

TGCTGGCTTCCTTCTGTGGGGGGGCTCTGGAGCCAATGCCAACTGAAGAGGATGAGGCAGATGACACATCAGCTAGCATCATCTCCGA

CCTGATCTGCCAGGGGGCTCAGCTTGGGGCACGGACTGACCGTACTGGCGAGACTGCTTTGCACCTGGCTGCCCGTTATGCCCGTGCT

GATGCAGCCAAGCGGCTGCTGGATGCTGGGGCAGACACCAATGCCCAGGACCACTCAGGCCGCACTCCCCTGCACACAGCTGTCACAG

CCGATGCCCAGGGTGTCTTCCAGATTCTCATCCGAAACCGCTCTACAGACTTGGATGCCCGCATGGCAGATGGCTCAACGGCACTGAT

CCTGGCGGCCCGCCTGGCAGTAGAGGGCATGGTGGAAGAGCTCATCGCCAGCCATGCTGATGTCAATGCTGTGGATGAGCTTGGGAAA

TCAGCCTTACACTGGGCTGCGGCTGTGAACAACGTGGAAGCCACTTTGGCCCTGCTCAAAAATGGAGCCAATAAGGACATGCAGGATA

GCAAGGAGGAGACCCCCCTATTCCTGGCCGCCCGCGAGGGCAGCTATGAGGCTGCCAAGCTGCTGTTGGACCACTTTGCCAACCGTGA

GATCACCGACCACCTGGACAGGCTGCCGCGGGACGTAGCCCAGGAGAGACTGCACCAGGACATCGTGCGCTTGCTGGATCAACCCAGT

GGGCCCCGCAGCCCCCCCGGTCCCCACGGCCTGGGGCCTCTGCTCTGTCCTCCAGGGGCCTTCCTCCCTGGCCTCAAAGCGGCACAGT

CGGGGTCCAAGAAGAGCAGGAGGCCCCCCGGGAAGGCGGGGCTGGGGCCGCAGGGGCCCCGGGGGCGGGGCAAGAAGCTGACGCTGGC

CTGCCCGGGCCCCCTGGCTGACAGCTCGGTCACGCTGTCGCCCGTGGACTCGCTGGACTCCCCGCGGCCTTTCGGTGGGCCCCCTGCT

TCCCCTGGTGGCTTCCCCCTTGAGGGGCCCTATGCAGCTGCCACTGCCACTGCAGTGTCTCTGGCACAGCTTGGTGGCCCAGGCCGGG

CGGGTCTAGGGCGCCAGCCCCCTGGAGGATGTGTACTCAGCCTGGGCCTGCTGAACCCTGTGGCTGTGCCCCTCGATTGGGCCCGGCT

GCCCCCACCTGCCCCTCCAGGCCCCTCGTTCCTGCTGCCACTGGCGCCGGGACCCCAGCTGCTCAACCCAGGGACCCCCGTCTCCCCG

CAGGAGCGGCCCCCGCCTTACCTGGCAGTCCCAGGACATGGCGAGGAGTACCCGGCGGCTGGGGCACACAGCAGCCCCCCAAAGGCCC

GCTTCCTGCGGGTTCCCAGTGAGCACCCTTACCTGACCCCATCCCCCGAATCCCCTGAGCACTGGGCCAGCCCCTCACCTCCCTCCCT

CTCAGACTGGTCCGAATCCACGCCTAGCCCAGCCACTGCCACTGGGGCCATGGCCACCACCACTGGGGCACTGCCTGCCCAGCCACTT

CCCTTGTCTGTTCCCAGCTCCCTTGCTCAGGCCCAGACCCAGCTGGGGCCCCAGCCGGAAGTTACCCCCAAGAGGCAAGTGTTGGCCT

GAGACGCTCGTCAGTTCTTAGATCTTGGGGGCCTAAAGAGACCCCCGTCCTGCCTCCTTTCTTTCTCTGTCTCTTCCTTCCTTTTAGT

CTTTTTCATCCTCTTCTCTTTCCACCAACCCTCCTGCATCCTTGCCTTGCAGCGTGACCGAGATAGGTCATCAGCCCAGGGCTTCAGT

CTTCCTTTATTTATAATGGGTGGGGGCTACCACCCACCCTCTCAGTCTTGTGAAGAGTCTGGGACCTCCTTCTTCCCCACTTCTCTCT

TCCCTCATTCCTTTCTCTCTCCTTCTGGCCTCTCATTTCCTTACACTCTGACATGAATGAATTATTATTATTTTTATTTTTCTTTTTT

TTTTTACATTTTGTATAGAAACAAATTCATTTAAACAAACTTATTATTATTATTTTTTACAAAATATATATATGGAGATGCTCCCTCC

CCCTGTGAACCCCCCAGTGCCCCCGTGGGGCTGAGTCTGTGGGCCCATTCGGCCAAGCTGGATTCTGTGTACCTAGTACACAGGCATG

ACTGGGATCCCGTGTACCGAGTACACGACCCAGGTATGTACCAAGTAGGCACCCTTGGGCGCACCCACTGGGGCCAGGGGTCGGGGGA

GTGTTGGGAGCCTCCTCCCCACCCCACCTCCCTCACTTCACTGCATTCCAGATGGGACATGTTCCATAGCCTTGCTGGGGAAGGGCCC

ACTGCCAACTCCCTCTGCCCCAGCCCCACCCTTGGCCATCTCCCTTTGGGAACTAGGGGGCTGCTGGTGGGAAATGGGAGCCAGGGCA

GATGTATGCATTCCTTTGTGTCCCTGTAAATGTGGGACTACAAGAAGAGGAGCTGCCTGAGTGGTACTTTCTCTTCCTGGTAATCCTC

TGGCCCAGCCTCATGGCAGAATAGAGGTATTTTTAGGCTATTTTTGTAATATGGCTTCTGGTCAAAATCCCTGTGTAGCTGAATTCCC

AAGCCCTGCATTGTACAGCCCCCCACTCCCCTCACCACCTAATAAAGGAATAGTTAACACTCAAAAAAAAAAAAAAAAAA

Human notch 4 (NOTCH4) mRNA NM_004557.3

(SEQ ID NO: 33)

AGACGTGAGGCTTGCAGCAGGCCGAGGAGGAAGAAGAGGGGCAGTGGGAGCAGAGGAGGTGGCTCCTGCCCCAGTGAGAGCTCTGAGG

GTCCCTGCCTGAAGAGGGACAGGGACCGGGGCTTGGAGAAGGGGCTGTGGAATGCAGCCCCCTTCACTGCTGCTGCTGCTGCTGCTGC

TGCTGCTGCTATGTGTCTCAGTGGTCAGACCCAGAGGGCTGCTGTGTGGGAGTTTCCCAGAACCCTGTGCCAATGGAGGCACCTGCCT

GAGCCTGTCTCTGGGACAAGGGACCTGCCAGTGTGCCCCTGGCTTCCTGGGTGAGACGTGCCAGTTTCCTGACCCCTGCCAGAACGCC

CAGCTCTGCCAAAATGGAGGCAGCTGCCAAGCCCTGCTTCCCGCTCCCCTAGGGCTCCCCAGCTCTCCCTCTCCATTGACACCCAGCT

TCTTGTGCACTTGCCTCCCTGGCTTCACTGGTGAGAGATGCCAGGCCAAGCTTGAAGACCCTTGTCCTCCCTCCTTCTGTTCCAAAAG

-continued

GGGCCGCTGCCACATCCAGGCCTCGGGCCGCCCACAGTGCTCCTGCATGCCTGGATGGACAGGTGAGCAGTGCCAGCTTCGGGACTTC

TGTTCAGCCAACCCATGTGTTAATGGAGGGGTGTGTCTGGCCACATACCCCCAGATCCAGTGCCACTGCCCACCGGGCTTCGAGGGCC

ATGCCTGTGAACGTGATGTCAACGAGTGCTTCCAGGACCCAGGACCCTGCCCCAAAGGCACCTCCTGCCATAACACCCTGGGCTCCTT

CCAGTGCCTCTGCCCTGTGGGGCAGGAGGGTCCACGTTGTGAGCTGCGGGCAGGACCCTGCCCTCCTAGGGGCTGTTCGAATGGGGGC

ACCTGCCAGCTGATGCCAGAGAAAGACTCCACCTTTCACCTCTGCCTCTGTCCCCCAGGTTTCATAGGCCCAGACTGTGAGGTGAATC

CAGACAACTGTGTCAGCCACCAGTGTCAGAATGGGGGCACTTGCCAGGATGGGCTGGACACCTACACCTGCCTCTGCCCAGAAACCTG

GACAGGCTGGGACTGCTCCGAAGATGTGGATGAGTGTGAGACCCAGGGTCCCCCTCACTGCAGAAACGGGGGCACCTGCCAGAACTCT

GCTGGTAGCTTTCACTGCGTGTGTGTGAGTGGCTGGGGCGGCACAAGCTGTGAGGAGAACCTGGATGACTGTATTGCTGCCACCTGTG

CCCCGGGATCCACCTGCATTGACCGGGTGGGCTCTTTCTCCTGCCTCTGCCCACCTGGACGCACAGGACTCCTGTGCCACTTGGAAGA

CATGTGTCTGAGCCAGCCGTGCCATGGGGATGCCCAATGCAGCACCAACCCCCTCACAGGCTCCACACTCTGCCTGTGTCAGCCTGGC

TATTCGGGGCCCACCTGCCACCAGGACCTGGACGAGTGTCTGATGGCCCAGCAAGGCCCAAGTCCCTGTGAACATGGCGGTTCCTGCC

TCAACACTCCTGGCTCCTTCAACTGCCTCTGTCCACCTGGCTACACAGGCTCCCGTTGTGAGGCTGATCACAATGAGTGCCTCTCCCA

GCCCTGCCACCCAGGAAGCACCTGTCTGGACCTACTTGCCACCTTCCACTGCCTCTGCCCGCCAGGCTTAGAAGGGCAGCTCTGTGAG

GTGGAGACCAACGAGTGTGCCTCAGCTCCCTGCCTGAACCACGCGGATTGCCATGACCTGCTCAACGGCTTCCAGTGCATCTGCCTGC

CTGGATTCTCCGGCACCCGATGTGAGGAGGATATCGATGAGTGCAGAAGCTCTCCCTGTGCCAATGGTGGGCAGTGCCAGGACCAGCC

TGGAGCCTTCCACTGCAAGTGTCTCCCAGGCTTTGAAGGGCCACGCTGTCAAACAGAGGTGGATGAGTGCCTGAGTGACCCATGTCCC

GTTGGAGCCAGCTGCCTTGATCTTCCAGGAGCCTTCTTTTGCCTCTGCCCCTCTGGTTTCACAGGCCAGCTCTGTGAGGTTCCCCTGT

GTGCTCCCAACCTGTGCCAGCCCAAGCAGATATGTAAGGACCAGAAAGACAAGGCCAACTGCCTCTGTCCTGATGGAAGCCCTGGCTG

TGCCCCACCTGAGGACAACTGCACCTGCCACCACGGGCACTGCCAGAGATCCTCATGTGTGTGTGACGTGGGTTGGACGGGGCCAGAG

TGTGAGGCAGAGCTAGGGGGCTGCATCTCTGCACCCTGTGCCCATGGGGGGACCTGCTACCCCCAGCCCTCTGGCTACAACTGCACCT

GCCCTACAGGCTACACAGGACCCACCTGTAGTGAGGAGATGACAGCTTGTCACTCAGGGCCATGTCTCAATGGCGGCTCCTGCAACCC

TAGCCCTGGAGGCTACTACTGCACCTGCCCTCCAAGCCACACAGGGCCCCAGTGCCAAACCAGCACTGACTACTGTGTGTCTGCCCCG

TGCTTCAATGGGGGTACCTGTGTGAACAGGCCTGGCACCTTCTCCTGCCTCTGTGCCATGGGCTTCCAGGGCCCGCGCTGTGAGGGAA

AGCTCCGCCCCAGCTGTGCAGACAGCCCCTGTAGGAATAGGGCAACCTGCCAGGACAGCCCTCAGGGTCCCCGCTGCCTCTGCCCCAC

TGGCTACACCGGAGGCAGCTGCCAGACTCTGATGGACTTATGTGCCCAGAAGCCCTGCCCACGCAATTCCCACTGCCTCCAGACTGGG

CCCTCCTTCCACTGCTTGTGCCTCCAGGGATGGACCGGGCCTCTCTGCAACCTTCCACTGTCCTCCTGCCAGAAGGCTGCACTGAGCC

AAGGCATAGACGTCTCTTCCCTTTGCCACAATGGAGGCCTCTGTGTCGACAGCGGCCCCTCCTATTTCTGCCACTGCCCCCCTGGATT

CCAAGGCAGCCTGTGCCAGGATCACGTGAACCCATGTGAGTCCAGGCCTTGCCAGAACGGGGCCACCTGCATGGCCCAGCCCAGTGGG

TATCTCTGCCAGTGTGCCCCAGGCTACGATGGACAGAACTGCTCAAAGGAACTCGATGCTTGTCAGTCCCAACCCTGTCACAACCATG

GAACCTGTACTCCCAAACCTGGAGGATTCCACTGTGCCTGCCCTCCAGGCTTTGTGGGGCTACGCTGTGAGGGAGACGTGGACGAGTG

TCTGGACCAGCCCTGCCACCCCACAGGCACTGCAGCCTGCCACTCTCTGGCCAATGCCTTCTACTGCCAGTGTCTGCCTGGACACACA

GGCCAGTGGTGTGAGGTGGAGATAGACCCCTGCCACAGCCAACCCTGCTTTCATGGAGGGACCTGTGAGGCCACAGCAGGATCACCCC

TGGGTTTCATCTGCCACTGCCCCAAGGGTTTTGAAGGCCCCACCTGCAGCCACAGGGCCCCTTCCTGCGGCTTCCATCACTGCCACCA

CGGAGGCCTGTGTCTGCCCTCCCCTAAGCCAGGCTTCCCACCACGCTGTGCCTGCCTCAGTGGCTATGGGGGTCCTGACTGCCTGACC

CCACCAGCTCCTAAAGGCTGTGGCCCTCCCTCCCCATGCCTATACAATGGCAGCTGCTCAGAGACCACGGGCTTGGGGGGCCCAGGCT

TTCGATGCTCCTGCCCTCACAGCTCTCCAGGGCCCCGGTGTCAGAAACCCGGAGCCAAGGGGTGTGAGGGCAGAAGTGGAGATGGGGC

CTGCGATGCTGGCTGCAGTGGCCCGGGAGGAAACTGGGATGGAGGGGACTGCTCTCTGGGAGTCCCAGACCCCTGGAAGGGCTGCCCC

TCCCACTCTCGGTGCTGGCTTCTCTTCCGGGACGGGCAGTGCCACCCACAGTGTGACTCTGAAGAGTGTCTGTTTGATGGCTACGACT

GTGAGACCCCTCCAGCCTGCACTCCAGCCTATGACCAGTACTGCCATGATCACTTCCACAACGGGCACTGTGAGAAAGGCTGCAACAC

TGCAGAGTGTGGCTGGGATGGAGGTGACTGCAGGCCTGAAGATGGGGACCCAGAGTGGGGGCCCTCCCTGGCCCTGCTGGTGGTACTG

-continued

```
AGCCCCCCAGCCCTAGACCAGCAGCTGTTTGCCCTGGCCCGGGTGCTGTCCCTGACTCTGAGGGTAGGACTCTGGGTAAGGAAGGATC

GTGATGGCAGGGACATGGTGTACCCCTATCCTGGGGCCCGGGCTGAAGAAAAGCTAGGAGGAACTCGGGACCCCACCTATCAGGAGAG

AGCAGCCCCTCAAACGCAGCCCCTGGGCAAGGAGACCGACTCCCTCAGTGCTGGGTTTGTGGTGGTCATGGGTGTGGATTTGTCCCGC

TGTGGCCCTGACCACCCGGCATCCCGCTGTCCCTGGGACCCTGGGCTTCTACTCCGCTTCCTTGCTGCGATGGCTGCAGTGGGAGCCC

TGGAGCCCCTGCTGCCTGGACCACTGCTGGCTGTCCACCCTCATGCAGGGACCGCACCCCCTGCCAACCAGCTTCCCTGGCCTGTGCT

GTGCTCCCCAGTGGCCGGGGTGATTCTCCTGGCCCTAGGGGCTCTTCTCGTCCTCCAGCTCATCCGGCGTCGACGCCGAGAGCATGGA

GCTCTCTGGCTGCCCCCTGGTTTCACTCGACGGCCTCGGACTCAGTCAGCTCCCCACCGACGCCGGCCCCCACTAGGCGAGGACAGCA

TTGGTCTCAAGGCACTGAAGCCAAAGGCAGAAGTTGATGAGGATGGAGTTGTGATGTGCTCAGGCCCTGAGGAGGGAGAGGAGGTGGG

CCAGGCTGAAGAAACAGGCCCACCCTCCACGTGCCAGCTCTGGTCTCTGAGTGGTGGCTGTGGGGCGCTCCCTCAGGCAGCCATGCTA

ACTCCTCCCCAGGAATCTGAGATGGAAGCCCCTGACCTGGACACCCGTGGACCTGATGGGGTGACACCCCTGATGTCAGCAGTTTGCT

GTGGGGAAGTACAGTCCGGGACCTTCCAAGGGGCATGGTTGGGATGTCCTGAGCCCTGGGAACCTCTGCTGGATGGAGGGGCCTGTCC

CCAGGCTCACACCGTGGGCACTGGGGAGACCCCCCTGCACCTGGCTGCCCGATTCTCCCGGCCAACCGCTGCCCGCCGCCTCCTTGAG

GCTGGAGCCAACCCCAACCAGCCAGACCGGGCAGGGCGCACACCCCTTCATGCTGCTGTGGCTGCTGATGCTCGGGAGGTCTGCCAGC

TTCTGCTCCGTAGCAGACAAACTGCAGTGGACGCTCGCACAGAGGACGGGACCACACCCTTGATGCTGGCTGCCAGGCTGGCGGTGGA

AGACCTGGTTGAAGAACTGATTGCAGCCCAAGCAGACGTGGGGGCCAGAGATAAATGGGGGAAAACTGCGCTGCACTGGGCTGCTGCC

GTGAACAACGCCCGAGCCGCCCGCTCGCTTCTCCAGGCCGGAGCCGATAAAGATGCCCAGGACAACAGGGAGCAGACGCCGCTATTCC

TGGCGGCGCGGGAAGGAGCGGTGGAAGTAGCCCAGCTACTGCTGGGGCTGGGGGCAGCCCGAGAGCTGCGGGACCAGGCTGGGCTAGC

GCCGGCGGACGTCGCTCACCAACGTAACCACTGGGATCTGCTGACGCTGCTGGAAGGGGCTGGGCCACCAGAGGCCCGTCACAAAGCC

ACGCCGGGCCGCGAGGCTGGGCCCTTCCCGCGCGCACGGACGGTGTCAGTAAGCGTGCCCCCGCATGGGGGCGGGGCTCTGCCGCGCT

GCCGGACGCTGTCAGCCGGAGCAGGCCCTCGTGGGGGCGGAGCTTGTCTGCAGGCTCGGACTTGGTCCGTAGACTTGGCTGCGCGGGG

GGGCGGGGCCTATTCTCATTGCCGGAGCCTCTCGGGAGTAGGAGCAGGAGGAGGCCCGACCCCTCGCGGCCGTAGGTTTTCTGCAGGC

ATGCGCGGGCCTCGGCCCAACCCTGCGATAATGCGAGGAAGATACGGAGTGGCTGCCGGGCGCGGAGGCAGGGTCTCAACGGATGACT

GGCCCTGTGATTGGGTGGCCCTGGGAGCTTGCGGTTCTGCCTCCAACATTCCGATCCCGCCTCCTTGCCTTACTCCGTCCCCGGAGCG

GGGATCACCTCAACTTGACTGTGGTCCCCCAGCCCTCCAAGAAATGCCCATAAACCAAGGAGGAGAGGGTAAAAAATAGAAGAATACA

TGGTAGGGAGGAATTCCAAAAATGATTACCCATTAAAAGGCAGGCTGGAAGGCCTTCCTGGTTTTAAGATGGATCCCCCAAAATGAAG

GGTTGTGAGTTTAGTTTCTCTCCTAAAATGAATGTATGCCCACCAGAGCAGACATCTTCCACGTGGAGAAGCTGCAGCTCTGGAAAGA

GGGTTTAAGATGCTAGGATGAGGCAGGCCCAGTCCTCCTCCAGAAAATAAGACAGGCCACAGGAGGGCAGAGTGGAGTGGAAATACCC

CTAAGTTGGAACCAAGAATTGCAGGCATATGGGATGTAAGATGTTCTTTCCTATATATGGTTTCCAAAGGGTGCCCCTATGATCCATT

GTCCCCACTGCCCACAAATGGCTGACAAATATTTATTGGGCACCTACTATGTGCCAGGCACTGTGTAGGTGCTGAAAAGTGGCCAAGG

GCCACCCCCGCTGATGACTCCTTGCATTCCCTCCCCTCACAACAAAGAACTCCACTGTGGGGATGAAGCGCTTCTTCTAGCCACTGCT

ATCGCTATTTAAGAACCCTAAATCTGTCACCCATAATAAAGCTGATTTGAAGTGTTAAAAAAAAAAAAAAAAAA
```

In some embodiments, the nucleic acid sequence encoding Notch, as described herein, is at least 80% identical to the sequence of SEQ ID NO: 29, SEQ ID NO: 30, SEQ ID NO: 31. SEQ ID NO: 32, or SEQ ID NO: 33. In some embodiments, the nucleic acid sequence encoding Notch is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 29, SEQ ID NO: 30, SEQ ID NO: 31. SEQ ID NO: 32, or SEQ ID NO: 33. In some embodiments, the nucleic acid sequence of Notch, as described herein, can vary from the sequence of SEQ ID NO: 29, SEQ ID NO: 30, SEQ ID NO: 31. SEQ ID NO: 32, or SEQ ID NO: 33 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

A "chimeric Notch receptor polypeptide" of the present disclosure comprises: a) an extracellular domain comprising a first member of a specific binding pair; b) a Notch receptor polypeptide, where the Notch receptor polypeptide has a length of from 50 amino acids to 1000 amino acids, and comprises one or more ligand-inducible proteolytic cleavage sites; and c) an intracellular domain Binding of the first member of the specific binding pair to a second member of the specific binding pair induces cleavage of the Notch receptor polypeptide at the one or more ligand-inducible proteolytic cleavage sites, thereby releasing the intracellular domain. Release of the intracellular domain modulates an activity of a cell that produces the chimeric Notch receptor polypeptide. The extracellular domain comprises a first member of a specific binding pair; the first member of a specific binding pair comprises an amino acid sequence that is heterologous to the Notch receptor polypeptide. The intracellular domain comprises an amino acid sequence that is heterologous to the Notch receptor polypeptide.

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein, including, without limitation, scFvs, or LBDs (Ligand Binding Domains) of growth factors. Additional examples of antigen-binding domains are known in the art.

As used herein, the term "antigen" refers generally to a binding partner specifically recognized by an antigen-binding domain described herein. Exemplary antigens include different classes of molecules, such as, but not limited to, polypeptides and peptide fragments thereof, small molecules, lipids, carbohydrates, and nucleic acids. Non-limiting examples of antigen or antigens that can be specifically bound by any of the antigen-binding domains are described herein. Additional examples of antigen or antigens that can be specifically bound by any of the antigen-binding domains are known in the art.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. Also encompassed by the term are Fab', Fv, F(ab').sub.2, and or other antibody fragments that retain specific binding to antigen, and monoclonal antibodies. A monoclonal antibody can be produced using hybridoma production technology, other production methods known to those skilled in the art can also be used (e.g., antibodies derived from antibody phage display libraries). An antibody can be monovalent or bivalent.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a complementarity-determining region (CDR) derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Boss et al., U.S. Pat. No. 4,816,397; Neuberger, M. S. et al., WO 86/01533; Winter, U.S. Pat. No. 5,225,539; See also, Ladner et al., U.S. Pat. No. 4,946,778; Huston, U.S. Pat. No. 5,476,786; and Bird, R. E. et al., Science, 242: 423-426 (1988)), regarding single chain antibodies.

The term "nanobody" (Nb) refers to the smallest antigen binding fragment or single variable domain (V.sub.HH) derived from naturally occurring heavy chain antibody. They are derived from heavy chain only antibodies, seen in camelids. In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a VHH antibody.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); domain antibodies (dAb; Holt et al., *Trends Biotechnol.* 21:484, 2003); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$fragment that has two antigen combining sites and is still capable of cross-linking antigen. "Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CHI) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b. "Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, Vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). Diabodies are described in EP 404,097; WO 93/11161; and Hollinger et al., *Proc. Natl. Acad. Sci. U.S.A.* 90:6444-6448, 1993.

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified to greater than 90%, greater than 95%, or greater than 98%, The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants, i.e., CAR variants are described, e.g., in PCT Application No. US2014/016527; Fedorov et al., *Sci Transl. Med.* 5(215):215ra172, 2013; Glienke et al., *Front. Pharmacol.* 6:21, 2015; Kakarla & Gottschalk, *Cancer J.* 20(2):151-155, 2014; Riddell et al., *Cancer J.* 20(2):141-144, 2014; Pegram et al., *Cancer J.* 20(2):127-33, 2014; Cheadle et al., *Immunol Rev.* 257(1):91-106, 2014; Barrett et al., *Ann. Rev. Med.* 65:333-347, 2014; Sadelain et al., *Cancer Discov.* 3(4):388-98, 2013; and Cartellieri et al., *J. Biomed. Biotechnol.* 956304, 2010; the disclosures of which are incorporated herein by reference in their entirety.

In the instant invention, transcription of a nucleotide sequence is activated by a transcriptional activator fusion protein composed of HNF1 DNA binding domain (e.g., a human HNF1 DNA-binding domain), which binds with high selectivity to selected DNA sequences, fused to different polypeptides responsible for the ligand-dependent activity of the transactivator and its transcriptional activity (e.g., a human RelA protein). The fusion proteins of the invention are useful for modulating the level of transcription of any target gene linked to the selected HNF1 DNA binding sites. The fusion proteins can be used to specifically activate transcription from genes controlled by HNF1 responsive promoters in tissues lacking endogenous HNF1 and vHNF1 proteins. The fusion proteins of the invention are composed primarily of human elements. Fully human proteins mitigate the risk of immune recognition of the transactivator. Repressors are also provided in similar fashion.

U.S. Pat. No. 9,670,281 describes various chimeric Notch receptors, how to construct them, and methods of using them. The examples described below which detail how to humanize chimeric Notch receptors to have low immunogenicity can employ the chimeric Notch receptors shown in U.S. Pat. No. 9,670,281, e.g., in cells of the monocyte/macrophage lineage.

Certain abbreviations are used throughout to describe the domains of the four human Notch proteins. These are: NEC: extracellular subunit; NTM: transmembrane subunit; EGF: epidermal growth factor; HD: heterodimerization domain; ICN: intracellular domain; LNR: cysteine-rich LNR repeats; TM: transmembrane domain; RAM: RAM domain; NLS: nuclear localizing signals; ANK: ankyrin repeat domain; NCR: cysteine response region; TAD: transactivation domain; PEST: region rich in proline (P), glutamine (E), serine (S) and threonine (T) residues.

Methods

Besides the use for gene therapy, ligand-dependent transcription factors incorporating a humanized DBD of the invention can be used to modulate expression of genes that are contained in recombinant viral vectors and that might interfere with the growth of the viruses in the packaging cell lines during the production processes. These recombinant viruses might be derivatives of Adenoviruses, Retroviruses, Lentiviruses, Herpesviruses, Adeno-associated viruses and other viruses which are familiar to those skilled in the art. Another use would be to provide large scale production of a toxic protein of interest using cultured cells in vitro that do not contain endogenous HNF1/vHNF1 and which have been modified to contain a nucleic acid encoding the transactivator carrying the DBD of the invention in a form suitable for expression of the transactivator in the cells and a gene encoding the protein of interest operatively linked to, for example, an HNF1-dependent promoter.

To induce or repress transcription in vivo the ligand may be administered to the body, or a tissue of interest (e.g. by injection). The body to be treated may be that of an animal, particularly a mammal, which may be human or non-human, such as rabbit, guinea pig, rat, mouse or other rodent, cat, dog, pig, sheep, goat, cattle or horse, or which is a bird, such as a chicken. Suitable routes of administration include oral, intraperitoneal, intramuscular, or i.v.

One convenient way of producing a polypeptide or fusion protein according to the present invention is to express nucleic acid encoding it, by use of nucleic acid in an expression system. Accordingly the present invention also provides in various aspects nucleic acid encoding the transcriptional activator or repressor of the invention, which may be used for production of the encoded protein.

Generally, whether encoding for a protein or component in accordance with the present invention, nucleic acid is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as encompassing reference to the RNA equivalent, with U substituted for T.

Nucleic acid sequences encoding a polypeptide or fusion protein in accordance with the present invention can be readily prepared by the skilled person using the information and references contained herein and techniques known in the art. Sambrook, et al., A Molecular Cloning, A Laboratory Manual, Cold Spring Harbor Laboratory Press (1989-2016), and Ausubel et al., Current Protocols in Molecular Biology, John Wiley and Sons, (1994-2016)). These techniques include (i) the use of the polymerase chain reaction (PCR) to amplify samples of such nucleic acid, e.g. from genomic sources, (ii) chemical synthesis, or (iii) preparing cDNA sequences. DNA encoding portions of full-length coding sequences (e.g. a DNA binding domain, or regulatory domain as the case may be) may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the relevant sequence may be made, e.g. using site directed mutagenesis, to lead to the expression of modified peptide or to take account of codon preference in the host cells used to express the nucleic acid.

In order to obtain expression of the nucleic acid sequences, the sequences may be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of *E. coli*, yeast, and eukaryotic cells such as COS or CHO cells.

Thus, the present invention also encompasses a method of making a polypeptide or fusion protein as disclosed, the method including expression from nucleic acid encoding the product (generally nucleic acid according to the invention). This may conveniently be achieved by growing a host cell in culture, containing such a vector, under appropriate conditions which cause or allow expression of the polypeptide. Polypeptides may also be expressed in in vitro systems.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli.*

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular cloning: a Laboratory Manual: 4th edition, Green and Sambrook et al., 2012, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al., Eds., John Wiley & Sons, 2016.

For use in mammalian cells, a recombinant expression vector's control functions may be provided by viral genetic material. Exemplary promoters include those derived from polyoma, Adenovirus 2, cytomegalovirus and SV40.

A regulatory sequences of a recombinant expression vector used in the present invention may direct expression of a polypeptide or fusion protein preferentially in a particular cell type, i.e., tissue-specific regulatory elements can be used. In one embodiment, the recombinant expression vector of the invention is a plasmid. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in Ausubel, et al. (supra). The genome of a virus such as adenovirus can be manipulated such that it encodes and expresses a transactivator or repressor protein but is inactivated in terms of its ability to replicate in a normal lytic viral life cycle.

Thus, a further aspect of the present invention provides a host cell containing heterologous nucleic acid as disclosed herein.

Still further, a recombinant expression vector can be designed to allow homologous recombination between the nucleic acid encoding the transactivator or repressor and a target gene in a host cell. Such homologous recombination vectors can be used to create homologous recombinant animals that express a fusion protein of the invention.

Examples of mammalian cell lines which may be used include CHO dhfr-cells (Urlaub and Chasin, *Proc. Natl. Acad. Sci. U.S.A.* 77:4216-4220, 1980), 293 cells (Graham et al., *J. Gen. Virol.* 36:59, 1977) and myeloma cells like SP2 or NS0 (*Meth. Enzymol.* 73(B):3-46, 2016). In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, muscle cells, neuronal cells and skin epithelium and airway epithelium. Additionally, for transgenic or homologous recombinant animals, embryonic stem cells and fertilized oocytes can be modified to contain nucleic acid encoding a transactivator or repressor fusion protein.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All four human Notch proteins (Notch 1-4) were tested for their ability of their core LNR, HD and transmembrane domains to selectively release a GAL4-VP16 transcription factor fused C-terminal to their intracellular portion in response to an N-terminal extracellular CD19 ScFv fusion binding to its cognate antigen. Human Notch2 and Notch3 released functional quantities of the transcription factor upon antigen binding. Human Notch1 released small amounts of transcription factor in response to antigen-binding, while human Notch 4 released no detectable amount of transcription factor. Human Notch3 showed the best functional release of transcription factor in response to antigen-binding, and was used for a number of designs.

We further improved the minimal LIN12-HD-transmembrane "core" Notch2 and Notch3 domains to include an extra, short (~60aa) intracellular domain that includes the natural Notch Nuclear Localization Sequence (NLS) to improve nuclear import upon self-cleavage and release of the transcription factor domain.

In order to minimize immunogenicity of the chimeric Notch receptor, a series of synthetic humanized transcription factors were designed and built from (1) a minimized human DNA-Binding Domain (DBD) and (2) a minimized, strong Transactivation Domain (TAD). The reason for creating an unnatural but humanized chimera is to eliminate unwanted endogenous cofactor interactions between the chimeric Notch receptor-released humanized transcription factor and the natural binding partners that a full-length human transcription factor would interact with. This is to improve the robustness and predictability of the chimeric antigen receptor induced transcriptional response in cellular applications utilizing a humanized antigen receptor.

A comprehensive screen of human transcription factors was undertaken in order to find natural DNA-Binding Domains to satisfy several criteria: (1) that the DNA Binding Domain belonged to a transcription factor that is generally not naturally expressed in the target host-cell-type. In the present embodiment we sought DNA-binding domains absent from any hematopoietic lineage, including especially lymphoid and T-cell lineages; and (2) that the DNA Binding Domain bound to its target DNA sequence with high affinities, with a dissociation constant at or lower than 10 nM.

The DNA-Binding Domains were first tested for their ability to bind to multisite synthetic promoters by expressing the DNA-binding domain fused to a natural transactivation domain to verify that it could upregulate GFP driven by the synthetic multisite promoter. This verifies that the designed cognate promoter-DNA-Binding Domain pair were correct.

The verified DNA-Binding Domains were then tested as fusions to synNotch along with a strong transactivation domain and assayed for their ability to upregulate the cognate-multisite-promoter driving GFP upon stimulation by external antigen and release to the nucleus.

Examples of human DNA-binding domains tested with this strategy were those taken from human CRX (Furukawa, Takahisa, Eric M. Morrow, and Constance L. Cepko. "Crx, a novel otx-like homeobox gene, shows photoreceptor-specific expression and regulates photoreceptor differentiation." Cell 91.4 (1997):531-541, //doi.org/10.1016/S0092-8674(00)80439-0), POU1F1 (Jacobson, Eric M., et al. "Structure of Pit-1 POU domain bound to DNA as a dimer: unexpected arrangement and flexibility." Genes & Development 11.2 (1997): 198-212, doi:10.1101/gad.11.2.198), HNF1A, EGR1 (Thiel, Gerald, and Giuseppe Cibelli. "Regulation of life and death by the zinc finger transcription factor Egr-1." Journal of cellular physiology 193.3 (2002): 287-292, DOI: 10.1002/jcp.10178) ZBTB18 (Najafabadi, Hamed S., et al. "C2H2 zinc finger proteins greatly expand the human regulatory lexicon." (Nature biotechnology 33.5 (2015): 555-562. doi:10.1038/nbt.3128), and ZNF528 (Najafabadi, Hamed S., et al. "C2H2 zinc finger proteins greatly expand the human regulatory lexicon." Nature biotechnology 33.5 (2015): 555-562, doi:10.1038/nbt.3128). All DNA-binding domains were able to induce strong GFP expression under control of their cognate promoters when expressed as soluble transcription factors. However, only the DNA-binding domains of HNF1A and EGR1 were able to induce detectable expression of GFP under their cognate promoter when expressed and released from a chimeric Notch fusion construct. Only a small fraction of the expressed chimeric Notch protein will self-cleave on response to stimulation by antigen-binding, so the effective concentration of the liberated, nuclear-imported transcription factor will be much lower than compared to a directly expressed transcription factor. Thus, a chimeric Notch-released transcription factor must exhibit extremely strong binding to its cognate promoter in order to be functional.

Human Transactivation Domains were screened for activity in the context of chimeric Notch designs by expressing them as fusions to a Gal4 DNA Binding Domain and measuring relative levels of GFP expression under control of a cognate Gal4 multisite promoter. These were also compared against the GFP expression levels induced by the non-human VP64 transactivation domain. Examples of human transactivation domains screened in this manner include RelA (p65) (Wang, Weixin, et al. "The nuclear factor-κB RelA transcription factor is constitutively activated in human pancreatic adenocarcinoma cells." Clinical Cancer Research 5.1 (1999): 119-127), YAP (Lian, Ian, et al. "The role of YAP transcription coactivator in regulating stem cell self-renewal and differentiation." Genes & development 24.11 (2010): 1106-1118, doi:10.1101/gad.1903310), WWTR1(TAZ) (Hong, Jeong-Ho, et al. "TAZ, a transcriptional modulator of mesenchymal stem cell differentiation." Science 309.5737 (2005): 1074-1078, doi: 10.1126/science.1110955), CREB3(LZIP) (Omori, Yoshihiro, et al. "CREB-H: a novel mammalian transcription factor belonging to the CREB/ATF family and functioning via the box-B element with a liver-specific expression." Nucleic acids research 29.10 (2001): 2154-2162, doi: //doi.org/10.1093/nar/29.10.2154), and MyoD (Weintraub, Harold, and Robert Davis. "The myoD gene family: nodal point during specification of the muscle cell lineage." Science 251.4995 (1991): 761, doi: 10.1126/science.1846704). Of these, the transactivation domains of RelA(p65), WWTR1(TAZ), and CREB3(LZIP) showed activity in chimeric Notch. The activity of the transactivation domain of RelA(p65) was measured to be the strongest in inducing GFP expression.

Combining the best performing human Notch domain, the best performing DNA-binding domain, and the best-performing Transactivation domain results in the Notch3-HNF1a-p65 design for a chimeric, humanized Notch receptor.

Applications of humanized chimeric Notch receptor are numerous. Such can, for example, deliver CARs or t-cell receptors to treat disease. U.S. Pat. No. 9,670,281.

Reference to nucleotide or protein sequences below, generally refer to sequences in the National Center for Biotechnology Information (NCBI) (ncbi.nlm.niv.gov). Nucleotide sequences are all 5' to 3.'

Example 1. Construction of Chimeric Notch with Notch3, DNA Binding Domain of HNF1alpha and p65 Transactivation Domain The following sequences were ordered as double-stranded synthetic DNA fragments (IDT gBlocks) or single-stranded long-oligonucleotides (IDT ultramers) which were made double-stranded by annealing with a short 3' reverse-complement oligo and second-strand synthesis by Phusion polymerase (Thermo Scientific™ Phusion™ High-Fidelity DNA Polymerase; Catalogue No. F534S).

Four synthetic dsDNA pieces were ordered from Integrated DNA Technologies (IDT) containing:

1. Human CD8a signal peptide 1-22 (NP_001139345 amino acids 1-22, (MALPVTALLLPLALLLHAARPS) (SEQ ID NO: 1)), Myc-tag (EQKLISEEDL) (SEQ ID NO: 2), Anti-Human B cell (CD19) Antibody, clone FMC63.
2. Human Notch3 core (gi|134244285|NP_000426.2 amino acids 1374-1734).
3. GS flexible Linker (GSAAAGGSGGSGGS) (SEQ ID NO: 3), Human HNF1alpha (gi|807201167|NP_001293108.1 amino acids 1-283), GS flexible Linker (GGGSGGGS) (SEQ ID NO: 4).
4. Human Rel-A (p65) (gi|223468676|NP_068810.3 amino acids 1-551) plus stop codon.

These were designed to incorporate 20 nt of homology with 5' and 3' neighboring fragments for in-vitro recombination by the In-fusion cloning system (Clontech). All fragments were assembled by the In-fusion into the MluI/NotI cut vector backbone of self-inactivating lentivirus vector pHR-SIN:SFFV (Addgene; Catalogue No. 79121.

A second reporter construct was constructed by assembling three synthetic dsDNA fragments:

1. a 4× repeated palindromic DNA binding sequence for the HNF1a DNA-binding domain dimer, immediately followed by a minimal CMV promoter (SEQ ID NO: 34)

atcgatGTTAATaATTAACatatatGTTAATcATTAACtatataGTTAAT tATTAACcgctatGTTAATgATTAACactagt*taggcgtgtacggtggga*

*ggcctatataagcagagctcgtttagtgaaccgtcagatcgcctggagac*

*gccatccacgctgttttgacctccatagaagacaccgggaccgatccagc*

2. A Kozak sequence (GCCGCCACC) (SEQ ID NO: 35) and coding sequence for EGFP.
3. An EF1α promoter sequence
4. A Kozak sequence (GCCGCCACC) (SEQ ID NO: 35) and coding sequence for mCherry.

These fragments were designed to incorporate an additional 20-25nt of homology with 5' and 3' neighboring fragments for in-vitro recombination by the In-fusion cloning system (Clontech). All fragments were assembled by the In-fusion reaction into the MluI/NotI cut vector backbone of self-inactivating lentivirus vector pHR-SIN:SFFV.

The lentiviral construct was then co-transfected into 293T cells together with the viral packaging plasmids pCMVdR8.91 and pMD2.G using the transfection reagent FuGENE HD (Roche). Amphotropic VSV-G pseudotyped lentiviral particles in the supernatant were collected 48 hours later.

Viral particles from both synnotch and reporter constructs were used to transduce simultaneously either Jurkat cells or primary CD4+/CD8+ pan-T cells from human donors. An extended description of lentiviral protocols can be found in Morsut et al. *Cell.* 2016 Feb. 11; 164(4):780-91.

Transduced Jurkat cells were tested for expression 2 days post-transduction, transduced human primary pan-T cells were tested for expression 7 days post-transduction. Expression of the synnotch construct was tested by labelling the expressed cell-surface Myc-tag marker with alexa-647-conjugated anti-myc antibody (Cell Signaling Techology, Myc-Tag (9B11) Mouse mAb (Alexa Fluor®647 Conjugate; Catalogue No. 2233).

Expression of the cognate reporter construct for the synnotch was tested by observing the constitutive mCherry expression produced from the reporter vector. Double-positive cells were sorted for further assays.

Cells expressing both synnotch constructs and its reporter were assayed for synnotch activity by stimulating the cells for 24 hours with magnetic beads coated with anti-Myc-tag antibodies (obtained from Thermofisher Scientific, Catalog number: 88842) or magnetic beads coated with anti-HA-tag antibodies as a negative control (obtained from Pierce™ Anti-HA Magnetic Beads, catalog number 88836). The mean fluorescence intensity of the reporter's EGFP expression in response to the antibody-binding stimulation was measured for the stimulated cells vs that of the negative-control stimulated cells.

Cells expressing both synnotch constructs and its reporter were additionally assayed for synnotch activity by stimulating the cells for 24 hours by coincubating with a Raji cell line expressing high-levels of CD19 antigen (American Type Culture Collection (ATCC) CCL-86™ (Raji)) as well as coincubating with cell lines negative for cell-surface CD19. The mean fluorescence intensity of the cotransduced reporter's9 EGFP expression in response to the cell-bound-antigen stimulation was measured for the stimulated cells vs that of the negative-control stimulated cells.

Example 2. Construction of Chimeric Notch with Notch3, DNA Binding Domain of EGR1 and p65 Transactivation Domain Vector construction was similar to that of Example 1 with the exception that the synthetic DNA fragment containing the DNA-binding domain of human HNF1a was substituted for the following containing the human EGR1 DNA-binding domain:

GS flexible Linker (GSAAAGGSGGSGGS) (SEQ ID NO: 3), Human EGR1 (genbank NP_001955 amino acids 333-423), GS flexible Linker (GGGSGGGS) (SEQ ID NO: 4)

The reporter construct contained a cognate 4× binding site a 5× repeated DNA binding sequence for the EGR1 DNA-binding domain dimer, immediately followed by a minimal CMV promoter:

(SEQ ID NO: 34)

acccgggggacagcagagatccagtttatcgatGCGTGGGCGataGCGG

GGGCGtatGCGTGGGCGattGCGGGGGCGttaGCGTGGGCGactagt*tag*

*gcgtgtacggtgggaggcctatataagcagagctcgtttagtgaaccgtc*

*agatcgcctggagacgccatccacgctgttttgacctccatagaagacac*

*cgggaccgatccagc*

Example 3. Construction of Above Examples with WWTR1 (TAZ) Transactivation Domain Vector construction was identical to that of Example 1&2 with the exception that the synthetic DNA fragment containing the transactivation domain of human RelA(p65) was replaced by the following containing the transactivation domain of human WWTR1:

Human WWTR1(TAZ) (Genpept NP_056287.1 amino acids 165-395) plus stop codon.

Example 4. Construction of Above Examples with CREB3(LZIP) Transactivation Domain Vector construction was identical to that of Example 1 & 2 with the exception that the synthetic DNA fragment containing the transactivation domain of human RelA(p65) was replaced by the following containing the transactivation domain of human CREB3(LZIP):

Human CREB3(LZIP) (Genpept NP_006359.3 amino acids 1-95) plus stop codon.

Example 5. Construction of the Above Examples Using the Human Notch 2 Domain Vector construction was identical to that of Examples above with the exception that the synthetic DNA fragment containing the minimized human notch3 lin12-HD-NLS domains were replaced by the following fragment containing the minimized LIN12-HD-NLS domains of human notch2:Human Notch2 core (gi|24041035|NP_077719.2) amino acids 1413-1780.

Example 6. Transduction of Monocyte-Derived Macrophages with a Chimeric Notch Made from Notch3, the DNA Binding Domain of HNF1alpha, and the p65 Transactivation Domain Mouse Notch 1 and human Notch 3 proteins were both tested for the ability of their core LNR, HD and transmembrane domains to selectively release a transcription factor, Gal4-VP64 for the mouse Notch protein or HNF1a-p65 for the human Notch protein, which was fused C-terminal to the intracellular portion of the protein, in response to the binding of the N-terminal extracellular CD19 scFv fusion portion of each protein to its cognate antigen in human monocyte-derived macrophages. The human Notch chimeric protein was constructed as described herein. The mouse Notch chimeric protein was constructed as described in U.S. Pat. No. 9,670,281.

Lentiviral constructs were co-transfected into 293T cells together with the viral packaging plasmids pCMV-dR8.91 and pMD2.G as well as the pVpx plasmid using the transfection reagent FuGENE HD (Roche). Amphotropic VSV-G pseudotyped lentiviral particles in the supernatant were collected 48 hours later. Jurkat cells were infected with different dilutions of viral supernatant and 7 days post infection and VCNs were determined by using the dd PCR.

Human macrophages were derived from monocytes isolated from freshly isolated (within 8 hours) healthy adult human blood (AllCells Inc.). CD14+ monocyte cells were enriched from blood utilizing RosetteSep negative selection (STEMCELL Technologies, RosetteSep™ Human Monocyte Enrichment Cocktail, Catalogue No. 15028). CD14+ cells were differentiated into macrophages as previously described (Hrecka et al., *Nature* 2011). Briefly, CD14% cells were placed in 24 well plates at a density of $3\times10^5$ cells/mL in 1 mL of media. Media was comprised of Dulbecco's Modified Eagle Media supplemented with 10% heat inactived foetal bovine serum, 2 mM L-glutamine, 100 u/ml Penicillin-G, 100 μg/mL streptomycin, 10 ng/mL macrophage-colony stimulating factor (M-CSF, Miltenyi Biotec) from day 0 to 2 than at 20 ng/mL from day 2 onwards.

Viral particles from both synNotch and reporter constructs were used to simultaneously to transduce monocyte-derived macrophage cells from human donors 4 days following isolation. Cells were transduced across a range of multiplicity of infections (0.1 to 1) with either the human Notch3, DNA binding domain of HNF1a and p65 transactivation domain (hNotch3/HNF1a/p65) or the mouse Notch 1, DNA binding domain of Gal4 and VP64 transactivation domain (mNotch1/Gal4/VP64). An extended description of lentiviral protocols can be found in Morsut L, et al. *Cell.* 2016 Feb. 11; 164(4):780-91.

Transduced human primary myeloid cells were tested for expression 7 days post-transduction by flow cytometry. Expression of the synNotch construct in myeloid cells was tested by labelling the myeloid cells with an PE-Cy7 anti-CD14+ antibody (BD Biosciences, PE-Cy™7 Mouse Anti-Human CD14 Antibody (Clone M5E2 (RUO)), Catalogue No. 557907) as well as the cell-surface expressed Myc-tag marker with an alexa-647-conjugated anti-my antibody (Cell Signaling Techology, Myc-Tag (9B11) Mouse mAb (Alexa Fluor® 647 Conjugate; Catalogue No. 2233).

Expression of the cognate reporter construct for the synNotch was tested by measuring the constitutive mCherry expression produced from the reporter vector by flow cytometry.

Cells were assayed for synNotch activity by stimulating the cells for 24 hours by co-culturing with a Daudi cell line expressing high-levels of CD19 antigen (American Type Culture Collection (ATCC) CCL-213™ cells (Daudi cells)) as well as cell lines negative for cell-surface CD19.

The fluorescence intensity of the cotransduced reporter's EGFP expression in response to the cell-bound-antigen stimulation was measured for these CD14+ monocyte-derived macrophages when stimulated with antigen positive CD19+ cells versus that of the negative-control stimulated cells.

Figure 2:
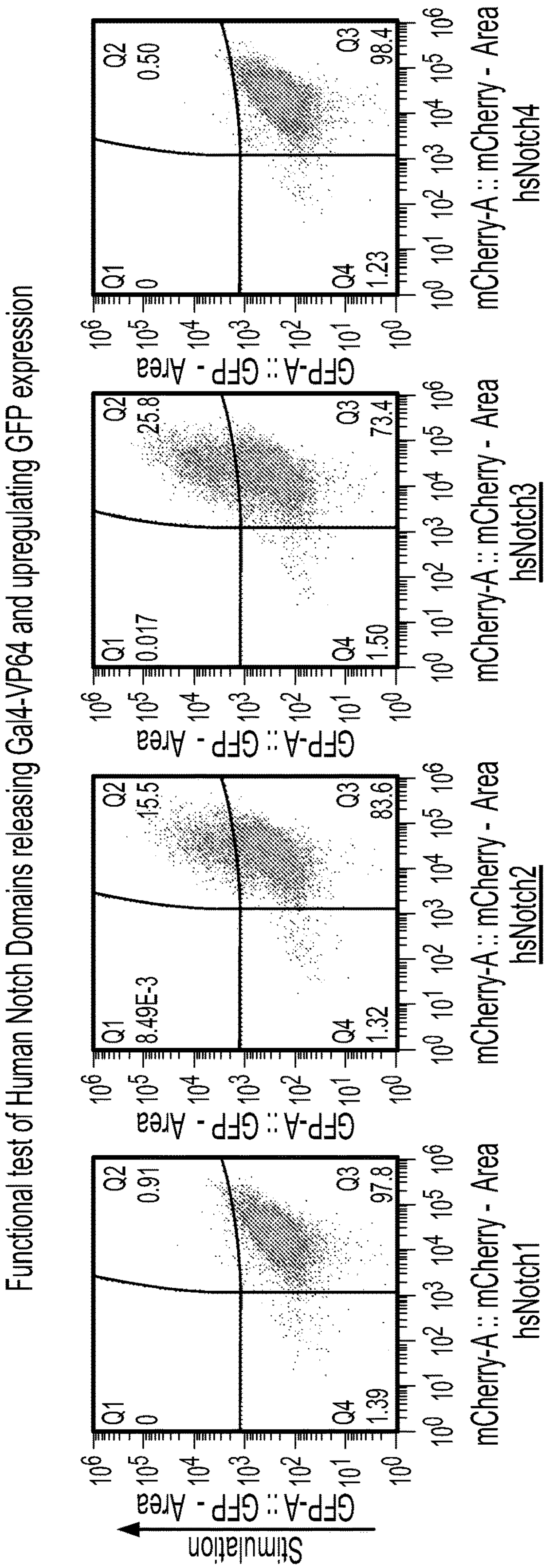
FIG. 2. Experimental data showing the relative performance of the four human Notch homologs in releasing GAL4-vp64 upon stimulation by an external myc-tag binding antigen to myc-bearing beads. hsNotch2 and hsNotch3 are the only homologs showing strong activity.
Figure 3A:
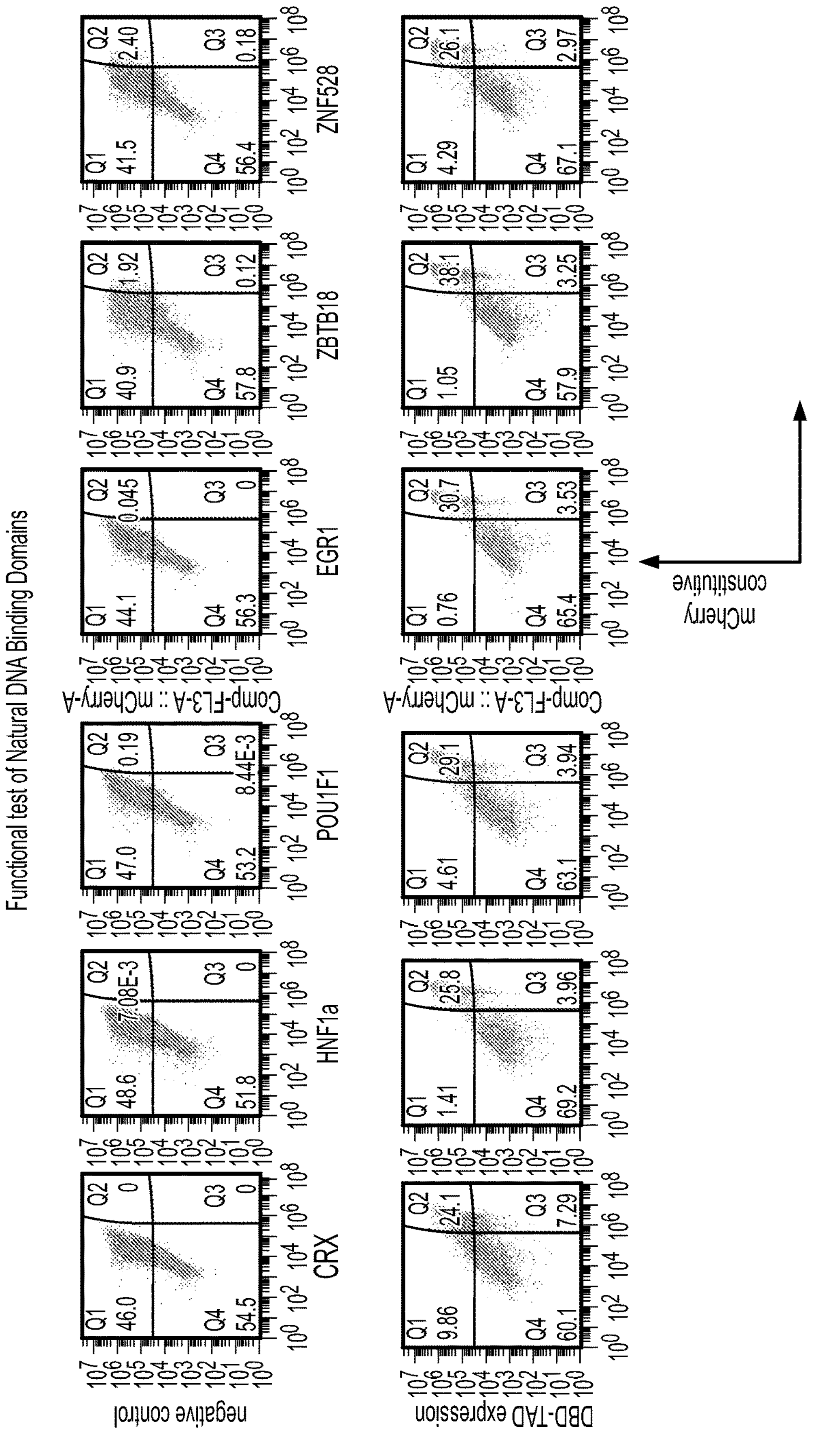
FIG. 3A. Experimental data showing the functional behavior of human DNA-binding domains fused to p65 transactivation domain upregulating GFP expression.
Figure 3B:
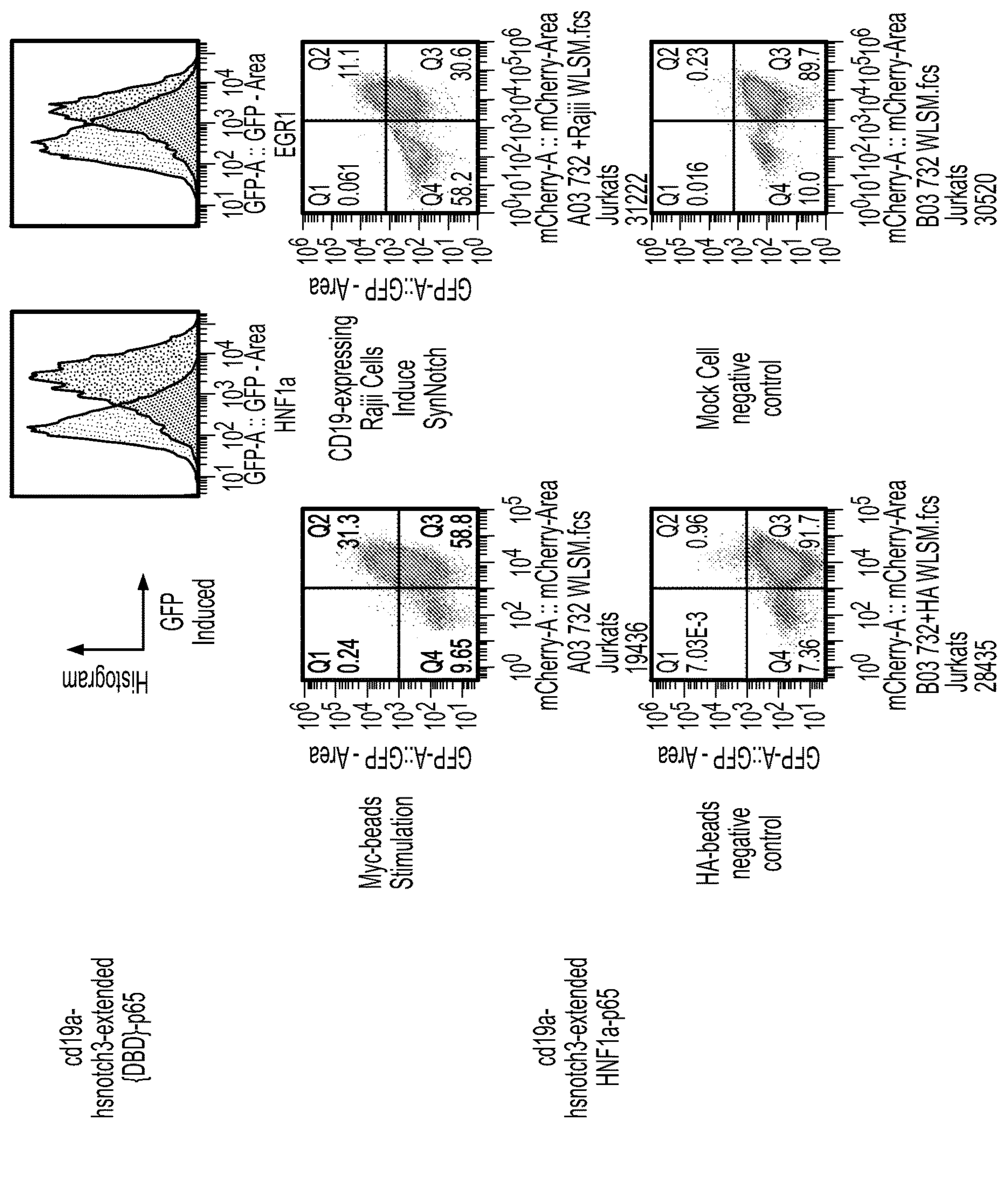
FIG. 3B. Experimental data showing the functional behavior of two working synthetic Notch human DNA-binding domains with p65 transactivation domains upregulating GFP expression.
Figure 4:
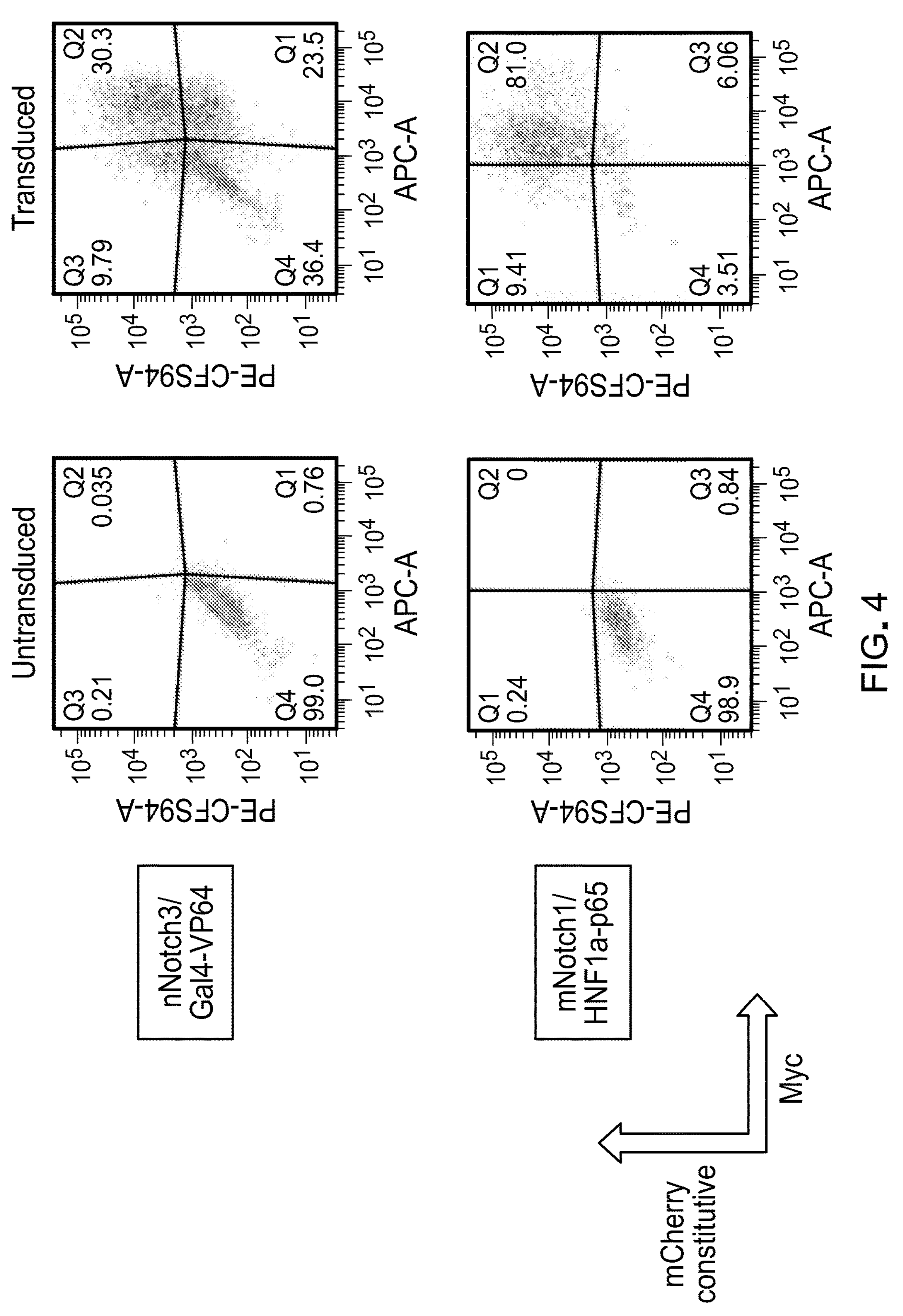
FIG. 4. Experimental data showing the expression of chimeric notch receptors in human monocyte-derived macrophage cells. Experimental data showing the percent transduction of mouse Notch 1 protein/Gal4 and VP64 transcription factors (top) and human Notch 3 protein/HNF1a and p65 transcription factors (bottom) relative to untransduced monocyte-derived macrophages (right).
Figure 5A:
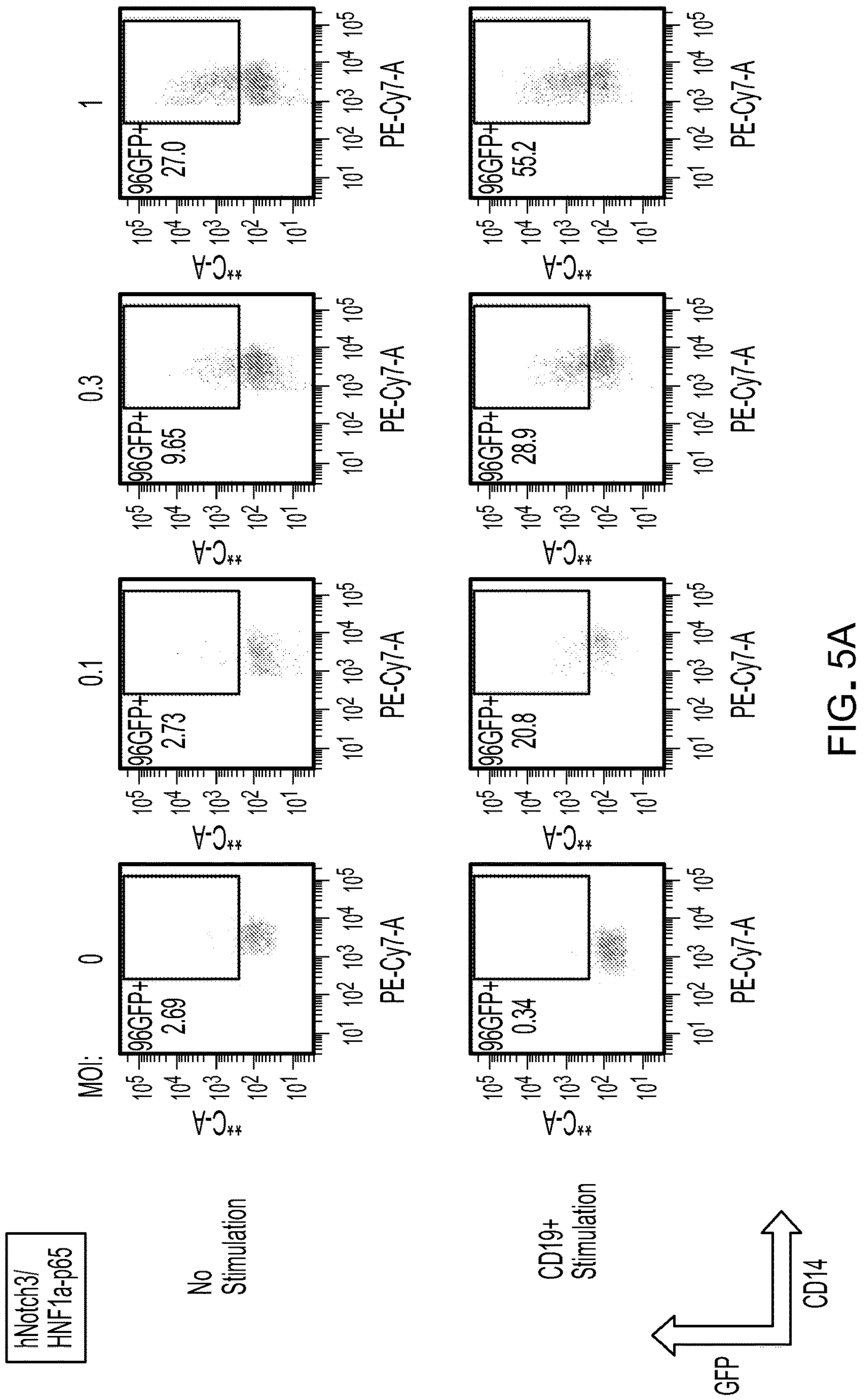
FIG. 5A. Experimental data showing the functional behavior of human Notch 3 and human DNA-binding domains fused to p65 transactivation domain upregulating GFP expression in human monocyte-derived macrophages.
Figure 5B:
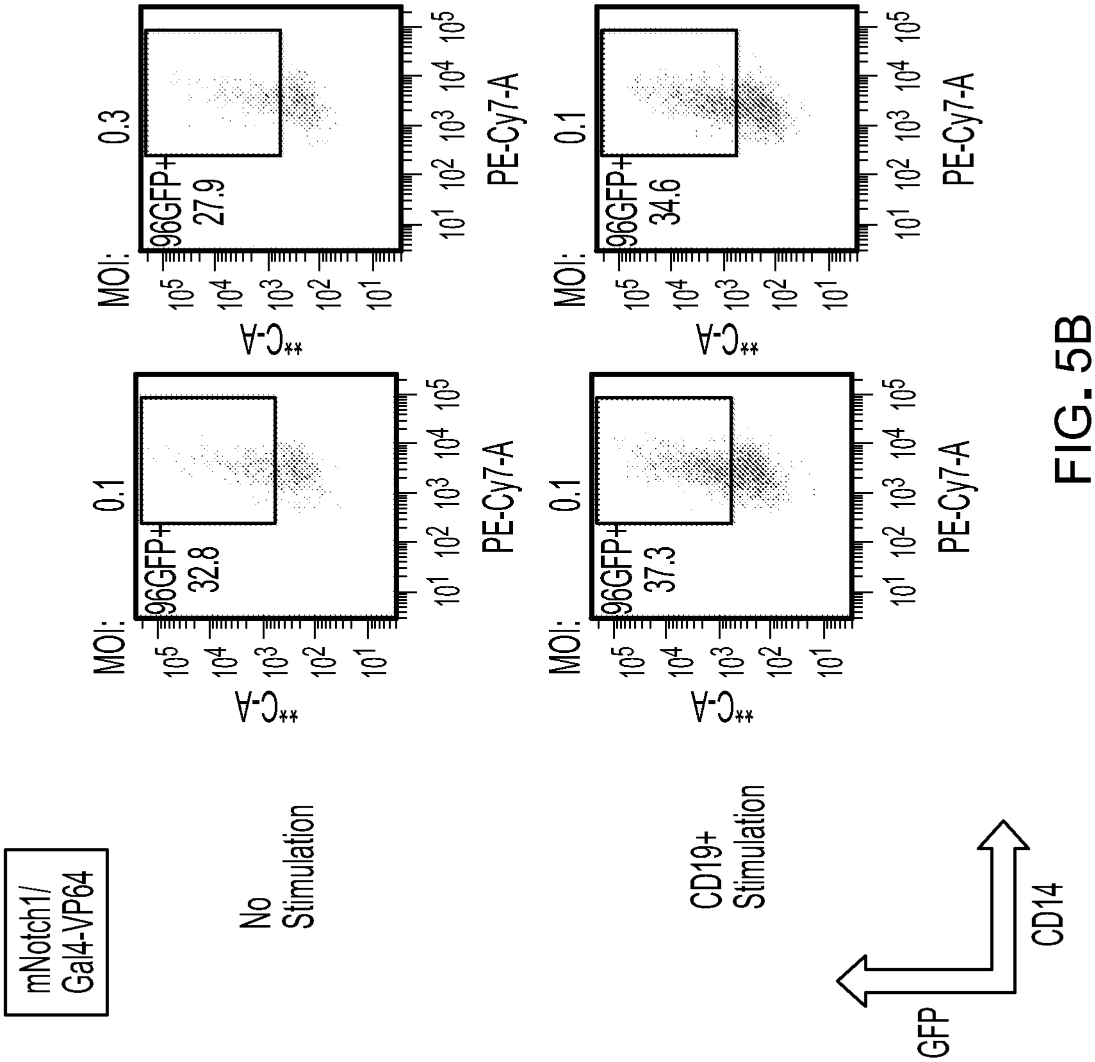
FIG. 5B. Experimental data showing the functional behavior of mouse Notch 1 and non-human Gal4 binding domains fused to VP64 transactivation upregulating GFP expression in human myeloid cells.

Overall, in monocyte-derived macrophages, the chimeric humanized Notch receptor, human Notch3-HNF1a-p65, induced unregulated expression of the reporter construct. The Notch, DNA-binding domain, and transactivation domain components of the protein were functional in macrophages. The chimeric mouse Notch receptor, Notch1-Gal4-VP64, did not induce the selective expression of GFP in response to an N-terminal extracellular CD19 scFv fusion binding to its cognate antigen compared to a negative control without any CD19 expression. See, FIGS. 2, 3A, 3B, 4, 5A, and 5B.

What is claimed is:

1. A chimeric Notch polypeptide comprising, from N-terminal to C-terminal and in covalent linkage: a) an extracellular domain comprising a binding agent that specifically binds to an antigen; b) a Notch 2 or Notch 3 core region; c) one or more proteolytic cleavage sites; and d) an intracellular domain comprising a transcriptional regulator; and wherein said transcriptional regulator is from the Hepatocyte Nuclear Factor (HNF) transcriptional regulator family.

2. The chimeric Notch polypeptide of claim 1, wherein said transcriptional regulator is HNF1 alpha or HNF1 beta.

3. The chimeric Notch polypeptide of claim 1, wherein binding of the binding agent to the antigen induces cleavage of the Notch polypeptide at the one or more proteolytic cleavage sites, thereby releasing the intracellular domain and the transcriptional regulator.

4. The chimeric Notch polypeptide of claim 1, wherein the transcriptional regulator comprises a DNA binding domain of human origin and a transactivation domain of human origin.

5. The chimeric Notch polypeptide of claim 4, wherein the transactivation domain is selected from the group consisting of RelA (p65), YAP, WWTR1(TAZ), and CREB3(LZIP).

6. The chimeric Notch polypeptide of claim 1, wherein said binding agent comprises an antibody.

7. The chimeric Notch polypeptide of claim 6, wherein said antibody is selected from the group consisting of scFv, bispecific antibody, nanobody, and bite.

8. The chimeric Notch polypeptide of claim 7, wherein said transcriptional regulator is a transcriptional activator.

9. The chimeric Notch polypeptide of claim 1, wherein the Notch 2 or Notch 3 core region comprises human Lin12 LNR.

* * * * *